United States Patent [19]
Queen et al.

[11] Patent Number: 5,693,761
[45] Date of Patent: Dec. 2, 1997

[54] POLYNUCLEOTIDES ENCODING IMPROVED HUMANIZED IMMUNOGLOBULINS

[75] Inventors: Cary L. Queen, Los Altos; William P. Schneider, Mountain View; Harold E. Selick, Belmont, all of Calif.

[73] Assignee: Protein Design Labs, Inc., Mountain View, Calif.

[21] Appl. No.: 474,040

[22] Filed: Jun. 7, 1995

Related U.S. Application Data

[62] Division of Ser. No. 634,278, Dec. 19, 1990, Pat. No. 5,530,101, which is a continuation of Ser. No. 590,274, Sep. 28, 1990, abandoned, and a continuation of Ser. No. 310,252, Feb. 13, 1989, abandoned, which is a continuation of Ser. No. 290,975, Dec. 28, 1988, abandoned.

[51] Int. Cl.$^6$ ........................... C07H 21/04
[52] U.S. Cl. .................. 536/23.53; 530/387.3; 435/320.1; 435/252.3
[58] Field of Search ............. 536/23.53; 530/387.3; 435/320.1, 252.3

[56] References Cited

U.S. PATENT DOCUMENTS

| | | | |
|---|---|---|---|
| 4,578,335 | 3/1986 | Urdal et al. | 530/351 |
| 4,816,397 | 3/1989 | Boss et al. | 435/68 |
| 4,816,565 | 3/1989 | Honjo et al. | 435/69.1 |
| 4,816,567 | 3/1989 | Cabilly et al. | 530/387 |
| 4,845,198 | 7/1989 | Urdal et al. | 530/387 |
| 4,867,973 | 9/1989 | Goers et al. | 424/85.91 |
| 5,198,359 | 3/1993 | Taniguchi et al. | 435/252.3 |
| 5,225,539 | 7/1993 | Winter | 530/387.3 |
| 5,476,786 | 12/1995 | Huston et al. | 435/85.8 |

FOREIGN PATENT DOCUMENTS

| | | |
|---|---|---|
| 0 120 694 | 10/1984 | European Pat. Off. . |
| 0171496 | 2/1986 | European Pat. Off. . |
| 0173494 | 3/1986 | European Pat. Off. . |
| 0184187 | 6/1986 | European Pat. Off. . |
| 0256654 | 7/1987 | European Pat. Off. . |
| 0239400 | 9/1987 | European Pat. Off. . |
| 0266663 | 6/1988 | European Pat. Off. . |
| 0 323 806 | 7/1989 | European Pat. Off. . |
| 0 328 404 | 8/1989 | European Pat. Off. . |
| 0 365 209 | 4/1990 | European Pat. Off. . |
| 0 365 997 | 5/1990 | European Pat. Off. . |
| 0 125 023 | 6/1991 | European Pat. Off. . |
| 0460167 | 12/1991 | European Pat. Off. . |
| 2188941 | 10/1987 | United Kingdom . |
| 8928874 | 12/1989 | United Kingdom . |
| WO 86/05513 | 9/1986 | WIPO . |
| WO 87/02671 | 5/1987 | WIPO . |
| WO 88/09344 | 12/1988 | WIPO . |
| WO 89/01783 | 3/1989 | WIPO . |
| 91/09967 | 7/1991 | WIPO . |

OTHER PUBLICATIONS

Better et al. "*Escherichia coli* Secretion of an Active Chimeric Antibody Fragment," *Science*, 240:1041–1043 (1988).

Bird et al., "Single-Chain Antigen-Binding Proteins," *Science*, 242:423–426 (1988).

Boulianne et al., "Production of functional chimeric mouse/human antibody," *Nature*, 312:643–646 (1984).

Carter et al., "Humanization of an anti-p185$^{HER2}$ antibody for human cancer therapy," *Proc. Natl. Acad. Sci.*, 89:4285–4289 (1992).

Chothia, C. and A.M. Lesk, "Canonical Structures for the Hypervariable Regions of Immunoglobulins," *J. Mol. Biol.*, 196:901–917 (1987).

Co et al., "Humanized antibodies for antiviral therapy," *Proc. Natl. Acad. Sci.*, 88:2869–2873 (1991).

Co et al., "Chimeric and humanized antibodies with specificity for the CD33 antigen," *J. Immunol.*, 148:1149–1154 (1992).

Daugherty et al., "Polymerase chain reaction facilitates the cloning, CDR-grafting, and rapid expansion of a murine monoclonal antibody directed against the CD18 component of leukocyte integrins," *Nuc. Acids. Res.*, 19:2471–2476 (1991).

Ellison et al., "The nucleotide sequence of a human immunoglobulin c(gamma)$_1$ gene," *Nucleic Acids Res.*, 10:4071– (1982).

Farrar, J., "The biochemistry, biology, and the role of interleukin-2 in the induction of cytotoxic T cell and antibody-forming B cell receptors," *Immunol. Rev.*, 63:129–166 (1982).

Foote et al., "Antibody framework residues affecting the conformation of hypervariable loops," *J. Mol. Biol.*, 224:487–499 (1992).

Gorman et al., "Reshaping a therapeutic CD4 antibody," *Proc. Natl. Acad. Sci.*, 88:4181–4185 (1991).

(List continued on next page.)

*Primary Examiner*—Lila Feisee
*Assistant Examiner*—Julie E. Reeves
*Attorney, Agent, or Firm*—Townsend and Townsend and Crew LLP

[57] ABSTRACT

Novel methods for producing, and compositions of, humanized immunoglobulins having one or more complementarity determining regions (CDR's) and possible additional amino acids from a donor immunoglobulin and a framework region from an accepting human immunoglobulin are provided. Each humanized immunoglobulin chain will usually comprise, in addition to the CDR's, amino acids from the donor immunoglobulin framework that are, e.g., capable of interacting with the CDR's to effect binding affinity, such as one or more amino acids which are immediately adjacent to a CDR in the donor immunoglobulin or those within about about 3 Å as predicted by molecular modeling. The heavy and light chains may each be designed by using any one or all of various position criteria. When combined into an intact antibody, the humanized immunoglobulins of the present invention will be substantially non-immunogenic in humans and retain substantially the same affinity as the donor immunoglobulin to the antigen, such as a protein or other compound containing an epitope.

37 Claims, 55 Drawing Sheets

OTHER PUBLICATIONS

Greene et al., "Growth of Human T Lymphocytes: An Analysis of Interleukin 2 and its Cellular receptor," *Progress in Hematology XIV*, E. Brown, ed., Grune and Statton, New York, pp. 283–301 (1986).

Hale et al., "Remission Induction in Non–Hodgkin Lymphoma with Reshaped Human Monoclonal Antibody CAMPATH–1H," *Lancet*, Dec. 17, 1988, pp. 1394–1399.

Hieter et al., "Cloned Human and Mouse Kappa Immunoglobulin Constant and J. Region Genes Conserve Homology in Functional Segments," *Cell*, 22:197–207 (1980).

Huston et al., "Protein engineering of antibody binding sites: Recovery of specific activity in an anti–digoxin single–chain Fv analogue produced in *Escherichia coli*," *Proc. Nat. Acad. Sci. USA*, 85:5879–5883 (1988), Progress in Hematology XIV, E. Brown, ed., Grune and Statton, New York, p. 283, (1986).

Jones et al., "Replacing the complementarity–determining regions in a human antibody with those from a mouse," *Nature*, 321:522–525 (1986).

Junghans et al., *Cancer Res.*, 50:1495–1502 (1990).

Kettleborough et al., "Humanization of a mouse monoclonal antibody by CDR–grafting: the importance of framework residues on loop conformation," *Protein Eng.*, 4:773–783 (1991).

Kirkman et al., *J. Exp. Med.*, 162:358 (1985).

Kupiec–Weglinski et al., *Proc. Natl. Acad. Sci.*, 3:2624 (1986).

Leonard et al., "The human receptor for T–cell growth factor," *J. Biol. Chem.*, 260:1872–1880 (1985).

Liu et al., "Expression of mouse::human immunoglobulin heavy–chain cDNA in lymphoid cells," *Gene*, 54:33–40 (1987).

Maeda et al., "Construction of reshaped human antibodies with HIV–neutralizing activity," *Hum. Antibod. Hybrid.*, 2:124–134 (1991).

Morrison et al., "Chimeric human antibody molecules: Mouse antigent binding–domains with human constant region domains," *Proc. Natl. Acad. Sci.*, 81:6851–6859 (1984).

Morrison, S.L., "Transfectomas Provide Novel Chimeric Antibodies," *Science*, 229:1202–1207 (1985).

Neuberger et al., "A hapten–specific chimeric IgE antibody with human physiological effector function," *Nature*, 314:268–270 (1985).

Queen et al., "A humanized antibody that binds to the interleukin 2 receptor," *Proc. Natl. Acad. Sci.*, 86:10029–10033 (1989).

Riechmann et al., "Reshaping human antibodies for therapy," *Nature*, 332:323–327 (1988).

Routledge et al., "A humanized monovalent CD3 antibody which can activate homologous complement," *Eur. J. Immunol.*, 21:2717–2725 (1991).

Sahagan et al., "A Genetically Engineered Murine/Human Chimeric Antibody Retains Specificity for Human Tumor––Associated Antigen," *J. Immunol.*, 137:1066–1074 (1986).

Shalaby et al., "Development of humanized bispecific antibodies reactive with cytotoxic lymphocytes and tumor cells overexpressing the HER2 protooncogene," *J. Exp. Med.*, 175:217–225 (1992).

Sharon et al., "Expression of a $V_H C_K$ chimaeric protein in mouse myeloma cells," *Nature*, 309:364–367 (1984).

Shearman et al., "Construction, expression and characterization of humanized antibodies directed against the human α/β T cell receptor," *J. Immunol.*, 147:4366–4373 (1991).

Takeda et al., "Construction of chimaeric processed immunoglobulin genes containing mouse variable and human constant region sequences," *Nature*, 314:452–454 (1985).

Saul et al., *J. Biol. Chem.*, 253(2), 585–597 (1978).

Sheriff et al., *PNAS–USA*, 84, 8075–8079 (1987).

Stanford and Wu, *J. Theor. Biol.*, 88, 421–439 (1981).

Tramontano et al., *J. Mol. Biol.*, 215, 175–182 (1990).

Verhoeyen et al., *BioEssays*, 8(2), 74–78 (1988).

Waldmann et al., *Cancer Research*, 45, 4559s–4562s (1985).

Wu and Kabat, *J. Exp. Med.*, 132, 211–250 (1970).

Tan et al., "A Human–Mouse Chimeric Immunoglobulin Gene with a Human Variable Region is Expressed in Mouse Myeloma Cells," *J. Immunol.*, 135:3564–3567 (1985).

Tempest et al., "Reshaping a human monoclonal antibody to inhibit human respiratory syncytial virus infection in vivo," *Bio/Technology*, 9:26–271 (1991).

Uchiyama et al., "A monoclonal antibody (anti–Tac) reactive with activated and functionally mature human T–cells," *J. Immunol.*, 126:1393–1397 (1981).

Verhoeyen et al., "Reshaping Human Antibodies: Grafting an Antilysozyme Activity," *Science*, 239:1534–1536 (1988).

Vitteta et al., "Redesigning nature's Poisons to Create Anti––Tumor Reagents," *Science*, 238:1098–1104 (1987).

Waldmann, T.A., "The Structure, Function, and Expression of Interleukin–2 Receptors on Normal and Malignant Lymphocytes," *Science*, 232:727–732 (1986).

Woodle et al., "Humanized OKT3 antibodies: successful transfer of immune modulating properties and idiotype expression," *J. Immunol.*, 148:2756–2763 (1992).

Amit et al., Science, 233, 747–753 (1986).

Cheetham, Protein Engineering, 2(3), 170–172 (1988).

Chothia et al., J. Mol. Biol., 186, 651–663 (1985).

Chothia et al., Nature, 342, 877–883 (1989).

Chothia et al., Science, 233, 755–758 (1986).

Chothia and Lesk, EMBO J., 5, 823–826 (1986).

Colman et al., Nature, 326, 358–362 (1987).

Davies et al., Ann. Rev. Immunol., 1, 87–117 (1983).

Davies et al., J. Biol. Chem., 263(22), 10541–10544 (1988).

Epp et al., Eur. J. Biochem., 45, 513–524 (1974).

Feldmann et al., Mol. Immunol., 18, 683–698 (1981).

Kabat, J. Immunol., 125, 961–969 (1980).

Lesk and Chothia, J. Mol. Biol., 160, 325–342 (1982).

Padlan, Mol. Immunol., 31, 169–217 (1994).

Palm et al., Hoppe Seyler's Z. Physiol. Chem., 354(12), 1651–1654 (1973).

Palm et al., Hoppe Seyler's Z. Physiol. Chem., 356, 167–191 (1975).

Panka et al., PNAS–USA, 85, 3080–3084 (1988).

Roberts et al., Nature, 328, 731–734 (1987).

Foote, Jefferson, "Humanized Antibodies", *Nova acta Leopoldine NF*, vol. 61, Nr. 269, pp. 103–110, 1989.

Groves et al. Hybridoma, vol. 6, No. 1, 1987 p. 71.

```
         10          20          30          40          50          60          70
AGCTTCTAGA TGGGATGGAG CTGGATCTTT CTCTTCCTCC TGTCAGGTAC CGGGGGCGTG CACTTCTCAGG
TCGAAGATCT ACCCTACCTC GACCTAGAAA GAGAAGGAGG ACAGTCCATG GCGCCCGCAC GTGAGAGTCC 80          90         100         110         120         130         140
TCCAGCTTCT CCAGTCTCGG GCTGAAGTCA AGAAACCTGG CTCGAGCGTG AAGGTCTCCT GCAAGGCTTC
AGGTCGAACA GGTCAGACCC CGACTTCAGT TCTTTGGACC GAGCTCGCAC TTCCAGAGGA CGTTCCGAAG 150         160         170         180         190         200         210
TGGCGGGACC TTTTCTAGCT ACAGGATGCA CTGGGTAAGG CAGGCCCCTG GACAGGGTCT GGAATGGATG
ACCGCCCTGG AAAGATCGA TGTCCTACGT GACCCATTCC GTCCGGGGAC CTGTCCCAGA CCTTACCTAC 220         230         240         250         260         270         280
GGATATATTA ATCCGTCGAC TGGGTATACT GAATACAATC AGAAGTTCAA GGACAGGGTC ACAATTACTG
CCTATATAAT TAGGCAGCTG ACCCATATGA CTTATGTTAG TCTTCAAGTT CCTGTCCCAG TGTTAATGAC 290         300         310         320         330         340         350
CAGACGAATC CACCAATACA GCCTACATGG AACTGAGCAG CCTGAGATCT GAGGACACCG CATTCTATTT
GTCTGCTTAG GTGGTTATGT CGGATGTACC TTGACTCGTC GGACTCTAGA CTCCTGTGGC GTAAGATAAA 360         370         380         390         400         410         420
CTGTGCAGGG GGTGGGGGAG TCTTTGACTA CGAATACAAT GGAGGGCTGG CCTCCCGACC AGTGTCAGAG
GACACGTCCC CCACCCCCTC AGAAACTGAT GCTTATGTTA CCTCCCGACC GGAGGGCTGG TCACAGTCTC 430         440
TCCTTAAAAC CTCTAGACGA TAT
AGGAATTTTG GAGATCTGCT ATA
```

FIGURE 11A

```
        10          20          30          40          50          60          70
CAAATCTAGA TGGAGACCGA TACCCTCCTG CTATGGGTCC TCCTGCTATG GGTCCCAGGA TCAACCGGAG
GTTTAGATCT ACCCTCTGGCT ATGGGAGGAC GATACCCAGG AGGACGATAC CCAGGGTCCT AGTTGGCCTC 80          90         100         110         120         130         140
ATATTCAGAT GACCCAGTCT CCATCTACCC TCTCTGCTAG CGTCGGGGAT AGGGTCACCA TAACCTGCTC
TATAAGTCTA CTGGGTCAGA GGTAGATGGG AGAGACGATC GCAGCCCCTA TCCCAGTGGT ATTGGACGAG 150         160         170         180         190         200         210
TGCCAGCTCA AGTATAAGTT ACATGCACTG GTACCAGCAG AAGCCAGGCA AAGCTCCCAA GCTTCTAATG
ACGGTCGAGT TCATATTCAA TGTACGTGAC CATGGTCGTC TTCGGTCCGT TTCGAGGGTT CGAAGATTAC 220         230         240         250         260         270         280
TATACCACAT CCAACCTGGC TTCTGGAGTC CCTTCTCGCT TCATTGGCAG TGGATCTGGG ACCGAGTTCA
ATATGGTGTA GGTTGGACCG AAGACCTCAG GGAAGAGCGA AGTAACCGTC ACCTAGACCC TGGCTCAAGT 290         300         310         320         330         340         350
CCCTCACAAT CAGCTCTCTG CAGCCAGATG ATTTCGCCAC TTATTACTGC CATCAAAGGA GTACTTACCC
GGGAGTGTTA GTCGAGAGAC GTCGGTCTAC TAAAGCGGTG AATAATGACG GTAGTTTCCT CATGAATGGG 360         370         380         390         400
ACTCACGTTC GGTCAGGGGA CCAAGGTGGA GGTCAAACGT AAGTACACTT TTCTAGATAT A
TGAGTGCAAG CCAGTCCCCT GGTTCCACCT CCAGTTTGCA TTCATGTGAA AAGATCTATA T
```

```
                10              20              30              40              50              60
       TCTAGATGGGATGGAGCTGGATCTTTCTCTTCCTCCTGTCAGGTACCGCGGGCGTGCACT
             M  G  W  S  W  I  F  L  F  L  L  S  G  T  A  G  V  H 70              80              90             100             110             120
       CTCAGGTCCAGCTTGTCCAGTCTGGGGCTGAAGTCAAGAAACCTGGCTCGAGCGTGAAGG
          S  Q  V  Q  L  V  Q  S  G  A  E  V  K  K  P  G  S  S  V  K 130             140             150             160             170             180
       TCTCCTGCAAGGCTTCTGGCTACACCTTTACTAGCTACAGGATGCACTGGGTAAGGCAGG
          V  S  C  K  A  S  G  Y  T  F  T  S  Y  R  M  H  W  V  R  Q 190             200             210             220             230             240
       CCCCTGGACAGGGTCTGGAATGGATTGGATATATTAATCCGTCGACTGGGTATACTGAAT
          A  P  G  Q  G  L  E  W  I  G  Y  I  N  P  S  T  G  Y  T  E 250             260             270             280             290             300
       ACAATCAGAAGTTCAAGGACAAGGCAACAATTACTGCAGACGAATCCACCAATACAGCCT
          Y  N  Q  K  F  K  D  K  A  T  I  T  A  D  E  S  T  N  T  A 310             320             330             340             350             360
       ACATGGAACTGAGCAGCCTGAGATCTGAGGACACCGCAGTCTATTACTGTGCAAGAGGGG
          Y  M  E  L  S  S  L  R  S  E  D  T  A  V  Y  Y  C  A  R  G 370             380             390             400             410             420
       GGGGGGTCTTTGACTACTGGGGCCAAGGAACCCTGGTCACAGTCTCCTCAGGTGAGTCCT
          G  G  V  F  D  Y  W  G  Q  G  T  L  V  T  V  S  S

430
       TAAAACCTCTAGA
```

FIGURE 17

```
         10         20         30         40         50         60
TCTAGATGGAGACCGATACCCTCCTGCTATGGGTCCTCCTGCTATGGGTCCCAGGATCAA
     M  E  T  D  T  L  L  L  W  V  L  L  L  W  V  P  G  S
         70         80         90        100        110        120
CCGGAGATATTCAGATGACCCAGTCTCCATCTACCCTCTCTGCTAGCGTCGGGGATAGGG
  T  G  D  I  Q  M  T  Q  S  P  S  T  L  S  A  S  V  G  D  R
        130        140        150        160        170        180
TCACCATAACCTGCTCTGCCAGCTCAAGTATAAGTTACATGCACTGGTACCAGCAGAAGC
  V  T  I  T  C  S  A  S  S  S  I  S  Y  M  H  W  Y  Q  Q  K
        190        200        210        220        230        240
CAGGCAAAGCTCCCAAGCTTCTAATTTATACCACATCCAACCTGGCTTCTGGAGTCCCTG
  P  G  K  A  P  K  L  L  I  Y  T  T  S  N  L  A  S  G  V  P
        250        260        270        280        290        300
CTCGCTTCAGTGGCAGTGGATCTGGGACCGAGTTCACCCTCACAATCAGCTCTCTGCAGC
  A  R  F  S  G  S  G  S  G  T  E  F  T  L  T  I  S  S  L  Q
        310        320        330        340        350        360
CAGATGATTTCGCCACTTATTACTGCCATCAAAGGAGTACTTACCCACTCACGTTCGGTC
  P  D  D  F  A  T  Y  Y  C  H  Q  R  S  T  Y  P  L  T  F  G
        370        380        390        400
AGGGGACCAAGGTGGAGGTCAAACGTAAGTACACTTTTCTAGA
  Q  G  T  K  V  E  V  K
```

FIGURE 18

HES12   AGCTTCTAGAGATGGGATGGAGGCTGGATCTTTCTCTTCCTGTCAGGTACCCGGGGCCGTG
        CACTCTCAGGTCCAGCTTGTCCAGCTCTGCGGGCTGAAGTCAAGAAACCTGGCTCGAGCGTG
        AAGGTC

HES13   GCCAGTCGACGGATTAATATATCCAATCCATTCCAGACCCTGTCCAGGGGCCTGCCTTAC
        CCAGTGCATCCTGTAGCTAGTAAAGGTGTAGCCAGAAGCCCTTGCAGGAGACCCTTCACGCT
        CGAGCCAGG

HES14   TATATTAATCCGTCGACTGGGTATACTGAATACAATCAGAAGTTCAAGGACAAGGCAACA
        ATTACTGCAGAGGAATCCACCAATACAGCCTACATGGAACTGAGCAGCCCTGAGATCTGAG
        GACA

HES15   ATATCGTCTAGAGGTTTTAAGGACTCACCTGAGGAGAGACTGTGACCAGGGTTCCTTGGCCC
        CAGTAGTCAAAGACCCCCCCCCCTCTTGCACAGTAATAGACTGCGGGTGTCCTCTCAGATCTC
        AGGCTGCT

FIGURE 19A

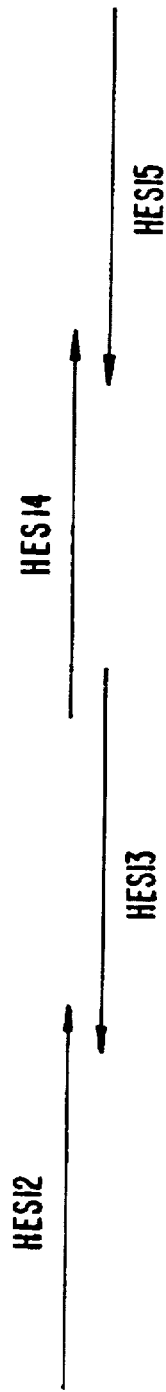

HES12

HES13

HES14

HES15

FIGURE 19B

JFD1  CAAATCTAGAGATGGAGAGACCGATACCCTCCTCCTGCTATGGGTCCTCCCAGGA
      TCAACCCGGAGATATTCAGAGACCCAGTCTCCATCTCCTCTCTGCTAGCGTCGGGAT

JFD2  ATAAATTAGAAGCTTGGGAGAGCTTGCCCTGGCTTCTGCTGGTACCAGTGCATGTAACTTAT
      ACTTGAGCTGGCAGAGCAGGTTATGGTGACCCTATCCCCGACGGCTAGCAGAGAG

JFD3  GCTCCCAAGCTTCTAATTTATACCACATCCAACCTCCAGTCCCTGCTCGGCTTC
      AGTGGCAGTGGATCTGGGACCGAGTTCACCCTCACAATCAGCTCTCTGCAGCCAGATGAT
      TTC

JFD4  TATATCTAGAAAAAGTGTACTTACGTTTGACCTTCCACCTTGGTCCCCTGACCGAACGTGAG
      TGGGTAAGTACTCCTTTGATGGCAGTAATAAGTGGCGAAATCATCTGGCTGCAGAGAGCT
      GA

FIGURE 20A

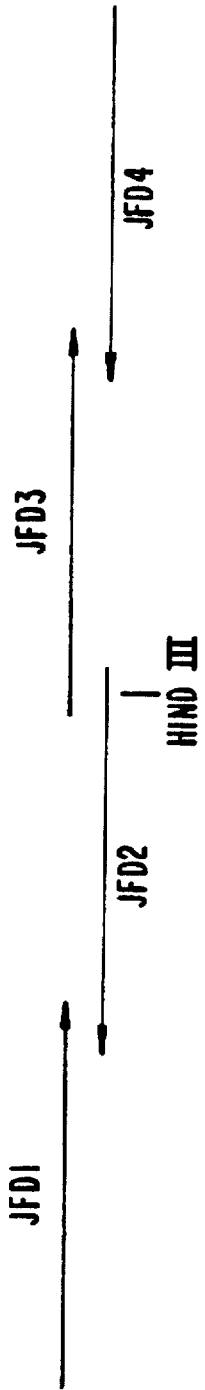

FIGURE 20B

```
                    •              •         30              •              •         60
ATGGATTTTCAAGTGCAGATTTTCAGCTTCCTGCTAATCAGTGCCTCAGTCATACTGTCC
 M  D  F  Q  V  Q  I  F  S  F  L  L  I  S  A  S  V  I  L  S

•              •         90              •              •        120
AGAGGACAAATTGTTCTCACCCAGTCTCCAGCAATCATGTCTGCGTCTCCAGGGGCGAAG
 R  G  Q  I  V  L  T  Q  S  P  A  I  M  S  A  S  P  G  E  K

•              •        150              •              •        180
GTCACCATGACCTGCAGTGGCAGCTCAAGTGTAAGTTTCATGTACTGGTACCAGCAGAGG
 V  T  M  T  C  S  G  S  S  S  V  S  F  M  Y  W  Y  Q  Q  R
                    ─────────────────────────────────

•              •        210              •              •        240
CCAGGATCCTCCCCCAGACTCCTGATTTATGACACATCCAACCTGGCTTCTGGAGTCCCT
 P  G  S  S  P  R  L  L  I  Y  D  T  S  N  L  A  S  G  V  P
                               ───────────────────

•              •        270              •              •        300
GTTCGCTTCAGTGGCAGTGGGTCTGGGACCTCTTACTCTCTCACAATCAGCCGAATGGAG
 V  R  F  S  G  S  G  S  G  T  S  Y  S  L  T  I  S  R  M  E

•              •        330              •              •        360
GCTGAAGATGCTGCCACTTATTACTGCCAGCAGTGGAGTACTTACCCGCTCACGTTCGGT
 A  E  D  A  A  T  Y  Y  C  Q  Q  W  S  T  Y  P  L  T  F  G
                           ──────────────────────────

•              •
GCTGGGACCAAGCTGGAGCTGAAA
 A  G  T  K  L  E  L  K
```

FIGURE 23A

```
                    •              •         30              •              •         60
ATGGCTGTCTTGGGGCTGCTCTTCTGCCTGGTGACATTCCCAAGCTGTGTCCTATCCCAG
 M  A  V  L  G  L  L  F  C  L  V  T  F  P  S  C  V  L  S  Q

•              •         90              •              •        120
GTGCAGCTGAAGCAGTCAGGACCTGGCCTAGTGCAGCCCTCACAGAGCCTGTCCATCACC
 V  Q  L  K  Q  S  G  P  G  L  V  Q  P  S  Q  S  L  S  I  T

•              •        150              •              •        180
TGCACAGTCTCTGGTTTCTCAGTAACAAGTTATGGTGTACACTGGATTCGCCAGTCTCCA
 C  T  V  S  G  F  S  V  T  S  Y  G  V  H  W  I  R  Q  S  P
                            ───────────────

•              •        210              •              •        240
GGAAAGGGTCTGGAGTGGCTGGGAGTGATATGGAGTGGTGGAAGCACAGACTATAATGCA
 G  K  G  L  E  W  L  G  V  I  W  S  G  G  S  T  D  Y  N  A
                             ────────────────────────────

•              •        270              •              •        300
GCTTTCATATCCAGACTGACCATCAGCAAGGACAACTCCAAGAGCCAAGTTTTCTTTAAA
 A  F  I  S  R  L  T  I  S  K  D  N  S  K  S  Q  V  F  F  K
 ─────────

•              •        330              •              •        360
GTGAACAGTCTGCAACCTGCTGACACAGCCATATACTATTGTGCCAGAGCTGGGGACTAT
 V  N  S  L  Q  P  A  D  T  A  I  Y  Y  C  A  R  A  G  D  Y
                                                ──────────

•              •        390              •
AATTACGACGGTTTTGCTTACTGGGGCCAAGGGACTCTGGTCACTGTCTCTGCG
 N  Y  D  G  F  A  Y  W  G  Q  G  T  L  V  T  V  S  A
 ──────────────────
```

```
         10         20         30         40         50         60
TTCTGCTGGT ACCAGTACAT GAAACTTACA CTTGAGCTGC CACTGCAGGT GATGGTGACG
         70         80         90        100
CGGTCACCCA CTGAGGCACT GAGGCTAGAT GGAGACTGGG TCATTTG
``` vc14

```
         10         20         30         40         50         60
CATGTACTGG TACCAGCAGA AGCCAGGAAA AGCTCCGAAA CTTCTGATTT ATGACACATC
         70         80         90        100        110        120
CAACCTGGCT TCTGGAGTCC CTTCCCGCTT CAGTGGCAGT GGGTCTGGGA CCGATTACAC
        130
CTTTACAATC TCTTCA
``` vc15

```
         10         20         30         40         50         60
TGTGTCTAGA AAAGTGTACT TACGTTTTAC CTCGACCTTG GTCCCTTGAC CGAACGTGAG
         70         80         90        100        110        120
CGGGTAAGTA CTCCACTGCT GGCAGTAATA AGTGGCTATA TCTTCCGGCT GAAGTGAAGA
        130
GATTGTAAAG GTGTAAT
``` vc16

```
         10         20         30         40         50         60
CACATCTAGA CCACCATGGA TTTTCAAGTG CAGATCTTCA GCTTCCTGCT AATCAGTGCC
         70         80         90        100
TCAGTCATAC TGTCCAGAGG AGATATTCAA ATGACCCAGT CTCCATCT
```

FIGURE 27A vcl1

```
        10         20         30         40         50         60
TAGTCTGTCG ACCCACCACT CCATATCACT CCCACCCACT CGAGTCCCTT TCCAGGAGCC 70         80         90        100        110        120
TGGCGGACCC AGTGTACACC ATAACTTGTT ACGGTGAAAC CACTGGCGGC ACAAGACAGT

130
CTCAGAGATC CTCCTGGC
``` vcl2

```
        10         20         30         40         50         60
TGGTGGGTCG ACAGACTATA ATGCAGCTTT CATATCCAGA TTTACCATCA GCAGAGACAA 70         80         90        100        110        120
CAGCAAGAAC ACACTGTATC TCCAAATGAA TAGCCTGCAA GCCGAGGACA CAGCCATATA

TTATTG
``` wps54

```
        10         20         30         40         50         60
ACACTCTAGA CCACCATGGC TGTCTTGGGG CTGCTCTTCT GCCTGGTGAC ATTCCCAAGC 70         80         90        100        110        120
TGTGTCCTAT CCGCTGTCCA GCTGCTAGAG AGTGGTGGCG GTCTGGTGCA GCCAGGAGGA

130
TCTCTGAGAC
``` wps57

```
        10         20         30         40         50         60
ACACTCTAGA AGTTAGGACT CACCTGAAGA GACAGTGACC AGAGTCCCTT GGCCCCAGTA 70         80         90        100        110
AGCAAACCG TCGTAATTAT AGTCCCAGC TCTGGCACAA TAATATATGG CTGTGTCC
```

```
                  •               •         30          •          •          60
        ATGGAGAAAGACACACTCCTGCTATGGGTCCTGCTTCTCTGGGTTCCAGGTTCCACAGGT
         M   E   K   D   T   L   L   W   V   L   L   L   W   V   P   G   S   T   G

•               •         90          •          •         120
        GACATTGTGCTGACCCAATCTCCAGCTTCTTTGGCTGTGTCTCTAGGGCAGAGGGCCACC
         D   I   V   L   T   Q   S   P   A   S   L   A   V   S   L   G   Q   R   A   T

•               •        150          •          •         180
        ATCTCCTGCAGAGCCAGCGAAAGTGTTGATAATTATGGCATTAGTTTTATGAACTGGTTC
         I   S   C   R   A   S   E   S   V   D   N   Y   G   I   S   F   M   N   W   F
                         ‾‾‾‾‾‾‾‾‾‾‾‾‾‾‾‾‾‾‾‾‾‾‾‾‾‾‾‾‾‾‾‾‾‾‾‾‾‾‾‾‾

•               •        210          •          •         240
        CAACAGAAACCAGGACAGCCACCCAAACTCCTCATCTATGCTGCATCCAACCAAGGATCC
         Q   Q   K   P   G   Q   P   P   K   L   L   I   Y   A   A   S   N   Q   G   S
                                                         ‾‾‾‾‾‾‾‾‾‾‾‾‾‾‾‾‾‾‾‾‾‾‾‾‾

•               •        270          •          •         300
        GGGGTCCCTGCCAGGTTTAGTGGCAGTGGGTCTGGGACAGACTTCAGCCTCAACATCCAT
         G   V   P   A   R   F   S   G   S   G   S   G   T   D   F   S   L   N   I   H

•               •        330          •          •         360
        CCTATGGAGGAGGATGATACTGCAATGTATTTCTGTCAGCAAAGTAAGGAGGTTCCGTGG
         P   M   E   E   D   D   T   A   M   Y   F   C   Q   Q   S   K   E   V   P   W
                                                         ‾‾‾‾‾‾‾‾‾‾‾‾‾‾‾‾‾‾‾‾‾‾‾‾‾

•               •        390
        ACGTTCGGTGGAGGCACCAAGCTGGAAATCAAA
         T   F   G   G   G   T   K   L   E   I   K
        ‾‾‾‾
```

FIGURE 34A

```
                  •               •         30          •          •          60
        ATGGGATGGAGCTGGATCTTTCTCTTCCTCCTGTCAGGAACTGCAGGCGTCCACTCTGAG
         M   G   W   S   W   I   F   L   F   L   L   S   G   T   A   G   V   H   S   E

•               •         90          •          •         120
        GTCCAGCTTCAGCAGTCAGGACCTGAGCTGGTGAAACCTGGGGCCTCAGTGAAGATATCC
         V   Q   L   Q   Q   S   G   P   E   L   V   K   P   G   A   S   V   K   I   S

•               •        150          •          •         180
        TGCAAGGCTTCTGGATACACATTCACTGACTACAACATGCACTGGGTGAAGCAGAGCCAT
         C   K   A   S   G   Y   T   F   T   D   Y   N   M   H   W   V   K   Q   S   H
                                             ‾‾‾‾‾‾‾‾‾‾‾‾‾‾‾‾‾

•               •        210          •          •         240
        GGAAAGAGCCTTGAGTGGATTGGATATATTTATCCTTACAATGGTGGTACTGGCTACAAC
         G   K   S   L   E   W   I   G   Y   I   Y   P   Y   N   G   G   T   G   Y   N
                                         ‾‾‾‾‾‾‾‾‾‾‾‾‾‾‾‾‾‾‾‾‾‾‾‾‾‾‾‾‾‾‾‾‾‾‾‾‾‾‾‾‾

•               •        270          •          •         300
        CAGAAGTTCAAGAGCAAGGCCACATTGACTGTAGACAATTCCTCCAGCACAGCCTACATG
         Q   K   F   K   S   K   A   T   L   T   V   D   N   S   S   S   T   A   Y   M
        ‾‾‾‾‾‾‾‾‾‾‾‾‾‾‾‾‾

•               •        330          •          •         360
        GACGTCCGCAGCCTGACATCTGAGGACTCTGCAGTCTATTACTGTGCAAGAGGGCGCCCC
         D   V   R   S   L   T   S   E   D   S   A   V   Y   Y   C   A   R   G   R   P
                                                                         ‾‾‾‾‾‾‾‾‾‾‾

•               •        390
        GCTATGGACTACTGGGGTCAAGGAACCTCAGTCACCGTCTCCTCA
         A   M   D   Y   W   G   Q   G   T   S   V   T   V   S   S
        ‾‾‾‾‾‾‾‾‾‾‾‾‾‾‾‾‾
```

```
         10         20         30         40         50         60
TATATCTAGA CCACCATGGG ATGGAGCTGG ATCTTTCTCT TCCTCCTGTC AGGAACTGCT 70         80         90        100        110        120
GGCGTCCACT CTCAGGTTCA GCTGGTGCAG TCTGGAGCTG AGGTGAAGAA GCCTGGAGC

130
TCAGTGAAGG TT
``` ma2

```
         10         20         30         40         50         60
AGCCGGTACC ACCATTGTAA GGATAAATAT ATCCAATCCA TTCCAGGCCT TGGCCAGGAG 70         80         90        100        110        120
CCTGCCTCAC CCAGTGCATG TTGTAGTCAG TGAAGGTGTA GCCAGAAGCT TTGCAGGAAA

130
CCTTCACTGA GCT
``` ma3

```
         10         20         30         40         50         60
TGGTGGTACC GGCTACAACC AGAAGTTCAA GAGCAAGGCC ACAATTACAG CAGACGAGAG 70         80         90        100        110
TACTAACACA GCCTACATGG AACTCTCCAG CCTGAGGTCT GAGGACACTG CA
``` ma4

```
         10         20         30         40         50         60
TATATCTAGA GGCCATTCTT ACCTGAAGAG ACAGTGACCA GAGTCCCTTG GCCCCAGTAG 70         80         90        100        110
TCCATAGCGG GGCGCCCTCT TGCGCAGTAA TAGACTGCAG TGTCCTCAGA C
```

FIGURE 37A ma5

```
         10         20         30         40         50         60
TATATCTAGA CCACCATGGA GAAAGACACA CTCCTGCTAT GGGTCCTGCT TCTCTGGGTT 70         80         90        100        110        120
CCAGGTTCCA CAGGTGACAT TCAGATGACC CAGTCTCCAG CTCTCTGTC CGCATCAGTA
```

GG ma6

```
         10         20         30         40         50         60
TCAGAAGCTT AGGAGCCTTC CCGGGTTTCT GTTGGAACCA GTTCATAAAG CTAATGCCAT 70         80         90        100        110        120
AATTGTCGAC ACTTTCGCTG GCTCTGCATG TGATGGTGAC CCTGTCTCCT ACTGATGCGG
```

AC ma7

```
         10         20         30         40         50         60
TCCTAAGCTT CTGATTTACG CTGCATCCAA CCAAGGCTCC GGGGTACCCT CTCGCTTCTC 70         80         90        100        110
AGGCAGTGGA TCTGGGACAG ACTTCACTCT CACCATTTCA TCTCTGCAGC CTGATGACT
``` ma8

```
         10         20         30         40         50         60
TATATCTAGA CTTTGGATTC TACTTACGTT TGATCTCCAC CTTGGTCCCT TGACCGAACG 70         80         90        100        110
TCCACGGAAC CTCCTTACTT TGCTGACAGT AATAGGTTGC GAAGTCATCA GGCTGCAG
```

FIGURE 37B

```
                    .         30          .         60
ATGGTTTTCACACCTCAGATACTTGGACTTATGCTTTTTGGATTTCAGCCTCCAGAGGT
 M  V  F  T  P  Q  I  L  G  L  M  L  F  W  I  S  A  S  R  G

.         90          .        120
GATATTGTGCTAACTCAGTCTCCAGCCACCCTGTCTGTGACTCCGGGAGATAGCGTCAGT
 D  I  V  L  T  Q  S  P  A  T  L  S  V  T  P  G  D  S  V  S

.        150          .        180
CTTTCCTGCAGGGCCAGCCAAAGTATTAGCAACAACCTACACTGGTATCAACAAAAATCA
 L  S  C  R  A  S  Q  S  I  S  N  N  L  H  W  Y  Q  Q  K  S

.        210          .        240
CATGAGTCTCCAAGGCTTCTCATCAAGTATGCTTCCCAGTCCATCTCTGGGATCCCCTCC
 H  E  S  P  R  L  L  I  K  Y  A  S  Q  S  I  S  G  I  P  S

.        270          .        300
AGGTTCAGTGGCAGTGGATCAGGGACAGATTTCACTCTCAGTGTCAACGGTGTGGAGACT
 R  F  S  G  S  G  S  G  T  D  F  T  L  S  V  N  G  V  E  T

.        330          .        360
GAAGATTTTGGAATGTATTTCTGTCAACACACTAACAGTTGGCCTCATACGTTCGGAGGG
 E  D  F  G  M  Y  F  C  Q  Q  S  N  S  W  P  H  T  F  G  G

.
GGGACCAAGCTGGAAATAAAA
 G  T  K  L  E  I  K
```

FIGURE 39A

```
                    .         30          .        ↓ 60
ATGGGATGGAGCTGGATCTTTCTCTTCCTCCTGTCAGGAACTGCAGGTGTCCACTCTGAG
 M  G  W  S  W  I  F  L  F  L  L  S  G  T  A  G  V  H  S  E

.         90          .        120
GTCCAGCTGCAACAGTCTGGACCTGAGCTGGTGAAGCCTGGAGCTTCAATGAAGATATCC
 V  Q  L  Q  Q  S  G  P  E  L  V  K  P  G  A  S  M  K  I  S

.        150          .        180
TGCAAGGCTTCTGTTTACTCATTCACTGGCTACACCATGAACTGGGTGAAGCAGAGCCAT
 C  K  A  S  V  Y  S  F  T  G  Y  T  M  N  W  V  K  Q  S  H

.        210          .        240
GGACAGAACCTTGAGTGGATTGGACTTATTAATCCTTACAATGGTGGTACTAGCTACAAC
 G  Q  N  L  E  W  I  G  L  I  N  P  Y  N  G  G  T  S  Y  N

.        270          .        300
CAGAAGTTCAAGGGGAAGGCCACATTAACTGTAGACAAGTCATCCAACACAGCCTACATG
 Q  K  F  K  G  K  A  T  L  T  V  D  K  S  S  N  T  A  Y  M

.        330          .        360
GAGCTCCTCAGTCTGACATCTGCGGACTCTGCAGTCTATTACTGTACAAGACGGGGGTTT
 E  L  L  S  L  T  S  A  D  S  A  V  Y  Y  C  T  R  R  G  F

.        390
CGAGACTATTCTATGGACTACTGGGGTCAAGGAACCTCAGTCACCGTCTCCTCA
 R  D  Y  S  M  D  Y  W  G  Q  G  T  S  V  T  V  S  S
```

```
          10         20         30         40         50         60
TAGATCTAGA CCACCATGGT TTTCACACCT CAGATACTAG GACTCATGCT CTTCTGGATT
          70         80         90        100        110        120
TCAGCCTCCA GAGGTGAAAT TGTGCTAACT CAGTCTCCAG GCACCCTAAG CTTATCACCG
```

GGAGAAAGG jb17

```
          10         20         30         40         50         60
TAGACAGAAT TCACGCGTAC TTGATAAGTA GACGTGGAGC TTGTCCAGGT TTTTGTTGGT
          70         80         90        100        110        120
ACCAGTGTAG GTTGTTGCTA ATACTTTGGC TGGCCCTGCA GGAAAGTGTA GCCCTTTCTC
```

CCGGTGAT jb18

```
          10         20         30         40         50         60
AAGAGAATTC ACGCGTCCCA GTCCATCTCT GGAATACCCG ATAGGTTCAG TGGCAGTGGA
          70         80         90        100        110
TCAGGGACAG ATTTCACTCT CACAATAAGT AGGCTCGAGC CGGAAGATTT TGC
``` jb19

```
          10         20         30         40         50         60
TAGATCTAGA GTTGAGAAGA CTACTTACGT TTTATTTCTA CCTTGGTCCC TTGTCCGAAC
          70         80         90        100        110
GTATGAGGCC AACTGTTACT CTGTTGACAA TAATACACAG CAAAATCTTC CGGCTC
```

FIGURE 41A jb20

```
           10         20         30         40         50         60
    TATATCTAGA CCACCATGGG ATGGAGCTGG ATCTTTCTCT TCCTCCTGTC AGGAACTGCA 70         80         90        100        110        120
    GGTGTCCACT CTCAAGTCCA ACTGGTACAG TCTGGAGCTG AGGTTAAAAA GCCTGGAAGT

130
    TCAGTAAGAG TTTC
``` jb21

```
           10         20         30         40         50         60
    TATATAGGTA CCACCATTGT AAGGATTAAT AAGTCCAACC CACTCAAGTC CTTTTCCAGG 70         80         90        100        110        120
    TGCCTGTCTC ACCCAGTTCA TGGTATACCC AGTGAATGAG TATCCGGAAG CTTTGCAGGA

130
    AACTCTTACT GAAC
``` jb22

```
           10         20         30         40         50         60
    TATATAGGTA CCAGCTACAA  CCAGAAGTTC AAGGGCACAG TTACAGTTC TTTGAAGCCT 70         80         90        100        110
    TCATTTAACC AGGCCTACAT GGAGCTCAGT AGTCTGTTTT CTGAAGACAC TGCAGT
``` jb23

```
           10         20         30         40         50         60
    TATATCTAGA GGCCATTCTT ACCTGAGGAG ACGGTGACTA AGGTTCCTTG ACCCCAGTAG 70         80         90        100        110
    TCCATAGAAT AGTCTCGAAA CCCCCGTCTT CTACAGTAAT AGACTGCAGT GTCTTC
```

FIGURE 41B

```
                    •               30              •               60
ATGCATCAGACCAGCATGGGCATCAAGATGGAATCACAGACTCTGGTCTTCATATCCATA
 M  H  Q  T  S  M  G  I  K  M  E  S  Q  T  L  V  F  I  S  I

•               90              •              120
CTGCTCTGGTTATATGGTGCTCATGGGAACATTGTTATGACCCAATCTCCCAAATCCATG
 L  L  W  L  Y  G  A  D  G  N  I  V  M  T  Q  S  P  K  S  M

•              150              •              180
TACGTGTCAATAGGAGAGAGGGTCACCTTGAGCTGCAAGGCCAGTGAAAATGTGGATACT
 Y  V  S  I  G  E  R  V  T  L  S  C  K  A  S  E  N  V  D  T

•              210              •              240
TATGTATCCTGGTATCAACAGAAACCAGAGCAGTCTCCTAAACTGCTGATATATGGGGCA
 Y  V  S  W  Y  Q  Q  K  P  E  Q  S  P  K  L  L  I  Y  G  A

•              270              •              300
TCCAACCGGTACACTGGGGTCCACGATCGCTTCACGGGCAGTGGATCTGCAACAGATTTC
 S  N  R  Y  T  G  V  H  D  R  F  T  G  S  G  S  A  T  D  F

•              330              •              360
ACTCTGACCATCAGCAGTGTGCAGGCTGAAGACCTTGCAGATTATCACTGTGGACAGAGT
 T  L  T  I  S  S  V  Q  A  E  D  L  A  D  Y  H  C  G  Q  S

•              390              •
TACAACTATCCATTCACGTTCGGCTCGGGGACAAAGTTGGAAATAAAG
 Y  N  Y  P  F  T  F  G  S  G  T  K  L  E  I  K
```

FIGURE 43A

```
                    •         •    30         •         •    60
ATGACATCACTGTTCTCTCTACAGTTACCGAGCACACAGGACCTCGCCATGGGATGGAGC
 M   T   S   L   F   S   L   Q   L   P   S   T   Q   D   L   A   M   G   W   S

•         •    90         •         •    120
TGTATCATCCTCTTCTTGGTAGCAACAGCTACAGGTGTCCTCTCCCAGGTCCAACTGCAG
 C   I   I   L   F   L   V   A   T   A   T   G   V   L   S   Q   V   Q   L   Q

•         •    150        •         •    180
CAGCCTGGGGCTGACCTTGTGATGCCTGGGGCTCCAGTGAAGCTGTCCTGCTTGGCTTCT
 Q   P   G   A   D   L   V   M   P   G   A   P   V   K   L   S   C   L   A   S

•         •    210        •         •    240
GGCTACATCTTCACCAGCTCCTGGATAAACTGGGTGAAGCAGAGGCCTGGACGAGGCCTC
 G   Y   I   F   T   S   S   W   I   N   W   V   K   Q   R   P   G   R   G   L

•         •    270        •         •    300
GAGTGGATTGGAAGGATTGATCCTTCCGATGGTGAAGTTCACTACAATCAAGATTTCAAG
 E   W   I   G   R   I   D   P   S   D   G   E   V   H   Y   N   Q   D   F   K

•         •    330        •         •    360
GACAAGGCCACACTGACTGTAGACAAATCCTCCAGCACAGCCTACATCCAACTCAACAGC
 D   K   A   T   L   T   V   D   K   S   S   S   T   A   Y   I   Q   L   N   S

•         •    390        •         •    420
CTGACATCTGAGGACTCTGCGGTCTATTACTGTGCTAGAGGATTTCTGCCCTGGTTTGCT
 L   T   S   E   D   S   A   V   Y   Y   C   A   R   G   F   L   P   W   F   A

•         •    450
GACTGGGGCCAAGGGACTCTGGTCACTGTCTCTGCA
 D   W   G   Q   G   T   L   V   T   V   S   A
```

```
         10         20         30         40         50         60
TTTTTTCTAG ACCACCATGG AGACCGATAC CCTCCTGCTA TGGGTCCTCC TGCTATGGGT 70         80         90        100        110
CCCAGGATCA ACCGGAGATA TTCAGATGAC CCAGTCTCCG TCGACCCTCT CTGCT
``` rh11

```
         10         20         30         40         50         60
TTTTAAGCTT GGGAGCTTTG CCTGGCTTCT GCTGATACCA GGATACATAA GTATCCACAT 70         80         90        100        110        120
TTTCACTGGC CTTGCAGGTT ATGGTGACCC TATCCCCGAC GCTAGCAGAG AGGTTCCACG
``` rh12

```
         10         20         30         40         50         60
TTTTAAGCTT CTAATTTATG GGGCATCCAA CCGGTACACT GGGGTACCTT CACGCTTCAG 70         80         90        100        110
TGGCAGTGGA TCTGGGACCG ATTTCACCCT CACAATCAGC TCTCTGCAGC CAGATGAT
``` rh13

```
         10         20         30         40         50         60
TTTTTTCTAG AGCAAAAGTC TACTTACGTT TGACCTCCAC CTTGGTCCCC TGACCGAACG 70         80         90        100        110        120
TGAATGGATA GTTGTAACTC TGTCCGCAGT AATAAGTGGC GAAATCATCT GGCTCCAGAG
```

FIGURE 45A rh20

```
         10         20         30         40         50         60
TTTTTCTAGA CCACCATGGG ATGGAGCTGG ATCTTTCTCT TCCTCCTGTC AGGTACCGCG
         70         80         90        100        110
GGCGTGCACT CTCAGGTCCA GCTTGTCCAG TCTGGGGCTG AAGTCAAGAA ACCT
``` rh21

```
         10         20         30         40         50         60
TTTTGAATTC TCGAGACCCT GTCCAGGGGC CTGCCTTACC CAGTTTATCC AGGAGCTAGT
         70         80         90        100        110        120
AAAGATGTAG CCAGAAGCTT TGCAGGAGAC CTTCACGGAG CTCCCAGGTT TCTTGACTTC
```

A rh22

```
         10         20         30         40         50         60
TTTTGAATTC TCGAGTGGAT GGGAAGGATT GATCCTTCCG ATGGTGAAGT TCACTACAAT
         70         80         90        100        110        120
CAAGATTTCA AGGACCGTGT TACAATTACA GCAGACGAAT CCACCAATAC AGCCTACATG
        130
GAACTGAGCA GCCTGAG
``` rh23

```
         10         20         30         40         50         60
TTTTTCTAGA GGTTTTAAGG ACTCACCTGA GGAGACTGTG ACCAGGGTTC CTTGGCCCCA
         70         80         90        100        110        120
GTCAGCAAAC CAGGGCAGAA ATCCTCTTGC ACAGTAATAG ACTGCAGTGT CCTCTGATCT
        130
CAGGCTGCTC AGTT
```

FIGURE 45B

POLYNUCLEOTIDES ENCODING IMPROVED HUMANIZED IMMUNOGLOBULINS

CROSS-REFERENCE TO RELATED APPLICATIONS

This is a Division of application Ser. No. 07/634,278 filed Dec. 19, 1990 issued 25 Jun. 1996 as U.S. Pat. No. 5,530, 101, which is a continuation-in-part application of commonly assigned patent application U.S. Ser. No. 07/590,274, filed Sep. 28, 1990 (now abandoned) and of U.S. Ser. No. 07/310,252, filed Feb. 13, 1989 (now abandoned), which is a contination-in-part of U.S. Ser. No. 07/290,975, filed Dec. 28, 1988 (now abandoned). All of these applications are specifically incorporated herein by reference.

FIELD OF THE INVENTION

The present invention relates generally to the combination of recombinant DNA and monoclonal antibody technologies for developing novel therapeutic agents and, more particularly, to the production of non-immunogenic antibodies having strong affinity for a predetermined antigen.

BACKGROUND OF THE INVENTION

The advent of monoclonal antibody technology in the mid 1970's heralded a new age of medicine. For the first time, researchers and clinicians had access to essentially unlimited quantities of uniform antibodies capable of binding to a predetermined antigenic site and having various immunological effector functions. These proteins, known as "monoclonal antibodies" were thought to hold great promise in, e.g., the removal of harmful cells in vivo. Indeed, the clinical value of monoclonal antibodies seemed limitless for this use alone.

Unfortunately, the development of appropriate therapeutic products based on these proteins has been severely hampered by a number of drawbacks inherent in monoclonal antibody production. For example, most monoclonal antibodies are mouse derived, and thus do not fix human complement well. They also lack other important immunoglobulin functional characteristics when used in humans.

Perhaps most importantly, non-human monoclonal antibodies contain substantial stretches of amino acid sequences that will be immunogenic when injected into a human patient. Numerous studies have shown that after injection of a foreign antibody, the immune response mounted by a patient can be quite strong, essentially eliminating the antibody's therapeutic utility after an initial treatment. Moreover, as increasing numbers of different mouse or other antigenic (to humans) monoclonal antibodies can be expected to be developed to treat various diseases, after one or several treatments with any non-human antibodies, subsequent treatments, even for unrelated therapies, can be ineffective or even dangerous in themselves, because of cross-reactivity.

While the production of so called "chimeric antibodies" (e.g., mouse variable regions joined to human constant regions) has proven somewhat successful, a significant immunogenicity problem remains. Moreover, efforts to immortalize human B-cells or generate human hybridomas capable of producing human immunoglobulins against a desired antigen have been generally unsuccessful, particularly with many important human antigens. Most recently, recombinant DNA technology has been utilized to produce immunoglobulins which have human framework regions combined with complementarity determining regions (CDR's) from a donor mouse or rat immunoglobulin (see, e.g., EPO Publication No. 0239400, which is incorporated herein by reference). These new proteins are called "reshaped" or "humanized" immunoglobulins and the process by which the donor immunoglobulin is converted into a human-like immunoglobulin by combining its CDR's with a human framework is called "humanization". Humanized antibodies are important because they bind to the same antigen as the original antibodies, but are less immunogenic when injected into humans.

However, a major problem with present humanization procedures has been a loss of affinity for the antigen (Jones et al., Nature, 321, 522–525 (1986)), in some instances as much as 10-fold or more, especially when the antigen is a protein (Verhoeyen et al., Science, 239, 1534–1536 (1988)). Loss of any affinity is, of course, highly undesirable. At the least, it means that more of the humanized antibody will have to be injected into the patient, at higher cost and greater risk of adverse effects. Even more critically, an antibody with reduced affinity may have poorer biological functions, such as complement lysis, antibody-dependent cellular cytotoxicity, or virus neutralization. For example, the loss of affinity in the partially humanized antibody HuVHCAMP may have caused it to lose all ability to mediate complement lysis (see, Riechmann et al., Nature, 332, 323–327 (1988); Table 1).

Thus, there is a need for improved means for producing humanized antibodies specifically reactive with strong affinity to a predetermined antigen. These humanized immunoglobulins should remain substantially non-immunogenic in humans, yet be easily and economically produced in a manner suitable for therapeutic formulation and other uses. The present invention fulfills these and other needs.

SUMMARY OF THE INVENTION

The present invention provides novel methods for preparing humanized immunoglobulin chains having generally one or more complementarity determining regions (CDR's) from a donor immunoglobulin and a framework region from a human immunoglobulin. The preferred methods comprise first comparing the framework or variable region amino acid sequence of the donor immunoglobulin to corresponding sequences in a collection of human immunoglobulin chains, and selecting as the human immunoglobulin one of the more homologous sequences from the collection. The human immunoglobulin, or acceptor immunoglobulin, sequence is typically selected from a collection of at least 10 to 20 immunoglobulin variable region sequences, and usually will have the highest homology to the donor immunoglobulin sequence of any sequence in the collection. The human immunoglobulin framework sequence will typically have about 65 to 70% homology or more to the donor immunoglobulin framework sequences. The donor immunoglobulin may be either a heavy chain or light chain, and the human collection will contain the same kind of chain. A humanized light and heavy chain can be used to form a complete humanized immunoglobulin or antibody, having two light/ heavy chain pairs, with or without partial or full-length human constant regions.

To form the humanized variable region, amino acids in the human acceptor sequence will be replaced by the corresponding amino acids from the donor sequence if they are in the category (1) the amino acid is in a CDR.

In another embodiment of the present invention, either in conjunction with the above comparison step or separately, additional amino acids in the acceptor immunoglobulin chain may be replaced with amino acids from the CDR-donor immunoglobulin chain. More specifically, further optional substitutions of a human framework amino acid of the acceptor immunoglobulin with the corresponding amino acid from a donor immunoglobulin will be made at positions which fall in one or more of the following categories:

(2) the amino acid in the human framework region of the acceptor immunoglobulin is rare for that position and the corresponding amino acid in the donor immunoglobulin is common for that position in human immunoglobulin sequences; or (3) the amino acid is immediately adjacent to one of the CDR's; or (4) the amino acid is predicted to be within about 3 Å of the CDR's in a three-dimensional immunoglobulin model and capable of interacting with the antigen or with the CDR's of the donor or humanized immunoglobulin.

Moreover, an amino acid in the acceptor sequence may optionally be replaced with an amino acid typical for human sequences at that position if (5) the amino acid in the acceptor immunoglobulin is rare for that position and the corresponding amino acid in the donor immunoglobulin is also rare, relative to other human sequences.

The humanized immunoglobulin chain will typically comprise at least about 3 amino acids from the donor immunoglobulin in addition to the CDR's, usually at least one of which is immediately adjacent to a CDR in the donor immunoglobulin. The heavy and light chains may each be designed by using any one or all three of the position criteria.

When combined into an intact antibody, the humanized light and heavy chains of the present invention will be substantially non-immunogenic in humans and retain substantially the same affinity as the donor immunoglobulin to the antigen (such as a protein or other compound containing an epitope). These affinity levels can vary from about $10^8$ $M^{-1}$ or higher, and may be within about 4 fold, preferably within about 2 fold of the donor immunoglobulin. Ideally, the humanized antibodies will exhibit affinity levels at least about 60 to 90% of the donor immunoglobulin's original affinity to the antigen.

Once designed, the immunoglobulins, including binding fragments and other immunoglobulin forms, of the present invention may be produced readily by a variety of recombinant DNA or other techniques. Preferably, polynucleotides encoding the desired amino acid sequences are produced synthetically and by joining appropriate nucleic acid sequences, with ultimate expression in transfected cells. Notably, the methods of the present invention maximize the likelihood of producing humanized immunoglobulins with optimum binding characteristics without the need for producing intermediate forms that may display stepwise improvements in binding affinity. The humanized immunoglobulins will be particularly useful in treating human disorders susceptible to monoclonal antibody therapy, but find a variety of other uses as well.

BRIEF DESCRIPTION OF THE FIGURES

FIG. 1A and FIG. 1B. Amino acid sequences (1-letter code) of the light chain (A) (SEQ ID NOS:1 and 2) and heavy chain (B) (SEQ ID NOS:3 and 4) variable regions of the mouse anti-Tac antibody (upper lines), compared with the human Eu antibody (lower lines), not including signal sequences. The three CDR's in each chain are underlined. Residues in the Eu antibody framework replaced with mouse amino acids in the humanized antibody are double underlined. The number of the first position on each line is given on the left.

FIG. 2A and FIG. 2B. Amino acid sequences (1-letter code) of the light chain (A) (SEQ ID NOS:46 and 47) and heavy chain (B) (SEQ ID NOS:48 AND 49) variable regions of the mouse Fd79 antibody (upper lines), compared with the humanized antibody (lower lines), not including signal sequences. The three CDR's in each chain are underlined. Residues in the humanized antibody framework replaced with mouse amino acids or typical human amino acids are double underlined. The number of the first position on each line is given on the left.

FIG. 3A and FIG. 3B. Amino acid sequences (1-letter code) of the light chain (A) (SEQ ID NOS:50 and 51) and heavy chain (B) (SEQ ID NOS:52 and 53) variable regions of the mouse Fd138-80 antibody (upper lines), compared with the humanized antibody (lower lines), not including signal sequences. The three CDR's in each chain are underlined. Residues in the humanized antibody framework replaced with mouse amino acids or typical human amino acids are double underlined. The number of the first position on each line is given on the left.

FIG. 4A and FIG. 4B. Amino acid sequences (1-letter code) of the light chain (A) (SEQ ID NOS:54 and 55) and heavy chain (B) (SEQ ID NOS:56 and 57) variable regions of the mouse M195 antibody (upper lines), compared with the humanized antibody (lower lines), not including signal sequences. The three CDR's in each chain are underlined. Residues in the humanized antibody framework replaced with mouse amino acids or typical human amino acids are double underlined. The number of the first position on each line is given on the left.

FIG. 5A and FIG. 5B. Amino acid sequences (1-letter code) of the light chain (A) (SEQ ID NOS:58 and 59) and heavy chain (B) (SEQ ID NOS:60 and 61) variable regions of the mouse mik-β1 antibody (upper lines), compared with the humanized antibody (lower lines), not including signal sequences. The three CDR's in each chain are underlined. Residues in the humanized antibody framework replaced with mouse amino acids or typical human amino acids are double underlined. The number of the first position on each line is given on the left.

FIG. 6A and FIG. 6B. Amino acid sequences (1-letter code) of the light chain (A) (SEQ ID NOS:62 and 63) and heavy chain (B) (SEQ ID NOS:64 and 65) variable regions of the mouse CMV5 antibody (upper lines), compared with the humanized antibody (lower lines), not including signal sequences. The three CDR's in each chain are underlined. Residues in the humanized antibody framework replaced with mouse amino acids or typical human amino acids are double underlined. The number of the first position on each line is given on the left.

FIG. 10A and FIG. 10B. Amino acid sequences of the heavy (A) (SEQ ID NOS:5 and 6) and light (B) (SEQ ID NOS:7 and 8) chain variable regions of the PDL and CDR-only humanized anti-Tac antibodies. The PDL sequence is shown on the upper line, the CDR-only sequence below. Amino acid differences are boxed. Complementarity Determining Regions (CDR's) are underlined.

FIG. 11A and FIG. 11B. Double-stranded DNA sequence of fragments encoding the heavy (A) (SEQ ID NO:9) and light (B) (SEQ ID NO:10) chain variable regions of the CDR-only humanized anti-Tac antibody including signal sequences. Oligonucleotides used for gene synthesis are marked by solid lines: above, for oligonucleotides from upper strand, and below, for oligonucleotides from lower strand. Restriction sites used for cloning are underlined.

FIG. 15. Comparison of sequences of anti-Tac heavy chain (upper lines) (SEQ ID NO:14) and Eu heavy chain (lower lines) (SEQ ID NO:15). The 1-letter code for amino acids is used. The first amino acid on each line is numbered at the left. Identical amino acids in the two sequences are connected by lines. The 3 CDRs are underlined. Other amino acid positions for which the anti-Tac amino acid rather than the Eu amino acid was used in the humanized anti-Tac heavy chain are denoted by an *.

FIG. 16. Comparison of sequences of anti-Tac light chain (upper lines) (SEQ ID NO:16) and Eu light chain (lower lines) (SEQ ID NO:17). The single-letter code for amino acids is used. The first amino acid on each line is numbered at the left. Identical amino acids in the two sequences are connected-by lines. The 3 CDRs are underlined. Other amino acid positions for which the anti-Tac amino acid rather than the Eu amino acid was used in the humanized anti-Tac heavy chain are denoted by an *.

FIG. 17. Nucleotide sequence of the gene for the humanized anti-Tac heavy chain variable region gene (SEQ ID NOS:18 and 19). The translated amino acid sequence for the part of the gene encoding protein is shown underneath the nucleotide sequence. The nucleotides TCTAGA at the beginning and end of the gene are Xba I sites. The mature heavy chain sequence begins with amino acid #20 Q.

FIG. 18. Nucleotide sequence of the gene for the humanized anti-Tac light chain variable region gene (SEQ ID NOS:20 and 21). The translated amino acid sequence for the part of the gene encoding protein is shown underneath the nucleotide sequence. The nucleotides TCTAGA at the beginning and end of the gene are Xba I sites. The mature light chain sequence begins with amino acid #21 D.

FIG. 19A and FIG. 19B. (A) Sequences of the four oligonucleotides (SEQ ID NOS:22, 23, 24, and 25) used to synthesize the humanized anti-Tac heavy chain gene, printed 5' to 3'. (B) Relative positions of the oligonucleotides. The arrows point in the 3' direction for each oligonucleotide.

FIG. 20A and FIG. 20B. (A) Sequences of the four oligonucleotides (SEQ ID NOS:26, 27, 28, and 29) used to synthesize the humanized anti-Tac light chain gene, printed 5' to 3'. (B) Relative positions of the oligonucleotides. The arrows point in the 3' direction for each oligonucleotide. The position of a Hind III site in the overlap of JFD2 and JFD3 is shown.

FIG. 23A and FIG. 23B. Sequences of the cDNA and translated amino acid sequences of the light chain (A) (SEQ ID NOS:30 and 31) and heavy chain (B) (SEQ ID NOS:32 and 33) variable regions of the antibody mik-β1. The CDR sequences are underlined. The mature light chain protein begins with amino acid 23 Q and the mature heavy chain protein with amino acid 20 Q, preceded by the respective signal sequences.

FIG. 24A and FIG. 24B. Schematic diagram of the plasmids pVg1-dhfr (A) and pVk (B). The plasmid pVg1- dhfr contains the following parts: an approximately 4200 base pair BamHI-EcoRI fragment containing the amp and dhfr genes; a 630-bp fragment containing the human cytomegalovirus IE1 gene promoter and enhancer (Boshart et al., *Cell* 41, 521 (1985), which is incorporated herein by reference) flanked at the 5' and 3' ends by EcoRI and XbaI linkers respectively; and a 2800 bp XbaI-BamHI fragment containing the human gamma-1 constant region gene with 215 bp of the preceding intron and the poly(A) signal. The plasmid pVk was similarly constructed, with a 1530-bp human kappa constant region gene replacing the gamma-1 gene and the gpt gene replacing the dhfr gene. The plasmids were constructed from the indicated parts using methods well-known in the art (see, Maniatis et al., *Molecular Cloning: A Laboratory Manual*, 2nd ed., Cold Spring Harbor Laboratory, Cold Spring Harbor, N.Y. (1989) and commonly assigned PCT Publication No. WO 89/09622, published Oct. 19, 1989. For example, pVg1-dhfr was constructed from the plasmid pVg1 by replacing the Hind III-Bgl II fragment containing the hyg gene with a 660 bp fragment containing the dhfr gene and extending to a Bgl II site (Simonsen et al., *Proc. Natl. Acad. Sci. USA* 80, 2495 (1983)).

Figure 25:
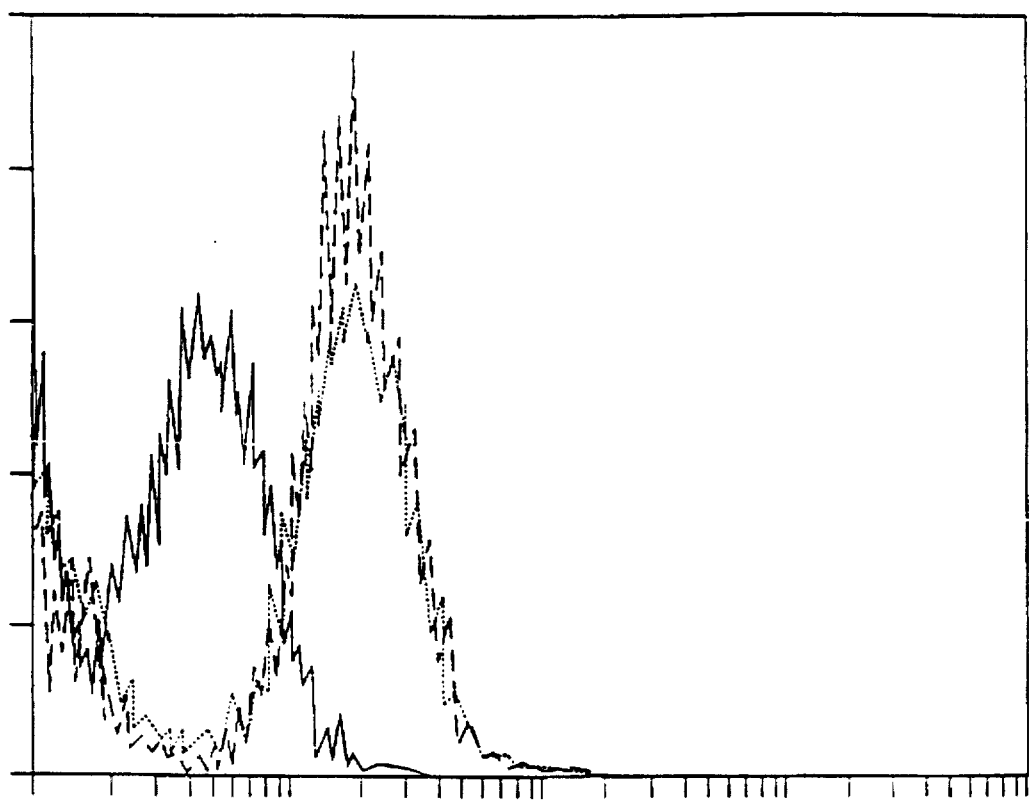

FIG. 25. Fluorocytometry of YTJB cells stained with (\_) Isotype matched control antibody, (- - -) humanized mik-β1 antibody, ( . . . ) chimeric mik-β1 antibody. Cells were suspended in FACS buffer (PBS+2% BSA+0.1% azide) at approximately 5×10⁶/ml. 100 ul of cell suspension was transferred to a polystyrene tube and incubated with 100 ng of purified antibody on ice for 30 min. The cells were washed with FACS buffer and incubated with goat anti-human Ig antibody on ice for another 30 min. Then the cells were washed and incubated with FITC labeled rabbit anti-goat Ig antibody for 30 min. The cells were washed again and finally resuspended in PBS+1% paraformaldehyde. Cells were analyzed on a FACSmate (Becton Dickinson).

FIG. 26A and FIG. 26B. Amino acid sequences of the light chain (A) (SEQ ID NOS:34 and 35) and the heavy chain (B) (SEQ ID NOS:36 and 37) of the humanized mik-β1 antibody, (lower lines) and human Lay antibody (upper lines), not including signal sequences. The three CDRs in each chain are underlined. Amino acids in the framework that have been replaced with mouse amino acids or consensus human amino acids in the humanized antibody are double underlined.

FIG. 27A and FIG. 27B. Oligonucleotides used in the construction of the humanized mik-β1 heavy chain (B) (SEQ ID NOS:42, 43, 44, and 45) and light chain (A) (SEQ ID NOS:38, 39, 40, and 41). The following pairs of oligonucleotides were mixed, extended with sequenase and cut with the indicated enzymes before ligation into the pBluescriptII ks (+) vector: wps54 and vc11 with Xba I and Sal I, vc12 and wps57 with Xba I and Sal I, vc16 and vc13 with Xba I and Kpn I, vc14 and vc15 with Xba I and Kpn I. Then the wps54–vc11 and vc12–wps57 fragments were excised with Xba I and Sal I ligated together into the Xba I site of pVg1-dhfr; and the vc16–vc13 fragments and vc14–vc15 fragments were excised with Xba I and Kpn I and ligated together into the Xba I site of pVk.

Figure 28:
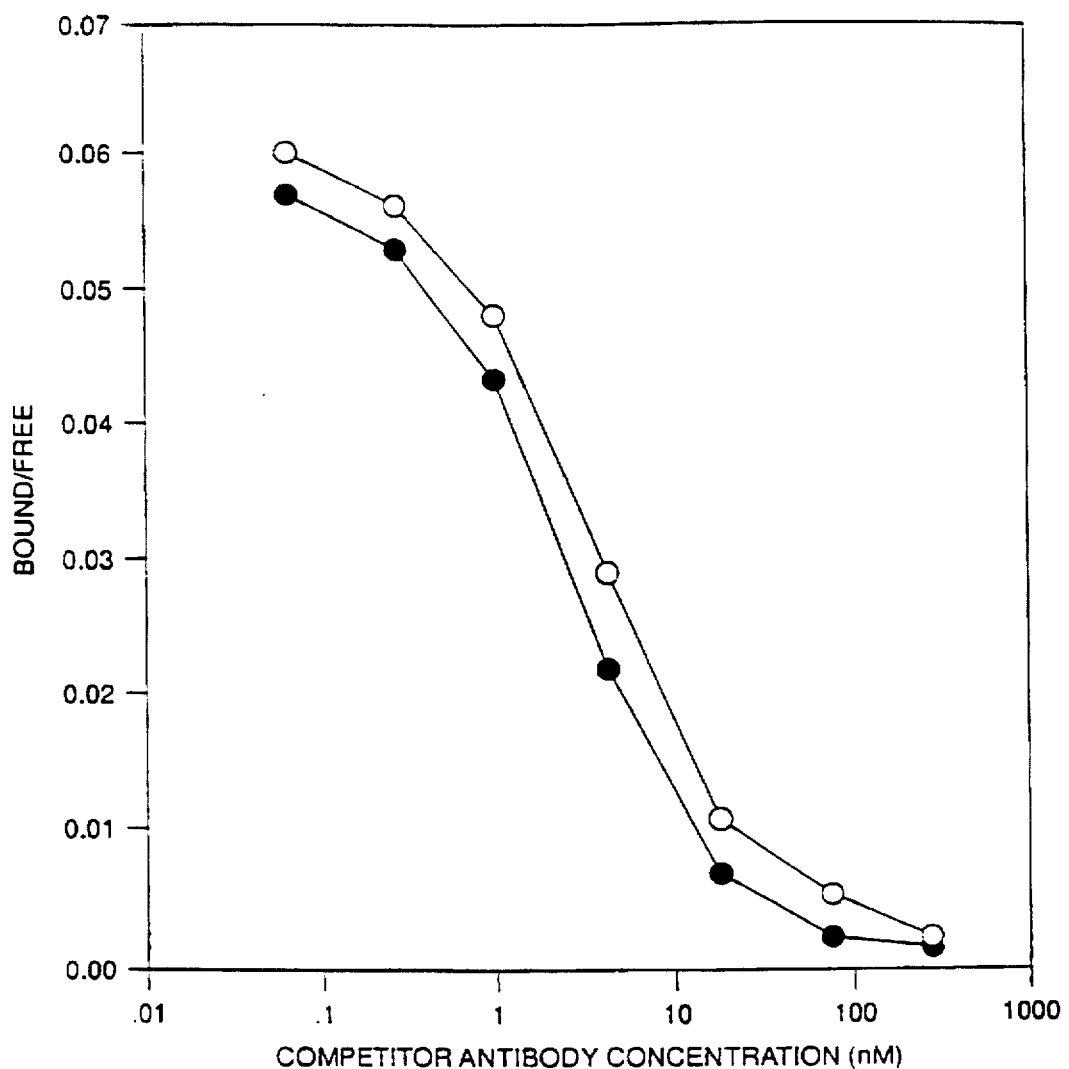

FIG. 28. Competitive binding of labeled mik-β1 tracer to YTJB cells. About 10⁶ YTJB cells were incubated with 3.0 ng of radio-iodinated mouse mik-β1 antibody (6 µCi/µg) and varing amounts of either unlabeled mouse mik-β1 antibody (●) or humanized mik-β1 antibody (○) in 200 ul of binding buffer (PBS+10% fetal calf serum+0.1% NaN₃+10 µg/ml mouse monoclonal Ig). After incubation for 2 hr at 0° C. the cells were washed twice with binding buffer without mouse Ig and collected by centrifugation. The radioactivity bound to cells was measured and expressed as the ratio of bound/free cpm.

Figure 29:
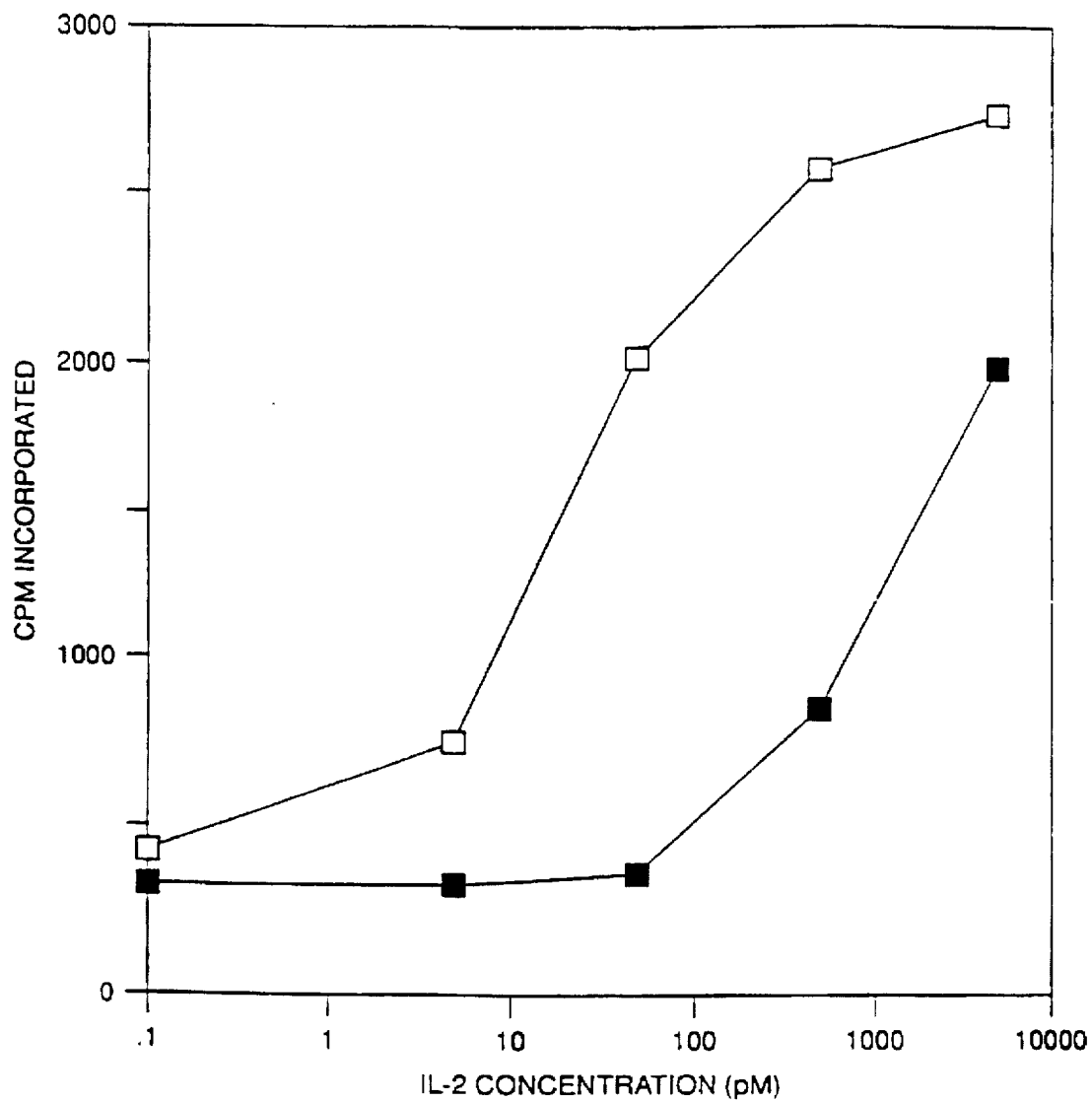

FIG. 29. Inhibition of IL-2 stimulated proliferation of human PHA blasts by humanized mik-β1+humanized anti-Tac antibodies. No antibody added (□), 2 ug each of humanized mik-β1 and humanized anti-Tac added (■).

FIG. 30A through FIG. 30D. Amino acid sequences of the heavy chain (A) (SEQ ID NOS:48 and 49) and the light chain (B) (SEQ ID NOS:46 and 47) of the murine and humanized Fd79 antibodies, and the heavy chain (C) (SEQ ID NOS:52 and 53) and the light chain (D) (SEQ ID NOS:50 and 51) of the murine and humanized Fd138-80 antibodies. The sequences of the murine antibody as deduced from the cDNA (upper lines) are shown aligned with the humanized antibody sequences (lower lines). The humanized Fd79 and Fd138-80 framework sequences are derived from Pom antibody and Eu antibody, respectively. Residues are numbered according to the Kabat system (E. A. Kabat et al., Sequences of Proteins of Immunological Interest (National Institutes of Health, Bethesda, Md.) (1987). The three CDRs in each chain are boxed. Residues in the Pom or Eu framework that have been replaced with murine sequences or consensus human sequences are underlined.

Figure 31A:
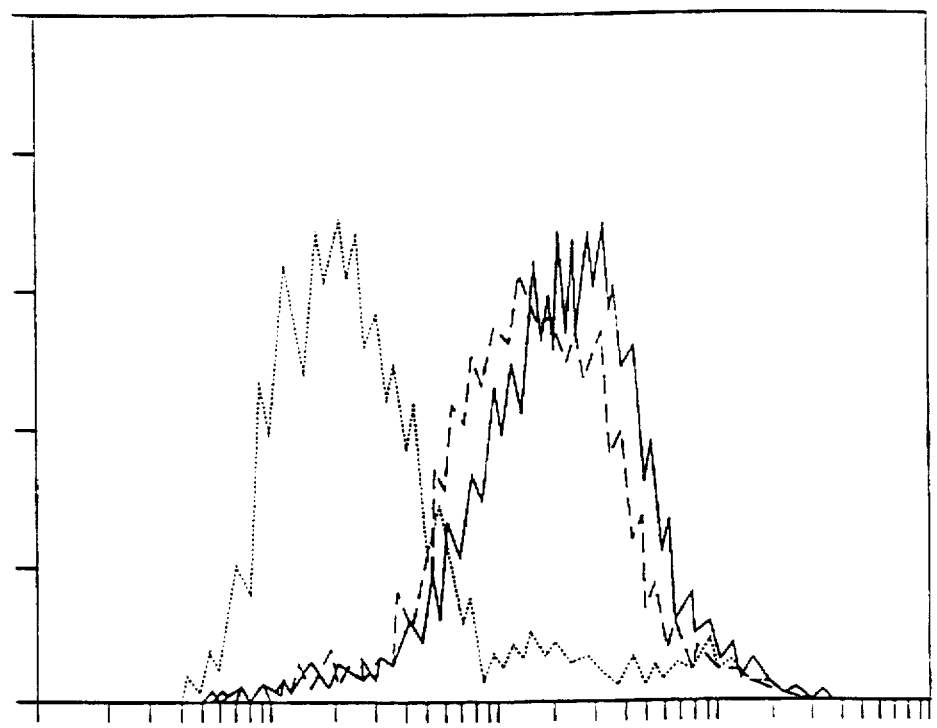
Figure 31B:
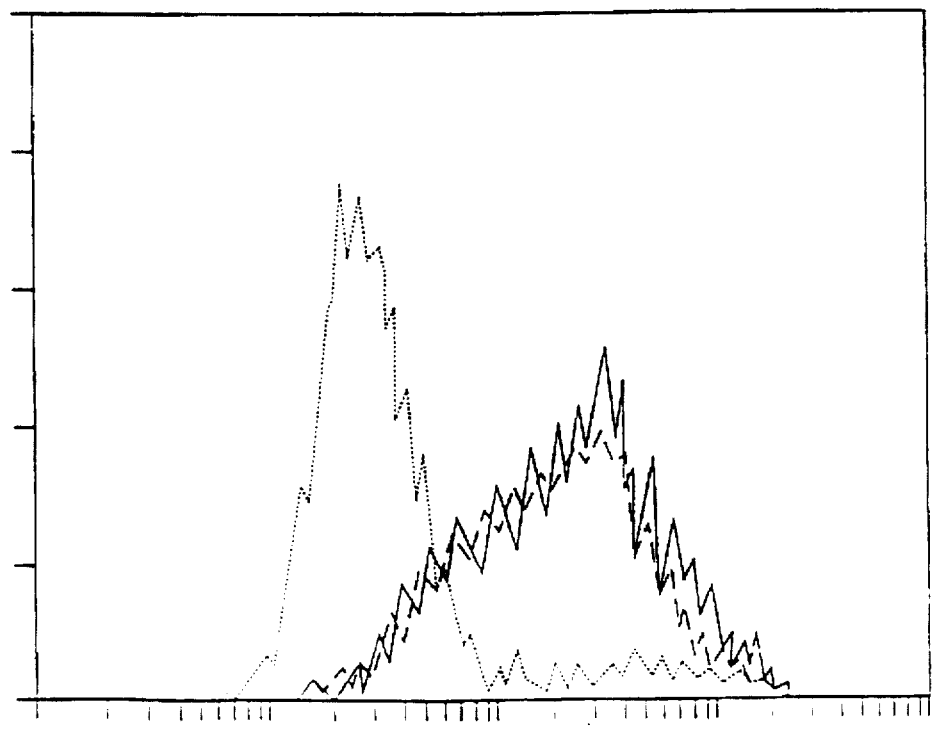

FIG. 31A and FIG. 31B. Fluorocytometry of HSV-1 infected Vero cells stained with Fd79 (A) and Fd138-80 (B) antibodies. ( . . ) Isotype matched control antibody, ( . . . ) humanized antibody, (\_) chimeric antibody. Vero cells were infected with HSV-1 (Δ305 mutant (F strain)) at 3 pfu/cell overnight. Cells were trypsinized at 0.5 mg/ml for 1 minute, washed extensively with PBS and resuspended in FACS buffer (PBS+2% BSA+0.1% azide) at approximately 5×10⁶/ml. 100 ul of cell suspension was transferred to a polystyrene tube and incubated with 100 ng of purified antibody on ice for 30 min. The cells were washed with FACS buffer and incubated with FITC labeled goat anti-human antibody (Cappel) on ice for another 30 min. The cells were washed again and finally resuspended in PBS+1% paraformaldehyde. Cells were analyzed on a FACSmate (Becton Dickinson).

Figure 32A:
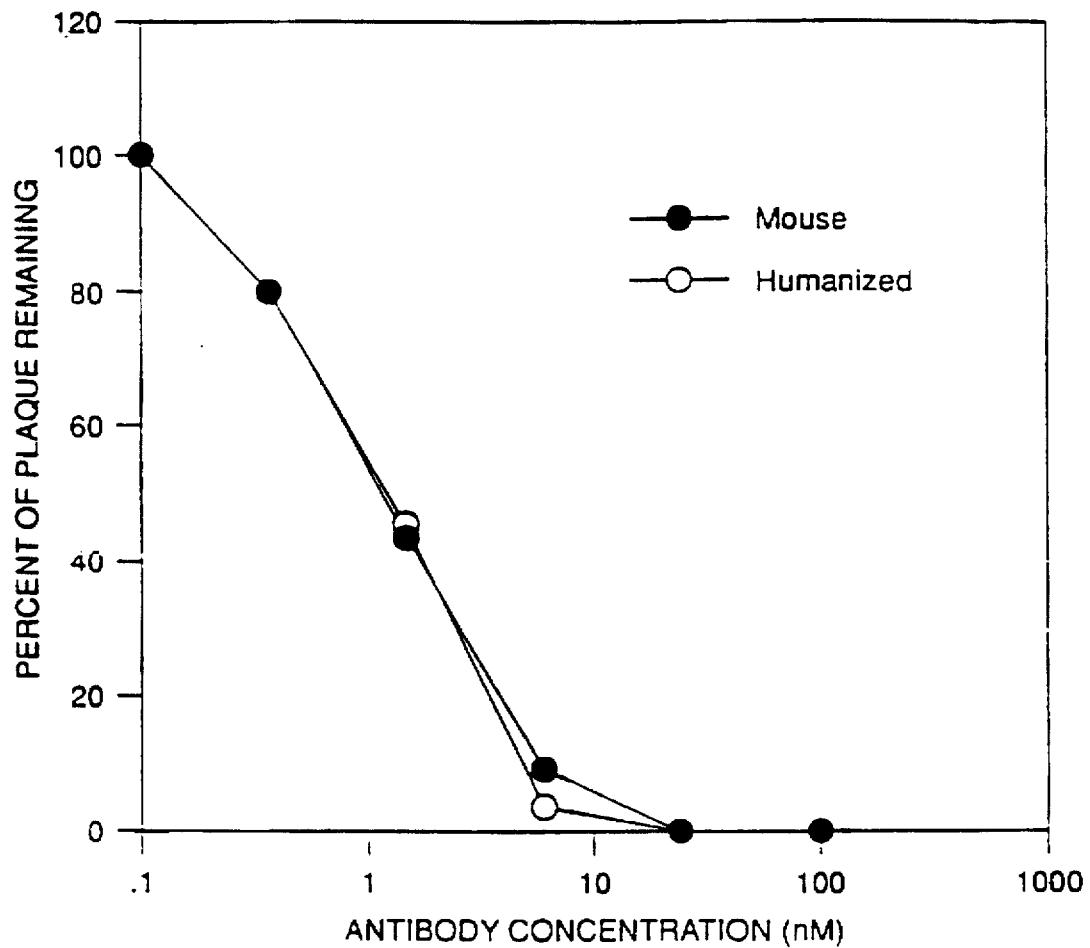
Figure 32B:
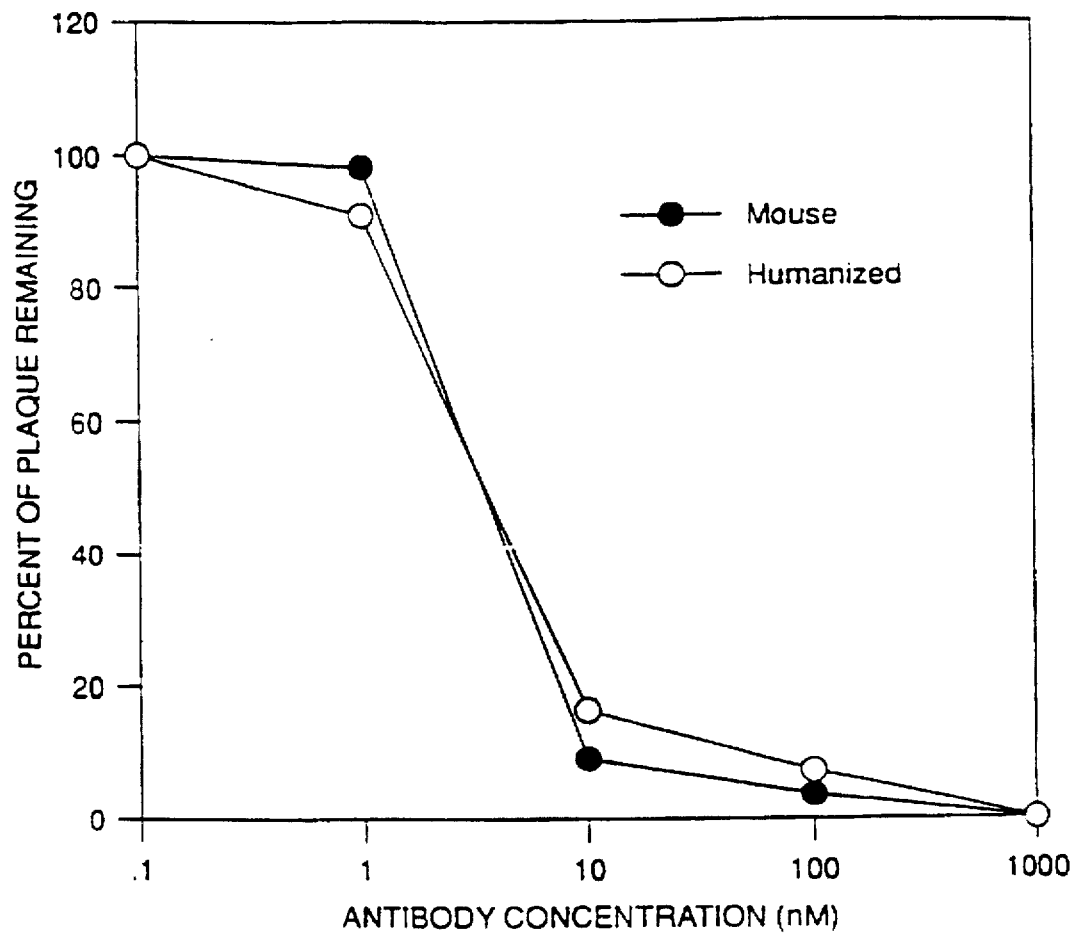

FIG. 32A and FIG. 32B. Neutralization of HSV-1 by Fd79 (A) and Fd138-80 (B). Serial dilutions of antibodies were mixed with 100 pfu of virus and incubated at 37° C. for 1 hr. The viruses were then inoculated onto 6-well plates with confluent Vero cells and adsorbed at 37° C. for 1 hr. Cells were overlayed with 1% agarose in medium and incubated for 4 days. Plaques were stained with neutral red.

Figure 33A:
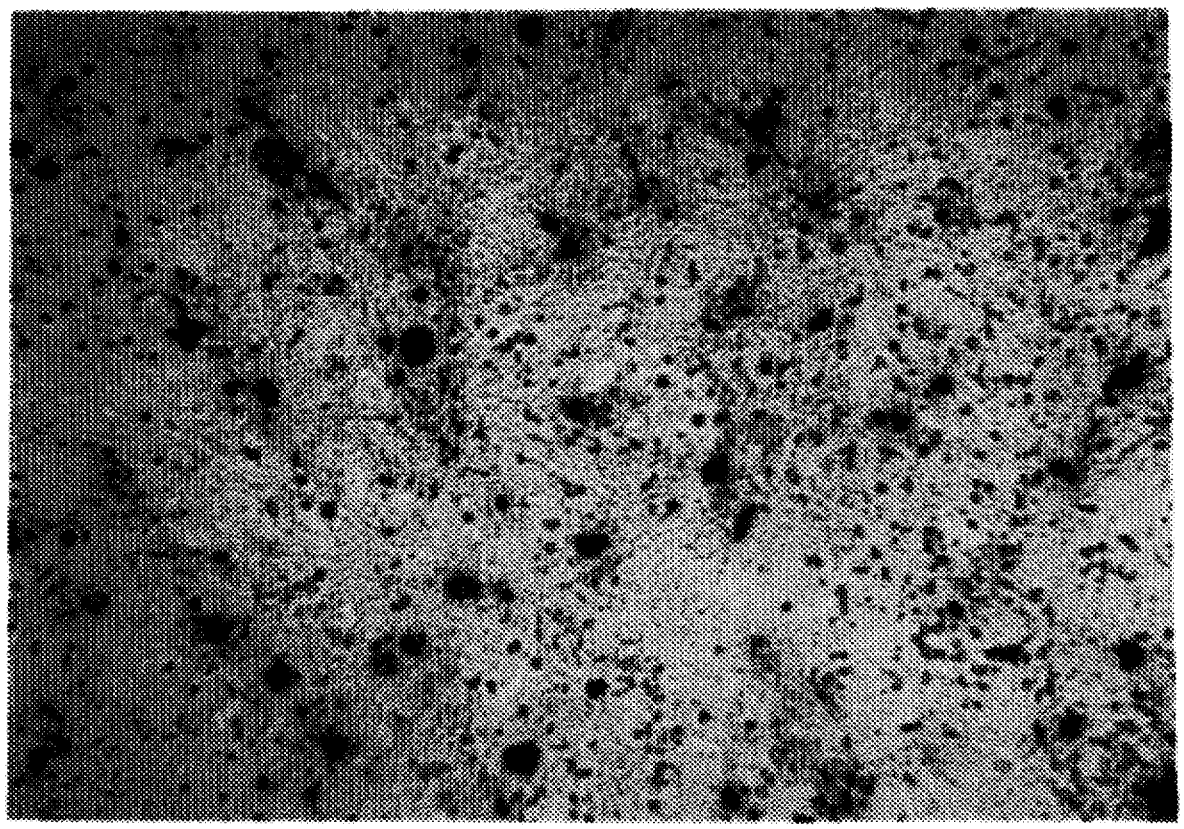
Figure 33B:
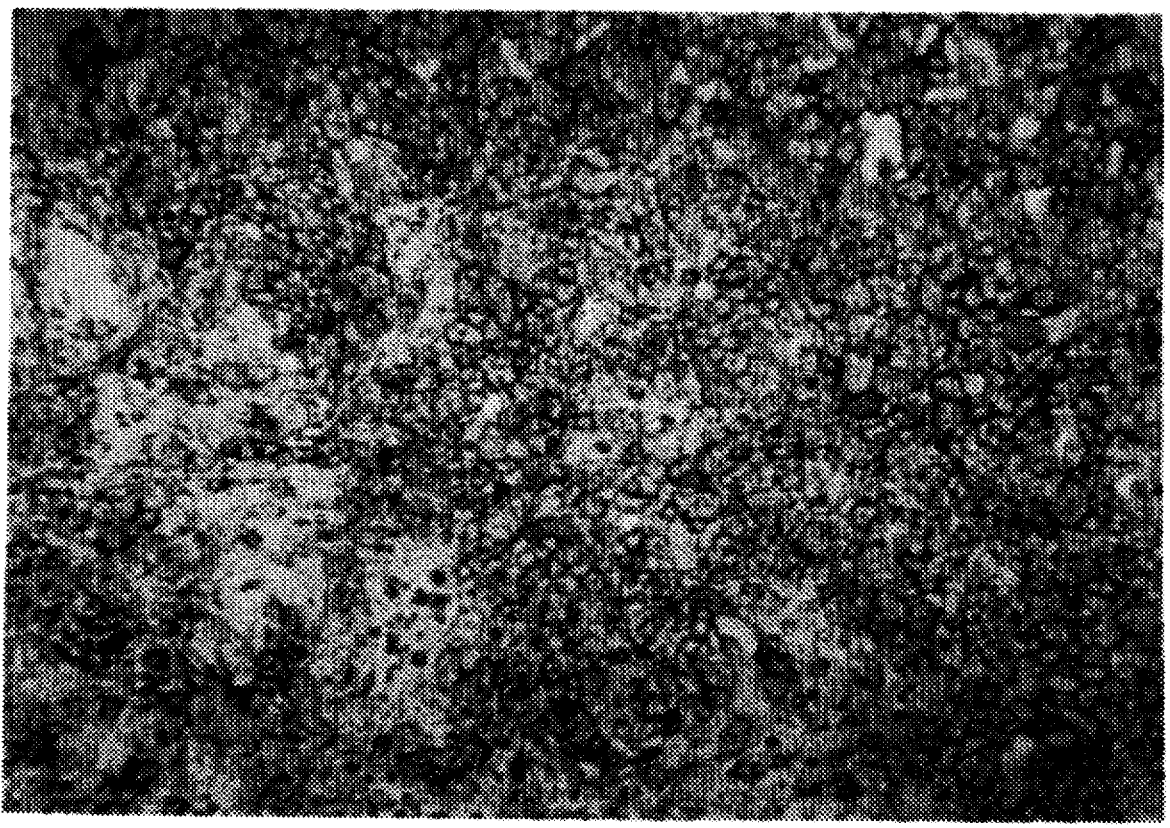

FIG. 33A and FIG. 33B. immunostaining of infected Vero cell monolayers to examine protection of cells from viral spread in tissue culture by (A) murine or humanized Fd79, (B) murine or humanized Fd138-80. 24-well plates of confluent Vero cells were inoculated with virus at 0.1 pfu/cell and allowed to adsorb for 2 hrs. at 37° C. before adding 200 ul of 10 ug/ml antibodies in medium. At the end of 4 days, culture medium was removed and plates were dried by placing overnight in a 37° C. incubator. To detect viral antigens, each well was incubated with 200 ul of anti-gB antibody at 0.5 ug/ml for 1 hr. at 37° C., washed twice and incubated with 200 ul of peroxidase conjugated goat anti-mouse IgG (Cappel, 1:300 dilution) for 1 hr. at 37° C. The plates were washed and then developed with the substrate 3-amino-9-ethyl-carbazole (AEC) (Sigma, St. Louis, Mo.) for 15 minutes at room temperature. Reaction was stopped by rinsing with water and air dried.

FIG. 34A and FIG. 34B. Sequences of the cDNA and translated amino acid sequences of the light chain (A) (SEQ ID NOS:66 and 67) and heavy chain (B) (SEQ ID NOS:68 and 69) variable regions of the antibody M195. The CDR sequences are underlined. The mature light chain protein begins with amino acid 21 D and the mature heavy chain protein with amino acid 20 E, preceded by the respective signal sequences.

Figure 35:
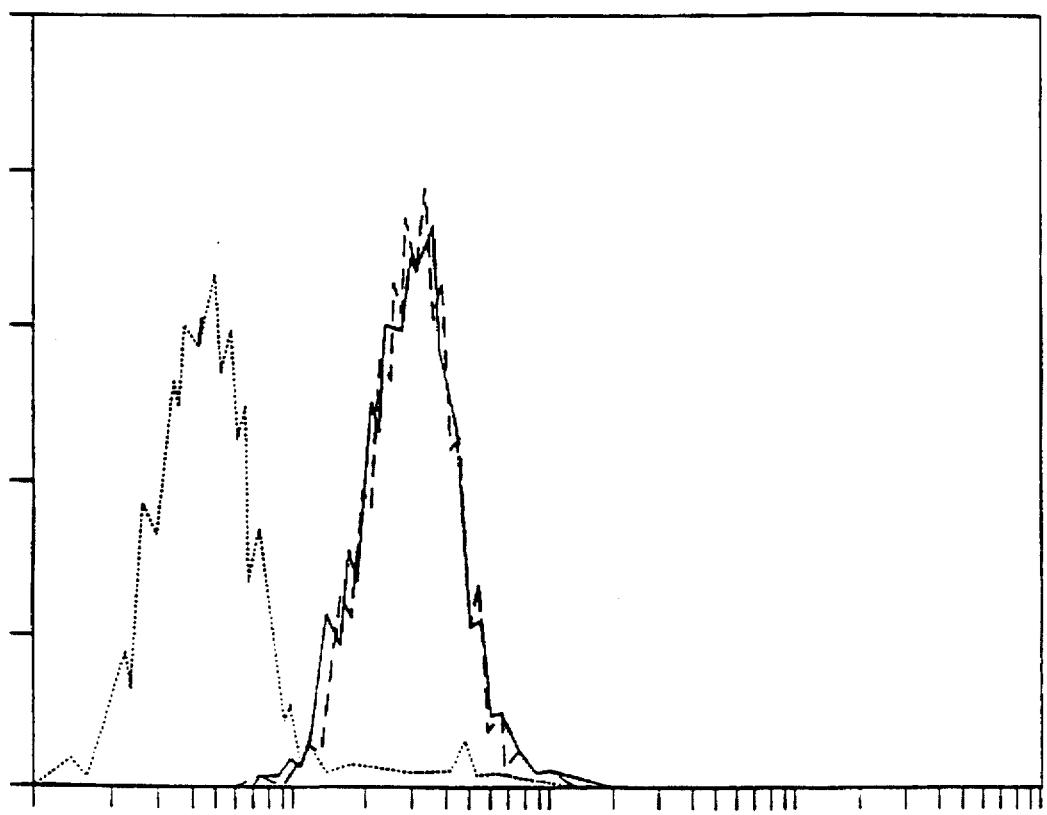

FIG. 35. Fluorocytometry of U937 cells stained with ( .. ) no antibody, ( . . . ) humanized M195 antibody, ( - - - ) chimeric M195 antibody. Cells were suspended in FACS buffer (PBS+2% FCS+0.1% azide) at approximately $5 \times 10^6$/ml. 100 ul of cell suspension was transferred to a polystyrene tube and incubated with 50 ng of purified antibody on ice for 30 min. The cells were washed with FACS buffer and incubated with FITC labeled goat anti-human Ig antibody on ice for another 30 min. The cells were washed again and finally resuspended in PBS+1% paraformaldehyde. Cells were analyzed on a FACSmate (Becton Dickinson).

FIG. 36A and FIG. 36B. Amino acid sequences of the light chain (A) (SEQ ID NOS:70 and 71) and the heavy chain (B) (SEQ ID NOS:72 and 73) of the humanized M195 antibody (lower lines) and human Eu antibody (upper lines), not including signal sequences. The three CDR's in each chain are underlined. Residues in the framework that have been replaced with mouse amino acids in the humanized antibody are double underlined.

FIG. 37A and FIG. 37B. Oligonucleotides used in the construction of the humanized M195 heavy chain (A; ma1–4) (SEQ ID NOS:74, 75, 76, and 77) and light chain (B; ma5–8) (SEQ ID NOS:78, 79, 80, and 81). The following pairs of oligonucleotides were mixed, extended with Klenow polymerase and cut with the indicated enzymes before ligation into pUC18: ma1 and ma2 with Xba I and Kpn I, ma3 and ma4 with Xba I and Kpn I, ma5 and ma6 with Xba I and Hind III, ma7 and ma8 with Xba I and Hind III. Then the ma1–ma2 and ma3–ma4 fragments were excised from pUC18 with Xba I and kpn I and ligated together into the Xba I site of pVg1-dhfr; and the ma5–ma6 and ma7–ma8 fragments were excised with Xba I and Hind III and ligated together into the Xba I site of pVk.

Figure 38:
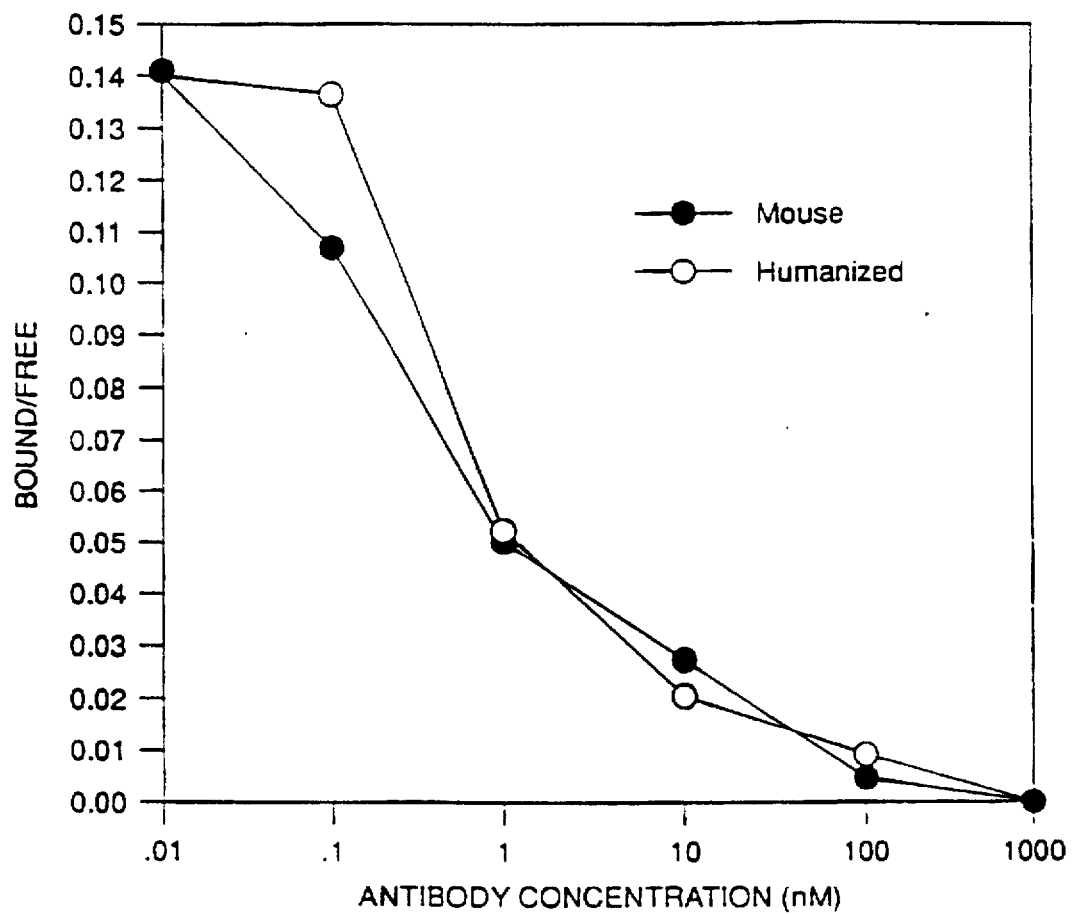

FIG. 38. Competitive binding of labeled M195 tracer to U937 cells. About $4 \times 10^5$ U937 cells were incubated with 4.5 ng of radio-iodinated mouse M195 antibody (6 µci/µg) and varying amounts of either unlabeled mouse M195 antibody (●) or humanized M195 antibody (○) in 200 ul of binding buffer (PBS+2% fetal calf serum+0.1% sodium azide). After incubation for 2 hr at 0° C., the cells were washed twice with binding buffer and collected by centrifugation. The radioactivity bound to cells was measured and is expressed as the ratio of bound/free cpm.

FIG. 39A and FIG. 39B. Sequences of the cDNA and translated amino acid sequences of the light chain (A) (SEQ ID NOS:82 and 83) and heavy chain (B) (SEQ ID NOS:84 and 85) variable regions of the antibody CMV5. The CDR sequences are underlined. The start of the mature protein sequences are indicated by arrows, preceded by the respective signal sequences.

FIG. 40A and FIG. 40B. Amino acid sequences of the light chain (A) (SEQ ID NOS:86 and 87) and the heavy chain (B) (SEQ ID NOS:88 and 89) of the humanized CMV5 antibody (lower lines) and human Wol antibody (upper lines), not including signal sequences. The three CDR's in each chain are underlined. Residues in the framework replaced with mouse amino acids or typical human amino acids in the humanized antibody are double underlined.

FIG. 41A and FIG. 41B. Oligonucleotides used in the construction of the humanized CMV5 light chain (A; jb16–jb19) (SEQ ID NOS:90, 91, 92, and 93) and heavy chain (B; jb20–jb22) (SEQ ID NOS:94, 95, 96, and 97). The following pairs of oligonucleotides were mixed, extended with Klenow polymerase and cut with the indicated enzymes before ligation into pUC18: jb16 and jb17 with Xba I and EcoR I, jb18 and jb19 with Xba I and EcoR I, jb20 and jb21 with Xba I and Kpn I, jb22 and jb23 with Xba I and Kpn I. Then the jb16–jb17 and jb18–jb19 fragments were excised with Xba I and Mlu I and ligated together into the Xba I site of pVk; and the jb20–jb21 and jb22–jb23 fragments were excised with Xba I and Kpn I and ligated together into the Xba I site of pVg1-dhfr.

Figure 42:
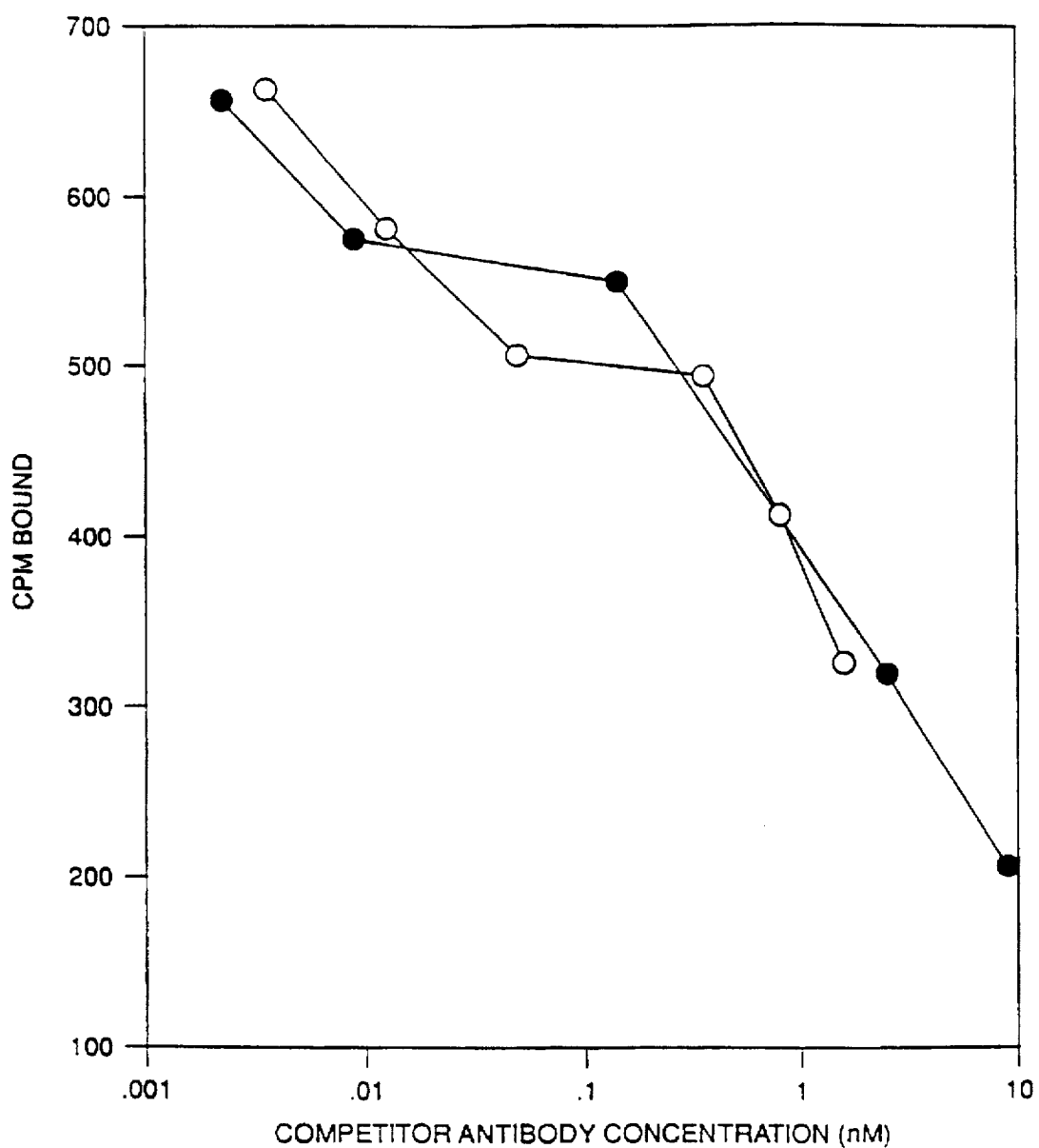

FIG. 42. Competitive binding of labeled CMV5 tracer to CMV-infected cells. Increasing amounts of mouse (●) or humanized (○) CMV5 antibody was added to CMV-infected HEL cells with tracer radio-iodinated mouse CMV5, and the amount of tracer bound to the cells was determined.

FIG. 43A and FIG. 43B. Sequences of the cDNA and translated amino acid sequences of the light chain (A) (SEQ ID NOS:98 and 99) and heavy chain (B) (SEQ ID NOS:100 and 101) variable regions of the antibody AF2. The CDR sequences are underlined. The mature light chain protein begins with amino acid 30 N and the mature heavy chain protein with amino acid 36 Q, preceded by the respective signal sequences.

FIG. 44A and FIG. 44B. Amino acid sequences of the light chain (A) (SEQ ID NOS:102 and 103) and the heavy chain (B) (SEQ ID NOS:104 and 105) of the humanized AF2 antibody (lower lines) and human Eu antibody (upper lines), not including signal sequences. The three CDR's in each chain are underlined. Residues in the framework that have been replaced with mouse amino acids or typical human amino acids in the humanized antibody are double underlined.

FIG. 45A and FIG. 45B. Oligonucleotides used in the construction of the humanized AF2 light chain (A; rh10–rh13) (SEQ ID NOS:106, 107, 108, and 109) and heavy chain (B; rh20–23) (SEQ ID NOS:110, 111, 112, and 113). The following pairs of oligonucleotides were mixed, extended with Klenow polymerase and cut with the indicated enzymes before ligation into pUC18: rh10 and rh11 with Xba I and Hind III, rh12 and rh13 with Xba I and Hind III, rh20 and rh21 with Xba I and EcoR I, rh22 and rh23 with Xba I and EcoR I. Then the rh10–rh11 and rh12–rh13 fragments were excised with Xba I and Hind III and ligated together into then Xba I site of pVk; and the rh20–rh21 and rh22–rh23 fragments were excised with Xba I and Xho I and ligated together into the Xba I site of pVg1-dhfr.

Figure 46:
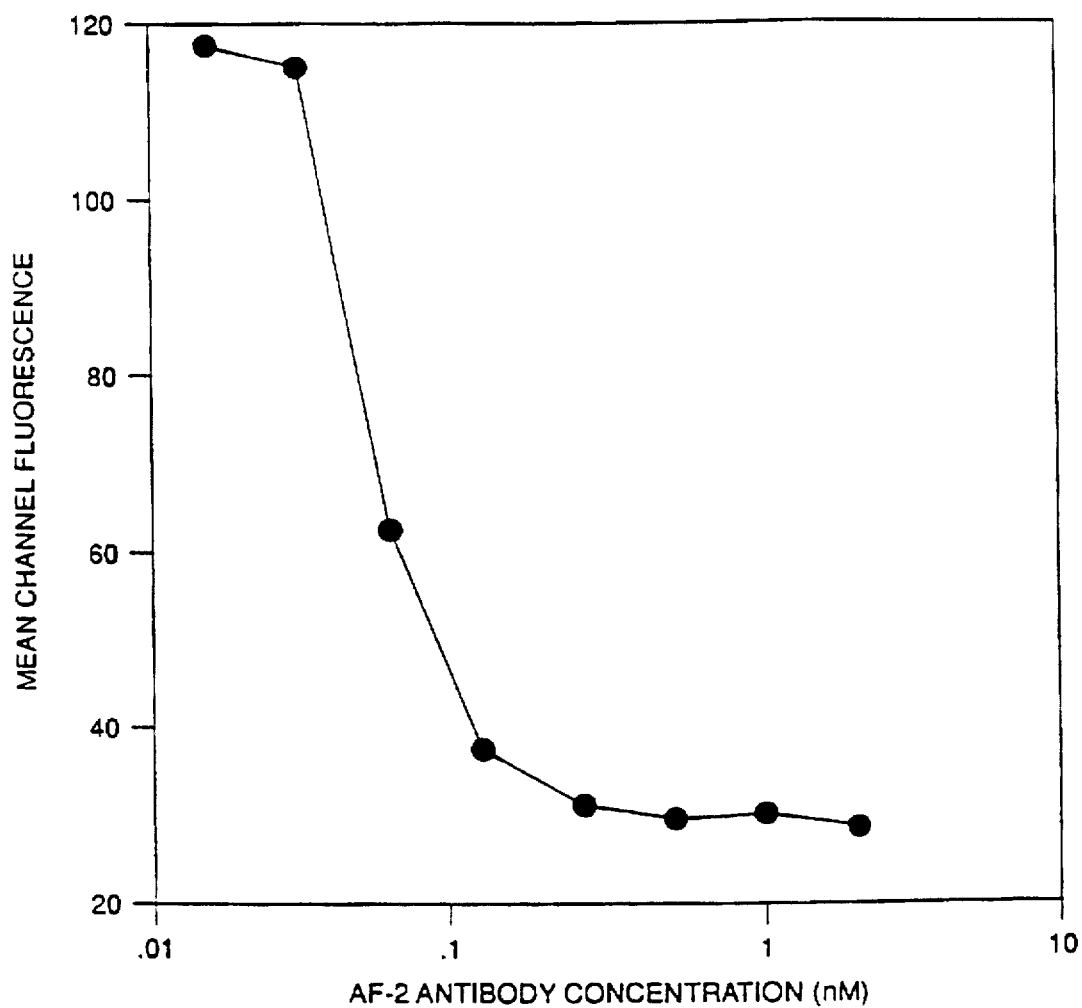

FIG. 46. Fluorescence of HS294T cells incubated with γ-IFN plus varying concentrations of mouse AF2 antibody, and stained with an anti-HLA-D antibody.

DETAILED DESCRIPTION OF THE INVENTION

In accordance with the present invention, novel means of designing humanized immunoglobulins capable of specifically binding to a predetermined antigen with strong affinity are provided. These improved methods produce immunoglobulins that are substantially non-immunogenic in humans but have binding affinities of at least about $10^8$ $M^{-1}$, preferably $10^9$ $M^{-1}$ to $10^{10}$ $M^{-1}$, or stronger. The humanized immunoglobulins will have a human framework and have one or more complementary determining regions (CDR's), plus a limited number of other amino acids, from a donor immunoglobulin specifically reactive with an antigen. The immunoglobulins can be produced economically in large quantities and find use, for example, in the treatment of various human disorders by a variety of techniques.

In order that the invention may be more completely understood, several definitions are set forth. As used herein, the term "immunoglobulin" refers to a protein consisting of one or more polypeptides substantially encoded by immunoglobulin genes. The recognized immunoglobulin genes include the kappa, lambda, alpha, gamma ($IgG_1$, $IgG_2$, $IgG_3$, $IgG_4$), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and (Fab')$_2$, as well as bifunctional hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879–5883 (1988) and Bird et al., *Science*, 242, 423–426 (1988), which are incorporated herein by reference). (See, generally, Hood et al., "Immunology", Benjamin, N.Y., 2nd ed. (1984), and Hunkapiller and Hood, *Nature*, 323, 15–16 (1986), which are incorporated herein by reference).

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90–95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant or effector domain from a human antibody (e.g., A.T.C.C. Accession No. CRL 9688 secretes an anti-Tac chimeric antibody), although other mammalian species may be used.

As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85–90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human. One says that the donor antibody has been "humanized", by the process of "humanization", because the resultant humanized antibody is expected to bind to the same antigen as the donor antibody that provides the CDR's.

It is understood that the humanized antibodies designed by the present method may have additional conservative amino acid substitutions which have substantially no effect on antigen binding or other immunoglobulin functions. By conservative substitutions is intended combinations such as gly, ala; val, ile, leu; asp, glu; asn, gln; ser, thr; lys, arg; and phe, tyr.

Humanized immunoglobulins, including humanized antibodies, have been constructed by means of genetic engineering. Most humanized immunoglobulins that have been previously described (Jones et al., op. cit.; Verhoeyen et al., op. cit.; Riechmann et al., op. cit.) have comprised a framework that is identical to the framework of a particular human immunoglobulin chain, the acceptor, and three CDR's from a non-human donor immunoglobulin chain. In one case (Riechmann et al., op. cit.), two additional amino acids in the framework were changed to be the same as amino acids in other human framework regions. The present invention includes criteria by which a limited number of amino acids in the framework of a humanized immunoglobulin chain are chosen to be the same as the amino acids at those positions in the donor rather than in the acceptor, in order to increase the affinity of an antibody comprising the humanized immunoglobulin chain.

The present invention is based in part on the model that two contributing causes of the loss of affinity in prior means of producing humanized antibodies (using as examples mouse antibodies as the source of CDR's) are:

(1) When the mouse CDR's are combined with the human framework, the amino acids in the framework close to the CDR's become human instead of mouse. Without intending to be bound by theory, we believe that these changed amino acids may slightly distort the CDR's, because they create different electrostatic or hydrophobic forces than in the donor mouse antibody, and the distorted CDR's may not make as effective contacts with the antigen as the CDR's did in the donor antibody;

(2) Also, amino acids in the original mouse antibody that are close to, but not part of, the CDR's (i.e., still part of the framework), may make contacts with the antigen that contribute to affinity. These amino acids are lost when the antibody is humanized, because all framework amino acids are made human.

To avoid these problems, and to produce humanized antibodies that have a very strong affinity for a desired antigen, the present invention uses one or more of the following principles for designing humanized immunoglobulins. Also, the criteria may be used singly, or when necessary in combination, to achieve the desired affinity or other characteristics.

A principle is that as acceptor, a framework is used from a particular human immunoglobulin that is unusually homologous to the donor immunoglobulin to be humanized, or use a consensus framework from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60–70%. By choosing as the acceptor immunoglobulin one of the human heavy (respectively light) chain variable regions that is most homologous to the heavy (respectively light) chain variable region of the donor immunoglobulin, fewer amino acids will be changed in going from the donor immunoglobulin to the humanized immunoglobulin. Hence, and again without intending to be bound by theory, it is believed that there is a smaller chance of changing an amino acid near the CDR's that distorts their conformation. Moreover, the precise overall shape of a humanized antibody comprising the humanized immunoglobulin chain may more closely resemble the shape of the donor antibody, also reducing the chance of distorting the CDR's.

Typically, one of the 3–5 most homologous heavy chain variable region sequences in a representative collection of at least about 10 to 20 distinct human heavy chains will be chosen as acceptor to provide the heavy chain framework, and similarly for the light chain. Preferably, one of the 1–3 most homologous variable regions will be used. The selected acceptor immunoglobulin chain will most preferably have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. In this case, the donor light and heavy chains will be compared only against chains from human antibodies whose complete sequence is known, e.g., the Eu, Lay, Pom, Wol, Sie, Gal, Ou and WEA antibodies (Kabat et al., op. cit.; occasionally, the last few amino acids of a human chain are not known and must be deduced by homology to other human antibodies). The human antibody will be chosen in which the light and heavy chain variable regions sequences, taken together, are overall most homologous to the donor light and heavy chain variable region sequences. Sometimes greater weight will be given to the heavy chain sequence. The chosen human antibody will then provide both light and heavy chain acceptor sequences. In practice, it is often found that the human Eu antibody will serve this role.

Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor. A second principle is that the following categories define what amino acids may be selected from the donor. Preferably, at many or all amino acid positions in one of these categories, the donor amino acid will in fact be selected.

Category 1: The amino acid position is in a CDR is defined by Kabat et al., op. cit.

Category 2: If an amino acid in the framework of the human acceptor immunoglobulin is unusual (i.e., "rare", which as used herein indicates an amino acid occurring at that position in less than about 20% but usually less than about 10% of human heavy (respectively light) chain V region sequences in a representative data bank), and if the donor amino acid at that position is typical for human sequences (i.e., "common", which as used herein indicates an amino acid occurring in more than about 25% but usually more than about 50% of sequences in a representative data bank), then the donor amino acid rather than the acceptor may be selected. This criterion helps ensure that an atypical amino acid in the human framework does not disrupt the antibody structure. Moreover, by replacing an unusual amino acid with an amino acid from the donor antibody that happens to be typical for human antibodies, the humanized antibody may be made less immunogenic.

All human light and heavy chain variable region sequences are respectively grouped into "subgroups" of sequences that are especially homologous to each other and have the same amino acids at certain critical positions (Kabat et al., op. cit.). When deciding whether an amino acid in a human acceptor sequence is "rare" or "common" among human sequences, it will often be preferable to consider only those human sequences in the same subgroup as the acceptor sequence.

Category 3: In the positions immediately adjacent to one or more of the 3 CDR's in the primary sequence of the humanized immunoglobulin chain, the donor amino acid(s) rather than acceptor amino acid may be selected. These amino acids are particularly likely to interact with the amino acids in the CDR's and, if chosen from the acceptor, to distort the donor CDR's and reduce affinity. Moreover, the adjacent amino acids may interact directly with the antigen (Amit et al., Science, 233, 747–753 (1986), which is incorporated herein by reference) and selecting these amino acids from the donor may be desirable to keep all the antigen contacts that provide affinity in the original antibody.

Category 4: A 3-dimensional model, typically of the original donor antibody, shows that certain amino acids outside of the CDR's are close to the CDR's and have a good probability of interacting with amino acids in the CDR's by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units of some atom in the CDR's and must contain an atom that could interact with the CDR atoms according to established chemical forces, such as those listed above.

In the case of atoms that may form a hydrogen bond, the 3 angstroms is measured between their nuclei, but for atoms that do not form a bond, the 3 angstroms is measured between their Van der Waals surfaces. Hence, in the latter case, the nuclei must be within about 6 angstroms (3+sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids in the framework that are capable of interacting with amino acids in the CDR's, and which therefore belong to Category 4, may be distinguished in another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a 3-dimensional model of an antibody, using algorithms known in the art (e.g., Connolly, *J. Appl. Cryst.* 16, 548 (1983) and Lee and Richards, *J. Mol. Biol.* 55, 379 (1971), both of which are incorporated herein by reference). Framework amino acids may also occasionally interact with the CDR's indirectly, by affecting the conformation of another framework amino acid that in turn contacts the CDR's.

The amino acids at several positions in the framework are known to be capable of interacting with the CDRs in many antibodies (Chothia and Lesk, *J. Mol. Biol.* 196, 901 (1987), Chothia et al., *Nature* 342, 877 (1989), and Tramontano et al., *J. Mol. Biol.* 215, 175 (1990), all of which are incorporated herein by reference), notably at positions 2, 48, 64 and 71 of the light chain and 26–30, 71 and 94 of the heavy chain (numbering according to Kabat, op. cit.), and therefore these amino acids will generally be in Category 4. Typically, humanized immunoglobulins, of the present invention will include donor amino acids (where different) in category 4 in addition to these. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain positions that may be in Category 4 such as the first 5 amino acids of the light chain may sometimes be chosen from the acceptor immunoglobulin without loss of affinity in the humanized immunoglobulin.

Chothia and Lesk (op. cit.) define the CDRs differently from Kabat et al. (op. cit.). Notably, CDR1 is defined as including residues 26–32. Accordingly, Riechmann et al., (op. cit.) chose these amino acids from the donor immunoglobulins.

Computer programs to create models of proteins such as antibodies are generally available and well known to those skilled in the art (see, Levy et al., *Biochemistry*, 28, 7168–7175 (1989; Bruccoleri et al., *Nature*, 335, 564–568 (1988); Chothia et al., *Science*, 233, 755–758 (1986), all of which are incorporated herein by reference). These do not form part of the invention. Indeed, because all antibodies have similar structures, the known antibody structures, which are available from the Brookhaven Protein Data Bank, can be used if necessary as rough models of other antibodies. Commercially available computer programs can be used to display these models on a computer monitor, to calculate the distance between atoms, and to estimate the likelihood of different amino acids interacting (see, Ferrin et al., *J. Mol. Graphics*, 6, 13–27 (1988)).

In addition to the above categories, which describe when an amino acid in the humanized immunoglobulin may be taken from the donor, certain amino acids in the humanized immunoglobulin may be taken from neither the donor nor acceptor, if then fall in:

Category 5: If the amino acid at a given position in the donor immunoglobulin is "rare" for human sequences, and the amino acid at that position in the acceptor immunoglobulin is also "rare" for human sequences, as defined above, then the amino acid at that position in the humanized immunoglobulin may be chosen to be some amino acid "typical" of human sequences. A preferred choice is the amino acid that occurs most often at that position in the known human sequences belonging to the same subgroup as the acceptor sequence.

Humanized antibodies generally have at least three potential advantages over mouse or in some cases chimeric antibodies for use in human therapy:

1) Because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or constant region of the humanized antibody as foreign, and therefore the antibody response against such an injected antibody should be less than against a totally foreign mouse antibody or a partially foreign chimeric antibody.

3) Injected mouse antibodies have been reported to have a half-life in the human circulation much shorter than the half-life of normal antibodies (D. Shaw et al., *J. Immunol.*, 138, 4534–4538 (1987)). Injected humanized antibodies will presumably have a half-life more similar to naturally occurring human antibodies, allowing smaller and less frequent doses to be given.

In one aspect, the present invention is directed to designing humanized immunoglobulins that are produced by expressing recombinant DNA segments encoding the heavy and light chain CDR's from a donor immunoglobulin capable of binding to a desired antigen, such as the human IL-2 receptor, attached to DNA segments encoding acceptor human framework regions. Exemplary DNA sequences designed in accordance with the present invention code for the polypeptide chains comprising heavy and light chain CDR's with substantially human framework regions shown in FIG. 1A through FIG. 6B. Due to codon degeneracy and non-critical amino acid substitutions, other DNA sequences can be readily substituted for those sequences, as detailed below. In general, the criteria of the present invention find applicability to designing substantially any humanized immunoglobulin.

The DNA segments will typically further include an expression control DNA sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, *Cells of Immunoglobulin Synthesis*, Academic Press, N.Y., (1979), which is incorporated herein by reference).

Human constant region DNA sequences can be isolated in accordance with well known procedures from a variety of human cells, but preferably immortalized B-cells (see, Kabat op. cit. and WP87/02671). The CDR's for producing the immunoglobulins of the present invention will be similarly derived from monoclonal antibodies capable of binding to the predetermined antigen, such as the human IL-2 receptor, and produced by well known methods in any convenient mammalian source including, mice, rats, rabbits, or other vertebrates, capable of producing antibodies. Suitable source cells for the constant region and framework DNA sequences, and host cells for immunoglobulin expression and secretion, can be obtained from a number of sources, such as the American Type Culture Collection ("Catalogue of Cell Lines and Hybridomas," sixth edition (1988) Rockville, Md., U.S.A., which is incorporated herein by reference).

In addition to the humanized immunoglobulins specifically described herein, other "substantially homologous" modified immunoglobulins to the native sequences can be readily designed and manufactured utilizing various recombinant DNA techniques well known to those skilled in the art. For example, the framework regions can vary specifically from the sequences in FIG. 1A through FIG. 6B at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, *Gene*, 8, 81–97 (1979) and S. Roberts et al., *Nature*, 328, 731–734 (1987), both of which are incorporated herein by reference).

Substantially homologous immunoglobulin sequences are those which exhibit at least about 85% homology, usually at least about 90%, and preferably at least about 95% homology with a reference immunoglobulin protein.

Figure 9B:
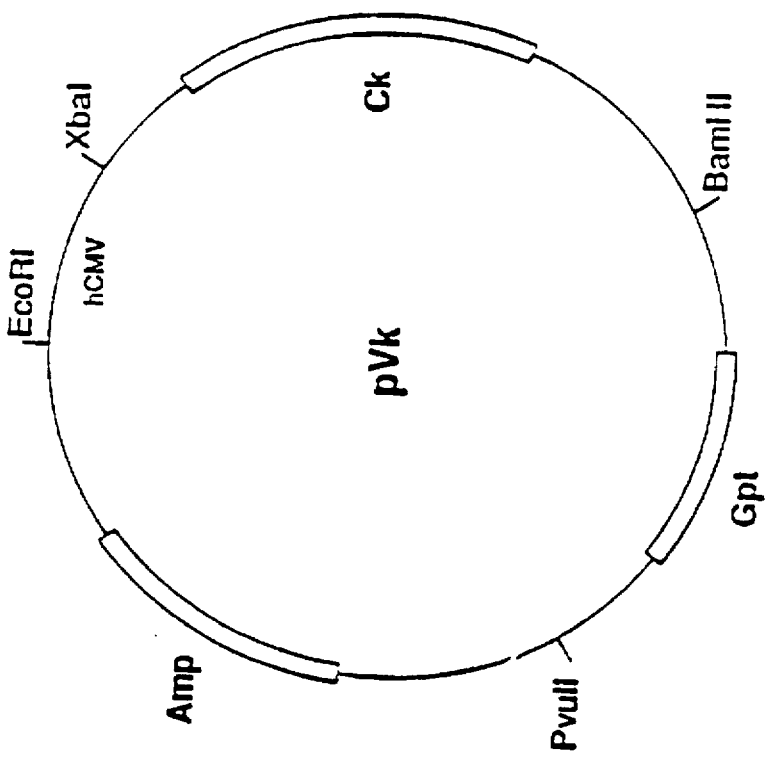
FIG. 9A and FIG. 9B. Schematic diagram of the plasmids pVg1 (A) and pVk (B). The plasmid pVg1 was constructed from the following fragments: an approximately 4850 base pair BamHI-EcoRI fragment from the plasmid pSV2hph containing the amp and hyg genes; a 630-pb fragment containing the human cytomegalovirus IE1 gene promoter and enhancer flanked at the 5' and 3' by EcoR1 and Xba1 linkers respectively; and a 2800 bp XbaI-BamHI fragment containing the human gamma-1 constant region gene with 215 bp of the preceding intron and the poly(A) signal. The plasmid pVk was similarly constructed, with a 1530-bp human kappa constant region gene replacing the gamma-1 gene and the gpt replacing the hyg gene.
Figure 9A:
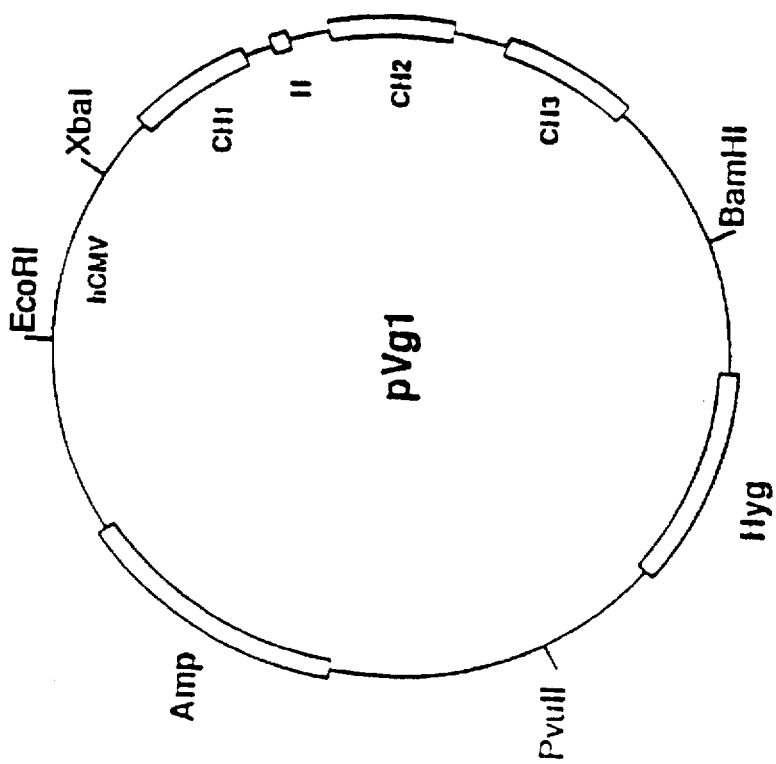

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in the vectors pVk and pVg1 (FIGS. 9A and 9B) using site-directed mutagenesis, such as after CH1 to produce Fab fragments or after the hinge region to produce (Fab')$_2$ fragments. Single chain antibodies may be produced by joining VL and VH with a DNA linker (see, Huston et al., op. cit., and Bird et al., op. cit.). Also because like many genes, the immunoglobulin-related genes contain separate functional regions, each having one or more distinct biological activities, the genes may be fused to functional regions from other genes (e.g., enzymes, see, commonly assigned U.S. Pat. No. 5,004,692) to produce fusion proteins (e.g., immunotoxins) having novel properties. The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate synthetic and genomic sequences is presently the most common method of production, but cDNA sequences may also be utilized (see, European Patent Publication No. 0239400 and L. Reichmann et al., *Nature*, 332, 323–327 (1988), both of which are incorporated herein by reference).

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilus*, and other enterobacteriaceae, such as *Salmonella*, *Serratia*, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc, and transformed B-cells or hybridomas. Expression vectors for these cells can include expression control sequences, such as an origin of replication, a promoter, an enhancer (Queen et al., *Immunol. Rev.*, 89, 49–68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, cytomegalovirus, Bovine Papilloma Virus, and the like.

The vectors containing the DNA segments of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis et al., Molecular Cloning: A Laboratory Manual, Cold Spring Harbor Press, (1982), which is incorporated herein by reference.)

Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like (see, generally, R. Scopes, "Protein Purification", Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods*, Vols. I and II, Lefkovits and Pernis, eds., Academic Press, New York, N.Y. (1979 and 1981)).

The antibodies of the present invention will typically find use individually in treating substantially any disease susceptible to monoclonal antibody-based therapy. In particular, the immunoglobulins can be used for passive immunization or the removal of unwanted cells or antigens, such as by complement mediated lysis, all without substantial immune reactions (e.g., anaphylactic shock) associated with many prior antibodies. For example, where the cell linked to a disease has been identified as IL-2 receptor bearing, then humanized antibodies that bind to the human IL-2 receptor are suitable (see, U.S. Ser. No. 085,707, entitled "Treating Human Malignancies and Disorders," which is incorporated herein by reference). For such a humanized immunoglobulin, typical disease states suitable for treatment include graft versus host disease and transplant rejection in patients undergoing an organ transplant, such as heart, lungs, kidneys, liver, etc. Other diseases include autoimmune diseases, such as Type I diabetes, multiple sclerosis, rheumatoid arthritis, systemic lupus erythematosus, and myasthenia gravis.

The method of producing humanized antibodies of the present invention can be used to humanize a variety of donor antibodies, especially monoclonal antibodies reactive with markers on cells responsible for a disease. For example, suitable antibodies bind to antigens on T-cells, such as those grouped into the so-called "Clusters of Differentiation," as named by the First International Leukocyte Differentiation Workshop, Leukocyte Typing, Bernard et al., Eds., Springer-Verlag, N.Y. (1984), which is incorporated herein by reference.

The antibodies of the present invention can also be used as separately administered compositions given in conjunction with chemotherapeutic or immunosuppressive agents. Possible agents include cyclosporin A or a purine analog (e.g., methotrexate, 6-mercaptopurine, or the like), but numerous additional agents (e.g., cyclophosphamide, prednisone, etc.) well-known to those skilled in the art of medicine may also be utilized.

A preferred pharmaceutical composition of the present invention comprises the use of the subject antibodies in immunotoxins. Immunotoxins are characterized by two components and are particularly useful for killing selected cells in vitro or in vivo. One component is a cytotoxic agent which is usually fatal to a cell when attached or absorbed. The second component, known as the "delivery vehicle," provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), which is incorporated herein by reference. The components may also be linked genetically (see, Chaudhary et al., *Nature* 339, 394 (1989), which is herein incorporated by reference).

A variety of cytotoxic agents are suitable for use in immunotoxins. Cytotoxic agents can include radionuclides, such as Iodine-131 or other isotopes of iodine, Yttrium-90, Rhenium-188, and Bismuth-212 or other alpha emitters; a number of chemotherapeutic drugs, such as vindesine, methotrexate, adriamycin, and cisplatinum; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). (See, generally, "Chimeric Toxins," Olsnes and Phil, *Pharmac. Ther.*, 25, 355–381 (1982), and "Monoclonal Antibodies for Cancer Detection and Therapy," eds. Baldwin and Byers, pp. 159–179, 224–266, Academic Press (1985), all of which are incorporated herein by reference.)

The delivery component of the immunotoxin will include the humanized immunoglobulins of the present invention. Intact immunoglobulins or their binding fragments, such as Fab, are preferably used. Typically, the antibodies in the immunotoxins will be of the human IgM or IgG isotype, but other mammalian constant regions may be utilized as desired.

For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels may be employed, such as radionuclides, fluors, enzymes, enzyme substrates, enzyme co-factors, enzyme inhibitors, ligands (particularly haptens), etc. Numerous types of immunoassays are available and are well known to those skilled in the art.

Anti-IL-2 Receptor Antibodies

To exert its biological effects, IL-2 interacts with a specific high-affinity membrane receptor (Greene, W., et al., *Progress in Hematology XIV*, E. Brown, Ed., Grune and Statton, New York (1986), at pgs. 283 ff and Waldmann, Ann. Rev. Biochem. 58, 875 (1989), both of which are incorporated herein by reference). The human IL-2 receptor is a complex multichain glycoprotein, with one chain, known as the Tac peptide, being about 55 kD in size (see, Leonard, W., et al., *J. Biol. Chem.* 260, 1872 (1985), which is incorporated herein by reference). A gene encoding this protein has been isolated, and predicts a 272 amino acid peptide, including a 21 amino acid signal peptide (see, Leonard, W., et al., *Nature* 311, 626 (1984)). The 219 $NH_2$-terminal amino acids of the p55 Tac protein apparently comprise an extracellular domain (see, Leonard, W., et al., *Science*, 230, 633–639 (1985), which is incorporated herein by reference).

Much of the elucidation of the human IL-2 receptor's structure and function is due to the development of specifically reactive monoclonal antibodies. In particular, one mouse monoclonal antibody, known as anti-Tac (Uchiyama, et al., *J. Immunol.* 126, 1393 (1981)) has been used to show that IL-2 receptors can be detected on T-cells, but also on cells of the monocyte-macrophage family, Kupffer cells of the liver, Langerhans' cells of the skin and, of course, activated T-cells. Importantly, resting T-cells, B-cells or circulating machrophages typically do not display the IL-2 receptor (Herrmann, et al., *J. Exp. Med.* 162, 1111 (1985)).

The anti-Tac monoclonal antibody has also been used to define lymphocyte functions that require IL-2 interaction, and has been shown to inhibit various T-cell functions, including the generation of cytotoxic and suppressor T lymphocytes in cell culture. Also, based on studies with anti-Tac and other antibodies, a variety of disorders are now associated with improper IL-2 receptor expression by T-cells, in particular adult T-cell leukemia.

More recently, the IL-2 receptor has been shown to be an ideal target for novel therapeutic approaches to T-cell mediated diseases. It has been proposed that IL-2 receptor specific antibodies, such as the anti-Tac monoclonal antibody, can be used either alone or as an immunoconjugate (e.g., with Ricin A, isotopes and the like) to effectively remove cells bearing the IL-2 receptor. These agents can, for example, theoretically eliminate IL-2 receptor-expressing leukemic cells, certain B-cells, or activated T-cells involved in a disease state, yet allow the retention of mature normal T-cells and their precursors to ensure the capability of mounting a normal T-cell immune response as needed. In general, most other T-cell specific agents can destroy essentially all peripheral T-cells, which limits the agents' therapeutic efficacy. Overall, the use of appropriate monoclonal antibodies specific for the IL-2 receptor may have therapeutic utility in autoimmune diseases, organ transplantation and any unwanted response by activated T-cells. Indeed, clinical trials have been initiated using, e.g., anti-Tac antibodies (see, generally, Waldmann, T., et al., *Cancer Res.* 45, 625 (1985), Waldmann, T., *Science* 232, 727–732 (1986) and Kirkman et al., *Transplant. Proc.* 21, 1766 (1989), all of which are incorporated herein by reference).

Unfortunately, the use of the anti-Tac and other non-human monoclonal antibodies have certain drawbacks, particularly in repeated therapeutic regimens as explained below. Mouse monoclonal antibodies, for example, do not fix human complement well, and lack other important immunoglobulin functional characteristics when used in humans.

Perhaps more importantly, anti-Tac and other non-human monoclonal antibodies contain substantial stretches of amino acid sequences that will be immunogenic when injected into a human patient. Numerous studies have shown that, after injection of a foreign antibody, the immune response elicited by a patient against an antibody can be quite strong, essentially eliminating the antibody's therapeutic utility after an initial treatment. Moreover, as increasing numbers of different mouse or other antigenic (to humans) monoclonal antibodies can be expected to be developed to treat various diseases, after the first or several treatments with any different non-human antibodies, subsequent treatments even for unrelated therapies can be ineffective or even dangerous in themselves, because of cross-reactivity.

While the production of so-called "chimeric antibodies" (e.g., mouse variable regions joined to human constant regions) has proven somewhat successful, a significant immunogenicity problem remains. In general, the production of human immunoglobulins reactive with the human IL-2 receptor, as with many human antigens, has been extremely difficult using typical human monoclonal antibody production techniques. Similarly, utilizing recombinant DNA technology to produce so-called "reshaped" or "humanized" antibodies (see, e.g., Riechmann et al., *Nature* 332, 323 (1988) and EPO Publication No. 0239400), provides uncertain results, in part due to unpredictable binding affinities.

Thus, there is a need for improved forms of human-like immunoglobulins specific for the human IL-2 receptor that are substantially non-immunogenic in humans, yet easily and economically produced in a manner suitable for therapeutic formulation and other uses. The present invention fulfills these and other needs.

The present invention provides novel compositions useful, for example, in the treatment of T-cell mediated human disorders, the compositions containing human-like immunoglobulins specifically capable of blocking the binding of human IL-2 to its receptor and/or capable of binding to the p55 Tac protein on human IL-2 receptors. The immunoglobulins can have two pairs of light chain/heavy chain complexes, typically at least one chain comprising mouse complementarity determining regions functionally joined to human framework region segments. For example, mouse complementarity determining regions, with or without additional naturally-associated mouse amino acid residues, can be used to produce human-like antibodies capable of binding to the human IL-2 receptor at affinity levels stronger than about $10^8$ $M^{-1}$.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for human-like immunoglobulin framework regions and a second sequence set coding for the desired immunoglobulin complementarity determining regions can be produced synthetically or by combining appropriate cDNA and genomic DNA segments.

The human-like immunoglobulins may be utilized alone in substantially pure form, or complexed with a cytotoxic agent, such as a radionuclide, a ribosomal inhibiting protein or a cytotoxic agent active at cell surfaces. All of these compounds will be particularly useful in treating T-cell mediated disorders. The human-like immunoglobulins or their complexes can be prepared in a pharmaceutically accepted dosage form, which will vary depending on the mode of administration.

In accordance with the present invention, human-like immunoglobulins specifically reactive with the IL-2 receptor on human T-cells are provided. These immunoglobulins, which have binding affinities of at least about $10^8$ $M^{-1}$, and preferably $10^9$ $M^{-1}$ to $10^{10}$ $M^{-1}$ or stronger, are capable of, e.g., blocking the binding of IL-2 to human IL-2 receptors. The human-like immunoglobulins will have a human-like framework and can have complementarity determining regions (CDR's) from an immunoglobulin, typically a mouse immunoglobulin, specifically reactive with an epitope on p55 Tac protein. The immunoglobulins of the present invention, which can be produced economically in large quantities, find use, for example, in the treatment of T-cell mediated disorders in human patients by a variety of techniques.

The basic antibody structural unit is known to comprise a tetramer. Each tetramer is composed of two identical pairs of polypeptide chains, each pair having one "light" (about 25 kD) and one "heavy" chain (about 50–70 kD). The $NH_2$-terminus of each chain begins a variable region of about 100 to 110 or more amino acids primarily responsible for antigen recognition. The COOH terminus of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 10 or more amino acids, with the heavy chain also including a "D" region of about 12 more amino acids. (See, generally, *Fundamental Immunology*, Paul, W., Ed., Chapter 7, pgs. 131–166, Raven Press, N.Y. (1984), which is incorporated herein by reference.)

The variable regions of each light/heavy chain pair form the antibody binding site. The chains all exhibit the same general structure of relatively conserved framework regions joined by three hypervariable regions, also called Complementarity Determining Regions or CDR's (see, "Sequences of Proteins of immunological Interest," Kabat, E., et al., U.S. Department of Health and Human Services, (1983); and Chothia and Lesk, *J. Mol. Biol.*, 196, 901–917 (1987), which are incorporated herein by reference). The CDR's from the two chains of each pair are aligned by the framework regions, enabling binding to a specific epitope.

In one aspect, the present invention is directed to recombinant DNA segments encoding the heavy and/or light chain CDR's from an immunoglobulin capable of binding to a desired epitope on the human IL-2 receptor, such as the anti-Tac monoclonal antibody. The DNA segments encoding these regions will typically be joined to DNA segments encoding appropriate human-like framework regions. Preferred DNA sequences, which on expression code for the polypeptide chains comprising the anti-Tac heavy and light chain hypervariable regions (with human-like framework regions), are included in FIGS. 15A and and 16A, respectively. Due to codon degeneracy and non-critical amino-acid substitutions, other DNA sequences can be readily substituted for those sequences, as detailed below.

The antibodies of the present invention will typically find use individually in treating a T-cell mediated disease state. Generally, where the cell linked to a disease has been identified as IL-2 receptor bearing, then the human-like antibodies capable of blocking the binding of IL-2 to the human IL-2 receptor are suitable.

For example, typical disease states suitable for treatment include graft versus host disease and transplant rejection in patients undergoing an organ transplant, such as heart, lungs, kidneys, liver, etc. Other diseases include autoimmune diseases, such as Type I diabetes, multiple sclerosis, rheumatoid arthritis, systemic lupus erythematosus, and myasthenia gravis.

The human-like antibodies of the present invention may also be used in combination with other antibodies, particularly human monoclonal antibodies reactive with other markers on cells responsible for the disease. For example, suitable T-cell markers can include those grouped into the so-called "Clusters of Differentiation," as named by the First international Leukocyte Differentiation Workshop, *Leukocyte Typing*, Bernard, et al., Eds., Springer-Verlag, N.Y. (1984), which is incorporated herein by reference.

The human-like antibodies and pharmaceutical compositions thereof of this invention are particularly useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, human albumin, etc. The concentration of antibody in these formulations can vary widely, i.e., from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for injection could be made up to contain 1 ml sterile buffered water, and 1 to 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, *Remington's Pharmaceutical Science*, 15th ed., Mack Publishing Company, Easton, Pa. (1980), which is incorporated herein by reference.

The antibodies of this invention can be frozen or lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human-like antibodies or a cocktail thereof can be administered for prophylactic and/or therapeutic treatments. In therapeutic application, compositions are administered to a patient already suffering from a disease, in an amount sufficient to cure or at least partially arrest the disease and its complications. An amount adequate to accomplish this is defined as a "therapeutically effective dose." Amounts effective for this use will depend upon the severity of the infection and the general state of the patient's own immune system, but generally range from about 1 to about 200 mg of antibody per dose, with dosages of from 5 to 25 mg being more commonly used. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the present human-like antibodies of this invention, it is possible and may be felt desirable by the treating physician to administer substantial excesses of these antibodies.

In prophylactic applications, compositions containing the present antibodies or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 25 mg per dose, especially 0.5 to 2.5 mg per dose. A preferred prophylactic use is for the prevention of kidney transplant rejection.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Human-like antibodies of the present invention can further find a wide variety of utilities in vitro. By way of example, the antibodies can be utilized for T-cell typing, for isolating specific IL-2 receptor bearing cells or fragments of the receptor, for vaccine preparation, or the like.

Kits can also be supplied for use with the subject antibodies in the protection against or detection of a cellular activity or for the presence of a selected antigen. Thus, the subject antibody composition of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimeric antibody is employed in an assay, this will usually be present in a separate vial. The second antibody is typically conjugated to a label and formulated in an analogous manner with the antibody formulations described above.

p75 Chain of IL-2 Receptor

The human IL-2 receptor is a complex multichain glycoprotein, with one chain, known as the Tac peptide or alpha chain, being about 55 kD in size (see, Leonard, W., et al., *J. Biol. Chem.* 260, 1872 (1985), which is incorporated herein by reference). The second chain is known as the p75 or beta chain (Tsudo et al., *Proc. Nat. Acad. Sci. USA*, 83, 9694 (1986) and Sharon et al., *Science* 234, 859 (1986), both of which are incorporated herein by reference)- The p55 or Tac chain and the p75 chain each independently bind IL-2 with low or intermediate affinity, while the IL-2 receptor complex of both chains binds IL-2 with high affinity. The p75 chain of the human IL-2 receptor will often be called herein simply the p75 protein.

The present invention provides novel compositions useful, for example, in the treatment of T-cell mediated human disorders, the compositions containing human-like immunoglobulins specifically capable of inhibiting the binding of human IL-2 to its receptor and/or capable of binding to the p75 protein of human IL-2 receptors. The immunoglobulins can have two pairs of light chain/heavy chain complexes, typically at least one chain comprising mouse complementarity determining regions functionally joined to human framework region segments. For example, mouse complementarity determining regions, with or without additional naturally-associated mouse amino acid residues, can be used to produce human-like antibodies capable of binding to the p75 protein at affinity levels stronger than about $10^7$ $M^{-1}$. These humanized immunoglobulins will also be capable of blocking the binding of the CDR-donating mouse monoclonal antibody to p75.

The human-like immunoglobulins may be utilized alone in substantially pure form, or complexed with a cytotoxic agent, such as a radionuclide, a ribosomal inhibiting protein or a cytotoxic agent active at cell surfaces. All of these compounds will be particularly useful in treating T-cell mediated disorders. The human-like immunoglobulins or their complexes can be prepared in a pharmaceutically accepted dosage form, which will vary depending on the mode of administration.

In accordance with the present invention, human-like immunoglobulins specifically reactive with the p75 chain of the human IL-2 receptor are provided. These immunoglobulins, which have binding affinities of at least $10^7$ to $10^8$ $M^{-1}$, and preferably $10^9$ $M^{-1}$ to $10^{10}$ $M^{-1}$ or stronger, are capable of, e.g., blocking the binding of IL-2 to human IL-2 receptors. The human-like immunoglobulins will have a human-like framework and can have complementarity determining regions (CDR's) from an immunoglobulin, typically a mouse immunoglobulin, specifically reactive with an epitope on p75 protein. The immunoglobulins of the present invention, which can be produced economically in large quantities, find use, for example, in the treatment of T-cell mediated disorders in human patients by a variety of techniques.

In one aspect, the present invention is directed to recombinant DNA segments encoding the heavy and/or light chain CDR's from an immunoglobulin capable of binding to a desired epitope on the human IL-2 receptor, such as the mik-β1 monoclonal antibody. The DNA segments encoding these regions will typically be joined to DNA segments encoding appropriate human-like framework regions. Exemplary DNA sequences, which on expression code for the polypeptide chains comprising the mik-β1 heavy and light chain CDRs, are included in FIG. 23A and FIG. 23B. Due to codon degeneracy and non-critical amino-acid substitutions, other DNA sequences can be readily substituted for those sequences, as detailed below.

The antibodies of the present invention will typically find use individually in treating a T-cell mediated disease state. Generally, where the cell linked to a disease has been identified as IL-2 receptor bearing, then the human-like antibodies capable of blocking the binding of IL-2 to the human IL-2 receptor are suitable.

For example, typical disease states suitable for treatment include graft-versus-host disease and transplant rejection in patients undergoing an organ transplant, such as heart, lungs, kidneys, liver, etc. Other diseases include autoimmune diseases, such as Type I diabetes, multiple sclerosis, rheumatoid arthritis, systemic lupus erythematosus, and myasthenia gravis.

The human-like antibodies of the present invention may also be used in combination with other antibodies, particularly human monoclonal antibodies reactive with other markers on cells responsible for the disease. For example, suitable T-cell markers can include those grouped into the so-called "Clusters of Differentiation," as named by the First International Leukocyte Differentiation Workshop, *Leukocyte Typing*, Bernard, et al., Eds., Springer-Verlag, N.Y. (1984), which is incorporated herein by reference. A preferred use is the simultaneous treatment of a patient with a human-like antibody binding to p55 and a human-like antibody binding to p75 of the IL-2 receptor, i.e., humanized anti-Tac plus humanized mik-β1.

Human-like antibodies of the present invention can further find a wide variety of utilities in vitro. By way of example, the antibodies can be utilized for T-cell typing, for isolating specific IL-2 receptor bearing cells or fragments of the receptor, for vaccine preparation, or the like.

Anti-HSV Antibodies

Herpes Simplex Virus types I and II (HSV-1 and HSV-2), are now estimated to be the second most frequent cause of sexually transmitted diseases in the world. Although completely accurate data are not available, infection estimates range from about 20 to 40% of the U.S. population.

A large number of diseases, from asymptomatic to life-threatening, are associated with HSV infection. Of particular clinical interest, encephalitis from HSV-1 infection and transmission of HSV-2 from a pregnant mother to her fetus are often fatal. Immunosuppressed patients are also subject to severe complications when infected with the virus.

More than 50 HSV polypeptides have been identified in HSV-infected cells, including at least seven major cell surface glycoproteins (see, Whitley, R., Chapt. 66, and Roizman and Sears, Chapt. 65, *Virology*, Eds. Fields et al., 2nd ed., Raven Press, N.Y., N.Y. (1990), which are incorporated herein by reference). The specific biologic functions of these glycoproteins are not well defined, although gB and gD have been shown to be associated with cell fusion activity (W. Cai et al., J. Virol. 62, 2596 (1988) and Fuller and Spear, Proc. Natl. Acad. Sci. USA 84, 5454 (1987)). gB and gD express both type-specific and type-common antigenic determinants. Oakes and Lausch demonstrated that monoclonal antibodies against gB and gE suppress replication of HSV-1 in trigeminal ganglia (Oakes and Lausch, J. Virol. 51, 656 (1984)). Dix et al. showed that anti-gC and gD antibodies protect mice against acute virus-induced neurological disease (Dix et al., Infect. Immun. 34, 192 (1981)). Whitley and colleagues produced a panel of murine monoclonal antibodies against HSV-1 and showed that several of the antibodies protected mice against encephalitis and death following ocular inoculation with the virus (see, Koga et al., Virology 151, 385 (1986); Metcalf et al., Cur. Eye Res. 6, 173 (1987) and Metcalf et al., Intervirology 29, 39 1988), all of which are incorporated herein by reference). Clone Fd79 (anti-gB) prevented encephalitis even when immunization was delayed until 48 hours post-infection. Fd79 and Fd138-80 (anti-gD) significantly reduced the severity of epithelial keratitis and lowered the frequency of persistent viral infection in an outbred mouse model.

Thus, there is a need for improved forms of humanized immunoglobulins specific for HSV antigens that are substantially non-immunogenic in humans, yet easily and economically produced in a manner suitable for therapeutic formulation and other uses. The present invention fulfills these and other needs.

The present invention provides novel compositions useful, for example, in the treatment of HSV mediated human disorders, the compositions containing humanized immunoglobulins specifically capable of blocking the binding of HSV to its receptors and/or capable of binding to the HSV specific proteins. The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to the HSV surface proteins at affinity levels stronger than about $10^7$ $M^{-1}$. These humanized immunoglobulins will also be capable of blocking the binding of the CDR donating mouse monoclonal antibody to HSV.

The humanized immunoglobulins may be utilized alone in substantially pure form, or together with an antiviral agent, such as acyclovir or a cytotoxic agent active at viral surfaces. All of these compounds will be particularly useful in treating HSV mediated disorders. The humanized immunoglobulins or their complexes can be prepared in a pharmaceutically accepted dosage form, which will vary depending on the mode of administration.

In accordance with the present invention, humanized immunoglobulins specifically reactive with HSV related epitopes either directly on the virus or on infected cells are provided. These immunoglobulins, which have binding affinities to HSV specific antigens of at least about $10^7$ $M^{-1}$, and preferably $10^8$ $M^{-1}$ to $10^{10}$ $M^{-1}$ or stronger, are capable of, e.g., protecting cells from HSV transmission. The humanized immunoglobulins will have a human framework and will have one or more complementarity determining regions (CDR's) from an immunoglobulin, typically a mouse immunoglobulin, specifically reactive with an HSV protein, such as gB and gD proteins. The immunoglobulins of the present invention, which can be produced economically in large quantities, find use, for example, in the treatment of HSV mediated disorders in human patients by a variety of techniques.

The HSVs are among the most intensively investigated of all viruses, and the HSV virion structure has been shown to contain about 33 proteins. Humanized immunoglobulins utilizing CDR's from monoclonal antibodies reactive with these proteins, particularly the eight surface glycoproteins (e.g., gB, gC, gD, gE, gG, gH and gI), represent preferred embodiments of the present invention (see, Spear, P. G., The Herpesviruses, vol. 3, pp. 315–356 (1984) (Roizman, B., ed), Plenum Press, N.Y., N.Y. and Spear, P. G., Immunochemistry of Viruses. The Basis for Serodiagnosis and Vaccines, pp. 425–446 (1985) (Neurath, A. R., eds.), Amsterdam: Elsevier, both of which are incorporated herein by reference).

In one aspect, the present invention is directed to recombinant DNA segments encoding the heavy and/or light chain CDR's from an immunoglobulin capable of binding to a desired epitope of an HSV protein, such as monoclonal antibodies reactive with HSV gB and gD glycoproteins. The DNA segments encoding these regions will typically be joined to DNA segments encoding appropriate humanized framework regions. Exemplary DNA sequences code for the polypeptide chains comprising the heavy and light chain hypervariable regions (with human framework regions) from monoclonal antibodies Fd79 and Fd138-80, shown in FIG. 30A through FIG. 30D. Due to codon degeneracy and non-critical amino-acid substitutions, other DNA sequences can be readily substituted for those sequences, as detailed below.

The antibodies of the present invention will typically find use individually in treating an HSV mediated disease state. For example, typical disease states suitable for treatment include any involving HSV infection. Specific diseases include neonatal herpes, herpes encephalitis, ocular herpes, genital herpes and disseminated herpes (see, Corey, L., Chapter 136, Harrison's Principles of Internal Medicine, 11th ed., McGraw-Hill Book Company, N.Y., N.Y. (1987), which is incorporated herein by reference).

Any humanized immunoglobulins of the present invention may also be used in combination with other antibodies, particularly humanized antibodies reactive with different HSV antigens. For example, suitable HSV antigens to which a cocktail of humanized immunoglobulins may react include gC, gE, gF, gG and gH (see, Rector, J. et al., Infect. Immun. 38, 168 (1982) and Fuller, A. et al., J. Virol. 63, 3435 (1989), both of which are incorporated herein by reference).

The antibodies can also be used as separately administered compositions given in conjunction with acyclovir or other antiviral agents. Typically, the agents may include idoxuridine or trifluorothymidine, but numerous additional agents (e.g., vidarabine) well-known to those skilled in the art for HSV treatment may also be utilized (see, Corey, L., op. cit.).

A preferred pharmaceutical composition of the present invention comprises the use of the subject immunoglobulins in immunotoxins to kill cells infected by HSV. Immunotoxins are characterized by two components and are particularly useful for killing selected cells in vitro or in vivo. One component is a cytotoxic agent which is usually fatal to a cell when attached or absorbed. The second component, known as the "delivery vehicle," provides a means for delivering the toxic agent to a particular cell type, such as cells expressing an HSV epitope.

The compositions containing the present humanized antibodies or a cocktail thereof can be administered for prophylactic and/or therapeutic treatments. In therapeutic application, compositions are administered to a patient already suffering from HSV infection, in an amount sufficient to cure or at least partially arrest the disease and its complications. An amount adequate to accomplish this is defined as a "therapeutically effective dose." Amounts effective for this use will depend upon the severity of the infection and the general state of the patient's own immune system, but generally range from about 1 to about 200 mg of antibody per dose, with dosages of from 5 to 25 mg being more commonly used. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the present humanized immunoglobulins of this invention, it is possible and may be felt desirable by the treating physician to administer substantial excesses of these antibodies.

In prophylactic applications, compositions containing the present immunoglobulins or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 25 mg per dose. A preferred prophylactic use is for the prevention of herpes in immunocompromised patients, such as organ transplant recipients.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Humanized antibodies of the present invention can further find a wide variety of utilities in vitro. By way of example, the antibodies can be utilized for detection of HSV antigens, for isolating specific HSV infected cells or fragments of the virus, for vaccine preparation, or the like.

Anti-CD33 Antibodies

There are about 10,000–15,000 new cases of myeloid (also called non-lymphocytic or granulocytic) leukemia in the U.S. per year (Cancer Facts & Figures, American Cancer Society, 1987). There are two major forms of myeloid leukemia: acute myelogenous leukemia (AML) and chronic myelogenous leukemia (CML). Despite treatment with chemotherapy, long-term survival in patients with AML is less than 10–20% (Clarkson et al., CRC Critical Review in Oncology/Hematology 4, 221 (1986)), and survival with CML and related diseases such as chronic myelomonocytic leukemia (CMML), chronic monocytic leukemia (CMMOL) and myelodysplastic syndrome (MDS) is even lower.

The p67 protein or CD33 antigen is found on the surface of progenitors of myeloid cells and of the leukemic cells of most cases of AML, but not on lymphoid cells or non-hematopoietic cells (see, Leucocyte Typing III, ed. by A. J. McMichael, Oxford University Press, pp. 622–629 (1987), which is incorporated herein by reference). Antibodies that are known to bind to the CD33 antigen include L4B3, L1B2 and MY9 (Andrews et al., Blood 62, 124 (1983) and Griffin et al., Leukemia Research 8, 521 (1984), both of which are incorporated herein by reference).

Another antibody that binds to CD33 is M195 (Tanimoto et al., Leukemia 3, 339 (1989) and Scheinberg et al., Leukemia 3, 440 (1989), both of which are incorporated herein by reference). The reactivity of M195 with a wide variety of cells and tissues was tested. Among normal cells, M195 was reported to bind only to some monocytes and myeloid progenitor cells. The research also reported that it does not bind to other hematopoietic cells or to non-hematopoietic tissues. M195 bound to cells of most cases of AML and all cases of CML in myeloblastic phase.

A phase I clinical trial of M195 in AML has been conducted (Scheinberg et al., Proc. ASCO 9, 207 (1990)). M195 radiolabeled with iodine-131 was found to rapidly and specifically target leukemic cells in both the blood and bone marrow.

Unfortunately, the use of non-human monoclonal antibodies such as M195 have certain drawbacks in human treatment, particularly in repeated therapeutic regimens as explained below. Mouse monoclonal antibodies, for example, do not fix human complement well, and lack other important immunoglobulin functional characteristics when used in humans.

Thus, there is a need for improved forms of humanized immunoglobulins specific for CD33 antigen that are substantially non-immunogenic in humans, yet easily and economically produced in a manner suitable for therapeutic formulation and other uses. The present invention fulfills these and other needs.

The present invention provides novel compositions useful, for example, in the treatment of myeloid leukemia-related human disorders, the compositions containing humanized immunoglobulins specifically capable of binding to CD33 antigen. The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to the CD33 antigen at affinity levels stronger than about $10^7$ $M^{-1}$. These humanized immunoglobulins will also be capable of blocking the binding of the CDR-donating mouse monoclonal antibody to CD33.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be utilized alone in substantially pure form, or together with a chemotherapeutic agent such as cytosine arabinoside or daunorubicin active against leukemia cells, or complexed with a radionuclide such as iodine-131. All of these compounds will be particularly useful in treating leukemia and myeloid cell-mediated disorders. The humanized immunoglobulins or their complexes can be prepared in a pharmaceutically accepted dosage form, which will vary depending on the mode of administration.

In accordance with the present invention, humanized immunoglobulins specifically reactive with CD33 related epitopes are provided. These immunoglobulins, which have binding affinities to CD33 of at least about $10^7$ $M^{-1}$, and preferably $10^8$ $M^{-1}$ to $10^{10}$ $M^{-1}$ or stronger, are capable of, e.g., destroying leukemia cells. The humanized immunoglobulins will have a human framework and will have one or more complementarity determining regions (CDR's) from an immunoglobulin, typically a mouse immunoglobulin, specifically reactive with CD33 antigen. In a preferred embodiment, one or more of the CDR's will come from the M195 antibody. Importantly, M195 does not bind to the ultimate hematopoietic stem cells, so M195 used in therapy will minimally interact with and destroy those cells, which are critical for generating all blood cells. Thus, the immunoglobulins of the present invention, which can be produced economically in large quantities, find use, for example, in the treatment of myeloid cell-mediated disorders in human patients by a variety of techniques.

In one aspect, the present invention is directed to recombinant DNA segments encoding the heavy and/or light chain CDR's from an immunoglobulin capable of binding to a desired epitope of CD33 antigen, such as monoclonal antibodies M195, L4B3, L1B2 or MY9. The DNA segments encoding these regions will typically be joined to DNA segments encoding appropriate human framework regions. Exemplary DNA sequences, which on expression code for the polypeptide chains comprising the heavy and light chain CDR's of monoclonal antibody M195 are included in FIG. 34A and FIG. 34B. Due to codon degeneracy and non-critical amino-acid substitutions, other DNA sequences can be readily substituted for those sequences, as detailed below.

The antibodies of the present invention will typically find use individually in treating hematologic malignancies. For example, typical disease states suitable for treatment include AML, CML, CMML, CMMOL and MDS (see, generally, Hoffbrand & Pettit, Essential Haematology, Blackwell Scientific Publications, Oxford (1980)). The antibodies may also be used for bone marrow ablation prior to bone marrow transplant.

Any humanized immunoglobulins of the present invention may also be used in combination with other antibodies, particularly humanized antibodies reactive with different myeloid antigens. For example, suitable antigens to which a cocktail of humanized immunoglobulins may react include CD13, CD14, CD15, CD16 and CD34 (see, Leukocyte Typing III, op. cit., pp. 576–732).

The antibodies can also be used as separately administered compositions given in conjunction with chemotherapeutic agents. Typically, the agents may include cytosine arabinoside and daunorubicin, but numerous additional agents (e.g., 6-thioguanine) well-known to those skilled in the art for leukemia treatment may also be utilized (see, Hoffbrund & Pettit., op. cit.).

A preferred pharmaceutical composition of the present invention comprises the use of the subject immunoglobulins in immunotoxins to kill leukemia cells. Immunotoxins are characterized by two components and are particularly useful for killing selected cells in vitro or in vivo. One component is a cytotoxic agent which is usually fatal to a cell when attached or absorbed. The second component, known as the "delivery-vehicle," provides a means for delivering the toxic agent to a particular cell type, such as cells expressing a CD33 epitope.

Humanized antibodies of the present invention can further find a wide variety of utilities in vitro. By way of example, the antibodies can be utilized for detection of CD33 antigens, for isolating specific myeloid cells, or the like.

It will be understood that although examples pertain to the M195 antibody, producing humanized antibodies with high binding affinity for the CD33 antigen is also contemplated using CDR's from L4B3, L1B2, MY9 or other monoclonal antibodies that bind to an epitope of CD33.

Anti-CMV Antibodies

Cytomegalovirus is a major pathogen of immunocompromised individuals, especially bone marrow transplant recipients, organ tansplant recipients, and AIDS patients (see, generally, Fields et al., Eds., Virology, 2nd ed., Raven Press, New York pp. 1981–2010 (1990), which is incorporated herein by reference). Approximately 15% of bone marrow transplant patients develop CMV pneumonia, with an 85% mortality rate (Meyers, Rev. Inf. Dis. 11 (suppl. 7), S1691 (1989)). About 10% of AIDS patients develop severe CMV disease; and congenitally acquired CMV, often with significant morbidity and mortality, affects 1% of newborns (Fields, op. cit.).

The drug ganciclovir is effective against certain forms of CMV infection, notably chorioretinitis and gastroenteritis, but is not very effective against CMV pneumonia, and it has serious toxicity. Use of pooled human imunoglobulin preparations has shown some beneficial effect for prophylaxis of CMV in bone marrow transplant patients (Meyers, op. cit.), and a combination of high-dose immune globulin and ganciclovir has been reported effective against CMV pneumonia (Emanuel et al., Trans. Proc. XIX (suppl. 7), 132 (1987)). However, the marginal effectiveness, variable potency and high cost of commercial human immune globulin remain serious problems. Hence, there is a great need for new drugs effective against CMV.

CMV is a member of the herpesvirus family of viruses, and as such, has a large double-stranded DNA core, a protein capsid, and an outer lipid envelope with viral glycoproteins on its surface. At least 8 proteins have been detected on the envelope of CMV (Britt et al., J. Virol. 62, 3309 (1988)) and others have been predicted to exist based on the DNA sequence of CMV (Chee et al., Nature 344, 774 (1990)). Murine monoclonal antibodies have been produced against two especially significant CMV glycoproteins: gB, also called p130/55 or gp55–116, and gH, also called p86 (Rasmussen et al., Virology 163, 308 (1988) and Britt et al., op. cit., both of which are incorporated herein by reference) and shown to neutralize infectivity of the virus. Three other neutralizing antibodies to gH are designated CMV5, CMV109 and CMV115. Human monoclonal antibodies to CMV have also been produced (Ehrlich et al., Hybridoma 6, 151 (1987)).

In animal models, murine monclonal antibodies have been shown effective in treating infections caused by various viruses, including members of the herpesvirus family (see, e.g., Metcalf et al., Intervirol. 29, 39 (1988)). Hence, such antibodies may be useful in treatment of CMV infections.

Unfortunately, the use of non-human monoclonal antibodies such as CMV5 and CMV115 have certain drawbacks in human treatment, particularly in repeated therapeutic regimens as explained below. Mouse monoclonal antibodies, for example, do not fix human complement well, and lack other important immunoglobulin functional characteristics when used in humans.

While the production of so-called "chimeric antibodies" (e.g., mouse variable regions joined to human constant regions) has proven somewhat successful, a significant immunogenicity problem remains. In general, the production of human immunoglobulins reactive with CMV antigens, as with many antigens, is difficult using typical human monoclonal antibody production techniques. Moreover, the human antibodies produced may lack certain desirable properties, such as high binding affinity and the ability to neutralize all clinical CMV strains. Similarly, utilizing recombinant DNA technology to produce so-called "humanized" or "reshaped" antibodies (see, e.g., Riechmann et al., Nature 332, 323 (1988) and EPO Publication No. 0239400, which are incorporated herein by reference), provides uncertain results, in part due to unpredictable binding affinities.

Thus, there is a need for improved forms of humanized immunoglobulins specific for CMV antigen that are substantially non-immunogenic in humans, yet easily and economically produced in a manner suitable for therapeutic formulation and other uses. The present invention fulfills these and other needs.

The present invention provides novel compositions useful, for example, in the treatment of CMV-mediated human disorders, the compositions containing humanized immunoglobulins specifically capable of blocking the binding of CMV to its receptors and/or capable of binding to CMV antigens. The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to CMV at affinity levels stronger than about $10^7$ $M^{-1}$. These humanized immunoglobulins will also be capable of blocking the binding of the CDR-donating mouse monoclonal antibody to CMV.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be utilized alone in substantially pure form, or together with a chemotherapeutic agent such a acyclovir or ganciclovir active against CMV-infected cells, or complexed with a cytotoxic agent. All of these compounds will be particularly useful in treating CMV-mediated disorders. The humanized immunoglobulins or their complexes can be prepared in a pharmaceutically accepted dosage form, which will vary depending on the mode of administration.

In accordance with the present invention, humanized immunoglobulins specifically reactive with CMV and CMV-infected cells are provided. These immunoglobulins, which have binding affinities to CMV specific antigens of at least about $10^7$ $M^{-1}$, and preferably $10^8$ $M^{-1}$ to $10^{10}$ $M^{-1}$ or stronger, are capable of, e.g., blocking CMV infection of cells. The humanized immunoglobulins will have a human framework and will have one or more complementarity determining regions (CDR's) from an immunoglobulin, typically a mouse immunoglobulin, specifically reactive with a CMV antigen. In a preferred embodiment, one or more of the CDR's will come from the CMV5, or CMV109 or CMV115 antibodies. The immunoglobulins of the present invention, which can be produced economically in large quantities, find use, for example, in the treatment of CMV-mediated disorders in human patients by a variety of techniques.

In one aspect, the present invention is directed to recombinant DNA segments encoding the heavy and/or light chain CDR's from an immunoglobulin capable of binding to a desired epitope of a CMV antigen, such as monoclonal antibodies CMV5 or CMV115. The DNA segments encoding these regions will typically be joined to DNA segments encoding appropriate human framework regions. Exemplary DNA sequences, which on expression code for the polypeptide chains comprising the heavy and light chain CDR's of monoclonal antibody CMV5 are included in FIG. 39A and FIG. 39B. Due to codon degeneracy and non-critical aminoacid substitutions, other DNA sequences can be readily substituted for those sequences, as detailed below.

Human constant region DNA sequences can be isolated in accordance with well known procedures from a variety of human cells, but preferably immortalized B-cells (see, Kabat op. cit. and WP87/02671). The CDR's for producing the immunoglobulins of the present invention will be similarly derived from monoclonal antibodies capable of binding to CMV and produced in any convenient mammalian source, including, mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection (*Catalogue of Cell Lines and Hybridomas*, Fifth edition (1985) Rockville, Md., U.S.A., which is incorporated herein by reference).

The antibodies of the present invention will typically find use individually in treating CMV-related disorders. For example, typical disease states suitable for treatment include CMV pneumonia, neonatal CMV infection, CMV mononucleosis and CMV-related chorioretinitis and gastroenteritis.

Any humanized immunoglobulins of the present invention may also be used in combination with other antibodies, particularly humanized antibodies reactive with different CMV antigens. For example, suitable antigens to which a cocktail of humanized immunoglobulins may react include the gB and gH proteins.

The antibodies can also be used as separately administered compositions given in conjunction with chemotherapeutic agents. Typically, the agents may include acyclovir or ganciclovir, but numerous additional agents well-known to those skilled in the art for CMV treatment may also be utilized.

A preferred pharmaceutical composition of the present invention comprises the use of the subject immunoglobulins in immunotoxins to kill CMV-infected cells. Immunotoxins are characterized by two components and are particularly useful for killing selected cells in vitro or in vivo. One component is a cytotoxic agent which is usually fatal to a cell when attached or absorbed. The second component, known as the "delivery vehicle," provides a means for delivering the toxic agent to a particular cell type, such as cells expressing a CMV epitope. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), which is incorporated herein by reference. The components may also be linked genetically (see Chaudhary et al., Nature 339, 394 (1989)).

In prophylactic applications, compositions containing the present immunoglobulins or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 1 to 50 mg per dose. A preferred prophylactic use is for the prevention of CMV infection in immunocompromised patients, such as organ or bone marrow transplant recipients.

Humanized antibodies of the present invention can further find a wide variety of utilities in vitro. By way of example, the antibodies can be utilized for detection of CMV antigens, for isolating specific CMV-infected cells, or the like.

In particular, the same method may be used to produce a humanized CMV109, CMV115 or other anti-CMV antibody as used to produce humanized CMV5 herein.

Anti-γ-IFN Antibodies

In mammals, the immune response is mediated by several types of cells that interact specifically with foreign material, i.e., antigens. One of these cell types, B cells, is responsible for the production of antibodies. Another cell type, T cells, include a wide variety of cellular subsets that destroy virally infected cells or control the in vivo function of both B cells and other hematopoietic cells, including T cells. A third cell type, macrophages, process and present antigens in conjunction with major histocompatibility complex (MHC) proteins to T cells. Communication between these cell types is mediated in a complex manner by lymphokines, such as interleukins 1–6 and γ-IFN (see, generally, Paul, W. E., ed., Fundamental Immunology, 2nd ed., Raven Press, New York (1989), which is incorporated herein by reference.)

One important lymphokine is γ-IFN, which is secreted by some T cells. In addition to its anti-viral activity, γ-IFN stimulates natual killer (NK) cells, activates macrophages, and stimulates the expression of MHC molecules on the surface of cells (Paul, op. cit., pp. 622–624). Hence γ-IFN generally serves to enhance many aspects of immune function, and is a logical candidate for a therapeutic drug in cases where such enhancement is desired, e.g., in treating cancer. Conversely, in disease states where the immune system is over-active, e.g., autoimmune diseases and organ transplant rejection, antagonists of γ-IFN may be used to treat the disease by neutralizing the stimulatory effects of γ-IFN.

One class of effective antagonists of γ-IFN are monoclonal antibodies that bind to and neutralize it (see, e.g., Van der Meide et al., J. Gen. Virol. 67, 1059 (1986)). In in vitro and in vivo mouse models of transplants, anti-γ-IFN antibodies have been shown to delay or prevent rejection (Landolfo et al., Science 229, 176 (1985) and Rosenberg et al., J. Immunol. 144, 4648 (1990), both of which are incorporated herein by reference). Treatment of mice prone to develop a syndrome like systemic lupus erythematosus (SLE) with a monoclonal antibody to γ-IFN significantly delayed onset of the disease (Jacob et al., J. Exp. Med. 166, 798 (1987)). Under some conditions, an anti-γ-IFN antibody alleviated adjuvant arthritis in rats (Jacob et al., J. Immunol. 142, 1500 (1989)), suggesting that anti-γ-IFN may be effective against some cases of rheumatoid arthritis in human patients. Multiple sclerosis (MS) in patients is made worse by treatment with γ-IFN (Panitch et al., Neurology 36 (suppl. 1), 285 (1986)), so an anti-γ-IFN antibody may alleviate MS. Thus, an anti-γ-IFN antibody may be effective in treating these and other autoimmune diseases.

For treatment of human patients, a murine monoclonal that binds to and neutralizes human γ-IFN (see, e.g., Yamamoto et al., Microbiol. Immunol. 32, 339 (1988)) may be used. Another murine monoclonal antibody designated AF2 that neutralizes human γ-IFN, and inhibits binding of γ-IFN to its cellular receptor, is disclosed herein. Unfortunately, the use of non-human monoclonal antibodies such as AF2 have certain drawbacks in human treatment, particularly in repeated therapeutic regimens as explained below. Mouse monoclonal antibodies, for example, have a relatively short circulating half-life in humans, and lack other important immunoglobulin functional characteristics when used in humans.

The present invention provides novel compositions useful, for example, in the treatment of human autoimmune disorders, the compositions containing humanized immunoglobulins specifically capable of binding to γ-IFN. The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to γ-IFN at affinity levels stronger than about $10^7$ $M^{-1}$. These humanized immunoglobulins will also be capable of blocking the binding of the CDR-donating mouse monoclonal antibody to γ-IFN.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be utilized alone in substantially pure form, or together with a chemotherapeutic agent such as a non-steroidal anti-inflammatory drug, a corticosteroid, or an immunosuppressant. All of these compounds will be particularly useful in treating autoimmune disorders. The humanized immunoglobulins or their complexes can be prepared in a pharmaceutically accepted dosage form, which will vary depending on the mode of administration.

In accordance with the present invention, humanized immunoglobulins specifically reactive with γ-IFN epitopes are provided. These immunoglobulins, which have binding affinities to γ-IFN of at least about $10^7$ $M^{-1}$, and preferably $10^8$ $M^{-1}$ to $10^{10}$ $M^{-1}$ or stronger, are capable of, e.g., neutralizing human γ-IFN. The humanized immunoglobulins will have a human framework and will have one or more complementarity determining regions (CDR's) from an immunoglobulin, typically a mouse immunoglobulin, specifically reactive with γ-IFN. In a preferred embodiment, one or more of the CDR's will come from the AF2 antibody. Thus, the immunoglobulins of the present invention, which can be produced economically in large quantities, find use, for example, in the treatment of autoimmune disorders in human patients by a variety of techniques.

The antibodies of the present invention will typically find use individually in treating autoimmune conditions. For example, typical disease states suitable for treatment include graft versus host disease and transplant rejection in patients undergoing an organ transplant, such as heart, lungs, kidneys, liver, etc. Other diseases include autoimmune diseases, such as Type I diabetes, multiple sclerosis, rheumatoid arthritis, systemic lupus erythematosus, and myasthenia gravis.

Any humanized immunoglobulins of the present invention may also be used in combination with other antibodies, particularly humanized antibodies reactive with other lymphokines or lymphokine receptors. For example, suitable antigens to which a cocktail of humanized immunoglobulins may react include interleukins 1 through 10 and the p55 and p75 chains of the IL-2 receptor (see, Waldmann, Annu. Rev. Biochem. 58, 875 (1989) and Queen et al., Proc. Natl. Acad. Sci. USA 86, 10029 (1989), both of which are incorporated herein by reference). Other antigens include those on cells responsible for the disease, e.g., the so-called "Clusters of Differentiation" (Leucocyte Typing III, ed. by A. J. McMichael, Oxford University Press (1987), which is incorporated herein by reference).

The antibodies can also be used as separately administered compositions given in conjunction with chemotherapeutic agents. Typically, the agents may include nonsteroidal anti-inflammatory agents (e.g., aspirin, ibuprofen), steroids (e.g., prednisone) and immunosuppressants (e.g., cyclosporin A, cytoxan), but numerous additional agents well-known to those skilled in the art may also be utilized.

A preferred pharmaceutical composition of the present invention comprises the use of the subject immunoglobulins in immunotoxins, e.g., to kill γ-IFN-secreting cells. Immunotoxins are characterized by two components and are particularly useful for killing selected cells in vitro or in vivo. One component is a cytotoxic agent which is usually fatal to a cell when attached or absorbed. The second component, known as the "delivery vehicle," provides a means for delivering the toxic agent to a particular cell type, such as cells expressing a γ-IFN epitope.

Humanized antibodies of the present invention can further find a wide variety of utilities in vitro. By way of example, the antibodies can be utilized for detection of γ-IFN antigens, or the like.

The following examples are offered by way of illustration, not by limitation.

EXPERIMENTAL

Example 1

Humanized anti-Tac Antibody

Design of Genes for Humanized anti-Tac Light and Heavy Chains

The sequence of the human antibody Eu (Sequences of Proteins of Immunological Interest, E. Kabat et al., U.S. Dept. of Health and Human Services, 1983) was used to provide the framework of the humanized antibody, because the amino acid sequence of the heavy chain variable region of anti-Tac is more homologous to the heavy chain of this antibody than to any other complete heavy chain variable region sequence in the National Biomedical Foundation Protein Identification Resource.

To select the sequence of the humanized heavy chain, the anti-Tac heavy chain sequence (FIG. 1B, upper lines; see, commonly assigned U.S. Ser. Nos. 07/223,037 filed Sep. 28, 1988, and 07/181,862 filed Apr. 15, 1988, both of which are now abandoned and which are incorporated herein by reference) was aligned with the sequence of the Eu heavy chain (FIG. 1B, lower lines). At each position, the Eu amino acid was selected for the humanized sequence, unless that position fell in any one of four categories defined above, in which case the anti-Tac amino acid was selected:

(1) The position fell within a complementarity determining region (CDR), as defined by Kabat, et al., op. cit. (amino acids 31–35, 50–66, 99–106);

(2) The Eu amino acid was rare for human heavy chains at that position, whereas the anti-Tac amino acid was common for human heavy chains at that position (amino acids 27, 93, 95, 98, 107–109, 111);

(3) The position was immediately adjacent to a CDR in the amino acid sequence of the anti-Tac heavy chain (amino acids 30 and 67); or (4) 3-dimensional modeling of the anti-Tac antibody suggested that the amino acid was physically close to the antigen binding region (amino acids 48 and 68).

Amino acid #27 is listed in category (2) because the acceptor Eu amino acid Gly is rare, and the donor anti-Tac amino acid Tyr is chemically similar to the amino acid Phe, which is common, but the substitution was actually made because #27 also fell in category (4). Although some amino acids fell in more than one of these categories, they are only listed in one. The amino acids in the humanized heavy and light chains are numbered according to the lower lines of FIG. 1A and FIG. 1B.

To select the sequence of the humanized light chain, the anti-Tac light chain sequence was aligned with the sequence of the Eu light chain (FIG. 1A, lower lines). The Eu amino acid was selected at each position for the humanized sequence, unless the position again fell into one of the categories (1)–(4):

(1) CDR's (amino acids 24–34, 50–56, 89–97);

(2) Anti-Tac amino acid more typical than Eu (amino acids 48 and 63);

(3) Adjacent to CDR's (no amino acids; Eu and anti-Tac were already the same at all these positions); or (4) Possible 3-dimensional proximity to binding region (amino acid 60).

The actual nucleotide sequence of the heavy and light chain genes were selected as follows:

(1) The nucleotide sequences code for the amino acid sequences chosen as described above;

(2) 5' of these coding sequences, the nucleotide sequences code for a leader (signal) sequence, namely the leader of the light chain of the antibody MOPC 63 and the leader of the heavy chain of the antibody PCH 108A (Kabat et al., op. cit.). These leader sequences were chosen as typical of antibodies;

(3) 3' of the coding sequences, the nucleotide sequences are the sequences that follow the mouse light chain J5 segment and the mouse heavy chain J2 segment, which are part of the anti-Tac sequences. These sequences are included because they contain splice donor signals; and (4) At each end of the sequence is an Xba I site to allow cutting at the Xba I sites and cloning into the Xba I site of a vector.

Construction of Humanized Light and Heavy Chain Genes

To synthesize the heavy chain, four oligonucleotides were synthesized using an Applied Biosystems 380B DNA synthesizer. Two of the oligonucleotides are part of each strand of the heavy chain, and each oligonucleotide overlaps the next one by about 20 nucleotides to allow annealing.

Together, the oligonucleotides cover the entire humanized heavy chain variable region with a few extra nucleotides at each end to allow cutting at the Xba I sites. The oligonucleotides were purified from polyacrylamide gels.

Each oligonucleotide was phosphorylated using ATP and T4 polynucleotide kinase by standard procedures (see, Maniatis, op. cit.). To anneal the phosphorylated oligonucleotides, they were suspended together in 40 ul of TA (33 mM Tris acetate, pH 7.9, 66 mM potassium acetate, 10 mM magnesium acetate) at a concentration of about 3.75 uM each, heated to 95° C. for 4 min. and cooled slowly to 4° C. To synthesize the complete gene from the oligonucleotides by synthesizing the opposite strand of each oligonucleotide, the following components were added in a final volume of 100 ul:

| 10 ul | annealed oligonucleotides |
| 0.16 mM each | deoxyribonucleotide |
| 0.5 mM | ATP |
| 0.5 mM | DTT |
| 100 ug/ml | BSA |
| 3.5 ug/ml | T4 g43 protein (DNA polymerase) |
| 25 ug/ml | T4 g44/62 protein (polymerase accessory protein) |
| 25 ug/ml | 45 protein (polymerase accessory protein) |

The mixture was incubated at 37° C. for 30 min. Then 10 u of T4 DNA ligase was added and incubation at 37° C. resumed for 30 min. The polymerase and ligase were inactivated by incubation of the reaction at 70° C. for 15 min. To digest the gene with Xba I, to the reaction was added 50 ul of 2× TA containing BSA at 200 ug/ml and DTT at 1 mM, 43 ul of water, and 50 u of Xba I in 5 ul. The reaction was incubated for 3 hr at 37° C., and run on a gel. The 431 bp Xba I fragment was purified from a gel and cloned into the Xba I site of the plasmid pUC19 by standard methods.

Four plasmid isolates were purified and sequenced using the dideoxy method. One of these had the correct sequence.

To synthesize the light chain, four oligonucleotides JFD1, JFD2, JFD3, JFD4 were synthesized. Two of the oligonucleotides are part of each strand of the light chain, and each oligonucleotide overlaps the next one by about 20 nucleotides to allow annealing. Together, the oligonucleotides cover the entire humanized light chain variable region with a few extra nucleotides at each end to allow cutting at the Xba I sites. The oligonucleotides were purified from polyacrylamide gels.

The light chain gene was synthesized from these oligonucleotides in two parts. 0.5 ug each of JFD1 and JFD2 were combined in 20 ul sequence buffer (40 mM Tris-HCl, pH 7.5, 20 mM magnesium chloride, 50 mM sodium chloride), heated at 70° C. for 3 min and allowed to cool slowly to 23° C. in order for the oligonucleotides to anneal. JFD3 and JFD4 were treated in the same way. Each reaction was made 10 mM in DTT and 0.5 mM in each deoxyribonucleotide and 6.5 u of sequenase (US Biochemicals) was added, in a final volume of 24 ul, and incubated for 1 hr at 37° C. to synthesize the opposite strands of the oligonucleotides. Xba I and Hind III were added to each reaction to digest the DNA (there is a Hind III site in the region where JFD2 and JFD3 overlap and therefore in each of the synthesized DNAs). The reactions were run on polyacrylamide gels, and the Xba I - Hind III fragments were purified and cloned into pUC18 by standard methods. Several plasmid isolates for each fragment were sequenced by the dideoxy method, and correct ones chosen.

Construction of Plasmids to Express Humanized Light and Heavy Chains

The heavy chain Xba I fragment was isolated from the pUG19 plasmid in which it had been inserted and then inserted into the Xba I site of the vector pVγ1 (see, commonly assigned U.S. Ser. No. 07/223,037 filed Sep. 28, 1988, now abandoned, which is incorporated herein by reference) in the correct orientation by standard methods, to produce the plasmid pHuGTAC1. This plasmid will express high levels of a complete heavy chain when transfected into an appropriate host cell.

The two light chain Xba I - Hind III fragments were isolated from the pUG18 plasmids in which they had been inserted. The vector plasmid pVκ1 (see, commonly assigned U.S. Ser. No. 07/223,037 filed Sep. 28, 1988, now abandoned, which is incorporated herein by reference) was cut with Xba I, dephosphorylated and ligated with the two fragments by standard methods. The desired reaction product has the circular form: vector - Xba I - fragment 1 - Hind III - fragment 2 - Xba I - vector. Several plasmid isolates were analyzed by restriction mapping and sequencing, and one with this form chosen. This plasmid, pHuLTAC, therefore contains the complete humanized light chain and will express high levels of the light chain when transfected into an appropriate host cell.

Synthesis and Affinity of Humanized Antibody

Figure 7A:
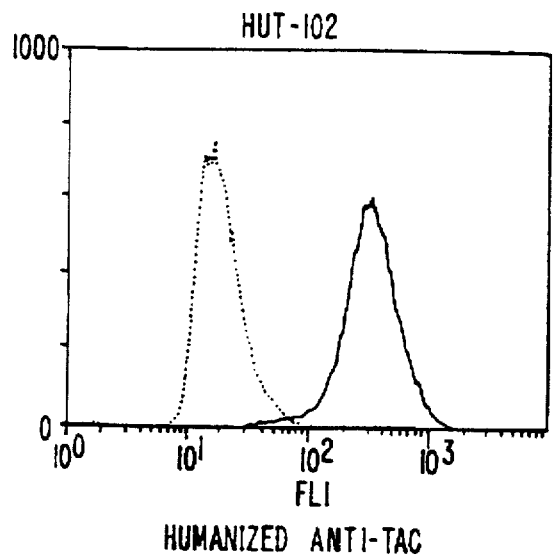
FIG. 7A through FIG. 7D. Fluorocytometry of HUT-102 and Jurkat cells stained with anti-Tac antibody or humanized anti-Tac antibody followed respectively by fluorescein-conjugated goat anti-mouse Ig antibody or goat anti-human Ig antibody, as labeled. In each panel, the dotted curve shows the results when the first antibody was omitted, and the solid curve the results when the first and second (conjugated) antibodies were included as described.
Figure 7B:
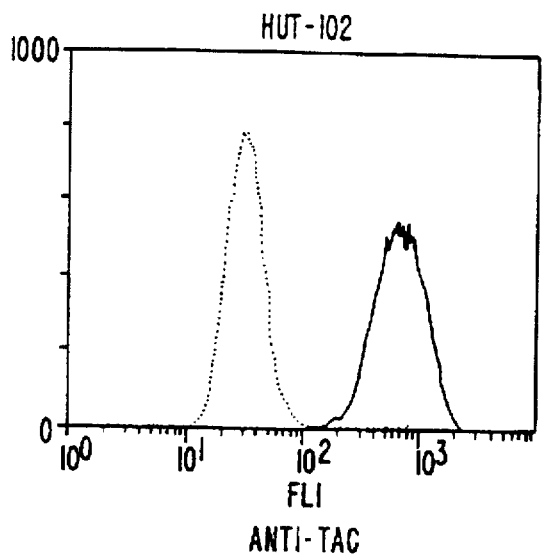
Figure 7C:
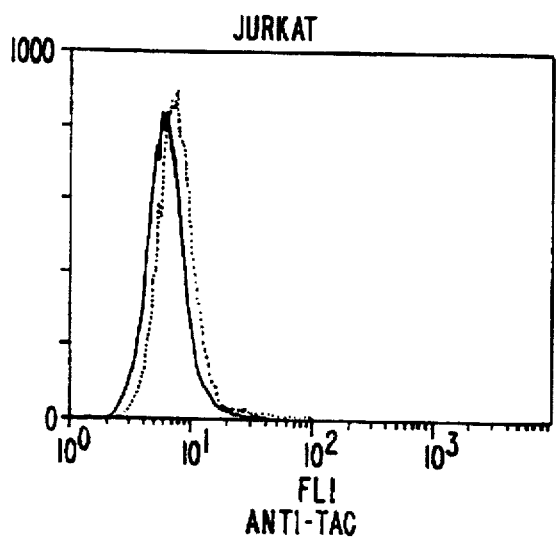
Figure 7D:
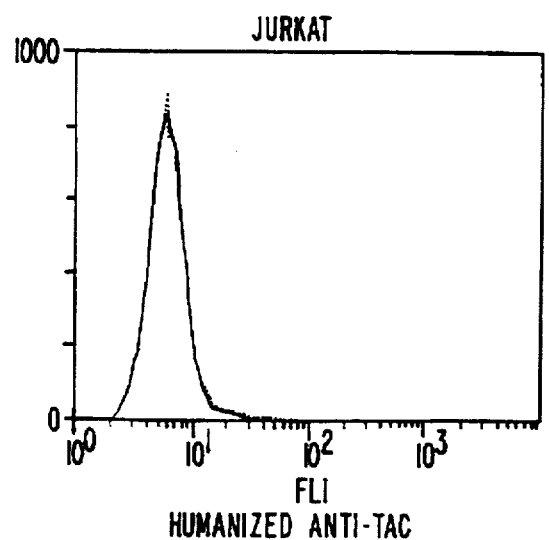

The plasmids pHuGTAC1 and pHuLTAC were transfected into mouse Sp2/0 cells, and cells that integrated the plasmids were selected on the basis of resistance to mycophenolic acid and/or hygromycin B conferred by the gpt and hyg genes on the plasmids by standard methods. To verify that these cells secreted antibody that binds to the IL-2 receptor, supernatant from the cells was incubated with HUT-102 cells that are known to express the IL-2 receptor. After washing, the cells were incubated with fluorescein-conjugated goat anti-human antibody, washed, and analyzed for fluorescence on a FACSCAN cytofluorometer. The results (FIG. 7A), clearly show that the humanized antibody binds to these cells, but not to Jurkat T-cells that do not express the IL-2 receptor (FIG. 7D). As controls, the original mouse anti-Tac antibody was also used to stain these cells, giving similar results.

For the next experiments, cells producing the humanized antibody were injected into mice, and the resultant ascites collected. Humanized antibody was purified to substantial homogeneity from the ascites by passage through an affinity column of goat anti-human immunoglobulin antibody, prepared on an Affigel-10 support (Bio-Rad Laboratories, Inc., Richmond, Calif.) according to standard techniques. To determine the affinity of the humanized antibody relative to the original anti-Tac antibody, a competitive binding experiment was performed. About $5 \times 10^5$ HUT-102 cells were incubated with known quantities (10–40 ng) of the anti-Tac antibody and the humanized anti-Tac antibody for 10 min at 4° C. Then 100 ng of biotinylated anti-Tac was added to the cells and incubated for 30 min at 4° C. This quantity of anti-Tac had previously been determined to be sufficient to saturate the binding sites on the cells, but not to be in large excess.

Then the cells were washed twice with 2 ml of phosphate buffered saline (PBS) containing 0.1% sodium azide. The cells were then incubated for 30 min at 4° C. with 250 ng of phycoerythrin-conjugated avidin, which bound to the biotinylated anti-Tac already bound to the cells. The cells were washed again as above, fixed in PBS containing 1% paraformaldehyde, and analyzed for fluorescence on a FACSCAN cytofluorometer.

Figure 8A:
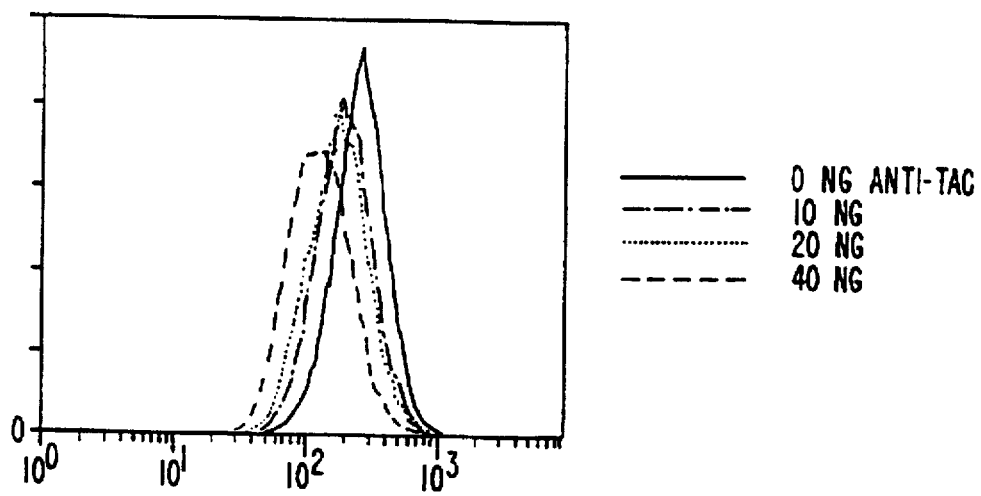
FIG. 8A and FIG. 8B. (A) Fluorocytometry of HUT-102 cells stained with 0–40 ng of anti-Tac as indicated, then with biotinylated anti-Tac, and then with phycoerythrin-conjugated avidin. (B) Fluorocytometry of HUT-102 cells stained with the indicated antibody, then with biotinylated anti-Tac, and then with phycoerythrin-conjugated avidin.
Figure 8B:
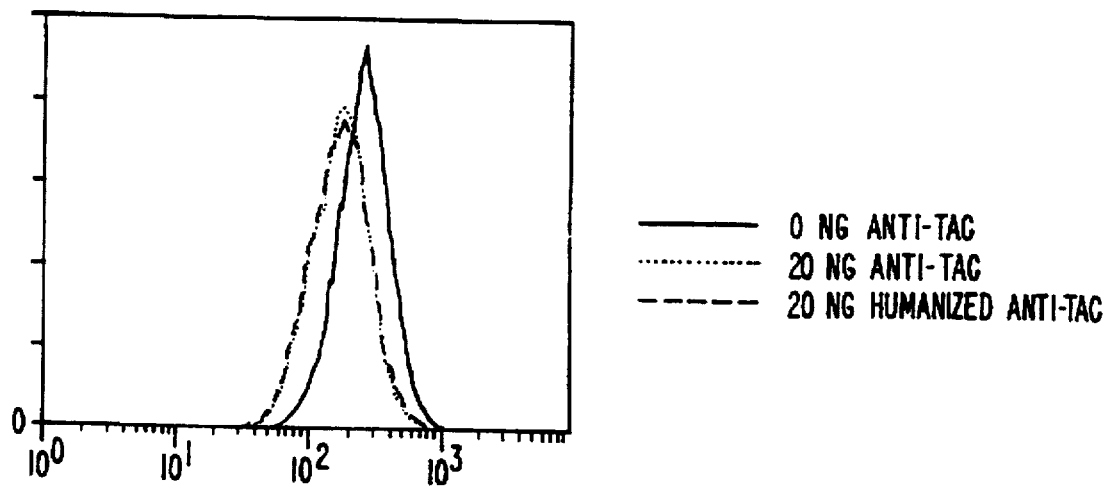

Use of increasing amounts (10–40 ng) of the anti-Tac antibody as competitor in the first step decreased the amount of biotinylated anti-Tac that could bind to the cells in the second step, and therefore the amount of phycoerythrin-conjugated avidin that bound in the last step, thus decreasing fluorescence (FIG. 8A). Equivalent amounts (20 ng) of anti-Tac, and humanized anti-Tac used as competitor decreased the fluorescence to approximately the same degree (FIG. 8B). This shows that these antibodies have approximately the same affinity, because if one had greater affinity, it would have more effectively competed with the biotinylated anti-Tac, thus decreasing fluorescence more.

Example 2

A Second Humanized anti-Tac Antibody

Higher Level Expression of the Humanized anti-Tac Antibody

Three new plasmid vectors were prepared for expression of the humanized antibodies. The plasmid pVg1 (FIG. 9A) contains a human cytomegalovirus IE1 promoter and enhancer (Boshart et al., *Cell* 41, 521 (1985), which is incorporated herein by reference), the human genomic Cγ1 segment including part of the preceding intron, and the hygomycin gene (Blochlinger et al., *Mol. Cell. Biol.* 4, 2929 (1984), which is incorporated herein by reference) for selection. The plasmid pVk (FIG. 9B) is similar to pVg1 but contains the human genomic Cκ segment and the gpt gene. The plasmid pVg1-dhfr was constructed similarly to pVg1 but contains a dihydrofolate reductase (dhfr) gene (Simonsen et al., *Proc. Natl. Acad. Sci. USA* 80, 2495 (1984), which is incorporated herein by reference) in place of the hygomycin gene.

Xba I fragments containing the humanized anti-Tac light chain and heavy chain variable regions were excised respectively from the plasmids pHuLTAC and the pHuGTAC1 and cloned into the Xba I sites of the plasmid vectors pVk and pVg1. To express the humanized anti-Tac antibody, the light chain encoding plasmid was introduced by electroporation into SP2/0 mouse myeloma cells followed by selection for gpt expression. Transfected cells expressing light chain were then transfected with the plasmid encoding the heavy chain followed by selection for hygromycin B resistance. Transfected cells producing the highest levels of humanized antibody as determined by ELISA were used for preparation of antibody. Humanized antibody was purified from culture supernatant of transfected cells by protein A sepharose chromatography.

Construction of the Second Humanized anti-Tac Antibody

Figure 10A:
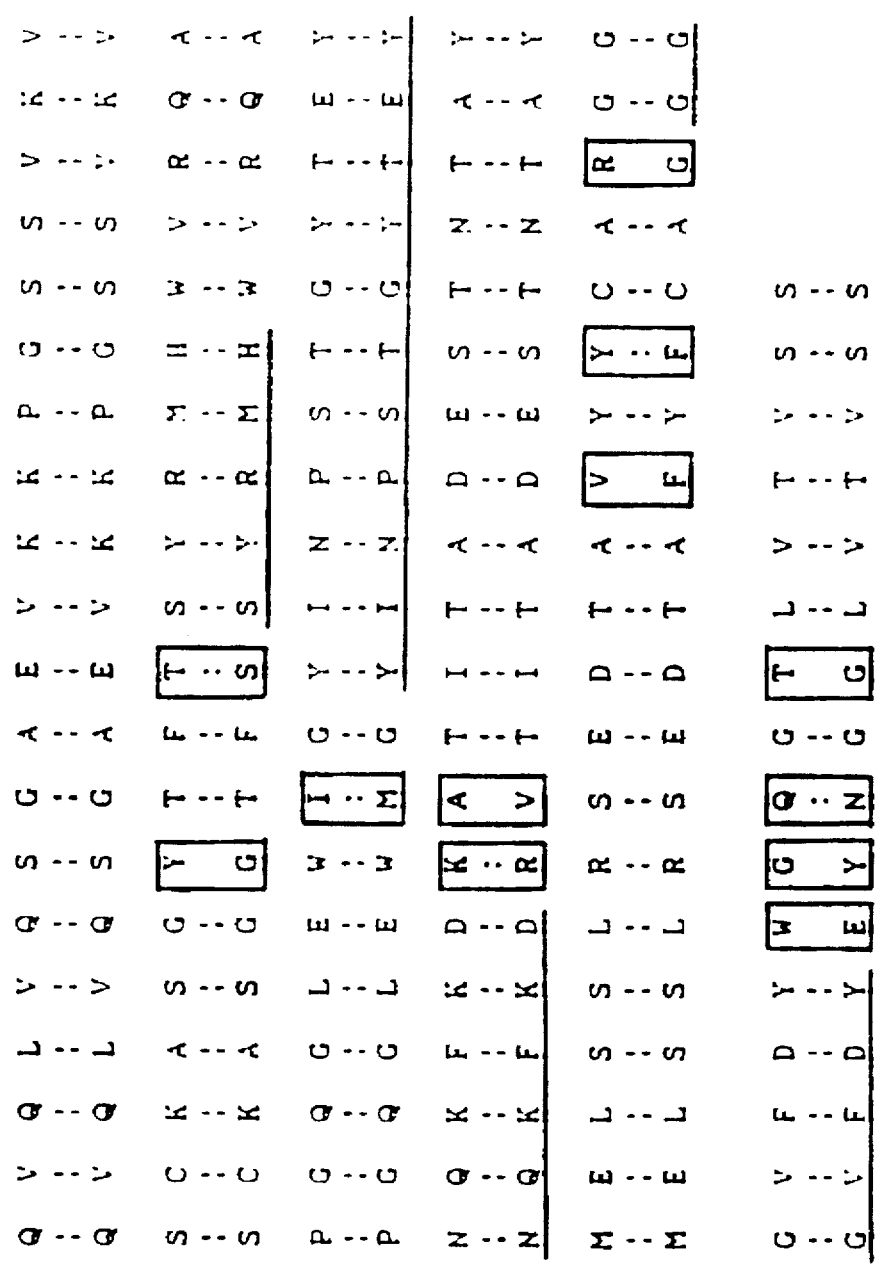
Figure 10B:
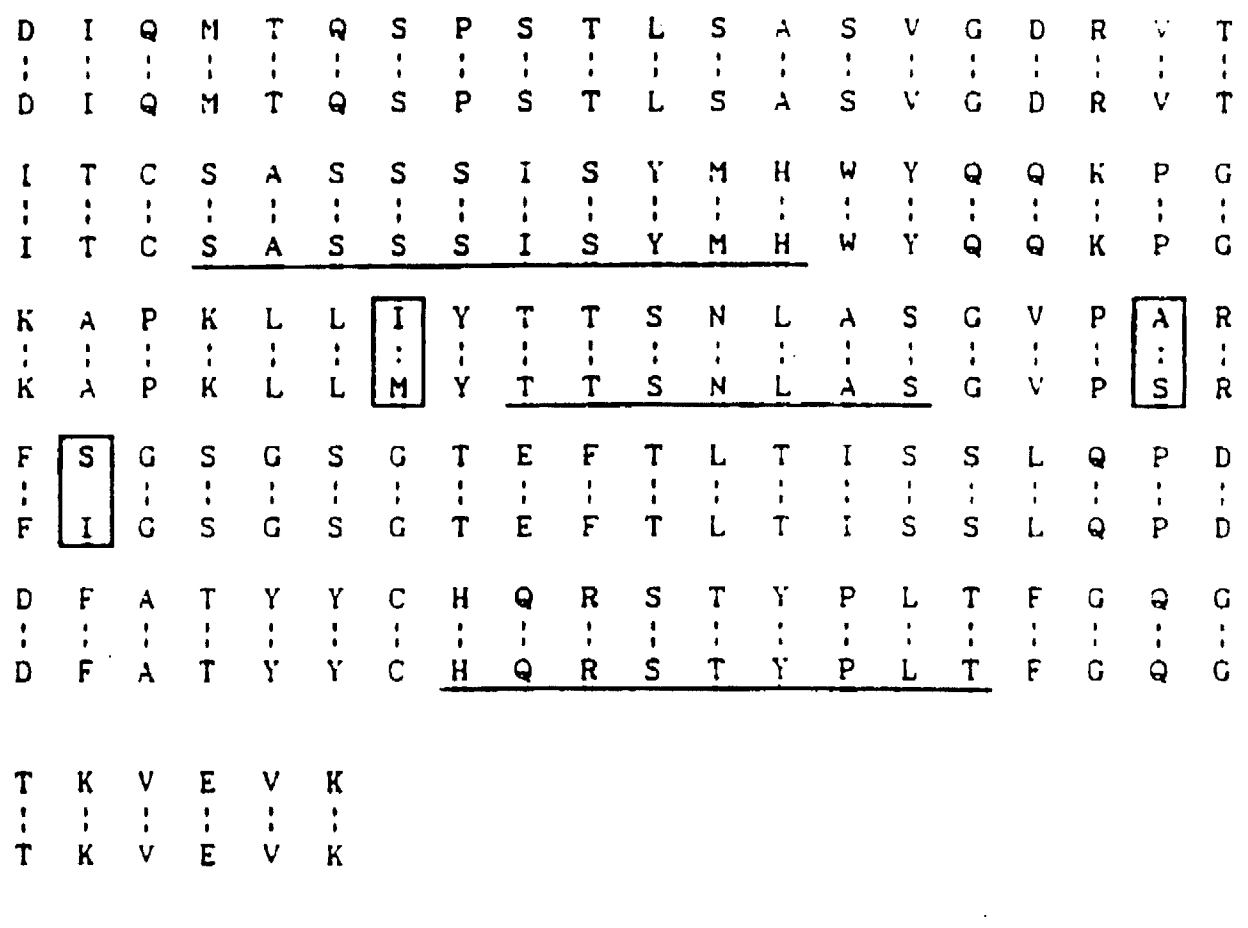

To determine whether it was actually necessary to use the mouse anti-Tac amino acids in categories (2)–(4) in the humanized anti-Tac antibody to retain binding affinity, a second humanized anti-Tac antibody was constructed. In the second antibody, only mouse anti-Tac amino acids in Category (1), i.e., in the CDR's themselves, were used, with all other amino acids coming from the human Eu framework. For purposes of this discussion, the original humanized anti-Tac antibody will be called the "PDL humanized antibody," and the second humanized antibody will be called the "CDR-only humanized antibody." The amino acid sequences of the PDL and CDR-only humanized antibody (variable regions) are compared in FIG. 10A and FIG. 10B.

The CDR-only humanized anti-Tac heavy and light chain variable (V) region gene segments were constructed in essentially the same manner as the light chain of the PDL humanized anti-Tac immunoglobulin, as described above. Specifically, each V region gene segment was synthesized in two halves. For each half, two overlapping, opposite-strand oligonucleotides, approximately 110 to 130 bases in length (FIG. 11A and FIG. 11B), were annealed and extended with sequenase (U.S. Biochemicals). The resulting double strand fragments were digested with either Xba I and Hind III (light chain) or-Xba I and Sal I (heavy chain) and inserted into plasmid pUC19. Clones with the correct sequence were identified by DNA sequencing. Complete heavy and light chain genes were generated by inserting the V region halves into the Xba I sites of pVg 1 and pVk respectively by three-fragment ligation.

The CDR-only humanized antibody was expressed in the same manner as the PDL humanized antibody, by transfecting first the light chain containing plasmid and then the heavy chain containing plasmid into SP2/0 cells. Transfected cells producing the highest levels of humanized antibody as determined by ELISA were used for preparation of antibody, which was purified by protein A sepharose chromatography. Antibody concentration was determined by ELISA using purified PDL humanized antibody as a standard. That the purified CDR-only humanized antibody is assembled into $H_2L_2$ tetramers as expected was shown by analysis using reducing and non-reducing polyacrylamide gel electrophoresis.

Figure 12:
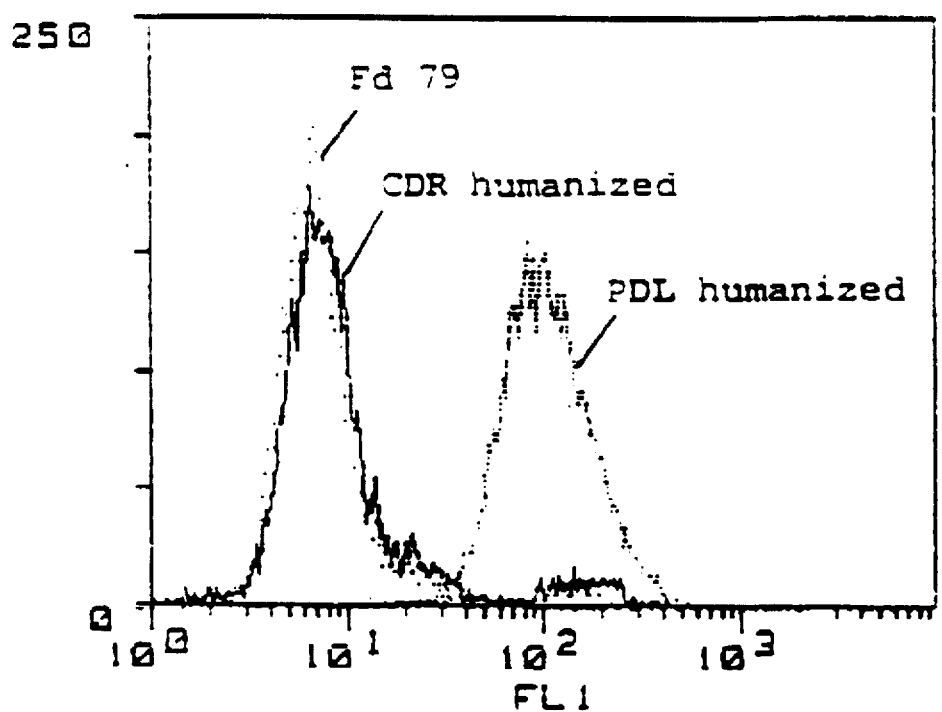
FIG. 12. FACS analysis of HUT-102 cells stained with PDL and CDR-only humanized anti-Tac antibodies and negative control antibody Fd79.

The ability of the CDR-only humanized immunoglobulin to bind to the IL-2 receptor was assessed by fluorescence staining. Approximately $3.4 \times 10^5$ HUT-102 cells, which are known to highly express the IL-2 receptor on their surface, were incubated with 200 ng of either the PDL or CDR-only humanized antibody, washed, and then incubated with fluorescein-conjugated goat anti-human IgG antisera. Cell fluorescence was measured by flow cytometry with a FACScan (Becton Dickinson). As shown in FIG. 12, the PDL humanized antibody strongly stained the cells. However, staining by the CDR-only antibody was indistinguishable from staining by the negative control antibody humanized Fd79, which binds the gB glycoprotein of herpes simplex virus and not HUT-102 cells. Hence, by this assay, the CDR-only humanized antibody does not detectably bind the IL-2 receptor.

Figure 13:
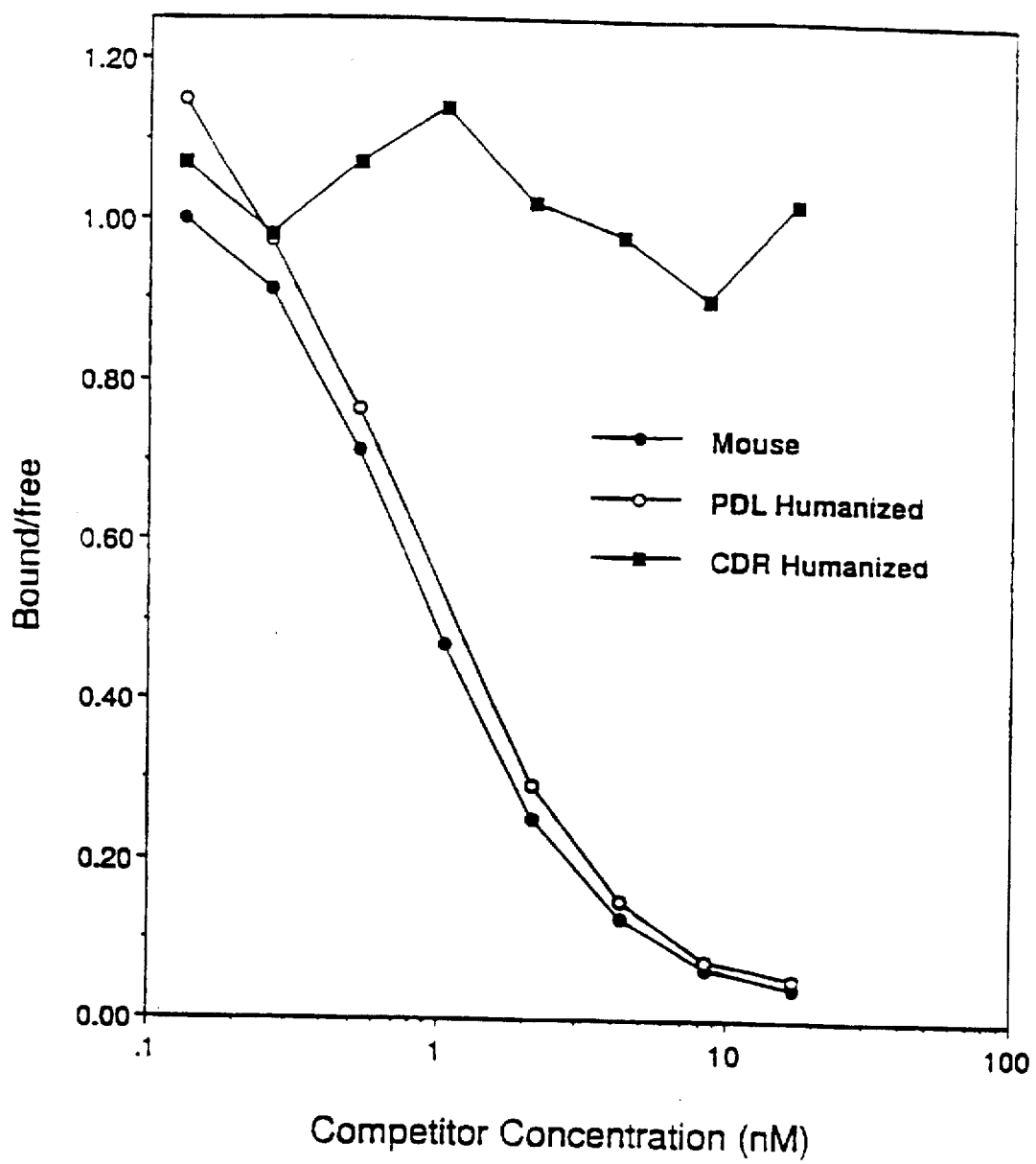
FIG. 13. Competition by mouse, PDL humanized, and CDR-only humanized anti-Tac antibodies with binding of radioiodinated mouse anti-Tac antibody to HUT-102 cells.

Binding of the PDL and CDR-only humanized anti-Tac antibodies to the IL-2 receptor were also compared in a competitive binding assay. Approximately 4×10⁵ HUT-102 cells were incubated with 1.5 ng of radioiodinated mouse anti-Tac antibody (7×10⁶ cpm/ug) and varying amounts of each humanized antibody (4 to 512 ng) in 200 ul total volume of binding buffer (RPMI 1040 medium, 10% fetal calf serum, 10 ug/ml murine IgG2a, 0.1% sodium azide). After incubation for 2 hours at 0° C., 800 ul of binding buffer was added, cells were collected by centrifugation and radioactivity was measured. The relative binding by the two humanized antibodies and by mouse anti-Tac is shown in a plot of bound/free labelled antibody versus competitor concentration (FIG. 13). The PDL humanized anti-Tac antibody affinity for IL-2 receptor is essentially equal to that of the mouse anti-Tac antibody, because it competes about equally well. But competition by the CDR-only humanized anti-Tac antibody to IL-2 receptor was undetectable at the antibody concentrations used, indicating a binding affinity reduction of at least 100-fold as compared to the PDL humanized anti-Tac antibody. Because the sequences of the PDL and CDR humanized anti-Tac antibodies differ only at positions where mouse framework residues in categories (2)–(4) were used in the PDL molecule, we conclude that at least one of these mouse framework residues are essential for high affinity binding.

Example 3

Construction of 5 Other Humanized Antibodies

Cloning of Heavy and Light Chain cDNAs

Figure 14:
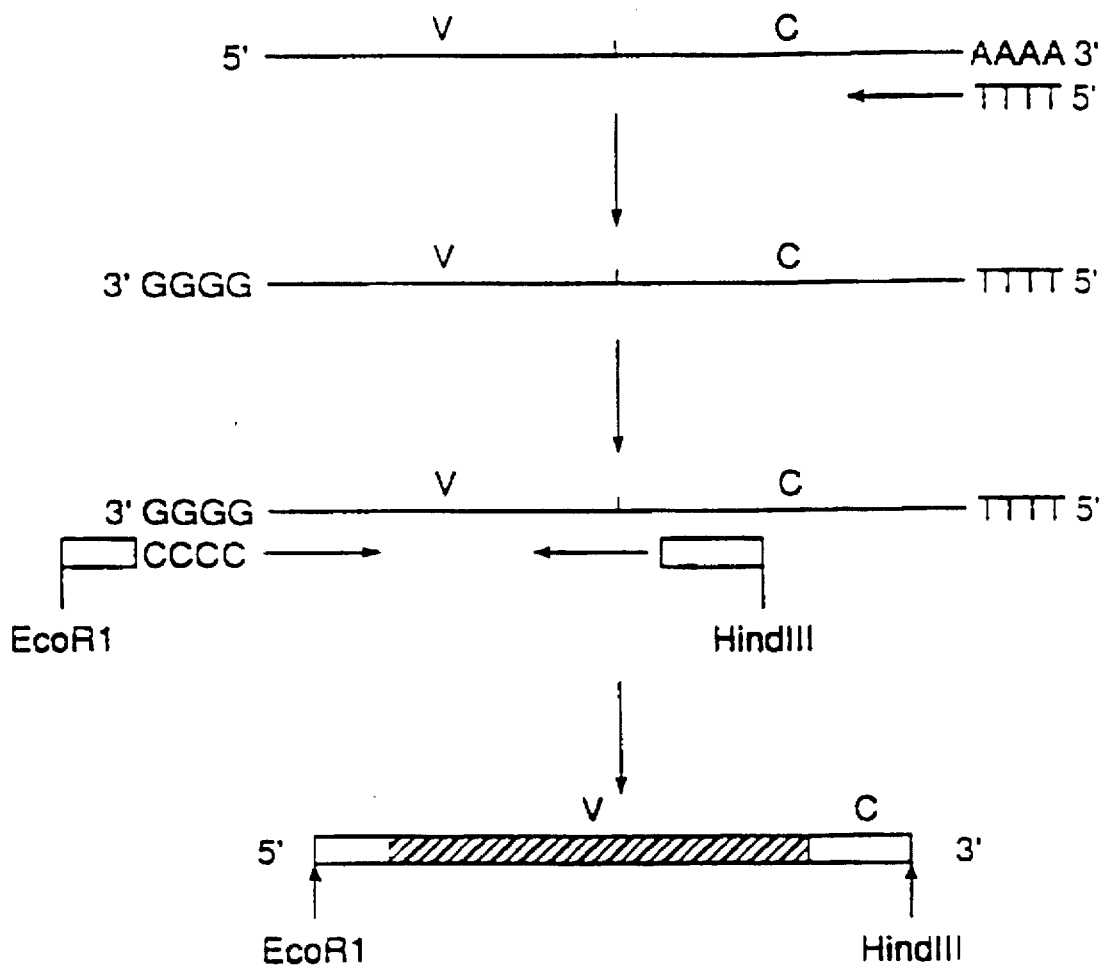
FIG. 14. Scheme for anchored polymerase chain reaction (PCR) cloning of the heavy and light chain variable domain cDNAs. RNA was prepared from about $10^7$ hybridoma cells using the hot phenol extraction method. Briefly, cells were resuspended and vortexed in 1 ml of RNA extraction buffer (50 mM sodium acetate pH 5.2/1% SDS), extracted with 0.5 ml of phenol pH 5.2 at 65° C. for 15 min, followed by another 15 min on ice. The aqueous phase was recovered and precipitated twice with ethanol. cDNA was synthesized from 10 ug of total RNA using reverse transcriptase (BRL, Betheseda, Md.) and oligo-dT$_{12-18}$ (Pharmacia, Piscatway, N.J.) as primers. A poly(dG) tail was attached to the 3' end of the cDNA using terminal deoxynucleotide transferase (BRL) (E. Y. Loh et al., Science 243, 217 (1989)), the variable domain genes (V) were amplified using AmpliTaq (Perkin Elmer-Cetus) with the primer mc045 (TAATCTAGAATTCCCCCCCCCCCCCCCCC) (SEQ ID NO:11) that hybridized to the poly(dG) tails and primers that hybridized to the constant region genes (C). For the light chain, the primer used was mc045 (TATAGAGCTCAAGCTTGGATGGTGGGAAGATGGA-TACAGTTGGTGC) (SEQ ID NO:12). For the heavy chain, the primer used was mc047 (TATAGAGCTCAAGCTTCCAGTGGATAGAC(CAT) GATGGGG(GC)TGT(TC)GTTTTGGC) (SEQ ID NO:13). The sequence in parenthesis indicates a base degeneracy. The degeneracy was introduced so that the primer would be able to hybridize to most gamma chains. The amplified fragments were then digested with EcoRI and HindIII and cloned into pUC18 vector for sequencing.

Five other humanized antibodies were designed and produced using the principles and categories disclosed herein. The antibodies are Fd79 and Fd138-80 which respectively bind to the gB and gD glycoproteins of herpes simplex virus (Metcalf et al., *Intervirology* 29, 39 (1988)), M195 (Tanimoto et al., *Leukemia* 3, 339 (1989)) which binds to the CD33 antigen, mik-β1 (Tusdo et al., *Proc. Natl. Acad. Sci. USA* 86, 1982 (1989)) which binds to the p75 chain of the IL-2 receptor, and CMV5 which binds to the gH glycoprotein of cytomegalovirus.

cDNAs for the heavy chain and light chain variable domain genes of each antibody were cloned using anchored polymerase chain reactions (Loh et al., *Science* 243, 219 (1989)), using 3' primers that hybridized to the constant regions and contained HindIII sites, and 5' primers that hybridized to the dG tails and contained EcoRI sites (Scheme shown in FIG. 14). The PCR amplified fragments were digested with EcoRI and HindIII and cloned into the pUC18 vector for sequencing. For each antibody, at least two heavy chain and two kappa clones were sequenced and found to have the same sequence. The deduced amino acid sequences of the mature light and heavy chain variable regions are shown in FIGS. 2A–6B, upper lines.

Design of Humanized Antibodies

In order to retain high binding affinity of the humanized antibodies, the principles and categories described above were utilized when designing the antibodies. Based on high sequence homology, human antibodies were selected to provide both the acceptor light and heavy chain human frameworks for the mouse antibodies, as follows: human Pom for Fd79, human Eu for Fd138-80, human Eu for M195, human Lay for mik-β1, and human Wol for CMV5.

The computer programs ABMOD and ENCAD (Levitt, *J. Mol. Biol.*, 168, 595 (1983) and Zilber et al., *Biochemistry* 29, 10032 (1990), both of which are incorporated herein by reference) was used to construct a model of the variable region of each mouse antibody. The model was used to determine the amino acids in each framework that were close enough to the CDR's to potentially interact with them (category 4 above). For each antibody, the positions found to fall in the categories (1)–(5) defined above are given in Table 1, numbered as in FIGS. 2A–6B.

TABLE 1

| Category | Light Chain | Heavy Chain |
|---|---|---|
| Fd79 Antibody | | |
| 1 | 24–38, 54–50, 93–100 | 31–35, 50–66, 99–111 |
| 2 | 9, 45, 46, 83 | 82, 112 |
| 3 | 53 | 112 |
| 4 | 53 | 97 |
| 5 | 81 | |
| Fd138-80 Antibody | | |
| 1 | 24–34, 50–56, 89–97 | 31–35, 50–66, 99–110 |
| 2 | 48, 63 | 93, 98, 111, 112, 113, 115 |
| 3 | — | 30, 67, 98, 111 |
| 4 | 36, 48, 87 | 27, 30, 37, 48, 67, 68, 98 |
| M195 Antibody | | |
| 1 | 24–38, 54–60, 93–101 | 31–35, 50–66, 95–105 |
| 2 | 10, 52, 67, 110 | 93, 95, 98, 106, 107, 108, 110 |
| 3 | — | 30, 67, 98, 106 |
| 4 | 40, 52, 74 | 27, 30, 48, 68, 98 |
| mik-β1 Antibody | | |
| 1 | 24–33, 49–55, 88–96 | 31–35, 50–65, 98–108 |
| 2 | 13 | 84, 89, 90 |
| 3 | — | 30, 49 |
| 4 | 70 | 29, 30, 72, 73 |
| 5 | 41 | 1 |
| CMV5 Antibody | | |
| 1 | 24–34, 50–56, 89–97 | 31–35, 50–66, 99–108 |
| 2 | — | 69, 80 |
| 3 | 49 | 30 |
| 4 | 49 | 24, 27, 28, 30, 97 |
| 5 | — | 5 |

In designing each humanized antibody, at each position the amino acid was selected to be the same as in the human acceptor sequence, unless the position fell in categories (1)–(4), in which case the amino acid from the mouse donor sequence was used, or in category (5), in which case an amino acid typical for human sequences at that position was used.

For the construction of genes for the humanized antibodies, nucleotide sequences were selected that encode the protein sequences of the humanized heavy and light chains, including signal peptides typically from the mouse antibody chains, generally utilizing codons found in the mouse sequence. Several degenerate codons were changed to create restriction sites or to remove undesirable ones. The nucleotide sequences also included splice donor signals typical for immunoglobulin genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal. The oligonucleotides were synthesized on an Applied Biosystems 380B DNA synthesizer. Each oligo was about 110–140 base long with a 15–20 base overlap. Double stranded DNA fragments were synthesized with Klenow or Taq polymerase or sequenase from each pair of oligonucleotides, digested with restriction enzymes, ligated to pUC18 vector and sequenced. Two fragments with the respectively correct half-sequences were then ligated into the XbaI sites of pVg1 (heavy chains of Fd79 and Fd138-80) or pVg1-dhfr (heavy chains of M195, mik-β1, CMV5) or pVk (all light chains) expression vectors in the appropriate orientations to produce the complete heavy and light chain genes. Reactions were carried out under conditions well-known in the art (Maniatis et al., op. cit.).

The heavy chain and light chain plasmids were transfected into Sp2/0 mouse myeloma cells by electroporation and cells were selected for gpt expression. Clones were screened by assaying human antibody production in the culture supernatant by ELISA, and antibody was purified from the best-producing clones. Antibody was purified by passing tissue culture supernatant over a column of staphylococcal protein A-Sepharose CL-4B (Pharmacia). The bound antibodies were eluted with 0.2M Glycine-HCl, pH 3.0 and neutralized with 1M Tris pH 8.0. The buffer was exchanged into PBS by passing over a PD10 column (Pharmacia).

Properties of the Humanized Antibodies

The binding of the humanized antibodies to cell types expressing the corresponding antigens was tested: HSV-infected cells for Fd79 and Fd138-80, U937 cells for M195, YTJB cells for mik-β1 and CMV-infected cells for CMV5. By fluorocytometry, the humanized antibodies bind approximately as well as the original mouse antibodies and the corresponding chimeric antibodies. Moreover, the humanized antibodies compete approximately as well as the corresponding mouse antibodies against the radiolabeled mouse antibodies for binding to the cells, so the humanized antibodies have approximately the same binding affinity as the mouse antibodies, typically within about 2 fold or better, see, e.g., Table 2.

TABLE 2

Binding affinities of murine and humanized antibodies.

| | Mouse $K_a$ (m$^{-1}$) | Humanized $K_a$ (M$^{-1}$) |
|---|---|---|
| Fd79 (anti-gB) | $1.1 \times 10^8$ | $5.3 \times 10^7$ |
| Fd138-80 (anti-gD) | $5.2 \times 10^7$ | $4.8 \times 10^7$ |

From the foregoing, it will be appreciated that the humanized immunoglobulins of the present invention offer numerous advantages over other antibodies. In comparison to other monoclonal antibodies, the present humanized immunoglobulin can be more economically produced and contain substantially less foreign amino acid sequences. This reduced likelihood of antigenicity after injection into a human patient represents a significant therapeutic improvement.

Example 4

Design of Genes for anti-Tac Human-like Light and Heavy Chains

The sequence of the human antibody Eu (Sequences of Proteins of Immunological Interest, Kabat, E., et al., U.S. Dept. of Health and Human Services, 1983) was used to provide the framework of the humanized antibody, because the amino acid sequence of the heavy chain of anti-Tac is more homologous to the heavy chain of this antibody than to any other heavy chain sequence in the National Biomedical Foundation Protein Identification Resource.

Figure 15:
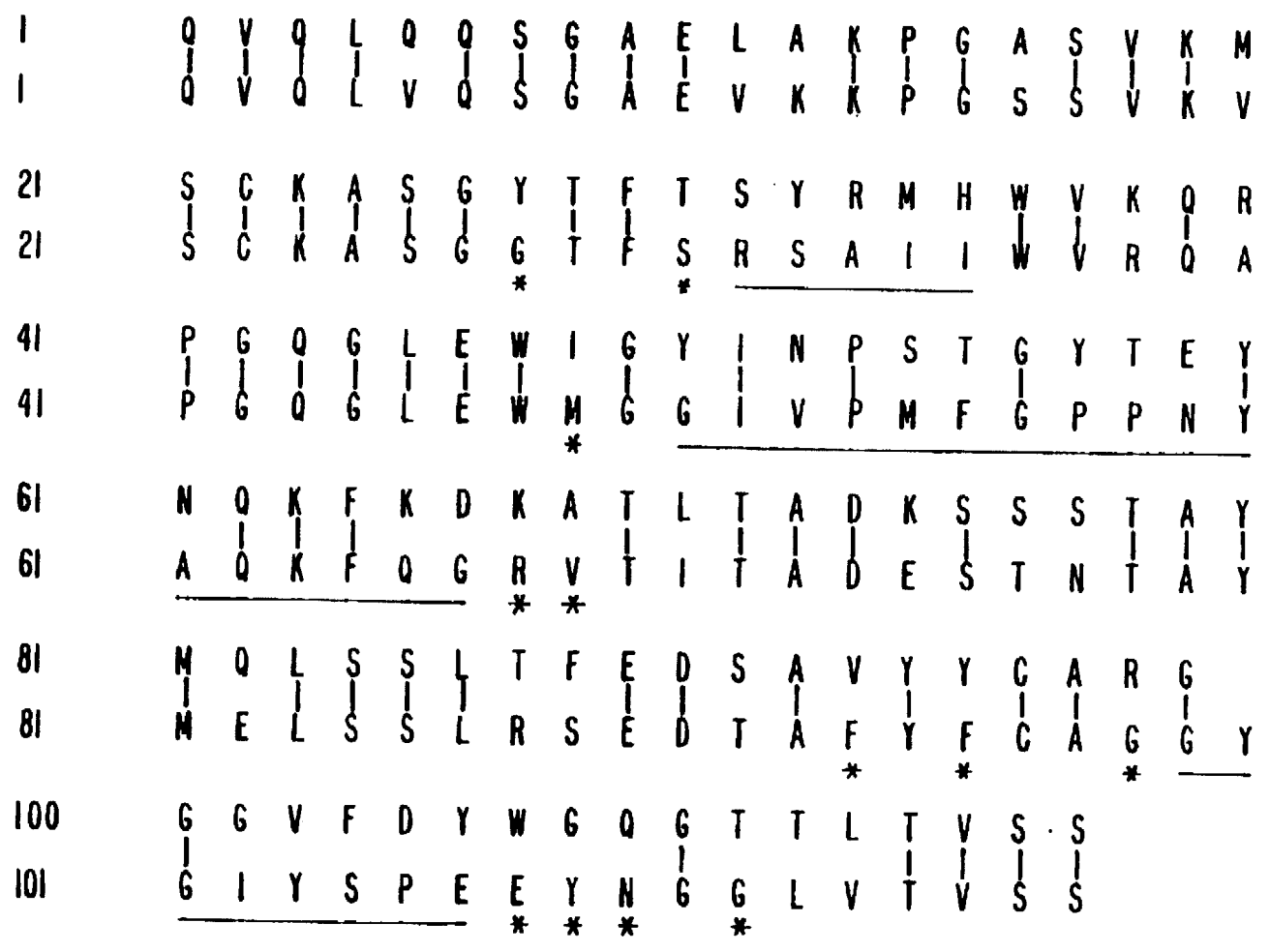

To select the sequence of the humanized heavy chain, the anti-Tac heavy chain sequence was aligned with the sequence of the Eu heavy chain (FIG. 15). At each position, the Eu amino acid was selected for the humanized sequence, unless that position fell in any one of the following categories, in which case the anti-Tac amino acid was selected.

(1) The position fell within a complementarity determining region (CDR), as defined by Kabat, et al., op. cit. (amino acids 31–35, 50–66, 99–106);

(2) The Eu amino acid was unusual for human heavy chains at that position, whereas the anti-Tac amino acid was typical for human heavy chains at that position (amino acids 27, 93, 95, 98, 107–109, 111);

(3) The position was immediately adjacent to a CDR in the amino acid sequence of the anti-Tac heavy chain (amino acids 30 and 67).

(4) 3-dimensional modeling of the anti-Tac antibody suggested that the amino acid was physically close to the antigen binding region (amino acids 48 and 68).

Some amino acids fell in more than one of these categories but are only listed in one.

Figure 16:
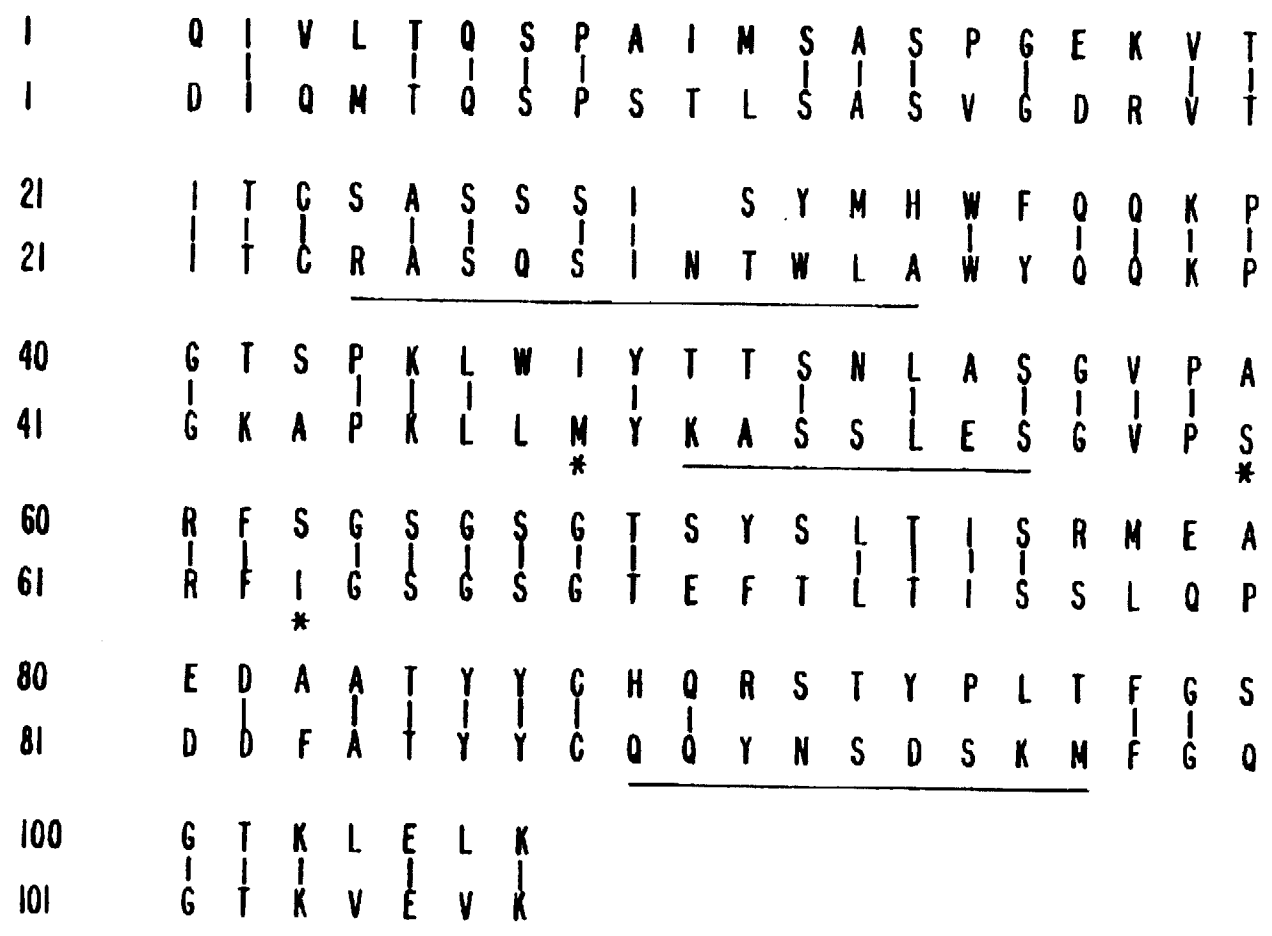

To select the sequence of the humanized light chain, the anti-Tac light chain sequence was aligned with the sequence of the Eu light chain (FIG. 16). The Eu amino acid was selected at each position, unless the position again fell into one of the categories (1)–(4), (with light chain replacing heavy chain in the category definitions):

(1) CDRs (amino acids 24–34, 50–56, 89–97).

(2) Anti-Tac amino acid more typical than Eu (amino acids 48 and 63).

(3) Adjacent to CDRs (no amino acids; Eu and anti-Tac were already the same at all these positions).

(4) Possible 3-dimensional proximity to binding region (amino acid 60).

The actual nucleotide sequence of the heavy (FIG. 17) and light chain (FIG. 18) genes were selected as follows:

(1) the nucleotide sequences code for the amino acid sequences chosen as described above.

(2) 5' of these coding sequences, the nucleotide sequences code for a leader (signal) sequence, namely the leader of the light chain of the antibody MOPC 63 and the leader of the heavy chain of the antibody PCH 108A (Kabat et al., op. cit.). These leader sequences were chosen as typical of antibodies.

(3) 3' of the coding sequences, the nucleotide sequences are the sequences that follow the mouse light chain J5 segment and the mouse heavy chain J2 segment, which are part of the anti-Tac sequences. These sequences are included because they contain splice donor signals.

(4) At each end of the sequence is an Xba I site to allow cutting at the Xba I sites and cloning into the Xba I site of a vector.

Construction of Humanized Light and Heavy Chain Genes

To synthesize the heavy chain, four oligonucleotides HES12, HES13, HES14, HES15 (FIG. 19A) were synthesized using an Applied Biosystems 380B DNA synthesizer. Two of the oligonucleotides are part of each strand of the heavy chain, and each oligonucleotide overlaps the next one by about 20 nucleotides to allow annealing (FIG. 19B). Together, the oligonucleotides cover the entire humanized heavy chain (FIG. 17) with a few extra nucleotides at each end to allow cutting at the Xba I sites. The oligonucleotides were purified from polyacrylamide gels.

Each oligonucleotide was phosphorylated using ATP and T4 polynucleotide kinase by standard procedures (see, Maniatis, op. cit.). To anneal the phosphorylated oligonucleotides, they were suspended together in 40 ul of TA (33 mM Tris acetate, pH 7.9, 66 mM potassium acetate, 10 mM magnesium acetate) at a concentration of about 3.75 uM each, heated to 95° C. for 4 min. and cooled slowly to 4° C. To synthesize the complete gene from the oligonucleotides by synthesizing the opposite strand of each oligonucleotide (FIG. 19B), the following components were added in a final volume of 100 ul:

| 10 ul | annealed oligonucleotides |
|---|---|
| 0.16 mM each | deoxyribonucleotide |
| 0.5 mM | ATP |
| 0.5 mM | DTT |
| 100 ug/ml | BSA |
| 3.5 ug/ml | T4 g43 protein (DNA polymerase) |
| 25 ug/ml | T4 944/62 protein (polymerase accessory protein) |
| 25 ug/ml | 45 protein (polymerase accessory protein) |

The mixture was incubated at 37° C. for 30 min. Then 10 U of T4 DNA ligase was added and incubation at 37° C. resumed for 30 min. The polymerase and ligase were inactivated by incubation of the reaction at 70° C. for 15 min. To digest the gene with Xba I, to the reaction was added 50 ul of 2× TA containing BSA at 200 ug/ml and DTT at 1 mM, 43 ul of water, and 50 U of Xba I in 5 ul. The reaction was incubated for 3 hr at 37° C., and run on a gel. The 431 bp Xba I fragment was purified from a gel and cloned into the Xba I site of the plasmid pUC19 by standard methods.

Four plasmid isolates were purified and sequenced using the dideoxy method. One of these had the correct sequence (FIG. 17).

To synthesize the light chain, four oligonucleotides JFD1, JFD2, JFD3, JFD4 (FIG. 20A) were synthesized. Two of the oligonucleotides are part of each strand of the light chain, and each oligonucleotide overlaps the next one by about 20 nucleotides to allow annealing (FIG. 20B). Together, the oligonucleotides cover the entire humanized light chain (FIG. 18) with a few extra nucleotides at each end to allow cutting at the Xba I sites. The oligonucleotides were purified from polyacrylamide gels.

The light chain gene was synthesized from these oligonucleotides in two parts. 0.5 ug each of JFD1 and JFD2 were combined in 20 ul sequenase buffer (40 mM Tris-HCl, pH 7.5, 20 mM magnesium chloride, 50 mM sodium chloride), heated at 70° C. for 3 min and allowed to cool slowly to 23° C. in order for the oligonucleotides to anneal. JFD3 and JFD4 were treated in the same way. Each reaction was made 10 mM in DTT and 0.5 mM in each deoxyribonucleotide and 6.5 U of sequenase (US Biochemicals) was added, in a final volume of 24 ul, and incubated for 1 hr at 37° C. to synthesize the opposite strands of the oligonucleotides. Xba I and Hind III were added to each reaction to digest the DNA (there is a Hind III site in the region where JFD2 and JFD3 overlap and therefore in each of the synthesized DNAs; FIG. 20B). The reactions were run on polyacrylamide gels, and the Xba I - Hind III fragments were purified and cloned into pUC18 by standard methods. Several plasmid isolates for each fragment were sequenced by the dideoxy method, and correct ones chosen.

Construction of Plasmids to Express Humanized Light and Heavy Chains

Figure 21:
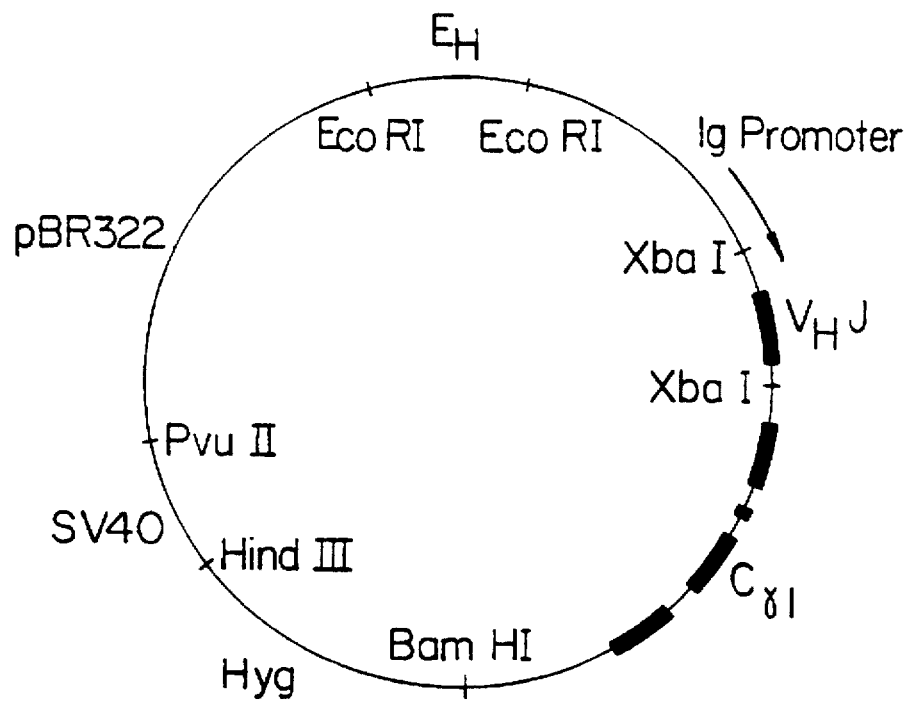
FIG. 21. Schematic diagram of the plasmid pHuGTAC1 used to express the humanized anti-Tac heavy chain. Relevant restriction sites are shown, and coding regions of the heavy chain are displayed as boxes. The direction of transcription from the immunoglobulin (Ig) promoter is shown by an arrow. $E_H$=heavy chain enhancer, Hyg=hygromycin resistance gene.

The heavy chain Xba I fragment was isolated from the pUC19 plasmid in which it had been inserted and then inserted into the Xba I site of the vector pVγ1 in the correct orientation by standard methods, to produce the plasmid pHuGTAC1 (FIG. 21). This plasmid will express high levels of a complete heavy chain when transfected into an appropriate host cell.

Figure 22:
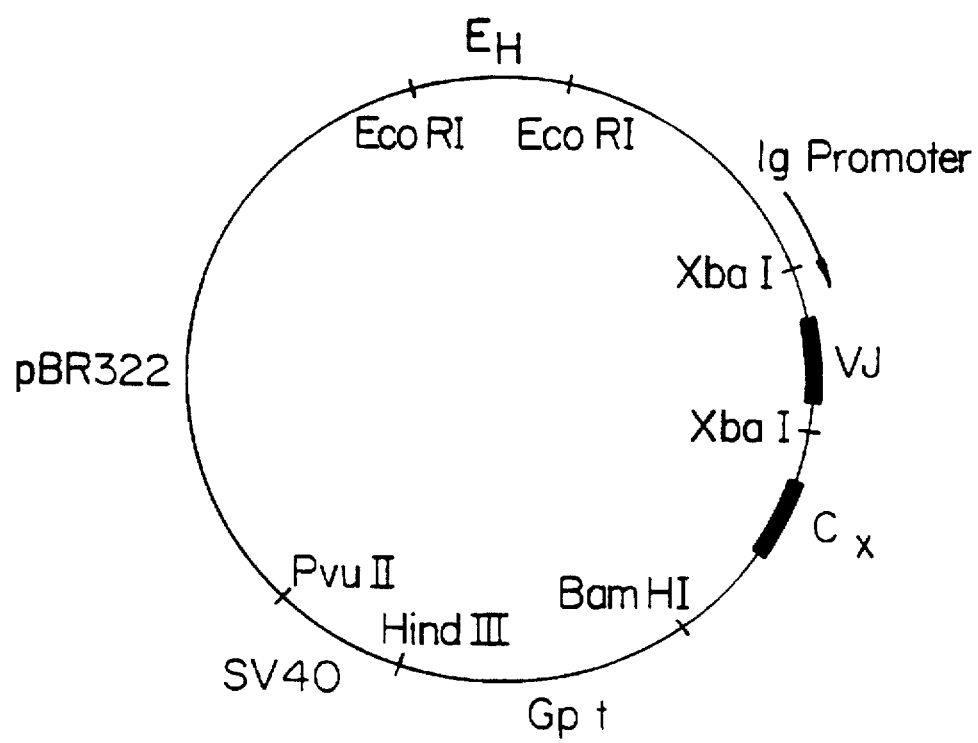
FIG. 22. Schematic diagram of the plasmid pHuLTAC used to express the humanized anti-Tac light chain. Relevant restriction sites are shown, and coding regions of the light chain are displayed as boxes. The direction of transcription from the Ig promoter is shown by an arrow.

The two light chain Xba I - Hind III fragments were isolated from the pUC18 plasmids in which they had been inserted. The vector plasmid pVκ1 was cut with Xba I, dephosphorylated and ligated with the two fragments by standard methods. The desired reaction product has the circular form: vector - Xba I - fragment 1 - Hind III - fragment 2 - Xba I - vector. Several plasmid isolates were analyzed by restriction mapping and sequencing, and one with this form chosen. This plasmid, pHuLTAC (FIG. 22), therefore contains the complete humanized light chain (FIG. 18) and will express high levels of the light chain when transfected into an appropriate host cell.

Synthesis and Affinity of Humanized Antibody

The plasmids pHuGTAC1 and pHuLTAC were transfected into mouse Sp2/0 cells, and cells that integrated the plasmids were selected on the basis of resistance to mycophenolic acid and/or hygromycin B conferred by the gpt and hyg genes on the plasmids (FIGS. 21, 22) by standard methods. To verify that these cells secreted antibody that binds to the IL-2 receptor, supernatant from the cells was incubated with HUT-102 cells that are known to express the IL-2 receptor. After washing, the cells were incubated with fluorescein-conjugated goat anti-human antibody, washed, and analyzed for fluorescence on a FACSCAN cytofluorometer. The results (FIG. 7A), clearly show that the humanized antibody binds to these cells, but not to Jurkat T-cells that do not express the IL-2 receptor (FIG. 7D). As controls, the original mouse anti-Tac antibody was also used to stain these cells (FIG. 7B and FIG. 7C), giving similar results.

For further experiments, cells producing the humanized antibody were injected into mice, and the resultant ascites collected. Humanized antibody was purified to substantial homogeneity from the ascites by passage through an affinity column of goat anti-human immunoglobulin antibody, prepared on an Affigel-10 support (Bio-Rad Laboratories, Inc., Richmond, Calif.) according to standard techniques. To determine the affinity of the humanized antibody relative to the original anti-Tac antibody, a competitive binding experiment was performed. About $5 \times 10^5$ HUT-102 cells were incubated with known quantities (10–40 ng) of the anti-Tac antibody and the humanized anti-Tac antibody for 10 min at 4° C. Then 100 ng of biotinylated anti-Tac was added to the cells and incubated for 30 min at 4° C. This quantity of anti-Tac had previously been determined to be sufficient to saturate the binding sites on the cells, but not to be in large excess. Then the cells were washed twice with 2 ml of phosphate buffered saline (PBS) containing 0.1% sodium azide. The cells were then incubated for 30 min at 4° C. with 250 ng of phycoerythrin-conjugated avidin, which bound to the biotinylated anti-Tac already bound to the cells. The cells were washed again as above, fixed in PBS containing 1% paraformaldehyde, and analyzed for fluorescence on a FACSCAN cytofluorometer.

Use of increasing amounts (10–40 ng) of the anti-Tac antibody as competitor in the first step decreased the amount of biotinylated anti-Tac that could bind to the cells in the second step, and therefore the amount of phycoerythrin-conjugated avidin that bound in the last step, thus decreasing fluorescence (FIG. 8A). Equivalent amounts (20 ng) of anti-Tac, and humanized anti-Tac used as competitor decreased the fluorescence to approximately the same degree (FIG. 8B). This shows that these antibodies have approximately the same affinity, because if one had greater affinity, it would have more effectively competed with the biotinylated anti-Tac, thus decreasing fluorescence more.

Biological Properties of the Humanized Antibody

For optimal use in treatment of human disease, the humanized antibody should be able to destroy T-cells in the body that express the IL-2 receptor. One mechanism by which antibodies may destroy target cells is antibody-dependent cell-mediated cytotoxicity, abbreviated ADCC (*Fundamental Immunology*, Paul, W., Ed., Raven Press, New York (1984), at pg. 681), in which the antibody forms a bridge between the target cell and an effector cell such as a macrophage that can lyse the target. To determine whether the humanized antibody and the original mouse anti-Tac antibody can mediate ADCC, a chromium release assay was performed by standard methods. Specifically, human leukemia HUT-102 cells, which express the IL-2 receptor, were incubated with $^{51}$Cr to allow them to absorb this radionuclide. The HUT-102 cells were then incubated with an excess of either anti-Tac or humanized anti-Tac antibody. The HUT-102 cells were next incubated for 4 hrs with either a 30:1 or 100:1 ratio of effector cells, which were normal purified human peripheral blood mononuclear cells that had been activated by incubation for about 20 hrs with human recombinant IL-2. Release of $^{51}$Cr, which indicated lysis of the target HUT-102 cells, was measured and the background subtracted (Table 3). The results show that at either ratio of effector cells, anti-Tac did not lyse a significant number of the target cells (less than 5%), while the humanized antibody did (more than 20%). Hence, the humanized antibody is likely to be more efficacious than the original mouse antibody in treating T-cell leukemia or other T-cell mediated diseases.

TABLE 3

| | Percent $^{51}$Cr release after ADCC | |
|---|---|---|
| | Effector: Target ratio | |
| Antibody | 30:1 | 100:1 |
| Anti-Tac | 4% | <1% |
| Humanized anti-Tac | 24% | 23% |

Higher Level Expression of the Humanized anti-Tac Antibody

Two new plasmid vectors were prepared for expression of the humanized antibody. The plasmid pVg1 (FIG. 9A) contains a human cytomegalovirus IE1 promoter and enhancer (Boshart et al., *Cell* 41, 521 (1985)), the human genomic Cγ1 segment including part of the preceding intron, and the hygomycin gene (Blochlinger et al., *Mol. Cell. Biol.* 4, 2929 (1984), which is incorporated herein by reference) for selection. The plasmid pVk (FIG. 9B) is similar to pVg1 but contains the human genomic Cκ segment and the gpt gene.

Xba I fragments containing the humanized anti-Tac light chain and heavy chain variable regions were excised respectively from the plasmids pHuLTAC and the pHuGTAC1 and cloned into the Xba I sites of the plasmid vectors pVk and pVG1. To express the humanized anti-Tac antibody, the light chain encoding plasmid was introduced by electroporation into SP2/0 mouse myeloma cells followed by selection for gpt expression. Transfected cells expressing light chain were then transfected with the plasmid encoding the heavy chain followed by selection for hygromycin B resistance. Transfected cells producing the highest levels of humanized antibody as determined by ELISA were used for preparation of antibody. Humanized antibody was purified from culture supernatant of transfected cells by protein A sepharose chromatography.

From the foregoing, it will be appreciated that the human-like immunoglobulins of the present invention offer numerous advantages of other human IL-2 receptor-specific antibodies. In comparison to anti-Tac mouse monoclonal antibodies, the present human-like immunoglobulin can be more economically produced and contain substantially less foreign amino acid sequences. This reduced likelihood of antigenicity after injection into a human patient represents a significant therapeutic improvement.

Example 5

Design of Genes for mikβ1 Humanized Light and Heavy Chains

To exert its biological effects, IL-2 interacts with a specific high-affinity membrane receptor (Greene, W., et al., *Progress in Hematology XIV*, E. Brown, Ed., Grune and Statton, New York (1986), at pgs. 283 ff and Waldmann, *Ann. Rev. Biochem.* 58, 875 (1989), which is incorporated herein by reference). The human IL-2 receptor is a complex multichain glycoprotein, with one chain, known as the Tac peptide or alpha chain, being about 55 kD in size (see, Leonard, W., et al., *J. Biol. Chem.* 260, 1872 (1985), which is incorporated herein by reference). The second chain is known as the p75 or beta chain (Tsudo et al., *Proc. Nat. Acad. Sci. USA*, 83, 9694 (1986) and Sharon et al., *Science* 234, 859 (1986), both of which are incorporated herein by reference). The p55 or Tac chain and the p75 chain each independently bind IL-2 with low or intermediate affinity, while the IL-2 receptor complex of both chains binds IL-2 with high affinity. The p75 chain of the human IL-2 receptor will often be called herein simply the p75 protein.

Much of the elucidation of the human IL-2 receptor's structure and function is due to the development of specifically reactive monoclonal antibodies. The antibody, mik-β1, binds to the p75 chain (Tsudo et al., *Proc. Nat. Acad. Sci. USA* 86, 1982 (1989), which is incorporated herein by reference).

Cloning of Heavy Chain and Light Chain cDNA cDNAs for the heavy chain and light chain variable domain genes were cloned using anchored polymerase chain reactions (E. Y. Loh et al., *Science* 243, 217 (1989)), using 3' primers that hybridized to the constant regions and contained HindIII sites, and 5' primers that hybridized to the dG tails and contained EcoRI sites (scheme shown in FIG. 14). The PCR amplified fragments were digested with EcoRI and HindIII and cloned into the pUC19 vector for sequencing. For mik-β1, two gamma-2a specific and two kappa specific clones were sequenced. The two gamma-2a clones and two kappa clones are respectively identical in sequence.

The cDNA variable domain sequences and the deduced amino acid sequences are shown in FIG. 23A and FIG. 23B.

Construction and Expression of Chimeric Antibody

Figure 24A:
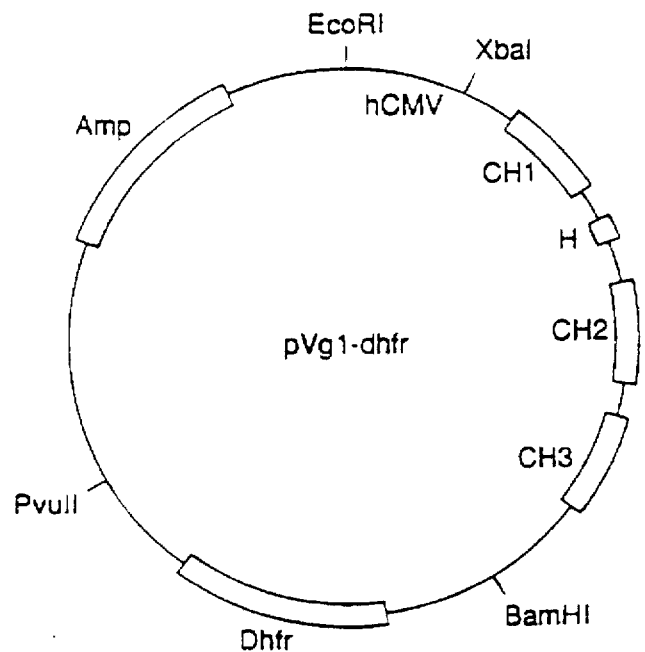
Figure 24B:
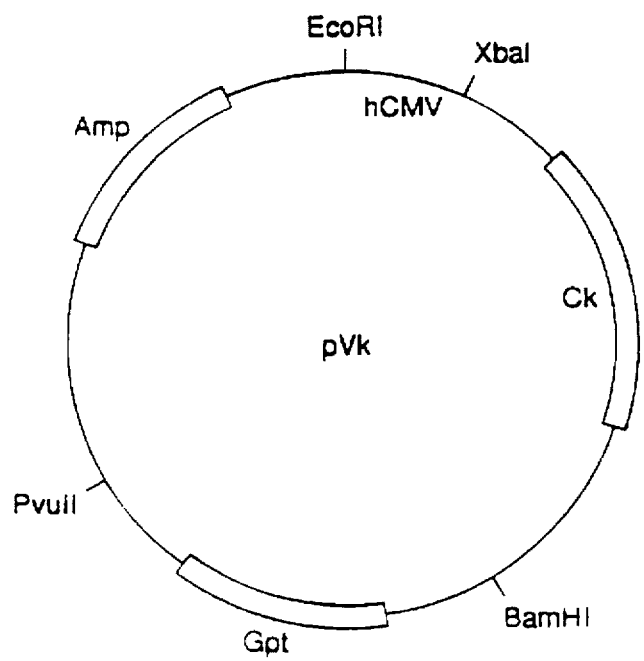

Two plasmid vectors were prepared for construction and expression of the chimeric antibody genes. The plasmid pVg1-dhfr (FIG. 24A) contains a human cytomegalovirus IE1 promoter and enhancer (M. Boshart et al., *Cell* 41, 521 (1985)), the human genomic $C_{\gamma}1$ segment including part of the preceding intron, and a dihydrofolate reductase (dhfr) gene (Simonsen et al., *Proc. Natl. Acad. Sci. USA* 80, 2495 (1983), which is incorporated herein by reference) for selection. The plasmid pVk (FIG. 24B) is similar to pVg1-dhfr but contains the human genomic CM segment and the gpt gene. Derivatives of the mik-β1 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, C. Queen et al., *Proc. Natl. Acad. Sci. USA* 86, 10029 (1989), which is incorporated herein by reference). The modified V regions were cloned into the XbaI sites of the respective plasmid vectors between the CMV promoter and the partial introns of the constant regions.

For expression of the chimeric antibody, the heavy chain and kappa chain plasmids were transfected into Sp2/0 mouse myeloma cells by electroporation and cells selected for gpt expression. Clones secreting a maximal amount of complete antibody were detected by ELISA. Purified chimeric mik-β1 antibody was shown to bind to YTJB cells, which express the p75 antigen, by flow cytometry (FIG. 25).

Computer Modeling of Humanized Antibodies

In order to retain high binding affinity in the humanized antibodies, the general procedures of Queen et al. were followed (C. Queen et al., *Proc. Natl. Acad. Sci. USA* 86, 10029 (1989), which is incorporated herein by reference). The more homologous a human antibody is to the original murine antibody, the less likely will combining the murine CDRs with the human framework be to introduce distortions into the CDRs that could reduce affinity. Normally the heavy chain and light chain from the same human antibody are chosen to provide the framework sequences, so as to reduce the possibility of incompatibility in the assembling of the two chains. Based on sequence database (performed with the MicrorGenie Sequence Analysis Software (Beckman)), the antibody Lay was chosen to provide the framework sequences for humanization of mik-β1.

The computer program ENCAD (M. Levitt, *J. Mol. Biol.* 168, 595 (1983), which is incorporated herein by reference) was used to construct a model of the mik-β1 variable region. The model was used to determine the amino acids in the mik-β1 framework that were close enough to the CDRs to potentially interact with them (category 4 below). To design the humanized light and heavy chain mik-β1 variable regions, at each position the amino acid was chosen to be the same as in the Lay antibody, unless that position fell in one or more of five categories:

(1) The position fell within a CDR, (2) The Lay amino acid was unusual for human antibodies at that position, whereas the mik-β1 amino acid was typical for human antibodies at that position.

(3) The position was immediately adjacent to a CDR, (4) The model described above suggested that the amino acid may be physically close to the antigen binding region (CDRs).

For positions in these categories, the amino acid from the (mouse) mik-β1 antibody was used. In addition, a position was in the fifth category if (5) The Lay amino acid was highly unusual for human antibodies at that position, and the mik-β1 amino acid was different but also unusual. Then an amino acid typical for human antibodies at that position may be used.

The amino acids in each category are shown in Table 4. Some amino acids may be in more than one category. The final sequences of the humanized mik-β1 light and heavy chain variable domains are shown in FIG. 26A and FIG. 26B, compared with the Lay sequences.

TABLE 4

| Category | Light Chain | Heavy Chain |
|---|---|---|
| 1 | 24–33, 49–55, 88–96 | 31–35, 50–65, 98–108 |
| 2 | 13 | 84, 89, 90 |
| 3 | 30, 49 | |
| 4 | 70 | 29, 30, 72, 73 |
| 5 | 41 | 1 |

For the construction of genes for the humanized antibodies, nucleotide sequences were selected that encode the protein sequences of the humanized heavy and light chains, including the same signal peptides as in the mouse mik-β1 chains (FIG. 23A and FIG. 23B), generally utilizing codons found in the mouse sequence. Several degenerate codons were changed to create restriction sites or to remove undesirable ones. The nucleotide sequences also included the same splice donor signals used in the chimeric genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal (FIG. 27A and FIG. 27B). The oligonucleotides were synthesized on an Applied Biosystems 380B DNA synthesizer. Each oligo was about 110–140 base long with about a 20 base overlap. Double stranded DNA fragments were synthesized with sequenase from each pair of oligonucleotides, digested with restriction enzymes, ligated to pBluescriptII KS (+) (Stratagene) vector and sequenced. Two fragments with the respectively correct half-sequences were then ligated into the XbaI sites of the pVg1-dhfr or pVk expression vectors. In vitro mutagenesis was used to change an Ala amino acid originally encoded by oligonucleotide wps54 to the Glu (E) at position 1 of the humanized heavy chain (FIG. 26B) by changing the nucleotides CT to AG. Reactions were carried out under conditions well-known in the art (Maniatis et al., op. cit.)

The heavy chain and light chain plasmids were transfected into Sp2/0 mouse myeloma cells by electroporation and cells were selected for gpt expression. Clones were screened by assaying human antibody production in the culture supernatant by ELISA, and antibody was purified from the best-producing clones. Antibody was purified by passing tissue culture supernatant over a column of staphylococcal protein A-Sepharose CL-4B (Pharmacia). The bound antibody was eluted with 0.2M Glycine-HCl, pH3.0 and neutralized with 1M Tris PH8.0. The buffer was exchanged into PBS by passing over a PD10 column (Pharmacia).

Properties of Humanized Antibodies

The humanized mik-β1 antibody was characterized in comparison to the murine and chimeric antibodies. The humanized antibody bound to YTJB cells, which express p75 chain at a high level, in a fluorocytometric analysis in a manner similar to the chimeric antibody (FIG. 25), showing that it recognizes the same p75 protein.

The affinity of the humanized antibody was determined by competition with the radio-iodinated mouse mik-β1 antibody (FIG. 28). The binding affinities were calculated according to the methods of Berzofsky (J. A. Berzofsky and I. J. Berkower, in *Fundamental Immunology* (ed. W. E. Paul), Raven Press (New York), 595 (1984), which is incorporated herein by reference). The binding affinity of the humanized mik-β1 antibody was within about 2-fold of the affinity of the mouse mik-β1 antibody.

The ability of humanized mik-β1 plus humanized anti-Tac antibody to inhibit IL-2 stimulated proliferation of human lymphocytes was determined. Human mononuclear cells, collected from human blood by centrifugation on Ficoll-Paque (Pharmacia), were diluted to $2 \times 10^6$ cells/ml in RPMI medium+10% fetal calf serum (FCS). A 1/200 volume of phytohemagglutinin P (Difco) was added and the cells were incubated for 4 days. The cells were incubated an additional 4 days in RPMI+10% FCS+10 u/ml IL-2. $10^5$ of these PHA activated blasts were then incubated with or without 2 μg each of humanized mik-β1 and humanized anti-Tac in 150 μl of RPMI+10% FCS in wells of a 96-well plate for 1 hr, to which various dilutions of IL-2 (Amgen) were then added in 50 μl medium. The cells were incubated 48 hr, 0.5 μCi methyl-$^3$H-thymidine (Amersham, 82 Ci/mmol) was added, and the cells were incubated 24 hr. Cells were harvested with a cell harvester and radioactivity determined. The combination of the antibodies greatly inhibited proliferation of the cells in response to IL-2 (FIG. 29), suggesting a combination of the antibodies will have strong immunosuppressive properties. Humanized mik-β1 plus humanized anti-Tac inhibited proliferation much more strongly than did either antibody alone.

From the foregoing, it will be appreciated that the humanized immunoglobulins of the present invention offer numerous advantages over other p75 specific antibodies. In comparison to mouse monoclonal antibodies, the present humanized immunoglobulin can be more economically produced and contain substantially less foreign amino acid sequences. This reduced likelihood of antigenicity after injection into a human patient represents a significant therapeutic improvement.

Example 6

Design of Genes for Fd79 and Fd138-80 Humanized Light and Heavy Chains

Exemplary DNA sequences coding for the polypeptide chains comprising the heavy and light chain hypervariable regions (with human framework regions) from monoclonal antibodies Fd79 and Fd138-80, are shown in FIG. 30A through FIG. 30D.

Cloning of Heavy Chain and Light Chain cDNA cDNAs for the heavy chain and light chain variable domain genes were cloned using anchored polymerase chain regions (E. Y. Loh et al., Science 243, 217 (1989)), using 3' primers that hybridized to the constant regions and contained HindIII sites, and 5' primers that hybridized to the dG tails and contained EcoRI sites (scheme shown in FIG. 14). This method yields clones with authentic variable domain sequences, in contrast to other methods using mixed primers designed to anneal to the variable domain sequence (J. W. Larrick et al., Bio/Technology 7, 934 (1989) and Y. L. Chiang et al., BioTech. 7, 360 (1989)). The PCR amplified fragments were digested with EcoRI and HindIII and cloned into the pUC18 vector for sequencing. For Fd79, two gamma-1 specific and 5 kappa specific clones were sequenced. The two gamma-1 specific clones are identical in sequence. This heavy chain cDNA fragment encodes a signal peptide of 19 amino acids, a V region in mouse heavy chain subgroup IIIB, a D segment, and a $J_H1$ segment with 4 alterations compared to the genomic $J_H1$ sequence. The deduced amino acid sequence is shown in FIG. 30A.

The five kappa specific clones belong to two groups. Two clones are identical and encode a kappa chain in which the conserved amino acid 23 cysteine has been substituted by a tyrosine, probably representing the non-productive allele. The other three clones have an identical sequence encoding a signal peptide sequence of 20 amino acids, a V region in mouse kappa chain subgroup III, and a $J_k2$ segment with a single alteration compared to the genomic $J_k2$ sequence (FIG. 30B). The validity of the heavy chain and the kappa chain sequences was subsequently confirmed by the construction and expression of a chimeric antibody as discussed below.

The heavy chain and the kappa chain of Fd138-80 were cloned similarly. Three clones each of the heavy chain and the kappa chain were sequenced. All three heavy chain clones have an identical sequence encoding a signal peptide sequence of 19 amino acids, a V region in mouse heavy chain subgroup II, a D segment and the $J_H3$ segment (FIG. 30C). The three kappa clones are also identical in sequence. This light chain fragment encodes a signal peptide sequence of 20 amino acids, a V region gene in mouse kappa chain subgroup V and the $J_k5$ segment (FIG. 30D). Both chains shown no irregularities in coding sequence; their validity was subsequently confirmed by construction and expression of a chimeric antibody.

Construction and Expression of Chimeric Antibodies

Two plasmid vectors were prepared for construction and expression of the chimeric antibody genes. The plasmid pVg1 (FIG. 9A) contains a human cytomegalovirus IE1 promoter and enhancer (M. Boshart et al., Cell 41, 521 (1985)), the human genomic $C_\gamma1$ segment including part of the preceding intron, and the hygromycin gene (Blochlinger et al., Mol. Cell. Biol. 4, 2929 (1984), which is incorporated herein by reference) for selection. The plasmid pVk (FIG. 9B) is similar to pVg1 but contains the human genomic $C_\kappa$ segment and the gpt gene. Derivatives of the Fd79 and Fd138-80 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, C. Queen et al., Proc. Natl. Acad. Sci. USA 86, 10029 (1989), which is incorporated herein by reference). The modified V regions were cloned into the XbaI sites of the respective plasmid vectors between the CMV promoter and the partial introns of the constant regions.

For expression of the chimeric antibodies, the heavy chain and kappa chain plasmids were transfected into Sp2/0 mouse myeloma cells by electroporation and cells selected for gpt expression. Clones secreting a maximal amount of complete antibody were detected by ELISA. Purified chimeric Fd79 and Fd138-80 antibodies were shown to bind to HSV-1 infected vero cells by flow cytometry. Viral neutralization assays also indicated that the chimeric antibodies retain the neutralization activities of the murine antibodies (data not shown, but see below for similar results with humanized antibodies).

Computer Modeling of Humanized Antibodies

In order to retain high binding affinity in the humanized antibodies, the general procedures of Queen et al. were followed (C. Queen et al., Proc. Natl. Acad. Sci. USA 86, 10029 (1989), which is incorporated herein by reference). The more homologous a human antibody is to the original murine antibody, the less likely will combining the murine CDRs with the human framework be to introduce distortions into the CDRs that could reduce affinity. Normally the heavy chain and light chain from the same human antibody are chosen to provide the framework sequences, so as to reduce the possibility of incompatibility in the assembling of the two chains. Based on sequence homology search against the NBRF protein sequence database (performed with the MicroGenie Sequence Analysis Software (Beckman)), the antibody Pom was chosen to provide the framework sequences for humanization of Fd79.

The computer program ENCAD (Levitt, J. Mol. Biol. 168, 595 (1983), which is incorporated herein by reference) was used to construct a model of the Fd79 variable region. Inspection of the refined model of murine Fd79 revealed two amino acid residues in the framework that are close enough to have significant contacts with the CDR residues (Table 5). Lys in light chain position 49 has contacts with 3 amino acids in CDR2 of the light chain (L50 Tyr, L53 Asn, L55 Glu) and 2 amino acids in CDR3 of the heavy chain (H99 Asp, H100 Tyr). Leu in heavy chain position 93 also shows interactions with 2 amino acids in CDR2 of the heavy chain (H35 Ser, H37 Val) and an amino acid in CDR3 of the heavy chain (H100C Phe). Hence, L49 Lys and H93 Leu were retained in the construction of humanized Fd79, as their replacement with human Pom framework residues would be likely to introduce distortions into the CDRs. Also, 7 other residues in the Pom framework (5 in the light chain and 2 in the heavy chain) were substituted with common human residues (identical to the murine Fd79 sequence in 6 of the choices) because of their rare occurrence in other human antibodies. The elimination of unusual amino acids in the framework may further reduce immunogenicity. The murine Fd79 sequences and the corresponding humanized sequences are shown in FIG. 30A and FIG. 30B. Substituted residues in the Pom framework are underlined.

TABLE 5

Residues in the framework sequence showing contacts with residues in the hypervariable regions.

| Residue No.[1] | Amino Acid | Contacting CDR residues[2] |
|---|---|---|
| Fd79 | | |
| L49 | Lys | L50Y, L53N, L55E, H99D, H100Y |
| H93 | Leu | H35S, H37V, H100CF |
| Fd138-80 | | |
| L36 | His | L34V, L89Q |
| H27 | Tyr | H32H, H34I |
| H30 | Tyr | H32H, H53R |
| H48 | Phe | H63F |
| H66 | Lys | H63F |
| H67 | Ala | H63F |

[1]. The amino acid residues are numbered according to the Kabat system (E. A. Kabat et al., Sequences of Proteins of Immunological Interest, National Institutes of Health, Bethesda, MD (1987)): the first letter (H or L) stands for the heavy chain or light chain. The following number is the residue number. The last letter is the amino acid one letter code.
[2]. The hypervariable regions are defined according to Kabat: Light chain CDR1: residue 24–34; CDR2: 50–56; CDR3: 89–97. Heavy chain CDR1: 31–35; CDR2: 50–65; CDR3: 95–102.

Similarly, the murine heavy chain and light chain sequences of Fd138-80 were subjected to sequence homology search against the NBRF protein sequence database. The sequences of the human antibody Eu were selected to provide the framework sequences for humanized Fd138-80. Inspection of a computer-generated model of Fd138-80 revealed 6 amino acid residues in the framework that are close enough to have important contacts with CDR residues.

The residues and their contacting counterparts are listed in Table 5; these murine residues were retained in the construction of humanized Fd138-80. Two other residues (L87 Phe and H37 Met) show significant contacts with L98 Phe, which is immediately adjacent to CDR3, so these two mouse residues were also retained. Eight amino acids in the Eu framework (2 in the light chain and 6 in the heavy chain) were substituted with the murine residues (which are also consistent with the human consensus residues) because of their rare occurrence in other human antibodies. The murine Fd138-80 sequences and the corresponding humanized sequences are shown in FIG. 30C and FIG. 30D. Substituted residues in the Eu framework are underlined.

For the construction of genes for the humanized antibodies, nucleotide sequences were selected that encode the protein sequences of the humanized heavy and light chains, including the signal peptides, generally utilizing codons found in the mouse sequence. Several degenerate codons were changed to create restriction sites or to remove undesirable ones. The nucleotide sequences also included the same splice donor signals used in the chimeric genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal. The oligonucleotides were synthesized on an Applied Biosystems 380B DNA synthesizer. Each oligo was about 110–140 bases long with a 15 base overlap. Double stranded DNA fragments were synthesized with Klenow polymerase, digested with restriction enzymes, ligated to pUC18 vector and sequenced. The two fragments with the correct sequences were then ligated into the XbaI sites of pVg1 or pVk expression vectors.

The synthetic genes were then cloned into the pVg1 and pVk expression vectors. For each humanized antibody constructed, the heavy chain and light chain plasmids were transfected into Sp2/0 mouse myeloma cells by electroporation and cells were selected for gpt expression. Clones were screened by assaying human antibody production in the culture supernatant by ELISA, and antibody was purified from the best-producing clones. Antibodies were purified by passing tissue culture supernatant over a column of staphylococcal protein A-Sepharose CL-4B (Pharmacia). The bound antibodies were eluted with 0.2M Glycine-HCl, pH3.0 and neutralized with 1M Tris PH8.0. The buffer was exchanged into PBS by passing over a PD10 column (Pharmacia).

Properties of Humanized Antibodies

The humanized Fd79 and Fd138-80 antibodies were characterized in comparison to the murine and chimeric antibodies. Both humanized antibodies bind to Vero cells infected with HSV-1 in a fluorocytometric analysis in a manner similar to the chimeric antibodies (FIG. 31A and FIG. 31B), suggesting that they recognize their respective viral antigens. To more quantitatively assess the binding activity, radioiodinated murine antibodies were bound to virally infected cells and Scatchard analysis performed.

The affinities of the humanized antibodies were determined by competition with the iodinated antibodies. Vero cells infected with HSV-1 were used as source of gB and gD antigens. Increasing amounts of competitor antibody (mouse or humanized) were added to 1.5 ng of radioiodinated tracer mouse antibody (2 uCi/ug) and incubated with $4 \times 10^5$ infected Vero cells in 0.2 ml of binding buffer (PBS+2%

FCS+0.1% azide) for 1 hr. at 4° C. Cells were washed and pelleted, and their radioactivities were measured. The concentrations of bound and free tracer antibody were calculated. The binding affinities were calculated according to the methods of Berzofsky (J. A. Berzofsky and I. J. Berkower, in *Fundamental Immunology* (ed. W. E. Paul), Raven Press (New York), 595 (1984), which is incorporated herein by reference).

The measurements indicate that there is no significant loss of binding affinities in the humanized antibodies (Table 6). Specifically, there is an approximately 2-fold decrease in affinity in humanized Fd79 compared to the murine Fd79 (Ka of $5.3 \times 10^7$ $M^{-1}$ vs. $1.1 \times 10^8$ $M^{-1}$). The affinity of humanized Fd138-80 is comparable to that of the murine antibody (Ka of $4.8 \times 10^7$ $M^{-1}$ vs $5.2 \times 10^7$ $M^{-1}$).

TABLE 6

Binding affinities of murine and humanized antibodies.

| | Mouse $K_a$ $(m^{-1})$ | Humanized $K_a$ $(m^{-1})$ |
|---|---|---|
| Fd79 (anti-gB) | $1.1 \times 10^8$ | $5.3 \times 10^7$ |
| Fd138-80 (anti-gD) | $5.2 \times 10^7$ | $4.8 \times 10^7$ |

Murine Fd79 and Fd138-80 have been shown to neutralize HSV-1 in vitro without complement (J. Koga et al., Virology 151, 385 (1986)), so the neutralizing activities of the humanized antibodies were compared with the mouse antibodies. Serial dilutions of equal quantities of murine and humanized antibodies were incubated with virus for 1 hr. before inoculation onto Vero cells. After 4 days, cells were stained with neutral red to visualize plaques. Results from these plaque reduction assays indicated that both humanized Fd79 and Fd138-80 neutralize virus as efficiently as their murine counterparts (FIGS. 32A and B). Both humanized and murine Fd79 cause a 90% reduction of plaques at an antibody concentration of 10 nM (1.5 ug/ml). Similarly, humanized and murine Fd138-80 were able to cause a 90% plaque reduction at equivalent levels.

The antibodies were also investigated for their ability to protect cells from viral spread in tissue culture. Vero cells were inoculated with virus at 0.1 pfu/cell and allowed to adsorb for 2 hrs. at 37° C. before addition of 10 ug/ml antibody. After four days, cells were stained with an anti-gB antibody for detection of viral antigens on infected cells. Results indicated that both murine and humanized Fd79 at 10 ug/ml protected culture cells from infection (FIG. 33A). However, neither murine nor humanized Fd138-80 were able to protect cells against viral spread (FIG. 33B), despite their ability to neutralize virus before inoculation. Both gB and gD are thought to be associated with cell fusion and virus infectivity (W. Cai et al., J. Virol. 62, 2596 (1988) and A. O. Fuller and P. G. Spear, Proc. Natl. Acad. Sci. USA 84, 5454 (1987)). However, it is possible that Fd79 blocks both the infectivity and cell fusion functions of gB, while Fd138-80 blocks only the infectivity function of gD, so virus can still spread cell-to-cell.

The binding, neutralization and protection results all indicate that the humanized Fd79 and Fd138-80 antibodies have retained the binding activities and the biological properties of the murine monoclonal antibodies. The availability of humanized antibodies with specificity for HSV gB and gD, inter alia, provides an opportunity for studies of the in vivo potency and immunogenicity of humanized antibodies in treating viral diseases. The recognition by Fd79 and Fd138-80 of type-common epitopes of gB and gD (J. Koga et al., Virology 151, 385 (1986)) expands the therapeutic potential to herpes simplex virus type 2 as well as type 1.

The use of a combination of two or more humanized antibodies in therapy is important for reducing the development of antibody resistant strains. Combination therapy of humanized antibodies with other antiviral agents such as acyclovir provides further opportunities to combat diseases when chemotherapeutic agents alone have not been effective. As Fd79 and Fd138-80 reduce the frequency of viral persistence in a murine ocular model (J. F. Metcalf et al., Cur. Eye Res. 6, 173 (1987)), the humanized antibodies, typically together with other antiviral agents, are capable of reducing episodes of recurrent genital infection, an area where traditional anti-viral agents have not been effective (L. Corey et al., N. Engl. J. Med. 306, 1313 (1982)). Incorporation of the human constant domains can also enhance effector functions, such as antibody-dependent cellular cytotoxicity, leading to greater therapeutic efficiency in human patients.

From the foregoing, it will be appreciated that the humanized immunoglobulins of the present invention offer numerous advantages over other HSV specific antibodies. In comparison to mouse monoclonal antibodies, the present humanized immunoglobulin can be more economically produced and contain substantially less foreign amino acid sequences. This reduced likelihood of antigenicity after injection into a human patient represents a significant therapeutic improvement.

Example 7

Design of Genes for M195 Humanized Light and Heavy Chains

The p67 protein or CD33 antigen is found on the surface of progenitors of myeloid cells and of the leukemic cells of most cases of AML, but not on lymphoid cells or non-hematopoietic cells (see, Leucocyte Typing III, ed. by A. J. McMichael, Oxford University Press, pp. 622–629 (1987), which is incorporated herein by reference). Antibodies that are known to bind to the CD33 antigen include L4B3, L1B2 and MY9 (Andrews et al., Blood 62, 124 (1983) and Griffin et al., Leukemia Research 8, 521 (1984), both of which are incorporated herein by reference).

Another antibody that binds to CD33 is M195 (Tanimoto et al., Leukemia 3, 339 (1989) and Scheinberg et al., Leukemia 3, 440 (1989), both of which are incorporated herein by reference).

Cloning of Heavy Chain and Light Chain cDNA cDNAs for the heavy chain and light chain variable domain genes were cloned using anchored polymerase chain reactions (E. Y. Loh et al., Science 243, 217 (1989)), using 3' primers that hybridized to the constant regions and contained HindIII sites, and 5' primers that hybridized to the dG tails and contained EcoRI sites (scheme shown in FIG. 14). The PCR amplified fragments were digested with EcoRI and HindIII and cloned into the pUC18 vector for sequencing. For M195, two gamma-2a specific and two kappa specific clones were sequenced. The two gamma-2a clones and two kappa clones are respectively identical in sequence. The cDNA variable domain sequences and the deduced amino acid sequences are shown in FIG. 34A and FIG. 34B.

Construction and Expression of Chimeric Antibody

Two plasmid vectors were prepared for construction and expression of the chimeric antibody genes. The plasmid pVg1-dhfr (FIG. 24A) contains a human cytomegalovirus IE1 promoter and enhancer (M. Boshart et al., Cell 41, 521 (1985)), the human genomic Cγ1 segment including part of the preceding intron, and a dihydrofolate reductase (dhfr) gene (Simonsen et al., Proc. Natl Acad. Sci. USA 80, 2495 (1984), which is incorporated herein by reference) for selection. The plasmid pVk (FIG. 24B) is similar to pVg1-dhfr but contains the human genomic Cκ segment and the gpt gene. Derivatives of the M195 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, Queen et al., Proc. Natl. Acad. Sci. USA 86, 10029 (1989), which is incorporated herein by reference). The modified V regions were cloned into the XbaI sites of the respective plasmid vectors between the CMV promoter and the partial introns of the constant regions.

For expression of the chimeric antibody, the heavy chain and kappa chain plasmids were transfected into Sp2/0 mouse myeloma cells by electroporation and cells selected for gpt expression. Clones secreting a maximal amount of complete antibody were detected by ELISA. Purified chimeric M195 antibody was shown to bind to U937 cells, which express the CD33 antigen, by flow cytometry (FIG. 35).

Computer Modeling of Humanized Antibodies

In order to retain high binding affinity in the humanized antibodies, the general procedures of Queen et al. were followed (see, Queen et al., Proc. Natl. Acad. Sci. USA 86, 10029 (1989) and WO 90/07861, which are incorporated herein by reference). The more homologous a human antibody is to the original murine antibody, the less likely will combining the murine CDR's with the human framework be to introduce distortions into the CDR's that could reduce affinity. Normally the heavy chain and light chain from the same human antibody are chosen to provide the framework sequences, so as to reduce the possibility of incompatibility in the assembling of the two chains. Based on sequence homology search against the NBRF protein sequence database (performed with the MicroGenie Sequence Analysis Software (Beckman)), the antibody Eu was chosen to provide the framework sequences for humanization of M195.

The computer program ENCAD (M. Levitt, J. Mol. Biol. 168, 595 (1983), which is incorporated herein by reference) was used to construct a model of the M195 variable region. The model was used to determine the amino acids in the M195 framework that were close enough to the CDR's to potentially interact with them (category 4 below). To design the humanized light and heavy chain M195 variable regions, at each position the amino acid was chosen to be the same as in the Eu antibody, unless that position fell in one or more of four categories:

(1) The position fell within a CDR,
(2) The Eu amino acid was unusual for human antibodies at that position, whereas the M195 amino acid was typical for human antibodies at that position,
(3) The position was immediately adjacent to a CDR,
(4) The model described above suggested that the amino acid may be physically close to the antigen binding region (CDR's).

In category (2), "unusual" is interpreted to include amino acids that occur in less than about 20% of the human sequences in the same subgroups (as defined by Kabat et al., op. cit.) as the Eu light and heavy chains, and "typical" is interpreted to include amino acids that occur in more than about 25% but generally more than 50% of the human sequences in those subgroups. For positions in these categories, the amino acid from the mouse M195 antibody was used: The amino acids in each category are shown in Table 7. Some amino acids may be in more than one category. The final sequences of the humanized M195 light and heavy chain variable domains are shown in FIG. 36A and FIG. 36B, compared with the Eu sequences.

TABLE 7

| Category | Light Chain | Heavy Chain |
| --- | --- | --- |
| 1 | 24–38, 54–60, 93–101 | 31–35, 50–66, 99–105 |
| 2 | 10, 52, 67, 110 | 93, 95, 98, 106, 107, 108, 110 |
| 3 | — | 30, 67, 98, 106 |
| 4 | 40, 52, 74 | 27, 30, 48, 68, 98 |

For the construction of genes for the humanized antibodies, nucleotide sequences were selected that encode the protein sequences of the humanized heavy and light chains, including the same signal peptides as in the mouse M195 chains (FIG. 34A and FIG. 34B), generally utilizing codons found in the mouse sequence. Several degenerate codons were changed to create restriction sites or to remove undesirable ones. The nucleotide sequences also included the same splice donor signals used in the chimeric genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal (FIG. 37A and FIG. 37B). The oligonucleotides were synthesized on an Applied Biosystems 380B DNA synthesizer. Each oligo was about 110–140 bases long with about a 15 base overlap. Double stranded DNA fragments were synthesized with Klenow polymerase from each pair of oligonucleotides, digested with restriction enzymes, ligated to the pUC18 vector and sequenced. Two fragments with the respectively correct half-sequences were then ligated into the XbaI sites of the pVg1-dhfr or pVk expression vectors in the appropriate orientations to produce the complete heavy and light chain genes. Reactions were carried out under conditions well-known in the art (Maniatis et al., op. cit.)

The heavy chain and light chain plasmids were transfected into Sp2/0 mouse myeloma cells by electroporation and cells were selected for gpt expression. Clones were screened by assaying human antibody production in the culture supernatant by ELISA, and antibody was purified from the best-producing clones. Antibody was purified by passing tissue culture supernatant over a column of staphylococcal protein A-Sepharose CL-4B (Pharmacia). The bound antibody was eluted with 0.2M Glycine-HCl, pH3.0 and neutralized with 1M Tris PH8.0. The buffer was exchanged into PBS by passing over a PD10 column (Pharmacia).

Properties of Humanized Antibodies

The humanized M195 antibody was characterized in comparison to the murine and chimeric antibodies. The humanized antibody bound to U937 cells in a fluorocytometric analysis in a manner similar to the chimeric antibody (FIG. 35), showing that it recognizes the same CD33 antigen.

The affinity of the humanized antibody was determined by competition with the radio-iodinated mouse M195 antibody (FIG. 38). The binding affinities were calculated according to the methods of Berzofsky (J. A. Berzofsky and I. J. Berkower, in *Fundamental Immunology* (ed. W. E. Paul), Raven Press (New York), 595 (1984), which is incorporated herein by reference). The mouse M195 had an affinity comparable to the published value (Tanimoto et al., op. cit.) and the humanized M195 antibody had an affinity the same as the mouse M195 to within experimental error.

Humanized M195 is useful to mediate antibody-dependent cellular cytotoxicity when human effector cells and human CD33-expressing cells are used. This is analogous to other humanized antibodies, such as reported by Junghans et al., Cancer Research 50, 1495 (1990), which is incorporated herein by reference.

From the foregoing, it will be appreciated that the humanized immunoglobulins of the present invention offer numerous advantages over other CD33 specific antibodies. In comparison to mouse monoclonal antibodies, the present humanized immunoglobulins can be more economically produced and contain substantially less foreign amino acid sequences. This reduced likelihood of antigenicity after injection into a human patient represents a significant therapeutic improvement.

Example 8

Design of Genes for CMV5 Humanized Light and Heavy Chains

Three neutralizing antibodies to the gH glycoprotein of human cytomegalovirus (CMV) are designated CMV5, CMV109 and CMV115.

Exemplary DNA sequences, which on expression code for the polypeptide chains comprising the heavy and light chain CDR's of monoclonal antibody CMV5 are included in FIG. 39A and FIG. 39B. Due to codon degeneracy and non-critical amino-acid substitutions, other DNA sequences can be readily substituted for those sequences, as detailed below. Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in the vectors pVk and pVg1-dhfr (FIGS. 24A and 24B) using site-directed mutagenesis, such as after CH1 to produce Fab fragments or after the hinge region to produce (Fab')$_2$ fragments.

Cloning of Heavy Chain and Light Chain cDNA cDNAs for the heavy chain and light chain variable domain genes were cloned using anchored polymerase chain reactions (E. Y. Loh et al., Science 243, 217 (1989)), using 3' primers that hybridized to the constant regions and contained HindIII sites, and 5' primers that hybridized to the dG tails and contained EcoR I sites (scheme shown in FIG. 14). The PCR amplified fragments were digested with EcoR I and HindIII and cloned into the pUC18 vector for sequencing. For CMV5, two gamma-2a specific and two kappa specific clones were sequenced. The two gamma-2a clones and two kappa clones are respectively identical in sequence. The cDNA variable domain sequences and the deduced amino acid sequences are shown in FIG. 39A and FIG. 39B. Similarly, by using techniques, which are well-known in the art, cDNAs for the CMV109 and CMV115 antibodies may be obtained and their sequence determined.

Construction and Expression of Chimeric Antibody

Two plasmid vectors were prepared for construction and expression of the chimeric antibody genes. The plasmid pVg1-dhfr (FIG. 24A) contains a human cytomegalovirus IE1 promoter and enhancer (M. Boshart et al., Cell 41, 521 (1985)), the human genomic Cγ1 segment including part of the preceding intron, and a dihydrofolate reductase (dhfr) gene (Simonsen et al., Proc. Natl. Acad. Sci. USA 80, 2495 (1983), which is incorporated herein by reference) for selection. The plasmid pVk (FIG. 24B) is similar to pVg1-dhfr but contains the human genomic Cκ segment and the gpt gene. Derivatives of the CMV5 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, Queen et al., Proc. Natl. Acad. Sci. USA 86, 10029 (1989), which is incorporated herein by reference). The modified V regions were cloned into the XbaI sites of the respective plasmid vectors between the cytomegalovirus promoter and the partial introns of the constant regions.

For expression of the chimeric antibody, the heavy chain and kappa chain plasmids were transfected into Sp2/0 mouse myeloma cells by electroporation and cells selected for gpt expression. Clones secreting a maximal amount of complete antibody were detected by ELISA. Purified chimeric CMV5 antibody was shown to bind to CMV-infected cells, which express the gH antigen, by immunostaining of CMV-infected human embryonic lung fibroblasts.

Computer Modeling of Humanized Antibodies

In order to retain high binding affinity in the humanized antibodies, the general procedures of Queen et al. were followed (see, Queen et al., Proc. Natl. Acad. Sci. USA 86, 10029 (1989) and WO 90/07861, which are incorporated herein by reference). The more homologous a human antibody is to the original murine antibody, the less likely will combining the murine CDR's with the human framework be to introduce distortions into the CDR's that could reduce affinity. Normally the heavy chain and light chain from the same human antibody are chosen to provide the framework sequences, so as to reduce the possibility of incompatibility in the assembling of the two chains. Based on sequence homology search against the NBRF protein sequence database (performed with the MicroGenie Sequence Analysis Software (Beckman)), the antibody Wol was chosen to provide the framework sequences for humanization of CMV5.

The computer program ENCAD (M. Levitt, J. Mol. Biol. 168, 595 (1983), which is incorporated herein by reference) was used to construct a model of the CMV5 variable region. The model was used to determine the amino acids in the CMV5 framework that were close enough to the CDR's to potentially interact with them (category 4 below). To design the humanized light and heavy chain CMV5 variable regions, at each position the amino acid was chosen to be the same as in the Wol antibody, unless that position fell in one or more of five categories:

(1) The position fell within a CDR, (2) The Wol amino acid was unusual for human antibodies at that position, whereas the CMV5 amino acid was typical for human antibodies at that position, (3) The position was immediately adjacent to a CDR, (4) The model described above suggested that the amino acid may be physically close to the antigen binding region (CDR's).

In category (2), "unusual" is interpreted to include amino acids that occur in less than about 20% of the human sequences in the same subgroups (as defined by Kabat et al., op. cit.) as the Wol light and heavy chains, and "typical" is interpreted to include amino acids that occur in more than about 25% but generally more than 50% of the human sequences in those subgroups. For positions in these categories, the amino acid from the mouse CMV5 antibody was used. In addition, a position was in the fifth category if the Wol amino acid was highly unusual for human antibodies at that position, and the CMV5 amino acid was different but also unusual. Then an amino acid typical for human antibodies at that position may be used.

The amino acids in each category are shown in Table 8. Some amino acids may be in more than one category. The final sequences of the humanized CMV5 light and heavy chain variable domains are shown in FIG. 40A and FIG. 40B, compared with the Wol sequences.

TABLE 8

| Category | Light Chain | Heavy Chain |
| --- | --- | --- |
| 1 | 24–34, 50–56, 89–97 | 31–35, 50–66, 99–108 |
| 2 | | 69, 80 |
| 3 | 49 | 30 |
| 4 | | 24, 27, 28, 30, 97 |
| 5 | | 5 |

For the construction of genes for the humanized antibodies, nucleotide sequences were selected that encode the protein sequences of the humanized heavy and light chains, including the same signal peptides as in the mouse CMV5 chains (FIG. 39A and FIG. 39B), generally utilizing codons found in the mouse sequence. Several degenerate codons were changed to create restriction sites or to remove undesirable ones. The nucleotide sequences also included the same splice donor signals used in the chimeric genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal (FIG. 41A and FIG. 41B). The oligonucleotides were synthesized on an Applied Biosystems 380B DNA synthesizer. Each oligo was about 110–140 bases long with about a 15 base overlap. Double stranded DNA fragments were synthesized with Klenow polymerase from each pair of oligonucleotides, digested with restriction enzymes, ligated to the pUC18 vector and sequenced. Two fragments with the respectively correct half-sequences were then ligated into the XbaI sites of the pVg1-dhfr or pVk expression vectors in the appropriate orientations to produce the complete heavy and light chain genes. Reactions were carried out under conditions well-known in the art (Maniatis et al., op. cit.)

The heavy chain and light chain plasmids are transfected into Sp2/0 mouse myeloma cells by electroporation and cells are selected for gpt expression. Clones are screened by assaying human antibody production in the culture supernatant by ELISA, and antibody purified from the best-producing clones. Antibody is purified by passing tissue culture supernatant over a column of staphylococcal protein A-Sepharose CL-4B (Pharmacia). The bound antibody is eluted with 0.2M Glycine-HCl, pH3.0 and neutralized with 1M Tris PH8.0. The buffer is exchanged into PBS by passing over a PD10 column (Pharmacia).

Humanized antibody was also produced by transient transfection. The heavy chain and light chain plasmids were transfected into S194 cells (ATCC TIB 19) by the DEAE-dextran method (Queen et al., Mol. Cell. Biol. 4, 1043 (1984), which is incorporated herein by reference), and humanized CMV5 antibody was purified from the media supernatant as above. Antibody was quantitated by ELISA assay for human Ig.

Properties of Humanized Antibodies

The humanized CMV5 antibody was characterized in comparison to the murine and chimeric antibodies. The humanized CMV5 antibody was shown to bind about as well as the mouse and chimeric antibodies to CMV antigen, by immunostaining of CMV-infected human embryonic lung (HEL) cells (ATCC CCL 137). HEL cells monolayers in 96-well plates were infected wtih CMV at 0.01 pfu/cell, incubated for 4 days, dried at 37° C. and stored wrapped at 4° C. 100 μl blotto (5% Carnation Instant Milk in PBS at pH 7.4) was added to each well and incubated at 37° C. for 30 min. The blotto was poured off and 75 μl of a series of 2-fold dilutions of mouse, chimeric and humanized CMV5 antibody was added to the wells. The plate was incubated 1 hr at 37° C. and washed twice with blotto (each wash was left on for 10 min). Then 75 μl of diluted peroxidase (HRP) conjugated goat anti-mouse or anti-human IgG (Tago) was added to each well and incubated for 1 hr at 37° C. The plate was washed 2× with PBS and 150 μl of HRP substrate solution was added to each well. Color was allowed to develop at room temperature. The plates were washed with water and air dried. The wells were examined under a microscope to determine the highest dilution of the antibodies that formed a colored precipitate on the CMV-infected cells. For all three antibodies, 63 ng/ml was the least amount of antibody that produced a detectable precipitate, indicating that humanized CMV5 binds about as well as the mouse and chimeric antibodies.

To compare the affinities of mouse and humanized CMV5 in another way, a competition experiment was performed. Plates of CMV-infected HEL cells as above were incubated with blotto for 30 min at 37° C. The blotto was poured off and dilutions of mouse or humanized CMV5 were added to each well in 75 μl of PBS. Then 125 μl of radio-iodinated mouse CMV5 (1 μCi/μg) in PBS, containing 28,000 cpm was added to each well and incubated at 37° C. for 2.5 hr. The plate was washed 5 times with PBS, and the contents of each well were solubilized with 200 μl of 2% SDS and counted. Increasing concentrations of mouse and humanized CMV5 inhibited binding of the radiolabeled CMV5 about equally well (FIG. 42), so humanized CMV5 has approximatley the same binding affinity as mouse CV5. An irrelevant antibody did not compete in this assay.

The ability of humanized CMV5 to neutralize CMV is compared to that of mouse CMV5. Mouse and humanized CMV5 are successively diluted by 2-fold in 100 μl of DME medium+2% FCS in wells of a 96-well plate. 100 μl of CMV, which has been diluted to contain 100 tissue culture infectious dose-50% (TCID50) units, are added to each well and incubated for 60 min at 37° C. Each well of antibody-virus mixture is added to a well of subconfluent HEL cells in a 96-well plate from which the medium has been removed. The cells are incubated for 5 days and cytopathic effect (CPE) is examined in each well under a microscope. The highest dilution of antibody that inhibits CPE by 90% is a measure of the neutralizing ability of the antibody. The humanized CMV5 antibody will neutralize CMV antibody approximately as well as the mouse CMV5 antibody.

From the foregoing, it will be appreciated that the humanized immunoglobulins of the present invention offer numerous advantages over other CMV specific antibodies. In comparison to mouse monoclonal antibodies, the present humanized immunoglobulins can be more economically produced and contain substantially less foreign amino acid sequences. This reduced likelihood of antigenicity after injection into a human patient represents a significant therapeutic improvement.

Example 9

Design of Genes for AF2 Human-like Light and Heavy Chains

This example is directed to recombinant DNA segments encoding the heavy and/or light chain CDR's from an immunoglobulin capable of binding to a desired epitope of γ-IFN, such as monoclonal antibody AF2. Exemplary DNA sequences, which on expression code for the polypeptide chains comprising the heavy and light chain CDR's of monoclonal antibody AF2 are included in FIG. 43A and FIG. 43B. Due to codon degeneracy and non-critical amino-acid substitutions, other DNA sequences can be readily substituted for those sequences.

Cloning of Heavy Chain and Light Chain cDNA cDNAs for the heavy chain and light chain variable domain genes were cloned using anchored polymerase chain reactions (E. Y. Loh et al., Science 243, 217 (1989)), using 3' primers that hybridized to the constant regions and contained HindIII sites, and 5' primers that hybridized to the dG tails and contained EcoR I sites (scheme shown in FIG. 14). The PCR amplified fragments were digested with EcoR I and HindIII and cloned into the pUC18 vector for sequencing. For AF2, two gamma-2b specific and two kappa specific clones were sequenced. The two gamma-2b clones and two kappa clones are respectively identical in sequence. The cDNA variable domain sequences and the deduced amino acid sequences are shown in FIG. 43A and FIG. 43B.

Construction and Expression of Chimeric Antibody

Two plasmid vectors were prepared for construction and expression of the chimeric antibody genes. The plasmid pVg1-dhfr (FIG. 24A) contains a human cytomegalovirus IE1 promoter and enhancer (M. Boshart et al., Cell 41, 521 (1985)), the human genomic Cγ1 segment including part of the preceding intron, and a dihydrofolate reductase (dhfr) gene (Simonsen et al., Proc. Natl. Acad. Sci. USA 80, 2495 (1984), which is incorporated herein by reference) for selection. The plasmid pVk (FIG. 24B) is similar to pVg1-dhfr but contains the human genomic Cκ segment and the gpt gene. Derivatives of the AF2 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, Queen et al., Proc. Natl. Acad. Sci. USA 86, 10029 (1989), which is incorporated herein by reference). The modified V regions were cloned into the XbaI sites of the respective plasmid vectors between the CMV promoter and the partial introns of the constant regions.

For expression of the chimeric antibody, the heavy chain and kappa chain plasmids were transfected into Sp2/0 mouse myeloma cells by electroporation and cells selected for gpt expression. Clones secreting a maximal amount of complete antibody were detected by ELISA. Chimeric AF2 antibody was shown to bind to human γ-IFN by ELISA.

Computer Modeling of Humanized Antibodies

In order to retain high binding affinity in the humanized antibodies, the general procedures of Queen et al. were followed (see, Queen et al., Proc. Natl. Acad. Sci. USA 86, 10029 (1989) and WO 90/07861, which are incorporated herein by reference). The more homologous a human antibody is to the original murine antibody, the less likely will combining the murine CDR's with the human framework be to introduce distortions into the CDR's that could reduce affinity. Normally the heavy chain and light chain from the same human antibody are chosen to provide the framework sequences, so as to reduce the possibility of incompatibility in the assembling of the two chains. Based on sequence homology search against the NBRF protein sequence database (performed with the MicroGenie Sequence Analysis Software (Beckman)), the antibody Eu was chosen to provide the framework sequences for humanization of AF2.

The computer program ENCAD (M. Levitt, J. Mol. Biol. 168, 595 (1983), which is incorporated herein by reference) was used to construct a model of the AF2 variable region. The model was used to determine the amino acids in the AF2 framework that were close enough to the CDR's to potentially interact with them (category 4 below). To design the humanized light and heavy chain AF2 variable regions, at each position the amino acid was chosen to be the same as in the Eu antibody, unless that position fell in one or more of five categories:

(1) The position fell within a CDR, (2) The Eu amino acid was unusual for human antibodies at that position, whereas the AF2 amino acid was typical for human antibodies at that position, (3) The position was immediately adjacent to a CDR, (4) The model described above suggested that the amino acid may be physically close to the antigen binding region (CDR's).

In category (2), "unusual" is interpreted to include amino acids that occur in less than about 20% of the human sequences in the same subgroups (as defined by Kabat et al., op. cit.) as the Eu light and heavy chains, and "typical" is interpreted to include amino acids that occur in more than about 25% but generally more than 50% of the human sequences in those subgroups. For positions in these categories, the amino acid from the mouse AF2 antibody was used. In addition, a position was in the fifth category if the Eu amino acid was highly unusual for human antibodies at that position, and the AF2 amino acid was different but also unusual. Then an amino acid typical for human antibodies at that position may be used.

The amino acids in each category are shown in Table 9. Some amino acids may be in more than one category. The final sequences of the humanized AF2 light and heavy chain variable domains are shown in FIG. 44A and FIG. 44B, compared with the Eu sequences.

TABLE 9

| Category | Light Chain | Heavy Chain |
| --- | --- | --- |
| 1 | 24–34, 50–56, 89–97 | 31–35, 50–66, 99–106 |
| 2 | 48 | 93, 95, 98, 107, 108, 109, 111 |
| 3 | | 30, 98, 107 |
| 4 | 48, 70 | 27, 28, 30, 98, 107 |
| 5 | 63 | |

For the construction of genes for the humanized antibodies, nucleotide sequences were selected that encode the protein sequences of the humanized heavy and light chains, plus typical immunoglobulin signal sequences, generally utilizing codons found in the mouse sequence. Several degenerate codons were changed to create restriction sites or to remove undesirable ones. The nucleotide sequences also included the same splice donor signals used in the chimeric genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal (FIG. 45A and FIG. 45B) The oligonucleotides were synthesized on an Applied Biosystems 380B DNA synthesizer. Each oligo was about 110–140 bases long with about a 15 base overlap. Double stranded DNA fragments were synthesized with Klenow polymerase from each pair of oligonucleotides, digested with restriction enzymes, ligated to the pUC18 vector and sequenced. Two fragments with the respectively correct half-sequences are then ligated into the XbaI sites of the pVg1-dhfr or pVk expression vectors in the appropriate orientations to produce the complete heavy and light chain genes. Reactions are carried out under conditions well-known in the art (Maniatis et al., op. cit.)

The heavy chain and light chain plasmids are transfected into Sp2/0 mouse myeloma cells by electroporation and cells selected for gpt expression. Clones are screened by assaying human antibody production in the culture supernatant by ELISA, and antibody purified from the best-producing clones. Antibody is purified by passing tissue culture supernatant over a column of staphylococcal protein A-Sepharose CL-4B (Pharmacia). The bound antibody is eluted with 0.2M Glycine-HCl, pH3.0 and neutralized with 1M Tris PH8.0. The buffer is exchanged into PBS by passing over a PD10 column (Pharmacia).

Properties of Humanized Antibodies

The humanized AF2 antibody is characterized in comparison to the murine and chimeric antibodies. The humanized antibody will bind to γ-IFN in an ELISA assay in a manner similar to the mouse and chimeric antibodies, showing that it recognizes γ-IFN.

To compare the binding affinities of mouse AF2 antibody and humanized AF2 antibody, a competitive ELISA assay is performed. An ELISA plate is coated with human recombinant γ-IFN by adding 100 μl of a 500 ng/ml solution of γ-IFN in PBS to each well and incubating overnight at 4° C. Subsequent steps are carried out at room temperature. The γ-IFN solution is removed and 200 μl of ELISA buffer (0.1% Tween-20, 1% Bovine serum albumin in PBS) is added to each well and incubated for 1 hr. After removing the solution, varying amounts of competitor antibody (mouse AF2 or humanized AF2) in 100 μl PBS is added to each well, along with an amount of biotinylated AF2 predetermined to give a good ELISA response. The plate is incubated for 1 hr and then washed 3 times with ELISA buffer. An amount of horseradish peroxidase (HRP)-conjugated strepavidin predetermined to be in excess is added in 100 μl PBS to each well and incubated for 30 min. The plate is washed 3 times in ELISA buffer, and 100 μl of substrate solution for HRP is added to each well. The plate is incubated for 10–30 min, and the optical density of each well is determined with an ELISA reader (BioRad). The decrease in optical density with increasing concentrations of competitor antibodies mouse AF2 and humanized AF2 are plotted. Mouse AF2 and humanized AF2 will compete similarly, showing that their binding affinities for γ-IFN are approximately the same. The procedures used are well known in the art (e.g., Harlow and Lane, op. cit.).

An important biological activity of γ-IFN is the induction of expression of class II HLA antigens on cells. To determine the ability of mouse and humanized AF2 to neutralize this activity, about $5 \times 10^4$ HS294T cells (Basham et al., J. Immunol. 130, 1492 (1983), which is incorporated herein by reference) are plated in 1.0 ml DMEM medium+10% FCS in each well of a 24-well plate. After overnight incubation, 0.1 nM interferon and varying amounts of mouse or humanized AF2 are added to the cells, and the plate is incubated for 72 hr. The cells are removed from the plate with 0.05M EDTA, stained with monoclonal antibody L243 from the American Type Culture Collection (ATCC) against HLA-D antigen, washed, stained with FITC conjugated goat anti-mouse Ig and analyzed with a FACScan (Becton-Dickinson). Increasing concentrations of mouse AF2 reduce fluorescence of the cells (FIG. 46), indicating the antibody is preventing induction of HLA-D by γ-IFN. The humanized AF2 will act similarly to mouse AF2 in this assay, showing that it neutralizes the biological activity of γ-IFN.

From the foregoing, it will be appreciated that the humanized immunoglobulins of the present invention offer numerous advantages over other γ-IFN specific antibodies. In comparison to mouse monoclonal antibodies, the present humanized immunoglobulins can be more economically produced and contain substantially less foreign amino acid sequences. This reduced likelihood of antigenicity after injection into a human patient represents a significant therapeutic improvement.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

---

What is claimed is:

1. First and second polynucleotides respectively encoding heavy and light chain variable regions of a humanized immunoglobulin having complementarity determining regions (CDRs) from a donor immunoglobulin and heavy and light chain variable region frameworks from human acceptor immunoglobulin heavy and light chain frameworks, which humanized immunoglobulin specifically binds to an antigen with an affinity constant of at least about $10^8$ $M^{-1}$ and no greater than about four-fold that of the donor immunoglobulin, wherein the sequence of the humanized immunoglobulin heavy chain variable region framework is at least 65% identical to the sequence of the donor immunoglobulin heavy chain variable region framework and comprises at least 70 amino acid residues identical to those in the acceptor human immunoglobulin heavy chain variable region framework.

2. First and second polynucleotides according to claim 1, wherein the humanized immunoglobulin binds to the antigen with an affinity constant no greater than about two-fold that of the donor immunoglobulin.

3. First and second polynucleotides according to claim 1, wherein the antigen is an interleukin-2 receptor or CD33 antigen.

4. First and second polynucleotides according to claim 1, wherein the donor immunoglobulin is the anti-Tac antibody or the M195 antibody.

5. First and second polynucleotides according to claim 1 wherein the acceptor immunoglobulin heavy and light chain frameworks are from the Eu human antibody.

6. A vector comprising first and second polynucleotides according to claim 1.

7. First and second polynucleotides respectively encoding heavy and light chain variable regions of a humanized immunoglobulin having complementarity determining regions (CDRs) from a donor immunoglobulin and heavy and light chain variable region frameworks from acceptor immunoglobulin heavy and light chain frameworks, which humanized immunoglobulin specifically binds to an antigen with an affinity constant of at least about $10^8$ $M^{-1}$ and no greater than about four-fold that of the donor immunoglobulin, wherein the sequence of the acceptor immunoglobulin heavy chain variable region framework is a consensus sequence of human immunoglobulin heavy chain variable region frameworks.

8. First and second polynucleotides according to claim 1 or 7 which are operably linked to promoters.

9. A vector comprising first and second polynucleotides according to claim 7.

10. First and second polynucleotides respectively encoding heavy and light chain variable regions of a humanized immunoglobulin having complementarity determining regions (CDRs) from a donor immunoglobulin and heavy and light chain variable region frameworks from human acceptor immunoglobulin heavy and light chains, which humanized immunoglobulin specifically binds to an antigen with an affinity constant of at least about $10^8$ $M^{-1}$ and no greater than about four-fold that of the donor immunoglobulin, wherein said humanized immunoglobulin heavy chain comprises one or more amino acids from the donor immunoglobulin heavy chain framework outside the Kabat and Chothia CDRs, wherein the donor amino acids substitute for corresponding amino acids in the acceptor immunoglobulin heavy chain framework, and each of these said donor amino acids:

(I) is adjacent to a CDR in the donor immunoglobulin sequence, or (II) contains an atom within a distance of 6 Å of a CDR in said humanized immunoglobulin.

11. First and second polynucleotides respectively encoding heavy and light chain variable regions of a humanized immunoglobulin having complementarity determining regions (CDRs) from a donor immunoglobulin and heavy and light chain variable region frameworks from human acceptor immunoglobulin heavy and light chains, which humanized immunoglobulin specifically binds to an antigen with an affinity constant of a least about $10^8$ $M^{-1}$ and no greater than about four-fold that of the donor immunoglobulin, wherein said humanized immunoglobulin heavy chain comprises one or more amino acids from the donor immunoglobulin heavy chain framework outside the Kabat and Chothia CDRs that substitute for the corresponding amino acids in the acceptor immunoglobulin heavy chain framework, wherein each of these said donor amino acids:

(I) is adjacent to a CDR in the donor immunoglobulin sequence, or (II) is capable of interacting with amino acids in the CDRs, or (III) is typical at its position for human immunoglobulin sequences, and the substituted amino acid in the acceptor is rare at its position for human immunoglobulin sequences.

12. First and second polynucleotides according to claim 10 or 11 which are operably linked to promoters.

13. First and second polynucleotides according to claim 10 or 11, wherein the antigen is a human interleukin-2 receptor or CD33 antigen.

14. First and second polynucleotides according to claim 10 or 11, wherein the donor immunoglobulin is the anti-Tac antibody or the M195 antibody.

15. A vector comprising first and second polynucleotides according to claim 10.

16. A vector comprising first and second polynucleotides according to claim 11.

17. A cell line transfected with a vector according to claim 6, 9, 15, or 16.

18. A cell line comprising first and second polynucleotides according to any one of claims 1, 7 10, or 11, which polynucleotides are expressed to produce the humanized immunoglobulin.

19. A method of producing an immunoglobulin comprising expressing first and second polynucleotides according to claim 10 or 11 in a cell.

20. First and second polynucleotides according to claim 10, wherein the second polynucleotide encodes a mature light chain variable region of the humanized immunoglobulin having the sequence:

D I Q M T Q S P S T L S A S V G D R Y T I T C S A S
S S I S Y M H W Y Q Q K P G K A P K L L I Y T T S
N L A S G V P A R F S G S G S G T E F T L T I S S L
Q P D D F A T Y Y C H Q R S T Y P L T F G Q G T K
V E V K.

21. First and second polynucleotides according to claim 20, wherein the second polynucleotide has the sequence:

GATATTCAGATGACCCAGTCTCCATC-
TACCCTCTCTGCTAGCGTCGGGGATAGGG TCAC-
CATAACCTGCTCTGCCAGCTCAAG-
TATAAGTTACATGCACTGGTACCAGCAGAAGC
CAGGCAAAGCTCCCAAGCTTCTAATT-
TATACCACATCCAACCTGGCTTCTGGAGTCCCTG
CTCGCTTCAGTGGCAGTGGATCTGGGAC-
CGAGTTCACCCTCACAATCAGCTCTCTGCAGC
CAGATGATTTCGCCACTTATTACTGC-
CATCAAAGGAGTACTTACCCACTCACGTTCGGTC
AGGGGACCAAGGTGGAGGTCAAA.

22. First and second polynucleotides according to claim 10, wherein the first polynucleotide encodes a mature heavy chain variable region of the humanized immunoglobulin having the sequence:

QVQLVQSGAEVKKPGSSVKVSCKAS
GYTFTSYRMHWVRQAPGQGLEWIG
YINPSTGYTEYNQKFKDKATITADE
STNTAYMELSSLRSEDTAVYYCARG
GGVFDYWGQGTLVTVSS.

23. First and second polynucleotides according to claim 22, wherein the first polynucleotide has the sequence:

CAGGTCCAGCTTGTCCAGTCTGGGGCT-
GAAGTCAAGAAACCTGGCTCGAGCGT-
G A A G G T C T C C T G
CAAGGCTTCTGGCTACACCTTTACTAGCTACAG-
GATGCACTGGGTAAGGCAGG- CCCCTGGACAGG
GTCTGGAATGGATTGGATATATTAATC-
CGTCGACTGGGTATACTGAATACAATCA-
G  A  A  G  T  T  C  A  A  G
GACAAGGCAACAATTACTGCAGACGAATCCACC-
AATACAGCCTACATGGAACTG- AGCAGCCTGAG
ATCTGAGGACACCGCAGTCTATTACTGT-
GCAAGAGGGGGGGGGGTCTTTGAC-
TACTGGGGCCAAG GAACCCTGGTCACAGTCTC-
CTCA.

24. First and second polynucleotides according to claim 10, wherein the second polynucleotide encodes a mature light chain variable region of the humanized immunoglobulin having the sequence:

DIQMTQSPSSLSASVGDRVTITCRAS
ESVDNYGISFMNWFQQKPGKAPKL
LIYAASNQGSGVPSRFSGSGSGTDF
TLTISSLQPDDFATYYCQQSKEVPW
TFGQGTKVEIK.

25. First and second polynucleotides according to claim 10, wherein the first polynucleotide encodes a mature heavy chain variable region of the humanized immunoglobulin having the sequence:

QVQLVQSGAEVKKPGSSVKVSCKAS
GYTFTDYNMHWVRQAPGQGLEWIG
YIYPYNGGTGYNQKFKSKATITADE
STNTAYMELSSLRSEDTAVYYCARG
RPAMDYWGQGTLVTVSS.

26. First and second polynucleotides according to any one of claims 1, 7 or 10, wherein the sequence of the humanized immunoglobulin light chain variable region framework is at least 65% identical to the sequence of the donor immunoglobulin light chain variable region framework and comprises at least 70 amino acid residues identical to those in the acceptor human immunoglobulin light chain variable region framework.

27. First and second polynucleotides according to any one of claims 1, 7 or 10, wherein the sequence of the acceptor immunoglobulin light chain variable region framework is a consensus sequence of human immunoglobulin light chain variable region frameworks.

28. First and second polynucleotides according to any one of claims 1, 7 or 10, wherein the humanized light chain comprises one or more amino acids from the donor immunoglobulin light chain framework outside the Kabat and Chothia CDRs, wherein the donor amino acids substitute for corresponding amino acids in the acceptor immunoglobulin light chain framework, and each of said donor amino acids:

(I) is adjacent to a CDR in the donor immunoglobulin sequence, or (II) contains an atom within a distance of 6 Å of a CDR in said humanized immunoglobulin.

29. First and second polynucleotides according to claim 10, wherein each of said donor amino acids:

(I) is adjacent to a CDR in the donor immunoglobulin sequence, or (II) contains an atom within a distance of 5 Å of a CDR in said humanized immunoglobulin.

30. First and second polynucleotides according to claim 10, wherein each of said donor amino acids:

(I) is adjacent to a CDR in the donor immunoglobulin sequence, or (II) contains an atom within a distance of 4 Å of a CDR in said humanized immunoglobulin.

31. First and second polynucleotides according to claim 1 or 7, wherein the heavy chain of the humanized immunoglobulin comprises one or more amino acids from the donor immunoglobulin heavy chain framework outside the Kabat and Chothia CDRs, wherein the donor amino acids substitute for corresponding amino acids in the acceptor immunoglobulin heavy chain framework, and each of these said donor amino acids:

(I) is adjacent to a CDR in the donor immunoglobulin sequence, or (II) contains an atom within a distance of 6 Å of a CDR in said humanized immunoglobulin.

32. First and second polynucleotides according to claim 1 or 7, wherein said humanized immunoglobulin heavy chain further comprises an amino acid from the donor immunoglobulin heavy chain framework outside the Kabat and Chothia CDRs that substitutes for the corresponding amino acid in the acceptor immunoglobulin heavy chain framework, wherein said amino acid is typical for its position in human immunoglobulin sequences and said corresponding amino acid in the acceptor immunoglobulin is rare for its position in human immunoglobulin sequences.

33. First and second polynucleotides according to any one of claims 1, 7, 10 or 11, wherein the polynucleotides are contained within an expression vector.

34. First and second polynucleotides according to any one of claims 1, 7, 10, or 11, wherein the first polynucleotide and the second polynucleotide are contained in separate vectors.

35. First and second polynucleotides respectively encoding heavy and light chain variable regions of a humanized immunoglobulin having complementarity determining regions (CDRs) from a donor immunoglobulin and heavy and light chain variable region frameworks from human acceptor immunoglobulin heavy and light chain frameworks, which humanized immunoglobulin specifically binds to an antigen with an affinity constant within about four-fold of that of the donor immunoglobulin, wherein the sequence of the humanized immunoglobulin heavy chain variable region framework is at least 65% identical to the sequence of the donor immunoglobulin heavy chain variable region framework and comprises at least 70 amino acid residues identical to those in the acceptor human immunoglobulin heavy chain variable region framework.

36. First and second polynucleotides respectively encoding heavy and light chain variable regions of a humanized immunoglobulin having complementarity determining regions (CDRs) from a donor immunoglobulin and heavy and light chain variable region frameworks from acceptor immunoglobulin heavy and light chain frameworks, which humanized immunoglobulin specifically binds to an antigen with an affinity constant within about four-fold of that of the donor immunoglobulin, wherein the sequence of the acceptor immunoglobulin heavy chain variable region framework is a consensus sequence of human immunoglobulin heavy chain variable region frameworks.

37. First and second polynucleotides respectively encoding heavy and light chain variable regions of a humanized immunoglobulin having complementarity determining regions (CDRs) from a donor immunoglobulin and heavy and light chain variable region frameworks from human acceptor immunoglobulin heavy and light chains, which humanized immunoglobulin specifically binds to an antigen with an affinity constant within about four-fold of the donor immunoglobulin, wherein said humanized immunoglobulin heavy chain comprises one or more amino acids from the donor immunoglobulin heavy chain framework outside the Kabat and Chothia CDRs, wherein the donor amino acids substitute for corresponding amino acids in the acceptor immunoglobulin heavy chain framework, and each of these said donor amino acids:

(I) is adjacent to a CDR in the donor immunoglobulin sequence, or (II) contains an atom within a distance of 6 Å of a CDR in said humanized immunoglobulin.

* * * * *

UNITED STATES PATENT AND TRADEMARK OFFICE
CERTIFICATE OF CORRECTION

PATENT NO. : 5,693,761
DATED : December 2, 1997
INVENTOR(S) : Cary L. Queen et al.

It is certified that error appears in the above-identified patent and that said Letters Patent is hereby corrected as shown below:

Title page,
Item [63], Related U.S. Application Data, should read:
-- Division of Ser. No. 634,278, Dec. 19, 1990, Pat. No. 5,530,101, which is a continuation-in-part of Ser. No. 590,274, Sep. 28, 1990, abandoned, and a continuation-in-part Ser. No. 310,252, Feb. 13, 1989, abandoned, which is a continuation-in-part of Ser. No. 290,975, Dec. 28, 1998, abandoned. --

Signed and Sealed this

Twelfth Day of April, 2005

JON W. DUDAS
*Director of the United States Patent and Trademark Office*

UNITED STATES PATENT AND TRADEMARK OFFICE
Certificate

Patent No. 5,693,761                                        Patented: December 2, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Cary L. Queen, Los Altos, CA (US); Man Sung Co, Cupertino, CA (US); William P. Schneider, Mountain View, CA (US); and Harold E. Selick, Belmont, CA (US).

Signed and Sealed this First Day of April 2008.

JULIE BURKE
Special Program Examiner
Technology Center 1600

SEQUENCE LISTING ( 1 ) GENERAL INFORMATION:

( i i i ) NUMBER OF SEQUENCES: 113

( 2 ) INFORMATION FOR SEQ ID NO:1:

( i ) SEQUENCE CHARACTERISTICS:
( A ) LENGTH: 106 amino acids (B) TYPE: amino acid
        (C) STRANDEDNESS: single
        (D) TOPOLOGY: unknown ( i i ) MOLECULE TYPE: protein ( i i i ) HYPOTHETICAL: NO ( i x ) FEATURE:
        (A) NAME/KEY: Protein
        (B) LOCATION: 1..106
        (D) OTHER INFORMATION: /note= "Variable region of the mouse
             anti-Tac antibody light chain."

( x i ) SEQUENCE DESCRIPTION: SEQ ID NO:1:

| Gln | Ile | Val | Leu | Thr | Gln | Ser | Pro | Ala | Ile | Met | Ser | Ala | Ser | Pro | Gly |
| 1 | | | | 5 | | | | | 10 | | | | | 15 | |
| Glu | Lys | Val | Thr | Ile | Thr | Cys | Ser | Ala | Ser | Ser | Ser | Ile | Ser | Tyr | Met |
| | | | 20 | | | | | 25 | | | | | 30 | | |
| His | Trp | Phe | Gln | Gln | Lys | Pro | Gly | Thr | Ser | Pro | Lys | Leu | Trp | Ile | Tyr |
| | | | 35 | | | | 40 | | | | | 45 | | | |
| Thr | Thr | Ser | Asn | Leu | Ala | Ser | Gly | Val | Pro | Ala | Arg | Phe | Ser | Gly | Ser |
| | 50 | | | | | 55 | | | | | 60 | | | | |
| Gly | Ser | Gly | Thr | Ser | Tyr | Ser | Leu | Thr | Ile | Ser | Arg | Met | Glu | Ala | Glu |
| 65 | | | | | 70 | | | | | 75 | | | | | 80 |
| Asp | Ala | Ala | Thr | Tyr | Tyr | Cys | His | Gln | Arg | Ser | Thr | Tyr | Pro | Leu | Thr |
| | | | | 85 | | | | | 90 | | | | | 95 | |
| Phe | Gly | Ser | Gly | Thr | Lys | Leu | Glu | Leu | Lys | | | | | | |
| | | | 100 | | | | | 105 | | | | | | | |

( 2 ) INFORMATION FOR SEQ ID NO:2:

( i ) SEQUENCE CHARACTERISTICS:
        (A) LENGTH: 107 amino acids
        (B) TYPE: amino acid
        (C) STRANDEDNESS: single
        (D) TOPOLOGY: unknown ( i i ) MOLECULE TYPE: protein ( i i i ) HYPOTHETICAL: NO ( i x ) FEATURE:
        (A) NAME/KEY: Protein
        (B) LOCATION: 1..107
        (D) OTHER INFORMATION: /note= "Variable region of the human
             Eu antibody light chain."

( x i ) SEQUENCE DESCRIPTION: SEQ ID NO:2:

| Asp | Ile | Gln | Met | Thr | Gln | Ser | Pro | Ser | Thr | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Ser | Ile | Asn | Thr | Trp |
| | | | 20 | | | | | 25 | | | | | 30 | | |
| Leu | Ala | Trp | Tyr | Gln | Gln | Lys | Pro | Gly | Lys | Ala | Pro | Lys | Leu | Leu | Met |
| | | | 35 | | | | 40 | | | | | 45 | | | |
| Tyr | Lys | Ala | Ser | Ser | Leu | Glu | Ser | Gly | Val | Pro | Ser | Arg | Phe | Ile | Gly |
| | 50 | | | | | 55 | | | | | 60 | | | | |
| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |
| Asp | Asp | Phe | Ala | Thr | Tyr | Tyr | Cys | Gln | Gln | Tyr | Asn | Ser | Asp | Ser | Lys |
| | | | | 85 | | | | | 90 | | | | | 95 | |
| Met | Phe | Gly | Gln | Gly | Thr | Lys | Val | Glu | Val | Lys | | | | | |
| | | | 100 | | | | | 105 | | | | | | | |

( 2 ) INFORMATION FOR SEQ ID NO:3:

( i ) SEQUENCE CHARACTERISTICS:
       ( A ) LENGTH: 116 amino acids
       ( B ) TYPE: amino acid
       ( C ) STRANDEDNESS: single
       ( D ) TOPOLOGY: unknown ( i i ) MOLECULE TYPE: protein ( i i i ) HYPOTHETICAL: NO ( i x ) FEATURE:
       ( A ) NAME/KEY: Protein
       ( B ) LOCATION: 1..116
       ( D ) OTHER INFORMATION: /note= "Variable region of the mouse anti-Tac antibody heavy chain."

( x i ) SEQUENCE DESCRIPTION: SEQ ID NO:3:

| Gln | Val | Gln | Leu | Gln | Gln | Ser | Gly | Ala | Glu | Leu | Ala | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Arg | Met | His | Trp | Val | Lys | Gln | Arg | Pro | Gly | Gln | Gly | Leu | Glu | Trp | Ile |
| | | | 35 | | | | | 40 | | | | | 45 | | |
| Gly | Tyr | Ile | Asn | Pro | Ser | Thr | Gly | Tyr | Thr | Glu | Tyr | Asn | Gln | Lys | Phe |
| | | 50 | | | | | 55 | | | | | 60 | | | |
| Lys | Asp | Lys | Ala | Thr | Leu | Thr | Ala | Asp | Lys | Ser | Ser | Ser | Thr | Ala | Tyr |
| 65 | | | | | 70 | | | | | 75 | | | | | 80 |
| Met | Gln | Leu | Ser | Ser | Leu | Thr | Phe | Glu | Asp | Ser | Ala | Val | Tyr | Tyr | Cys |
| | | | | 85 | | | | | 90 | | | | | 95 | |
| Ala | Arg | Gly | Gly | Gly | Val | Phe | Asp | Tyr | Trp | Gly | Gln | Gly | Thr | Thr | Leu |
| | | | 100 | | | | | 105 | | | | | 110 | | |
| Thr | Val | Ser | Ser | | | | | | | | | | | | |
| | | | 115 | | | | | | | | | | | | |

( 2 ) INFORMATION FOR SEQ ID NO:4:

( i ) SEQUENCE CHARACTERISTICS:
       ( A ) LENGTH: 117 amino acids
       ( B ) TYPE: amino acid
       ( C ) STRANDEDNESS: single
       ( D ) TOPOLOGY: unknown ( i i ) MOLECULE TYPE: protein ( i i i ) HYPOTHETICAL: NO ( i x ) FEATURE:
       ( A ) NAME/KEY: Protein
       ( B ) LOCATION: 1..117
       ( D ) OTHER INFORMATION: /note= "Variable region of the human Eu antibody heavy chain."

( x i ) SEQUENCE DESCRIPTION: SEQ ID NO:4:

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |
| Ser | Val | Lys | Val | Ser | Cys | Lys | Ala | Ser | Gly | Gly | Thr | Phe | Ser | Arg | Ser |
| | | | 20 | | | | | 25 | | | | | 30 | | |
| Ala | Ile | Ile | Trp | Val | Arg | Gln | Ala | Pro | Gly | Gln | Gly | Leu | Glu | Trp | Met |
| | | | 35 | | | | | 40 | | | | | 45 | | |
| Gly | Gly | Ile | Val | Pro | Met | Phe | Gly | Pro | Pro | Asn | Tyr | Ala | Gln | Lys | Phe |
| | | | 50 | | | | 55 | | | | | 60 | | | |
| Gln | Gly | Arg | Val | Thr | Ile | Thr | Ala | Asp | Glu | Ser | Thr | Asn | Thr | Ala | Tyr |
| 65 | | | | | 70 | | | | | 75 | | | | | 80 |

```
            Met   Glu   Leu   Ser   Ser   Leu   Arg   Ser   Glu   Asp   Thr   Ala   Phe   Tyr   Phe   Cys
                                    85                        90                        95

Ala   Gly   Gly   Tyr   Gly   Ile   Tyr   Ser   Pro   Glu   Glu   Tyr   Asn   Gly   Gly   Leu
                              100                           105                         110

Val   Thr   Val   Ser   Ser
                        115
```

( 2 ) INFORMATION FOR SEQ ID NO:5:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..116
        ( D ) OTHER INFORMATION: /note= "Variable region of the PDL
            humanized anti-Tac antibody heavy chain."

( x i ) SEQUENCE DESCRIPTION: SEQ ID NO:5:

```
            Gln   Val   Gln   Leu   Val   Gln   Ser   Gly   Ala   Glu   Val   Lys   Lys   Pro   Gly   Ser
            1                       5                         10                        15

Ser   Val   Lys   Val   Ser   Cys   Lys   Ala   Ser   Gly   Tyr   Thr   Phe   Thr   Ser   Tyr
                              20                            25                        30

Arg   Met   His   Trp   Val   Arg   Gln   Ala   Pro   Gly   Gln   Gly   Leu   Glu   Trp   Ile
                        35                            40                        45

Gly   Tyr   Ile   Asn   Pro   Ser   Thr   Gly   Tyr   Thr   Glu   Tyr   Asn   Gln   Lys   Phe
                  50                            55                        60

Lys   Asp   Lys   Ala   Thr   Ile   Thr   Ala   Asp   Glu   Ser   Thr   Asn   Thr   Ala   Tyr
            65                            70                        75                              80

Met   Glu   Leu   Ser   Ser   Leu   Arg   Ser   Glu   Asp   Thr   Ala   Val   Tyr   Tyr   Cys
                                    85                        90                        95

Ala   Arg   Gly   Gly   Gly   Val   Phe   Asp   Tyr   Trp   Gly   Gln   Gly   Thr   Leu   Val
                              100                           105                         110

Thr   Val   Ser   Ser
                        115
```

( 2 ) INFORMATION FOR SEQ ID NO:6:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..116
        ( D ) OTHER INFORMATION: /note= "Variable region of the CDR-only
            humanized anti-Tac antibody heavy chain."

( x i ) SEQUENCE DESCRIPTION: SEQ ID NO:6:

```
            Gln   Val   Gln   Leu   Val   Gln   Ser   Gly   Ala   Glu   Val   Lys   Lys   Pro   Gly   Ser
            1                       5                         10                        15

Ser   Val   Lys   Val   Ser   Cys   Lys   Ala   Ser   Gly   Gly   Thr   Phe   Ser   Ser   Tyr
                              20                            25                        30
```

| | | | | | | | | | | | | | | | |
|---|---|---|---|---|---|---|---|---|---|---|---|---|---|---|---|
| Arg | Met | His | Trp | Val | Arg | Gln | Ala | Pro | Gly | Gln | Gly | Leu | Glu | Trp | Met |
| | | 35 | | | | 40 | | | | | | 45 | | | |
| Gly | Tyr | Ile | Asn | Pro | Ser | Thr | Gly | Tyr | Thr | Glu | Tyr | Asn | Gln | Lys | Phe |
| | | 50 | | | | 55 | | | | | 60 | | | | |
| Lys | Asp | Arg | Val | Thr | Ile | Thr | Ala | Asp | Glu | Ser | Thr | Asn | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Phe | Tyr | Phe | Cys |
| | | | | 85 | | | | | 90 | | | | | 95 | |
| Ala | Gly | Gly | Gly | Gly | Val | Phe | Asp | Tyr | Glu | Tyr | Asn | Gly | Gly | Leu | Val |
| | | | 100 | | | | | 105 | | | | | 110 | | |
| Thr | Val | Ser | Ser | | | | | | | | | | | | |
| | | 115 | | | | | | | | | | | | | |

( 2 ) INFORMATION FOR SEQ ID NO:7:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..106
        ( D ) OTHER INFORMATION: /note= "Variable region of the PDL
            humanized anti-Tac antibody light chain."

( x i ) SEQUENCE DESCRIPTION: SEQ ID NO:7:

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Thr | Leu | Ser | Ala | Ser | Val | Gly |
| 1 | | | | 5 | | | | | 10 | | | | | 15 | |
| Asp | Arg | Val | Thr | Ile | Thr | Cys | Ser | Ala | Ser | Ser | Ser | Ile | Ser | Tyr | Met |
| | | | 20 | | | | | 25 | | | | | 30 | | |
| His | Trp | Tyr | Gln | Gln | Lys | Pro | Gly | Lys | Ala | Pro | Lys | Leu | Leu | Ile | Tyr |
| | | 35 | | | | | 40 | | | | | 45 | | | |
| Thr | Thr | Ser | Asn | Leu | Ala | Ser | Gly | Val | Pro | Ala | Arg | Phe | Ser | Gly | Ser |
| | 50 | | | | | 55 | | | | | 60 | | | | |
| Gly | Ser | Gly | Thr | Glu | Phe | Thr | Leu | Thr | Ile | Ser | Ser | Leu | Gln | Pro | Asp |
| 65 | | | | | 70 | | | | | 75 | | | | | 80 |
| Asp | Phe | Ala | Thr | Tyr | Tyr | Cys | His | Gln | Arg | Ser | Thr | Tyr | Pro | Leu | Thr |
| | | | | 85 | | | | | 90 | | | | | 95 | |
| Phe | Gly | Gln | Gly | Thr | Lys | Val | Glu | Val | Lys | | | | | | |
| | | | 100 | | | | | 105 | | | | | | | |

( 2 ) INFORMATION FOR SEQ ID NO:8:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..106
        ( D ) OTHER INFORMATION: /note= "Variable region of the CDR-only
            humanized anti-Tac antibody light chain."

( x i ) SEQUENCE DESCRIPTION: SEQ ID NO:8:

| Asp | Ile | Gln | Met | Thr | Gln | Ser | Pro | Ser | Thr | Leu | Ser | Ala | Ser | Val | Gly |
| 1 | | | | 5 | | | | | 10 | | | | | 15 | |

| Asp | Arg | Val | Thr | Ile | Thr | Cys | Ser | Ala | Ser | Ser | Ser | Ile | Ser | Tyr | Met |
| | | | 20 | | | | | 25 | | | | | 30 | | |

| His | Trp | Tyr | Gln | Gln | Lys | Pro | Gly | Lys | Ala | Pro | Lys | Leu | Leu | Met | Tyr |
| | | | 35 | | | | 40 | | | | | 45 | | | |

| Thr | Thr | Ser | Asn | Leu | Ala | Ser | Gly | Val | Pro | Ser | Arg | Phe | Ile | Gly | Ser |
| | 50 | | | | | 55 | | | | | 60 | | | | |

| Gly | Ser | Gly | Thr | Glu | Phe | Thr | Leu | Thr | Ile | Ser | Ser | Leu | Gln | Pro | Asp |
| 65 | | | | | 70 | | | | 75 | | | | | | 80 |

| Asp | Phe | Ala | Thr | Tyr | Tyr | Cys | His | Gln | Arg | Ser | Thr | Tyr | Pro | Leu | Thr |
| | | | | 85 | | | | | 90 | | | | | 95 | |

| Phe | Gly | Gln | Gly | Thr | Lys | Val | Glu | Val | Lys |
| | | | 100 | | | | | 105 | |

( 2 ) INFORMATION FOR SEQ ID NO:9:

( i ) SEQUENCE CHARACTERISTICS:
        ( A ) LENGTH: 443 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..443
        ( D ) OTHER INFORMATION: /note= "Sequence encoding heavy
        chain variable region of CDR-only humanized
        anti-Tac antibody including signal sequence."

( x i ) SEQUENCE DESCRIPTION: SEQ ID NO:9:

| AGCTTCTAGA | TGGGATGGAG | CTGGATCTTT | CTCTTCCTCC | TGTCAGGTAC | CGCGGGCGTG | 60 |
| CACTCTCAGG | TCCAGCTTGT | CCAGTCTGGG | GCTGAAGTCA | AGAAACCTGG | CTCGAGCGTG | 120 |
| AAGGTCTCCT | GCAAGGCTTC | TGGCGGGACC | TTTTCTAGCT | ACAGGATGCA | CTGGGTAAGG | 180 |
| CAGGCCCCTG | GACAGGGTCT | GGAATGGATG | GGATATATTA | ATCCGTCGAC | TGGGTATACT | 240 |
| GAATACAATC | AGAAGTTCAA | GGACAGGGTC | ACAATTACTG | CAGACGAATC | CACCAATACA | 300 |
| GCCTACATGG | AACTGAGCAG | CCTGAGATCT | GAGGACACCG | CATTCTATTT | CTGTGCAGGG | 360 |
| GGTGGGGGAG | TCTTTGACTA | CGAATACAAT | GGAGGGCTGG | TCACAGTCTC | CTCAGGTGAG | 420 |
| TCCTTAAAAC | CTCTAGACGA | TAT | | | | 443 |

( 2 ) INFORMATION FOR SEQ ID NO:10:

( i ) SEQUENCE CHARACTERISTICS:
        ( A ) LENGTH: 411 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..411
        ( D ) OTHER INFORMATION: /note= "Sequence encoding light
        chain variable region of the CDR-only humanized
        anti-Tac antibody including signal sequence."

( x i ) SEQUENCE DESCRIPTION: SEQ ID NO:10:

| CAAATCTAGA | TGGAGACCGA | TACCCTCCTG | CTATGGGTCC | TCCTGCTATG | GGTCCCAGGA | 60 |
| TCAACCGGAG | ATATTCAGAT | GACCCAGTCT | CCATCTACCC | TCTCTGCTAG | CGTCGGGGAT | 120 |
| AGGGTCACCA | TAACCTGCTC | TGCCAGCTCA | AGTATAAGTT | ACATGCACTG | GTACCAGCAG | 180 |
| AAGCCAGGCA | AAGCTCCCAA | GCTTCTAATG | TATACCACAT | CCAACCTGGC | TTCTGGAGTC | 240 |
| CCTTCTCGCT | TCATTGGCAG | TGGATCTGGG | ACCGAGTTCA | CCCTCACAAT | CAGCTCTCTG | 300 |
| CAGCCAGATG | ATTTCGCCAC | TTATTACTGC | CATCAAAGGA | GTACTTACCC | ACTCACGTTC | 360 |
| GGTCAGGGGA | CCAAGGTGGA | GGTCAAACGT | AAGTACACTT | TTCTAGATAT | A | 411 |

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..29
        ( D ) OTHER INFORMATION: /standard_name= "Primer mc045"

( x i ) SEQUENCE DESCRIPTION: SEQ ID NO:11:

| TAATCTAGAA | TTCCCCCCCC | CCCCCCCC | | | | 29 |

( 2 ) INFORMATION FOR SEQ ID NO:12:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..46
        ( D ) OTHER INFORMATION: /standard_name= "Primer mc045"

( x i ) SEQUENCE DESCRIPTION: SEQ ID NO:12:

| TATAGAGCTC | AAGCTTGGAT | GGTGGGAAGA | TGGATACAGT | TGGTGC | 46 |

( 2 ) INFORMATION FOR SEQ ID NO:13:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..50
        ( D ) OTHER INFORMATION: /standard_name= "Primer mc047"

( x i ) SEQUENCE DESCRIPTION: SEQ ID NO:13:

TATAGAGCTC AAGCTTCCAG TGGATAGACH GATGGGGSTG TYGTTTTGGC                                    50

( 2 ) INFORMATION FOR SEQ ID NO:14:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..116
        ( D ) OTHER INFORMATION: /note= "Anti-Tac heavy chain amino
            acid sequence."

( x i ) SEQUENCE DESCRIPTION: SEQ ID NO:14:

```
Gln  Val  Gln  Leu  Gln  Gln  Ser  Gly  Ala  Glu  Leu  Ala  Lys  Pro  Gly  Ala
 1                    5                        10                       15

Ser  Val  Lys  Met  Ser  Cys  Lys  Ala  Ser  Gly  Tyr  Thr  Phe  Thr  Ser  Tyr
               20                       25                       30

Arg  Met  His  Trp  Val  Lys  Gln  Arg  Pro  Gly  Gln  Gly  Leu  Glu  Trp  Ile
          35                        40                       45

Gly  Tyr  Ile  Asn  Pro  Ser  Thr  Gly  Tyr  Thr  Glu  Tyr  Asn  Gln  Lys  Phe
     50                        55                       60

Lys  Asp  Lys  Ala  Thr  Leu  Thr  Ala  Asp  Lys  Ser  Ser  Ser  Thr  Ala  Tyr
 65                        70                       75                       80

Met  Gln  Leu  Ser  Ser  Leu  Thr  Phe  Glu  Asp  Ser  Ala  Val  Tyr  Tyr  Cys
               85                       90                       95

Ala  Arg  Gly  Gly  Gly  Val  Phe  Asp  Tyr  Trp  Gly  Gln  Gly  Thr  Thr  Leu
               100                      105                      110

Thr  Val  Ser  Ser
               115
```

( 2 ) INFORMATION FOR SEQ ID NO:15:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..117
        ( D ) OTHER INFORMATION: /note= "Eu heavy chain amino acid
            sequence."

( x i ) SEQUENCE DESCRIPTION: SEQ ID NO:15:

```
Gln  Val  Gln  Leu  Val  Gln  Ser  Gly  Ala  Glu  Val  Lys  Lys  Pro  Gly  Ser
 1                    5                        10                       15

Ser  Val  Lys  Val  Ser  Cys  Lys  Ala  Ser  Gly  Gly  Thr  Phe  Ser  Arg  Ser
               20                       25                       30

Ala  Ile  Ile  Trp  Val  Arg  Gln  Ala  Pro  Gly  Gln  Gly  Leu  Glu  Trp  Met
          35                        40                       45

Gly  Gly  Ile  Val  Pro  Met  Phe  Gly  Pro  Pro  Asn  Tyr  Ala  Gln  Lys  Phe
     50                        55                       60
```

| Gln | Gly | Arg | Val | Thr | Ile | Thr | Ala | Asp | Glu | Ser | Thr | Asn | Thr | Ala | Tyr |
| 65 | | | | 70 | | | | | 75 | | | | | | 80 |

| Met | Glu | Leu | Ser | Ser | Leu | Arg | Ser | Glu | Asp | Thr | Ala | Phe | Tyr | Phe | Cys |
| | | | | 85 | | | | | 90 | | | | | 95 | |

| Ala | Gly | Gly | Tyr | Gly | Ile | Tyr | Ser | Pro | Glu | Glu | Tyr | Asn | Gly | Gly | Leu |
| | | | | 100 | | | | 105 | | | | | 110 | | |

| Val | Thr | Val | Ser | Ser |
| | | | 115 | |

( 2 ) INFORMATION FOR SEQ ID NO:16:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..106
        ( D ) OTHER INFORMATION: /note= "Anti-Tac light chain amino
            acid sequence."

( x i ) SEQUENCE DESCRIPTION: SEQ ID NO:16:

| Gln | Ile | Val | Leu | Thr | Gln | Ser | Pro | Ala | Ile | Met | Ser | Ala | Ser | Pro | Gly |
| 1 | | | | 5 | | | | | 10 | | | | | 15 | |

| Glu | Lys | Val | Thr | Ile | Thr | Cys | Ser | Ala | Ser | Ser | Ser | Ile | Ser | Tyr | Met |
| | | | 20 | | | | | 25 | | | | | 30 | | |

| His | Trp | Phe | Gln | Gln | Lys | Pro | Gly | Thr | Ser | Pro | Lys | Leu | Trp | Ile | Tyr |
| | | | 35 | | | | | 40 | | | | | 45 | | |

| Thr | Thr | Ser | Asn | Leu | Ala | Ser | Gly | Val | Pro | Ala | Arg | Phe | Ser | Gly | Ser |
| | 50 | | | | | 55 | | | | | 60 | | | | |

| Gly | Ser | Gly | Thr | Ser | Tyr | Ser | Leu | Thr | Ile | Ser | Arg | Met | Glu | Ala | Glu |
| 65 | | | | | 70 | | | | | 75 | | | | | 80 |

| Asp | Ala | Ala | Thr | Tyr | Tyr | Cys | His | Gln | Arg | Ser | Thr | Tyr | Pro | Leu | Thr |
| | | | | 85 | | | | | 90 | | | | | 95 | |

| Phe | Gly | Ser | Gly | Thr | Lys | Leu | Glu | Leu | Lys |
| | | | | 100 | | | | 105 | |

( 2 ) INFORMATION FOR SEQ ID NO:17:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..107
        ( D ) OTHER INFORMATION: /note= "Eu light chain amino acid
            sequence."

( x i ) SEQUENCE DESCRIPTION: SEQ ID NO:17:

| Asp | Ile | Gln | Met | Thr | Gln | Ser | Pro | Ser | Thr | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Ser | Ile | Asn | Thr | Trp |

```
                         20                      25                       30
           Leu  Ala  Trp  Tyr  Gln  Gln  Lys  Pro  Gly  Lys  Ala  Pro  Lys  Leu  Leu  Met
                     35                      40                      45

Tyr  Lys  Ala  Ser  Ser  Leu  Glu  Ser  Gly  Val  Pro  Ser  Arg  Phe  Ile  Gly
                50                       55                      60

Ser  Gly  Ser  Gly  Thr  Glu  Phe  Thr  Leu  Thr  Ile  Ser  Ser  Leu  Gln  Pro
           65                      70                      75                           80

Asp  Asp  Phe  Ala  Thr  Tyr  Tyr  Cys  Gln  Gln  Tyr  Asn  Ser  Asp  Ser  Lys
                          85                      90                           95

Met  Phe  Gly  Gln  Gly  Thr  Lys  Val  Glu  Val  Lys
                          100                     105
```

( 2 ) INFORMATION FOR SEQ ID NO:18:

( i ) SEQUENCE CHARACTERISTICS:
       ( A ) LENGTH: 433 base pairs
       ( B ) TYPE: nucleic acid
       ( C ) STRANDEDNESS: single
       ( D ) TOPOLOGY: linear ( i i ) MOLECULE TYPE: DNA ( i i i ) HYPOTHETICAL: NO ( i x ) FEATURE:
       ( A ) NAME/KEY: CDS
       ( B ) LOCATION: 6..410
       ( D ) OTHER INFORMATION: /product="Humanized anti-Tac heavy
            chain variable region, Seq ID. 19"

( x i ) SEQUENCE DESCRIPTION: SEQ ID NO:18:

```
TCTAG ATG  GGA  TGG  AGC  TGG  ATC  TTT  CTC  TTC  CTC  CTG  TCA  GGT  ACC                 47
      Met  Gly  Trp  Ser  Trp  Ile  Phe  Leu  Phe  Leu  Leu  Ser  Gly  Thr
      1                  5                            10

GCG  GGC  GTG  CAC  TCT  CAG  GTC  CAG  CTT  GTC  CAG  TCT  GGG  GCT  GAA  GTC             95
Ala  Gly  Val  His  Ser  Gln  Val  Gln  Leu  Val  Gln  Ser  Gly  Ala  Glu  Val
15                      20                      25                      30

AAG  AAA  CCT  GGC  TCG  AGC  GTG  AAG  GTC  TCC  TGC  AAG  GCT  TCT  GGC  TAC            143
Lys  Lys  Pro  Gly  Ser  Ser  Val  Lys  Val  Ser  Cys  Lys  Ala  Ser  Gly  Tyr
                     35                      40                      45

ACC  TTT  ACT  AGC  TAC  AGG  ATG  CAC  TGG  GTA  AGG  CAG  GCC  CCT  GGA  CAG            191
Thr  Phe  Thr  Ser  Tyr  Arg  Met  His  Trp  Val  Arg  Gln  Ala  Pro  Gly  Gln
               50                      55                      60

GGT  CTG  GAA  TGG  ATT  GGA  TAT  ATT  AAT  CCG  TCG  ACT  GGG  TAT  ACT  GAA            239
Gly  Leu  Glu  Trp  Ile  Gly  Tyr  Ile  Asn  Pro  Ser  Thr  Gly  Tyr  Thr  Glu
          65                      70                      75

TAC  AAT  CAG  AAG  TTC  AAG  GAC  AAG  GCA  ACA  ATT  ACT  GCA  GAC  GAA  TCC            287
Tyr  Asn  Gln  Lys  Phe  Lys  Asp  Lys  Ala  Thr  Ile  Thr  Ala  Asp  Glu  Ser
     80                      85                      90

ACC  AAT  ACA  GCC  TAC  ATG  GAA  CTG  AGC  AGC  CTG  AGA  TCT  GAG  GAC  ACC            335
Thr  Asn  Thr  Ala  Tyr  Met  Glu  Leu  Ser  Ser  Leu  Arg  Ser  Glu  Asp  Thr
95                       100                     105                     110

GCA  GTC  TAT  TAC  TGT  GCA  AGA  GGG  GGG  GGG  GTC  TTT  GAC  TAC  TGG  GGC            383
Ala  Val  Tyr  Tyr  Cys  Ala  Arg  Gly  Gly  Gly  Val  Phe  Asp  Tyr  Trp  Gly
               115                     120                     125

CAA  GGA  ACC  CTG  GTC  ACA  GTC  TCC  TCA  GGTGAGTCCT  TAAAACCTCT                        430
Gln  Gly  Thr  Leu  Val  Thr  Val  Ser  Ser
               130                     135

AGA                                                                                        433
```

( 2 ) INFORMATION FOR SEQ ID NO:19:

( i ) SEQUENCE CHARACTERISTICS:

(A) LENGTH: 135 amino acids
(B) TYPE: amino acid
(D) TOPOLOGY: linear (ii) MOLECULE TYPE: protein (xi) SEQUENCE DESCRIPTION: SEQ ID NO:19:

| Met | Gly | Trp | Ser | Trp | Ile | Phe | Leu | Phe | Leu | Leu | Ser | Gly | Thr | Ala | Gly |
|---|---|---|---|---|---|---|---|---|---|---|---|---|---|---|---|
| 1 | | | | 5 | | | | | 10 | | | | | 15 | |

| Val | His | Ser | Gln | Val | Gln | Leu | Val | Gln | Ser | Gly | Ala | Glu | Val | Lys | Lys |
|---|---|---|---|---|---|---|---|---|---|---|---|---|---|---|---|
| | | | 20 | | | | | 25 | | | | | 30 | | |

| Pro | Gly | Ser | Ser | Val | Lys | Val | Ser | Cys | Lys | Ala | Ser | Gly | Tyr | Thr | Phe |
|---|---|---|---|---|---|---|---|---|---|---|---|---|---|---|---|
| | | 35 | | | | | 40 | | | | | 45 | | | |

| Thr | Ser | Tyr | Arg | Met | His | Trp | Val | Arg | Gln | Ala | Pro | Gly | Gln | Gly | Leu |
|---|---|---|---|---|---|---|---|---|---|---|---|---|---|---|---|
| | 50 | | | | | 55 | | | | | 60 | | | | |

| Glu | Trp | Ile | Gly | Tyr | Ile | Asn | Pro | Ser | Thr | Gly | Tyr | Thr | Glu | Tyr | Asn |
|---|---|---|---|---|---|---|---|---|---|---|---|---|---|---|---|
| 65 | | | | | 70 | | | | | 75 | | | | | 80 |

| Gln | Lys | Phe | Lys | Asp | Lys | Ala | Thr | Ile | Thr | Ala | Asp | Glu | Ser | Thr | Asn |
|---|---|---|---|---|---|---|---|---|---|---|---|---|---|---|---|
| | | | | 85 | | | | | 90 | | | | | 95 | |

| Thr | Ala | Tyr | Met | Glu | Leu | Ser | Ser | Leu | Arg | Ser | Glu | Asp | Thr | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Arg | Gly | Gly | Gly | Val | Phe | Asp | Tyr | Trp | Gly | Gln | Gly |
|---|---|---|---|---|---|---|---|---|---|---|---|---|---|---|---|
| | | 115 | | | | | 120 | | | | | 125 | | | |

| Thr | Leu | Val | Thr | Val | Ser | Ser |
|---|---|---|---|---|---|---|
| | 130 | | | | | 135 |

(2) INFORMATION FOR SEQ ID NO:20:

(i) SEQUENCE CHARACTERISTICS:
(A) LENGTH: 403 base pairs
(B) TYPE: nucleic acid
(C) STRANDEDNESS: single
(D) TOPOLOGY: linear (ii) MOLECULE TYPE: DNA (iii) HYPOTHETICAL: NO (ix) FEATURE:
(A) NAME/KEY: CDS
(B) LOCATION: 6..383
(D) OTHER INFORMATION: /product="Humanized anti-Tac light chain variable region: Seq ID. 21"

(xi) SEQUENCE DESCRIPTION: SEQ ID NO:20:

| TCTAG | ATG | GAG | ACC | GAT | ACC | CTC | CTG | CTA | TGG | GTC | CTC | CTG | CTA | TGG | 47 |
|---|---|---|---|---|---|---|---|---|---|---|---|---|---|---|---|
| | Met | Glu | Thr | Asp | Thr | Leu | Leu | Leu | Trp | Val | Leu | Leu | Leu | Trp | |
| | 1 | | | | 5 | | | | | 10 | | | | | |

| GTC | CCA | GGA | TCA | ACC | GGA | GAT | ATT | CAG | ATG | ACC | CAG | TCT | CCA | TCT | ACC | 95 |
|---|---|---|---|---|---|---|---|---|---|---|---|---|---|---|---|---|
| Val | Pro | Gly | Ser | Thr | Gly | Asp | Ile | Gln | Met | Thr | Gln | Ser | Pro | Ser | Thr | |
| 15 | | | | | 20 | | | | | 25 | | | | | 30 | |

| CTC | TCT | GCT | AGC | GTC | GGG | GAT | AGG | GTC | ACC | ATA | ACC | TGC | TCT | GCC | AGC | 143 |
|---|---|---|---|---|---|---|---|---|---|---|---|---|---|---|---|---|
| Leu | Ser | Ala | Ser | Val | Gly | Asp | Arg | Val | Thr | Ile | Thr | Cys | Ser | Ala | Ser | |
| | | | | 35 | | | | | 40 | | | | | 45 | | |

| TCA | AGT | ATA | AGT | TAC | ATG | CAC | TGG | TAC | CAG | CAG | AAG | CCA | GGC | AAA | GCT | 191 |
|---|---|---|---|---|---|---|---|---|---|---|---|---|---|---|---|---|
| Ser | Ser | Ile | Ser | Tyr | Met | His | Trp | Tyr | Gln | Gln | Lys | Pro | Gly | Lys | Ala | |
| | | | 50 | | | | | 55 | | | | | 60 | | | |

| CCC | AAG | CTT | CTA | ATT | TAT | ACC | ACA | TCC | AAC | CTG | GCT | TCT | GGA | GTC | CCT | 239 |
|---|---|---|---|---|---|---|---|---|---|---|---|---|---|---|---|---|
| Pro | Lys | Leu | Leu | Ile | Tyr | Thr | Thr | Ser | Asn | Leu | Ala | Ser | Gly | Val | Pro | |
| | | | 65 | | | | | 70 | | | | | 75 | | | |

| GCT | CGC | TTC | AGT | GGC | AGT | GGA | TCT | GGG | ACC | GAG | TTC | ACC | CTC | ACA | ATC | 287 |
|---|---|---|---|---|---|---|---|---|---|---|---|---|---|---|---|---|
| Ala | Arg | Phe | Ser | Gly | Ser | Gly | Ser | Gly | Thr | Glu | Phe | Thr | Leu | Thr | Ile | |
| | 80 | | | | | 85 | | | | | 90 | | | | | |

| | | | | | | | | | | | | | | | | |
|---|---|---|---|---|---|---|---|---|---|---|---|---|---|---|---|---|
| AGC | TCT | CTG | CAG | CCA | GAT | GAT | TTC | GCC | ACT | TAT | TAC | TGC | CAT | CAA | AGG | 335 |
| Ser | Ser | Leu | Gln | Pro | Asp | Asp | Phe | Ala | Thr | Tyr | Tyr | Cys | His | Gln | Arg | |
| 95 | | | | 100 | | | | | 105 | | | | | | 110 | |
| AGT | ACT | TAC | CCA | CTC | ACG | TTC | GGT | CAG | GGG | ACC | AAG | GTG | GAG | GTC | AAA | 383 |
| Ser | Thr | Tyr | Pro | Leu | Thr | Phe | Gly | Gln | Gly | Thr | Lys | Val | Glu | Val | Lys | |
| | | | | 115 | | | | | 120 | | | | | 125 | | |

CGTAAGTACA CTTTTCTAGA        403

( 2 ) INFORMATION FOR SEQ ID NO:21:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro |
| 1 | | | | 5 | | | | | 10 | | | | | 15 | |
| Gly | Ser | Thr | Gly | Asp | Ile | Gln | Met | Thr | Gln | Ser | Pro | Ser | Thr | Leu | Ser |
| | | | 20 | | | | | 25 | | | | | 30 | | |
| Ala | Ser | Val | Gly | Asp | Arg | Val | Thr | Ile | Thr | Cys | Ser | Ala | Ser | Ser | Ser |
| | | 35 | | | | | 40 | | | | | 45 | | | |
| Ile | Ser | Tyr | Met | His | Trp | Tyr | Gln | Gln | Lys | Pro | Gly | Lys | Ala | Pro | Lys |
| | 50 | | | | | 55 | | | | | 60 | | | | |
| Leu | Leu | Ile | Tyr | Thr | Thr | Ser | Asn | Leu | Ala | Ser | Gly | Val | Pro | Ala | Arg |
| 65 | | | | | 70 | | | | | 75 | | | | | 80 |
| Phe | Ser | Gly | Ser | Gly | Ser | Gly | Thr | Glu | Phe | Thr | Leu | Thr | Ile | Ser | Ser |
| | | | | 85 | | | | | 90 | | | | | 95 | |
| Leu | Gln | Pro | Asp | Asp | Phe | Ala | Thr | Tyr | Tyr | Cys | His | Gln | Arg | Ser | Thr |
| | | | 100 | | | | | 105 | | | | | 110 | | |
| Tyr | Pro | Leu | Thr | Phe | Gly | Gln | Gly | Thr | Lys | Val | Glu | Val | Lys | | |
| | | | 115 | | | | | 120 | | | | | 125 | | |

( 2 ) INFORMATION FOR SEQ ID NO:22:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..126
        ( D ) OTHER INFORMATION: /standard_name= "Oligo HES12"
        / note= "One of four oligonucleotides used to
        synthesize the humanized anti-Tac heavy chain
        gene."

( x i ) SEQUENCE DESCRIPTION: SEQ ID NO:22:

AGCTTCTAGA TGGGATGGAG CTGGATCTTT CTCTTCCTCC TGTCAGGTAC CGCGGGCGTG        60

CACTCTCAGG TCCAGCTTGT CCAGTCTGGG GCTGAAGTCA AGAAACCTGG CTCGAGCGTG        120

AAGGTC        126

( 2 ) INFORMATION FOR SEQ ID NO:23:

( i ) SEQUENCE CHARACTERISTICS:
        ( A ) LENGTH: 129 base pairs ( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i x ) FEATURE:
( A ) NAME/KEY: misc_feature
( B ) LOCATION: 1..129
( D ) OTHER INFORMATION: /standard_name= "Oligo HES13"
/ note= "One of four oligonucleotides used to
synthesize the humanized anti-Tac heavy chain
gene."

( x i ) SEQUENCE DESCRIPTION: SEQ ID NO:23:

| | | | | | |
|---|---|---|---|---|---|
| CCCAGTCGAC | GGATTAATAT | ATCCAATCCA | TTCCAGACCC | TGTCCAGGGG | CCTGCCTTAC | 60 |
| CCAGTGCATC | CTGTAGCTAG | TAAAGGTGTA | GCCAGAAGCC | TTGCAGGAGA | CCTTCACGCT | 120 |
| CGAGCCAGG | | | | | | 129 |

( 2 ) INFORMATION FOR SEQ ID NO:24:

( i ) SEQUENCE CHARACTERISTICS:
( A ) LENGTH: 124 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i x ) FEATURE:
( A ) NAME/KEY: misc_feature
( B ) LOCATION: 1..124
( D ) OTHER INFORMATION: /standard_name= "Oligo HES14"
/ note= "One of four oligonucleotides used to
synthesize the humanized anti-Tac heavy chain
gene."

( x i ) SEQUENCE DESCRIPTION: SEQ ID NO:24:

| | | | | | |
|---|---|---|---|---|---|
| TATATTAATC | CGTCGACTGG | GTATACTGAA | TACAATCAGA | AGTTCAAGGA | CAAGGCAACA | 60 |
| ATTACTGCAG | ACGAATCCAC | CAATACAGCC | TACATGGAAC | TGAGCAGCCT | GAGATCTGAG | 120 |
| GACA | | | | | | 124 |

( 2 ) INFORMATION FOR SEQ ID NO:25:

( i ) SEQUENCE CHARACTERISTICS:
( A ) LENGTH: 128 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i x ) FEATURE:
( A ) NAME/KEY: misc_feature
( B ) LOCATION: 1..128
( D ) OTHER INFORMATION: /standard_name= "Oligo HES15"
/ note= "One of four oligonucleotides used to
synthesize the humanized anti-Tac heavy chain
gene."

( x i ) SEQUENCE DESCRIPTION: SEQ ID NO:25:

| | | | | | |
|---|---|---|---|---|---|
| ATATCGTCTA | GAGGTTTTAA | GGACTCACCT | GAGGAGACTG | TGACCAGGGT | TCCTTGGCCC | 60 |
| CAGTAGTCAA | AGACCCCCCC | CCCTCTTGCA | CAGTAATAGA | CTGCGGTGTC | CTCAGATCTC | 120 |

AGGCTGCT                                                                                                    128

( 2 ) INFORMATION FOR SEQ ID NO:26:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..120
        ( D ) OTHER INFORMATION: /standard_name= "Oligo JFD1"
            / note= "One of four oligonucleotides used to
            synthesize the humanized anti-Tac light chain
            gene."

( x i ) SEQUENCE DESCRIPTION: SEQ ID NO:26:

CAAATCTAGA TGGAGACCGA TACCCTCCTG CTATGGGTCC TCCTGCTATG GGTCCAGGA          60

TCAACCGGAG ATATTCAGAT GACCCAGTCT CCATCTACCC TCTCTGCTAG CGTCGGGAT         120

( 2 ) INFORMATION FOR SEQ ID NO:27:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..114
        ( D ) OTHER INFORMATION: /standard_name= "Oligo JFD2"
            / note= "One of four oligonucleotides used to
            synthesize the humanized anti-Tac light chain
            gene."

( x i ) SEQUENCE DESCRIPTION: SEQ ID NO:27:

ATAAATTAGA AGCTTGGGAG CTTTGCCTGG CTTCTGCTGG TACCAGTGCA TGTAACTTAT          60

ACTTGAGCTG GCAGAGCAGG TTATGGTGAC CCTATCCCCG ACGCTAGCAG AGAG              114

( 2 ) INFORMATION FOR SEQ ID NO:28:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..123
        ( D ) OTHER INFORMATION: /standard_name= "Oligo JFD3"
            / note= "One of four oligonucleotides used to
            synthesize the humanized anti-Tac light chain
            gene."

( x i ) SEQUENCE DESCRIPTION: SEQ ID NO:28:

GCTCCCAAGC TTCTAATTTA TACCACATCC AACCTGGCTT CTGGAGTCCC TGCTCGCTTC          60

```
AGTGGCAGTG GATCTGGGAC CGAGTTCACC CTCACAATCA GCTCTCTGCA GCCAGATGAT      120

TTC                                                                    123
```

( 2 ) INFORMATION FOR SEQ ID NO:29:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..122
        ( D ) OTHER INFORMATION: /standard_name= "Oligo JFD4"
        / note= "One of four oligonucleotides used to
        synthesize the humanized anti-Tac light chain
        gene."

( x i ) SEQUENCE DESCRIPTION: SEQ ID NO:29:

```
TATATCTAGA AAAGTGTACT TACGTTTGAC CTCCACCTTG GTCCCCTGAC CGAACGTGAG       60

TGGGTAAGTA CTCCTTTGAT GGCAGTAATA AGTGGCGAAA TCATCTGGCT GCAGAGAGCT      120

GA                                                                     122
```

( 2 ) INFORMATION FOR SEQ ID NO:30:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..384
        ( D ) OTHER INFORMATION: /product="Light chain variable
        region of mik-beta1: Seq ID No. 31"

( x i ) SEQUENCE DESCRIPTION: SEQ ID NO:30:

```
ATG GAT TTT CAA GTG CAG ATT TTC AGC TTC CTG CTA ATC AGT GCC TCA         48
Met Asp Phe Gln Val Gln Ile Phe Ser Phe Leu Leu Ile Ser Ala Ser
 1               5                  10                  15

GTC ATA CTG TCC AGA GGA CAA ATT GTT CTC ACC CAG TCT CCA GCA ATC         96
Val Ile Leu Ser Arg Gly Gln Ile Val Leu Thr Gln Ser Pro Ala Ile
             20                  25                  30

ATG TCT GCG TCT CCA GGG GAG AAG GTC ACC ATG ACC TGC AGT GGC AGC        144
Met Ser Ala Ser Pro Gly Glu Lys Val Thr Met Thr Cys Ser Gly Ser
         35                  40                  45

TCA AGT GTA AGT TTC ATG TAC TGG TAC CAG CAG AGG CCA GGA TCC TCC        192
Ser Ser Val Ser Phe Met Tyr Trp Tyr Gln Gln Arg Pro Gly Ser Ser
     50                  55                  60

CCC AGA CTC CTG ATT TAT GAC ACA TCC AAC CTG GCT TCT GGA GTC CCT        240
Pro Arg Leu Leu Ile Tyr Asp Thr Ser Asn Leu Ala Ser Gly Val Pro
 65                  70                  75                  80

GTT CGC TTC AGT GGC AGT GGG TCT GGG ACC TCT TAC TCT CTC ACA ATC        288
Val Arg Phe Ser Gly Ser Gly Ser Gly Thr Ser Tyr Ser Leu Thr Ile
                 85                  90                  95

AGC CGA ATG GAG GCT GAA GAT GCT GCC ACT TAT TAC TGC CAG CAG TGG        336
```

|   |   |   |   |   |   |   |   |   |   |   |   |   |   |   |
|---|---|---|---|---|---|---|---|---|---|---|---|---|---|---|
| Ser | Arg | Met | Glu<br>100 | Ala | Glu | Asp | Ala | Ala<br>105 | Thr | Tyr | Tyr | Cys | Gln<br>110 | Gln | Trp |

| AGT | ACT | TAC | CCG | CTC | ACG | TTC | GGT | GCT | GGG | ACC | AAG | CTG | GAG | CTG | AAA | 384 |
|---|---|---|---|---|---|---|---|---|---|---|---|---|---|---|---|---|
| Ser | Thr | Tyr<br>115 | Pro | Leu | Thr | Phe | Gly<br>120 | Ala | Gly | Thr | Lys | Leu<br>125 | Glu | Leu | Lys | |

( 2 ) INFORMATION FOR SEQ ID NO:31:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

| Met<br>1 | Asp | Phe | Gln | Val<br>5 | Gln | Ile | Phe | Ser | Phe<br>10 | Leu | Leu | Ile | Ser | Ala<br>15 | Ser |
|---|---|---|---|---|---|---|---|---|---|---|---|---|---|---|---|
| Val | Ile | Leu | Ser<br>20 | Arg | Gly | Gln | Ile | Val<br>25 | Leu | Thr | Gln | Ser | Pro<br>30 | Ala | Ile |
| Met | Ser | Ala<br>35 | Ser | Pro | Gly | Glu | Lys<br>40 | Val | Thr | Met | Thr | Cys<br>45 | Ser | Gly | Ser |
| Ser | Ser<br>50 | Val | Ser | Phe | Met | Tyr<br>55 | Trp | Tyr | Gln | Gln | Arg<br>60 | Pro | Gly | Ser | Ser |
| Pro<br>65 | Arg | Leu | Leu | Ile | Tyr<br>70 | Asp | Thr | Ser | Asn | Leu<br>75 | Ala | Ser | Gly | Val | Pro<br>80 |
| Val | Arg | Phe | Ser | Gly<br>85 | Ser | Gly | Ser | Gly | Thr<br>90 | Ser | Tyr | Ser | Leu | Thr<br>95 | Ile |
| Ser | Arg | Met | Glu<br>100 | Ala | Glu | Asp | Ala | Ala<br>105 | Thr | Tyr | Tyr | Cys | Gln<br>110 | Gln | Trp |
| Ser | Thr | Tyr<br>115 | Pro | Leu | Thr | Phe | Gly<br>120 | Ala | Gly | Thr | Lys | Leu<br>125 | Glu | Leu | Lys |

( 2 ) INFORMATION FOR SEQ ID NO:32:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..414
        ( D ) OTHER INFORMATION: /product="Heavy chain var. region
                of the antibody mik-beta1: SeqID 33"

( x i ) SEQUENCE DESCRIPTION: SEQ ID NO:32:

| ATG | GCT | GTC | TTG | GGG | CTG | CTC | TTC | TGC | CTG | GTG | ACA | TTC | CCA | AGC | TGT | 48 |
|---|---|---|---|---|---|---|---|---|---|---|---|---|---|---|---|---|
| Met<br>1 | Ala | Val | Leu | Gly<br>5 | Leu | Leu | Phe | Cys | Leu<br>10 | Val | Thr | Phe | Pro | Ser<br>15 | Cys | |

| GTC | CTA | TCC | CAG | GTG | CAG | CTG | AAG | CAG | TCA | GGA | CCT | GGC | CTA | GTG | CAG | 96 |
|---|---|---|---|---|---|---|---|---|---|---|---|---|---|---|---|---|
| Val | Leu | Ser | Gln<br>20 | Val | Gln | Leu | Lys | Gln<br>25 | Ser | Gly | Pro | Gly | Leu<br>30 | Val | Gln | |

| CCC | TCA | CAG | AGC | CTG | TCC | ATC | ACC | TGC | ACA | GTC | TCT | GGT | TTC | TCA | GTA | 144 |
|---|---|---|---|---|---|---|---|---|---|---|---|---|---|---|---|---|
| Pro | Ser | Gln<br>35 | Ser | Leu | Ser | Ile | Thr<br>40 | Cys | Thr | Val | Ser | Gly<br>45 | Phe | Ser | Val | |

| ACA | AGT | TAT | GGT | GTA | CAC | TGG | ATT | CGC | CAG | TCT | CCA | GGA | AAG | GGT | CTG | 192 |
|---|---|---|---|---|---|---|---|---|---|---|---|---|---|---|---|---|
| Thr | Ser | Tyr<br>50 | Gly | Val | His | Trp<br>55 | Ile | Arg | Gln | Ser | Pro<br>60 | Gly | Lys | Gly | Leu | |

-continued

| | | | | | | | | | | | | | | | | |
|---|---|---|---|---|---|---|---|---|---|---|---|---|---|---|---|---|
| GAG | TGG | CTG | GGA | GTG | ATA | TGG | AGT | GGT | GGA | AGC | ACA | GAC | TAT | AAT | GCA | 240 |
| Glu | Trp | Leu | Gly | Val | Ile | Trp | Ser | Gly | Gly | Ser | Thr | Asp | Tyr | Asn | Ala | |
| 65 | | | | 70 | | | | | 75 | | | | | | 80 | |
| GCT | TTC | ATA | TCC | AGA | CTG | ACC | ATC | AGC | AAG | GAC | AAC | TCC | AAG | AGC | CAA | 288 |
| Ala | Phe | Ile | Ser | Arg | Leu | Thr | Ile | Ser | Lys | Asp | Asn | Ser | Lys | Ser | Gln | |
| | | | | 85 | | | | | 90 | | | | | 95 | | |
| GTT | TTC | TTT | AAA | GTG | AAC | AGT | CTG | CAA | CCT | GCT | GAC | ACA | GCC | ATA | TAC | 336 |
| Val | Phe | Phe | Lys | Val | Asn | Ser | Leu | Gln | Pro | Ala | Asp | Thr | Ala | Ile | Tyr | |
| | | | 100 | | | | | 105 | | | | | 110 | | | |
| TAT | TGT | GCC | AGA | GCT | GGG | GAC | TAT | AAT | TAC | GAC | GGT | TTT | GCT | TAC | TGG | 384 |
| Tyr | Cys | Ala | Arg | Ala | Gly | Asp | Tyr | Asn | Tyr | Asp | Gly | Phe | Ala | Tyr | Trp | |
| | | | 115 | | | | | 120 | | | | | 125 | | | |
| GGC | CAA | GGG | ACT | CTG | GTC | ACT | GTC | TCT | GCG | | | | | | | 414 |
| Gly | Gln | Gly | Thr | Leu | Val | Thr | Val | Ser | Ala | | | | | | | |
| | 130 | | | | | 135 | | | | | | | | | | |

( 2 ) INFORMATION FOR SEQ ID NO:33:

( i ) SEQUENCE CHARACTERISTICS:
  ( A ) LENGTH: 138 amino acids
  ( B ) TYPE: amino acid
  ( D ) TOPOLOGY: linear ( i i ) MOLECULE TYPE: protein ( x i ) SEQUENCE DESCRIPTION: SEQ ID NO:33:

| | | | | | | | | | | | | | | | |
|---|---|---|---|---|---|---|---|---|---|---|---|---|---|---|---|
| Met | Ala | Val | Leu | Gly | Leu | Leu | Phe | Cys | Leu | Val | Thr | Phe | Pro | Ser | Cys |
| 1 | | | | 5 | | | | | 10 | | | | | 15 | |
| Val | Leu | Ser | Gln | Val | Gln | Leu | Lys | Gln | Ser | Gly | Pro | Gly | Leu | Val | Gln |
| | | | 20 | | | | | 25 | | | | | 30 | | |
| Pro | Ser | Gln | Ser | Leu | Ser | Ile | Thr | Cys | Thr | Val | Ser | Gly | Phe | Ser | Val |
| | | | 35 | | | | | 40 | | | | | 45 | | |
| Thr | Ser | Tyr | Gly | Val | His | Trp | Ile | Arg | Gln | Ser | Pro | Gly | Lys | Gly | Leu |
| | | 50 | | | | | 55 | | | | | 60 | | | |
| Glu | Trp | Leu | Gly | Val | Ile | Trp | Ser | Gly | Gly | Ser | Thr | Asp | Tyr | Asn | Ala |
| 65 | | | | | 70 | | | | | 75 | | | | | 80 |
| Ala | Phe | Ile | Ser | Arg | Leu | Thr | Ile | Ser | Lys | Asp | Asn | Ser | Lys | Ser | Gln |
| | | | | 85 | | | | | 90 | | | | | 95 | |
| Val | Phe | Phe | Lys | Val | Asn | Ser | Leu | Gln | Pro | Ala | Asp | Thr | Ala | Ile | Tyr |
| | | | 100 | | | | | 105 | | | | | 110 | | |
| Tyr | Cys | Ala | Arg | Ala | Gly | Asp | Tyr | Asn | Tyr | Asp | Gly | Phe | Ala | Tyr | Trp |
| | | | 115 | | | | | 120 | | | | | 125 | | |
| Gly | Gln | Gly | Thr | Leu | Val | Thr | Val | Ser | Ala | | | | | | |
| | 130 | | | | | 135 | | | | | | | | | |

( 2 ) INFORMATION FOR SEQ ID NO:34:

( i ) SEQUENCE CHARACTERISTICS:
  ( A ) LENGTH: 107 amino acids
  ( B ) TYPE: amino acid
  ( C ) STRANDEDNESS: single
  ( D ) TOPOLOGY: unknown ( i i ) MOLECULE TYPE: protein ( i i i ) HYPOTHETICAL: NO ( i x ) FEATURE:
  ( A ) NAME/KEY: Protein
  ( B ) LOCATION: 1..107
  ( D ) OTHER INFORMATION: /note= "Amino acid sequence of the
   light chain for humane Lay antibody."

( x i ) SEQUENCE DESCRIPTION: SEQ ID NO:34:

```
Asp Ile Gln Met Thr Gln Ser Pro Ser Ser Leu Ser Val Ser Val Gly
 1               5                  10                  15

Asp Arg Val Thr Ile Thr Cys Gln Ala Ser Gln Asn Val Asn Ala Tyr
            20                  25                  30

Leu Asn Trp Tyr Gln Gln Lys Pro Gly Leu Ala Pro Lys Leu Leu Ile
        35                  40                  45

Tyr Gly Ala Ser Thr Arg Glu Ala Gly Val Pro Ser Arg Phe Ser Gly
    50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asn Asn Trp Pro Pro
                85                  90                  95

Thr Phe Gly Gln Gly Thr Lys Val Glu Val Lys
                100                 105
```

( 2 ) INFORMATION FOR SEQ ID NO:35:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..106
        ( D ) OTHER INFORMATION: /note= "Amino acid sequence of the
        light chain of the humanized mik-beta1 antibody."

( x i ) SEQUENCE DESCRIPTION: SEQ ID NO:35:

```
Asp Ile Gln Met Thr Gln Ser Pro Ser Ser Leu Ser Ala Ser Val Gly
 1               5                  10                  15

Asp Arg Val Thr Ile Thr Cys Ser Gly Ser Ser Ser Val Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Thr Tyr Pro Leu Thr
                85                  90                  95

Phe Gly Gln Gly Thr Lys Val Glu Val Lys
                100                 105
```

( 2 ) INFORMATION FOR SEQ ID NO:36:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..122
        ( D ) OTHER INFORMATION: /note= "Amino acid sequence of the heavy chain of the human Lay antibody."

( x i ) SEQUENCE DESCRIPTION: SEQ ID NO:36:

| Ala | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ala | Ser |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Trp | Lys | Tyr | Glu | Asn | Gly | Asn | Asp | Lys | His | Tyr | Ala | Asp | Ser | Val |
|---|---|---|---|---|---|---|---|---|---|---|---|---|---|---|---|
| | 50 | | | | | 55 | | | | | 60 | | | | |

| Asn | Gly | Arg | Phe | Thr | Ile | Ser | Arg | Asn | Asp | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Gly | Leu | Gln | Ala | Glx | Val | Ser | Ala | Ile | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Ala | Gly | Pro | Tyr | Val | Ser | Pro | Thr | Phe | Phe | Ala | His | Trp |
|---|---|---|---|---|---|---|---|---|---|---|---|---|---|---|---|
| | | | 100 | | | | 105 | | | | | 110 | | | |

| Gly | Gln | Gly | Thr | Leu | Val | Thr | Val | Ser | Ser |
|---|---|---|---|---|---|---|---|---|---|
| | | 115 | | | | | 120 | | |

( 2 ) INFORMATION FOR SEQ ID NO:37:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..119
        ( D ) OTHER INFORMATION: /note= "Amino acid sequence of the
        heavy chain of the humanized mik-beta1 antibody."

( x i ) SEQUENCE DESCRIPTION: SEQ ID NO:37:

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Val | Thr | Ser | Tyr |
|---|---|---|---|---|---|---|---|---|---|---|---|---|---|---|---|
| | | | 20 | | | | | 25 | | | | | 30 | | |

| Gly | Val | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Val | Ile | Trp | Ser | Gly | Gly | Ser | Thr | Asp | Tyr | Asn | Ala | Ala | Phe | Ile |
|---|---|---|---|---|---|---|---|---|---|---|---|---|---|---|---|
| | 50 | | | | | 55 | | | | | 60 | | | | |

| Ser | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Gln | Ala | Glu | Asp | Thr | Ala | Ile | Tyr | Tyr | Cys | Ala |
|---|---|---|---|---|---|---|---|---|---|---|---|---|---|---|---|
| | | | | 85 | | | | | 90 | | | | | 95 | |

| Arg | Ala | Gly | Asp | Tyr | Asn | Tyr | Asp | Gly | Phe | Ala | Tyr | Trp | Gly | Gln | Gly |
|---|---|---|---|---|---|---|---|---|---|---|---|---|---|---|---|
| | | | 100 | | | | 105 | | | | | 110 | | | |

| Thr | Leu | Val | Thr | Val | Ser | Ser |
|---|---|---|---|---|---|---|
| | | 115 | | | | |

( 2 ) INFORMATION FOR SEQ ID NO:38:

( i ) SEQUENCE CHARACTERISTICS:
        ( A ) LENGTH: 107 base pairs
        ( B ) TYPE: nucleic acid
        ( C ) STRANDEDNESS: single (D) TOPOLOGY: linear (ii) MOLECULE TYPE: DNA (iii) HYPOTHETICAL: NO (ix) FEATURE:
   (A) NAME/KEY: misc_feature
   (B) LOCATION: 1..107
   (D) OTHER INFORMATION: /standard_name= "Oligo vc13"

(xi) SEQUENCE DESCRIPTION: SEQ ID NO:38:

```
TTCTGCTGGT ACCAGTACAT GAAACTTACA CTTGAGCTGC CACTGCAGGT GATGGTGACG      60

CGGTCACCCA CTGAGGCACT GAGGCTAGAT GGAGACTGGG TCATTTG                   107
```

(2) INFORMATION FOR SEQ ID NO:39:

(i) SEQUENCE CHARACTERISTICS:
      (A) LENGTH: 136 base pairs
      (B) TYPE: nucleic acid
      (C) STRANDEDNESS: single
      (D) TOPOLOGY: linear (ii) MOLECULE TYPE: DNA (iii) HYPOTHETICAL: NO (ix) FEATURE:
      (A) NAME/KEY: misc_feature
      (B) LOCATION: 1..136
      (D) OTHER INFORMATION: /standard_name= "Oligo vc14"

(xi) SEQUENCE DESCRIPTION: SEQ ID NO:39:

```
CATGTACTGG TACCAGCAGA AGCCAGGAAA AGCTCCGAAA CTTCTGATTT ATGACACATC      60

CAACCTGGCT TCTGGAGTCC CTTCCCGCTT CAGTGGCAGT GGGTCTGGGA CCGATTACAC     120

CTTTACAATC TCTTCA                                                    136
```

(2) INFORMATION FOR SEQ ID NO:40:

(i) SEQUENCE CHARACTERISTICS:
      (A) LENGTH: 137 base pairs
      (B) TYPE: nucleic acid
      (C) STRANDEDNESS: single
      (D) TOPOLOGY: linear (ii) MOLECULE TYPE: DNA (iii) HYPOTHETICAL: NO (ix) FEATURE:
      (A) NAME/KEY: misc_feature
      (B) LOCATION: 1..137
      (D) OTHER INFORMATION: /standard_name= "Oligo vc15"

(xi) SEQUENCE DESCRIPTION: SEQ ID NO:40:

```
TGTGTCTAGA AAAGTGTACT TACGTTTTAC CTCGACCTTG GTCCCTTGAC CGAACGTGAG      60

CGGGTAAGTA CTCCACTGCT GGCAGTAATA AGTGGCTATA TCTTCCGGCT GAAGTGAAGA     120

GATTGTAAAG GTGTAAT                                                   137
```

(2) INFORMATION FOR SEQ ID NO:41:

(i) SEQUENCE CHARACTERISTICS:
      (A) LENGTH: 108 base pairs
      (B) TYPE: nucleic acid
      (C) STRANDEDNESS: single
      (D) TOPOLOGY: linear (ii) MOLECULE TYPE: DNA (iii) HYPOTHETICAL: NO (ix) FEATURE:
    (A) NAME/KEY: misc_feature
    (B) LOCATION: 1..108
    (D) OTHER INFORMATION: /standard_name= "Oligo vc16"

(xi) SEQUENCE DESCRIPTION: SEQ ID NO:41:

| | | | | | |
|---|---|---|---|---|---|
| CACATCTAGA | CCACCATGGA | TTTTCAAGTG | CAGATCTTCA | GCTTCCTGCT | AATCAGTGCC | 60 |
| TCAGTCATAC | TGTCCAGAGG | AGATATTCAA | ATGACCCAGT | CTCCATCT | | 108 |

(2) INFORMATION FOR SEQ ID NO:42:

(i) SEQUENCE CHARACTERISTICS:
    (A) LENGTH: 138 base pairs
    (B) TYPE: nucleic acid
    (C) STRANDEDNESS: single
    (D) TOPOLOGY: linear (ii) MOLECULE TYPE: DNA (iii) HYPOTHETICAL: NO (ix) FEATURE:
    (A) NAME/KEY: misc_feature
    (B) LOCATION: 1..138
    (D) OTHER INFORMATION: /standard_name= "Oligo vc11"

(xi) SEQUENCE DESCRIPTION: SEQ ID NO:42:

| | | | | | |
|---|---|---|---|---|---|
| TAGTCTGTCG | ACCCACCACT | CCATATCACT | CCCACCCACT | CGAGTCCCTT | TCCAGGAGCC | 60 |
| TGGCGGACCC | AGTGTACACC | ATAACTTGTT | ACGGTGAAAC | CACTGGCGGC | ACAAGACAGT | 120 |
| CTCAGAGATC | CTCCTGGC | | | | | 138 |

(2) INFORMATION FOR SEQ ID NO:43:

(i) SEQUENCE CHARACTERISTICS:
    (A) LENGTH: 126 base pairs
    (B) TYPE: nucleic acid
    (C) STRANDEDNESS: single
    (D) TOPOLOGY: linear (ii) MOLECULE TYPE: DNA (iii) HYPOTHETICAL: NO (ix) FEATURE:
    (A) NAME/KEY: misc_feature
    (B) LOCATION: 1..126
    (D) OTHER INFORMATION: /standard_name= "Oligo vc12"

(xi) SEQUENCE DESCRIPTION: SEQ ID NO:43:

| | | | | | |
|---|---|---|---|---|---|
| TGGTGGGTCG | ACAGACTATA | ATGCAGCTTT | CATATCCAGA | TTTACCATCA | GCAGAGACAA | 60 |
| CAGCAAGAAC | ACACTGTATC | TCCAAATGAA | TAGCCTGCAA | GCCGAGGACA | CAGCCATATA | 120 |
| TTATTG | | | | | | 126 |

(2) INFORMATION FOR SEQ ID NO:44:

(i) SEQUENCE CHARACTERISTICS:
    (A) LENGTH: 130 base pairs
    (B) TYPE: nucleic acid
    (C) STRANDEDNESS: single
    (D) TOPOLOGY: linear (ii) MOLECULE TYPE: DNA (iii) HYPOTHETICAL: NO (ix) FEATURE:
    (A) NAME/KEY: misc_feature ( B ) LOCATION: 1..130
              ( D ) OTHER INFORMATION: /standard_name= "Oligo wps54"

( x i ) SEQUENCE DESCRIPTION: SEQ ID NO:44:

ACACTCTAGA CCACCATGGC TGTCTTGGGG CTGCTCTTCT GCCTGGTGAC ATTCCCAAGC    60

TGTGTCCTAT CCGCTGTCCA GCTGCTAGAG AGTGGTGGCG GTCTGGTGCA GCCAGGAGGA    120

TCTCTGAGAC                                                          130

( 2 ) INFORMATION FOR SEQ ID NO:45:

( i ) SEQUENCE CHARACTERISTICS:
              ( A ) LENGTH: 118 base pairs
              ( B ) TYPE: nucleic acid
              ( C ) STRANDEDNESS: single
              ( D ) TOPOLOGY: linear ( i i ) MOLECULE TYPE: DNA ( i i i ) HYPOTHETICAL: NO ( i x ) FEATURE:
              ( A ) NAME/KEY: misc_feature
              ( B ) LOCATION: 1..118
              ( D ) OTHER INFORMATION: /standard_name= "Oligo wps57"

( x i ) SEQUENCE DESCRIPTION: SEQ ID NO:45:

ACACTCTAGA AGTTAGGACT CACCTGAAGA GACAGTGACC AGAGTCCCTT GGCCCCAGTA    60

AGCAAAACCG TCGTAATTAT AGTCCCAGC TCTGGCACAA TAATATATGG CTGTGTCC      118

( 2 ) INFORMATION FOR SEQ ID NO:46:

( i ) SEQUENCE CHARACTERISTICS:
              ( A ) LENGTH: 111 amino acids
              ( B ) TYPE: amino acid
              ( C ) STRANDEDNESS: single
              ( D ) TOPOLOGY: linear ( i i ) MOLECULE TYPE: peptide ( x i ) SEQUENCE DESCRIPTION: SEQ ID NO:46:

Asp  Ile  Val  Leu  Thr  Gln  Ser  Pro  Ala  Ser  Leu  Ala  Val  Ser  Leu  Gly
 1                   5                        10                        15

Gln  Arg  Ala  Thr  Ile  Ser  Cys  Arg  Ala  Ser  Gln  Ser  Val  Ser  Thr  Ser
                20                       25                       30

Thr  Tyr  Asn  Tyr  Met  His  Trp  Tyr  Gln  Gln  Lys  Pro  Gly  Gln  Pro  Pro
           35                       40                       45

Lys  Leu  Leu  Ile  Lys  Tyr  Ala  Ser  Asn  Leu  Glu  Ser  Gly  Val  Pro  Ala
      50                       55                       60

Arg  Phe  Ser  Gly  Ser  Gly  Phe  Gly  Thr  Asp  Phe  Thr  Leu  Asn  Ile  His
 65                       70                       75                       80

Pro  Val  Glu  Glu  Glu  Asp  Thr  Val  Thr  Tyr  Tyr  Cys  Gln  His  Ser  Trp
                     85                       90                       95

Glu  Ile  Pro  Tyr  Thr  Phe  Gly  Gly  Gly  Thr  Lys  Leu  Glu  Ile  Lys
               100                      105                      110

( 2 ) INFORMATION FOR SEQ ID NO:47:

( i ) SEQUENCE CHARACTERISTICS:
              ( A ) LENGTH: 111 amino acids
              ( B ) TYPE: amino acid
              ( C ) STRANDEDNESS: single
              ( D ) TOPOLOGY: linear ( i i ) MOLECULE TYPE: peptide ( x i ) SEQUENCE DESCRIPTION: SEQ ID NO:47:

| | | | | | | | | | | | | | | | |
|---|---|---|---|---|---|---|---|---|---|---|---|---|---|---|---|
| Glu<br>1 | Ile | Val | Met | Thr<br>5 | Gln | Ser | Pro | Ala | Thr<br>10 | Leu | Ser | Val | Ser | Pro<br>15 | Gly |
| Glu | Arg | Ala | Thr<br>20 | Leu | Ser | Cys | Arg | Ala<br>25 | Ser | Gln | Ser | Val | Ser<br>30 | Thr | Ser |
| Thr | Tyr | Asn<br>35 | Tyr | Met | His | Trp | Tyr<br>40 | Gln | Gln | Lys | Pro | Gly<br>45 | Gln | Ser | Pro |
| Arg | Leu<br>50 | Leu | Ile | Lys | Tyr | Ala<br>55 | Ser | Asn | Leu | Glu | Ser<br>60 | Gly | Ile | Pro | Ala |
| Arg<br>65 | Phe | Ser | Gly | Ser | Gly<br>70 | Ser | Gly | Thr | Glu | Phe<br>75 | Thr | Leu | Thr | Ile | Ser<br>80 |
| Arg | Leu | Glu | Ser | Glu<br>85 | Asp | Phe | Ala | Val | Tyr<br>90 | Tyr | Cys | Gln | His | Ser<br>95 | Trp |
| Glu | Ile | Pro | Tyr<br>100 | Thr | Phe | Gly | Gln | Gly<br>105 | Thr | Arg | Val | Glu | Ile<br>110 | Lys | |

( 2 ) INFORMATION FOR SEQ ID NO:48:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

| | | | | | | | | | | | | | | | |
|---|---|---|---|---|---|---|---|---|---|---|---|---|---|---|---|
| Glu<br>1 | Met | Ile | Leu | Val<br>5 | Glu | Ser | Gly | Gly | Gly<br>10 | Leu | Val | Lys | Pro | Gly<br>15 | Ala |
| Ser | Leu | Lys | Leu<br>20 | Ser | Cys | Ala | Ala | Ser<br>25 | Gly | Phe | Thr | Phe | Ser<br>30 | Asn | Tyr |
| Gly | Leu | Ser<br>35 | Trp | Val | Arg | Gln | Thr<br>40 | Ser | Asp | Arg | Arg | Leu<br>45 | Glu | Trp | Val |
| Ala | Ser<br>50 | Ile | Ser | Arg | Gly | Gly<br>55 | Gly | Arg | Ile | Tyr | Ser<br>60 | Pro | Asp | Asn | Leu |
| Lys<br>65 | Gly | Arg | Phe | Thr | Ile<br>70 | Ser | Arg | Glu | Asp | Ala<br>75 | Lys | Asn | Thr | Leu | Tyr<br>80 |
| Leu | Gln | Met | Ser | Ser<br>85 | Leu | Lys | Ser | Glu | Asp<br>90 | Thr | Ala | Leu | Tyr | Tyr<br>95 | Cys |
| Leu | Arg | Glu | Gly<br>100 | Ile | Tyr | Tyr | Ala | Asp<br>105 | Tyr | Gly | Phe | Phe | Asp<br>110 | Val | Trp |
| Gly | Thr | Gly<br>115 | Thr | Thr | Val | Ile | Val<br>120 | Ser | Ser | | | | | | |

( 2 ) INFORMATION FOR SEQ ID NO:49:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

| | | | | | | | | | | | | | | | |
|---|---|---|---|---|---|---|---|---|---|---|---|---|---|---|---|
| Glu<br>1 | Val | Gln | Leu | Leu<br>5 | Glu | Ser | Gly | Gly | Gly<br>10 | Leu | Val | Gln | Pro | Gly<br>15 | Gly |
| Ser | Leu | Arg | Leu<br>20 | Ser | Cys | Ala | Ala | Ser<br>25 | Gly | Phe | Thr | Phe | Ser<br>30 | Asn | Tyr |
| Gly | Leu | Ser | Trp | Val | Arg | Gln | Ala | Pro | Gly | Lys | Gly | Leu | Glu | Trp | Val |

```
                    35                          40                          45
     Ala  Ser  Ile  Ser  Arg  Gly  Gly  Arg  Ile  Tyr  Ser  Pro  Asp  Asn  Leu
          50                       55                       60

Lys  Gly  Arg  Phe  Thr  Ile  Ser  Arg  Asn  Asp  Ser  Lys  Asn  Thr  Leu  Tyr
     65                       70                       75                       80

Leu  Gln  Met  Asn  Ser  Leu  Gln  Ala  Glu  Asp  Thr  Ala  Leu  Tyr  Tyr  Cys
                    85                       90                       95

Leu  Arg  Glu  Gly  Ile  Tyr  Tyr  Ala  Asp  Tyr  Gly  Phe  Phe  Asp  Val  Trp
                    100                      105                      110

Gly  Gln  Gly  Thr  Leu  Val  Thr  Val  Ser  Ser
                    115                      120
```

( 2 ) INFORMATION FOR SEQ ID NO:50:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
     Asp  Ile  Val  Met  Thr  Gln  Ser  His  Lys  Phe  Met  Ser  Thr  Ser  Val  Gly
     1                  5                       10                      15

Asp  Arg  Val  Ser  Ile  Thr  Cys  Lys  Ala  Ser  Gln  Asp  Val  Gly  Ser  Ala
                    20                       25                       30

Val  Val  Trp  His  Gln  Gln  Lys  Ser  Gly  Gln  Ser  Pro  Lys  Leu  Leu  Ile
                    35                       40                       45

Tyr  Trp  Ala  Ser  Thr  Arg  His  Thr  Gly  Val  Pro  Asp  Arg  Phe  Thr  Gly
          50                       55                       60

Ser  Gly  Ser  Gly  Thr  Asp  Phe  Thr  Leu  Thr  Ile  Thr  Asn  Val  Gln  Ser
     65                       70                       75                       80

Glu  Asp  Leu  Ala  Asp  Tyr  Phe  Cys  Gln  Gln  Tyr  Ser  Ile  Phe  Pro  Leu
                    85                       90                       95

Thr  Phe  Gly  Ala  Gly  Thr  Arg  Leu  Glu  Leu  Lys
                    100                      105
```

( 2 ) INFORMATION FOR SEQ ID NO:51:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
     Asp  Ile  Gln  Met  Thr  Gln  Ser  Pro  Ser  Thr  Leu  Ser  Ala  Ser  Val  Gly
     1                  5                       10                      15

Asp  Arg  Val  Thr  Ile  Thr  Cys  Lys  Ala  Ser  Gln  Asp  Val  Gly  Ser  Ala
                    20                       25                       30

Val  Val  Trp  His  Gln  Gln  Lys  Pro  Gly  Lys  Ala  Pro  Lys  Leu  Leu  Ile
                    35                       40                       45

Tyr  Trp  Ala  Ser  Thr  Arg  His  Thr  Gly  Val  Pro  Ser  Arg  Phe  Thr  Gly
          50                       55                       60

Ser  Gly  Ser  Gly  Thr  Glu  Phe  Thr  Leu  Thr  Ile  Ser  Ser  Leu  Gln  Pro
     65                       70                       75                       80

Asp  Asp  Phe  Ala  Thr  Tyr  Phe  Cys  Gln  Gln  Tyr  Ser  Ile  Phe  Pro  Leu
```

```
                            8 5                    9 0                    9 5
        Thr  Phe  Gly  Gln  Gly  Thr  Lys  Val  Glu  Val  Lys
                            100                   105
```

( 2 ) INFORMATION FOR SEQ ID NO:52:

( i ) SEQUENCE CHARACTERISTICS:
    ( A ) LENGTH: 121 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:52:

```
Gln  Val  Gln  Leu  Gln  Gln  Ser  Asp  Ala  Glu  Leu  Val  Lys  Pro  Gly  Ala
1                 5                      10                     15

Ser  Val  Lys  Ile  Ser  Cys  Lys  Val  Ser  Gly  Tyr  Thr  Phe  Thr  Asp  His
                20                      25                     30

Thr  Ile  His  Trp  Met  Lys  Gln  Arg  Pro  Glu  Gln  Gly  Leu  Glu  Trp  Phe
           35                           40                     45

Gly  Tyr  Ile  Tyr  Pro  Arg  Asp  Gly  His  Thr  Arg  Tyr  Ser  Glu  Lys  Phe
     50                           55                      60

Lys  Gly  Lys  Ala  Thr  Leu  Thr  Ala  Asp  Lys  Ser  Ala  Ser  Thr  Ala  Tyr
65                           70                      75                      80

Met  His  Leu  Asn  Ser  Leu  Thr  Ser  Glu  Asp  Ser  Ala  Val  Tyr  Phe  Cys
                85                           90                      95

Ala  Arg  Gly  Arg  Asp  Ser  Arg  Glu  Arg  Asn  Gly  Phe  Ala  Tyr  Trp  Gly
               100                          105                     110

Gln  Gly  Thr  Leu  Val  Thr  Val  Ser  Ala
              115                     120
```

( 2 ) INFORMATION FOR SEQ ID NO:53:

( i ) SEQUENCE CHARACTERISTICS:
    ( A ) LENGTH: 121 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:53:

```
Gln  Val  Gln  Leu  Val  Gln  Ser  Gly  Ala  Glu  Val  Lys  Lys  Pro  Gly  Ser
1                 5                      10                     15

Ser  Val  Lys  Val  Ser  Cys  Lys  Ala  Ser  Gly  Tyr  Thr  Phe  Thr  Asp  His
                20                      25                     30

Thr  Ile  His  Trp  Met  Arg  Gln  Ala  Pro  Gly  Gln  Gly  Leu  Glu  Trp  Phe
           35                           40                     45

Gly  Tyr  Ile  Tyr  Pro  Arg  Asp  Gly  His  Thr  Arg  Tyr  Ser  Glu  Lys  Phe
     50                           55                      60

Lys  Gly  Lys  Ala  Thr  Ile  Thr  Ala  Asp  Glu  Ser  Thr  Asn  Thr  Ala  Tyr
65                           70                      75                      80

Met  Glu  Leu  Ser  Ser  Leu  Arg  Ser  Glu  Asp  Thr  Ala  Val  Tyr  Phe  Cys
                85                           90                      95

Ala  Arg  Gly  Arg  Asp  Ser  Arg  Glu  Arg  Asn  Gly  Phe  Ala  Tyr  Trp  Gly
               100                          105                     110

Gln  Gly  Thr  Leu  Val  Thr  Val  Ser  Ser
              115                     120
```

(2) INFORMATION FOR SEQ ID NO:54:

(i) SEQUENCE CHARACTERISTICS:
      (A) LENGTH: 111 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:54:

```
Asp Ile Val Leu Thr Gln Ser Pro Ala Ser Leu Ala Val Ser Leu Gly
 1               5                  10                  15
Gln Arg Ala Thr Ile Ser Cys Arg Ala Ser Glu Ser Val Asp Asn Tyr
            20                  25                  30
Gly Ile Ser Phe Met Asn Trp Phe Gln Gln Lys Pro Gly Gln Pro Pro
            35                  40                  45
Lys Leu Leu Ile Tyr Ala Ala Ser Asn Gln Gly Ser Gly Val Pro Ala
 50                      55                  60
Arg Phe Ser Gly Ser Gly Ser Gly Thr Asp Phe Ser Leu Asn Ile His
 65                  70                  75                  80
Pro Met Glu Glu Asp Asp Thr Ala Met Tyr Phe Cys Gln Gln Ser Lys
                 85                  90                  95
Glu Val Pro Trp Thr Phe Gly Gly Gly Thr Lys Leu Glu Ile Lys
             100                 105                 110
```

(2) INFORMATION FOR SEQ ID NO:55:

(i) SEQUENCE CHARACTERISTICS:
      (A) LENGTH: 111 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:55:

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Glu Ser Val Asp Asn Tyr
            20                  25                  30
Gly Ile Ser Phe Met Asn Trp Phe Gln Gln Lys Pro Gly Lys Ala Pro
            35                  40                  45
Lys Leu Leu Ile Tyr Ala Ala Ser Asn Gln Gly Ser Gly Val Pro Ser
 50                      55                  60
Arg Phe Ser Gly Ser Gly Ser Gly Thr Asp Phe Thr Leu Thr Ile Ser
 65                  70                  75                  80
Ser Leu Gln Pro Asp Asp Phe Ala Thr Tyr Tyr Cys Gln Gln Ser Lys
                 85                  90                  95
Glu Val Pro Trp Thr Phe Gly Gln Gly Thr Lys Val Glu Ile Lys
             100                 105                 110
```

(2) INFORMATION FOR SEQ ID NO:56:

(i) SEQUENCE CHARACTERISTICS:
      (A) LENGTH: 116 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:56:

```
Glu  Val  Gln  Leu  Gln  Gln  Ser  Gly  Pro  Glu  Leu  Val  Lys  Pro  Gly  Ala
 1              5                    10                       15

Ser  Val  Lys  Ile  Ser  Cys  Lys  Ala  Ser  Gly  Tyr  Thr  Phe  Thr  Asp  Tyr
               20                   25                       30

Asn  Met  His  Trp  Val  Lys  Gln  Ser  His  Gly  Lys  Ser  Leu  Glu  Trp  Ile
          35                        40                       45

Gly  Tyr  Ile  Tyr  Pro  Tyr  Asn  Gly  Gly  Thr  Gly  Tyr  Asn  Gln  Lys  Phe
          50                        55                       60

Lys  Ser  Lys  Ala  Thr  Leu  Thr  Val  Asp  Asn  Ser  Ser  Thr  Ala  Tyr
 65                       70                   75                       80

Met  Asp  Val  Arg  Ser  Leu  Thr  Ser  Glu  Asp  Ser  Ala  Val  Tyr  Tyr  Cys
                    85                        90                       95

Ala  Arg  Gly  Arg  Pro  Ala  Met  Asp  Tyr  Trp  Gly  Gln  Gly  Thr  Ser  Val
                    100                      105                      110

Thr  Val  Ser  Ser
               115
```

( 2 ) INFORMATION FOR SEQ ID NO:57:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:57:

```
Gln  Val  Gln  Leu  Val  Gln  Ser  Gly  Ala  Glu  Val  Lys  Lys  Pro  Gly  Ser
 1              5                    10                       15

Ser  Val  Lys  Val  Ser  Cys  Lys  Ala  Ser  Gly  Tyr  Thr  Phe  Thr  Asp  Tyr
               20                   25                       30

Asn  Met  His  Trp  Val  Arg  Gln  Ala  Pro  Gly  Gln  Gly  Leu  Glu  Trp  Ile
          35                        40                       45

Gly  Tyr  Ile  Tyr  Pro  Tyr  Asn  Gly  Gly  Thr  Gly  Tyr  Asn  Gln  Lys  Phe
          50                        55                       60

Lys  Ser  Lys  Ala  Thr  Ile  Thr  Ala  Asp  Glu  Ser  Thr  Asn  Thr  Ala  Tyr
 65                       70                   75                       80

Met  Glu  Leu  Ser  Ser  Leu  Arg  Ser  Glu  Asp  Thr  Ala  Val  Tyr  Tyr  Cys
                    85                        90                       95

Ala  Arg  Gly  Arg  Pro  Ala  Met  Asp  Tyr  Trp  Gly  Gln  Gly  Thr  Leu  Val
                    100                      105                      110

Thr  Val  Ser  Ser
               115
```

( 2 ) INFORMATION FOR SEQ ID NO:58:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Gln  Ile  Val  Leu  Thr  Gln  Ser  Pro  Ala  Ile  Met  Ser  Ala  Ser  Pro  Gly
 1              5                    10                       15

Glu  Lys  Val  Thr  Met  Thr  Cys  Ser  Gly  Ser  Ser  Ser  Val  Ser  Phe  Met
               20                   25                       30
```

```
     Tyr  Trp  Tyr  Gln  Gln  Arg  Pro  Gly  Ser  Ser  Pro  Arg  Leu  Leu  Ile  Tyr
               35                       40                      45

Asp  Thr  Ser  Asn  Leu  Ala  Ser  Gly  Val  Pro  Val  Arg  Phe  Ser  Gly  Ser
          50                       55                      60

Gly  Ser  Gly  Thr  Ser  Tyr  Ser  Leu  Thr  Ile  Ser  Arg  Met  Glu  Ala  Glu
     65                       70                      75                          80

Asp  Ala  Ala  Thr  Tyr  Tyr  Cys  Gln  Gln  Trp  Ser  Thr  Tyr  Pro  Leu  Thr
                         85                       90                      95

Phe  Gly  Ala  Gly  Thr  Lys  Leu  Glu  Leu  Lys
                    100                      105
```

( 2 ) INFORMATION FOR SEQ ID NO:59:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
     Asp  Ile  Gln  Met  Thr  Gln  Ser  Pro  Ser  Ser  Leu  Ser  Ala  Ser  Val  Gly
     1                        5                       10                          15

Asp  Arg  Val  Thr  Ile  Thr  Cys  Ser  Gly  Ser  Ser  Ser  Val  Ser  Phe  Met
                    20                       25                      30

Tyr  Trp  Tyr  Gln  Gln  Lys  Pro  Gly  Lys  Ala  Pro  Lys  Leu  Leu  Ile  Tyr
               35                       40                      45

Asp  Thr  Ser  Asn  Leu  Ala  Ser  Gly  Val  Pro  Ser  Arg  Phe  Ser  Gly  Ser
          50                       55                      60

Gly  Ser  Gly  Thr  Asp  Tyr  Thr  Phe  Thr  Ile  Ser  Ser  Leu  Gln  Pro  Glu
     65                       70                      75                          80

Asp  Ile  Ala  Thr  Tyr  Tyr  Cys  Gln  Gln  Trp  Ser  Thr  Tyr  Pro  Leu  Thr
                         85                       90                      95

Phe  Gly  Gln  Gly  Thr  Lys  Val  Glu  Val  Lys
                    100                      105
```

( 2 ) INFORMATION FOR SEQ ID NO:60:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

```
     Gln  Val  Gln  Leu  Lys  Gln  Ser  Gly  Pro  Gly  Leu  Val  Gln  Pro  Ser  Gln
     1                        5                       10                          15

Ser  Leu  Ser  Ile  Thr  Cys  Thr  Val  Ser  Gly  Phe  Ser  Val  Thr  Ser  Tyr
                    20                       25                      30

Gly  Val  His  Trp  Ile  Arg  Gln  Ser  Pro  Gly  Lys  Gly  Leu  Glu  Trp  Leu
               35                       40                      45

Gly  Val  Ile  Trp  Ser  Gly  Gly  Ser  Thr  Asp  Tyr  Asn  Ala  Ala  Phe  Ile
          50                       55                      60

Ser  Arg  Leu  Thr  Ile  Ser  Lys  Asp  Asn  Ser  Lys  Ser  Gln  Val  Phe  Phe
     65                       70                      75                          80

Lys  Val  Asn  Ser  Leu  Gln  Pro  Ala  Asp  Thr  Ala  Ile  Tyr  Tyr  Cys  Ala
                    85                       90                      95
```

```
       Arg  Ala  Gly  Asp  Tyr  Asn  Tyr  Asp  Gly  Phe  Ala  Tyr  Trp  Gly  Gln  Gly
                      100                      105                      110

Thr  Leu  Val  Thr  Val  Ser  Ala
                      115
```

(2) INFORMATION FOR SEQ ID NO:61:

(i) SEQUENCE CHARACTERISTICS:
    (A) LENGTH: 119 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:61:

```
       Glu  Val  Gln  Leu  Leu  Glu  Ser  Gly  Gly  Gly  Leu  Val  Gln  Pro  Gly  Gly
        1              5                        10                       15

Ser  Leu  Arg  Leu  Ser  Cys  Ala  Ala  Ser  Gly  Phe  Thr  Val  Thr  Ser  Tyr
                      20                       25                       30

Gly  Val  His  Trp  Val  Arg  Gln  Ala  Pro  Gly  Lys  Gly  Leu  Glu  Trp  Val
                      35                       40                       45

Gly  Val  Ile  Trp  Ser  Gly  Gly  Ser  Thr  Asp  Tyr  Asn  Ala  Ala  Phe  Ile
                 50                       55                       60

Ser  Arg  Phe  Thr  Ile  Ser  Arg  Asp  Asn  Ser  Lys  Asn  Thr  Leu  Tyr  Leu
        65                      70                       75                      80

Gln  Met  Asn  Ser  Leu  Gln  Ala  Glu  Asp  Thr  Ala  Ile  Tyr  Tyr  Cys  Ala
                           85                       90                       95

Arg  Ala  Gly  Asp  Tyr  Asn  Tyr  Asp  Gly  Phe  Ala  Tyr  Trp  Gly  Gln  Gly
                      100                      105                      110

Thr  Leu  Val  Thr  Val  Ser  Ser
                      115
```

(2) INFORMATION FOR SEQ ID NO:62:

(i) SEQUENCE CHARACTERISTICS:
    (A) LENGTH: 107 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:62:

```
       Asp  Ile  Val  Leu  Thr  Gln  Ser  Pro  Ala  Thr  Leu  Ser  Val  Thr  Pro  Gly
        1              5                        10                       15

Asp  Ser  Val  Ser  Leu  Ser  Cys  Arg  Ala  Ser  Gln  Ser  Ile  Ser  Asn  Asn
                      20                       25                       30

Leu  His  Trp  Tyr  Gln  Gln  Lys  Ser  His  Glu  Ser  Pro  Arg  Leu  Leu  Ile
                      35                       40                       45

Lys  Tyr  Ala  Ser  Gln  Ser  Ile  Ser  Gly  Ile  Pro  Ser  Arg  Phe  Ser  Gly
                 50                       55                       60

Ser  Gly  Ser  Gly  Thr  Asp  Phe  Thr  Leu  Ser  Val  Asn  Gly  Val  Glu  Thr
        65                      70                       75                      80

Glu  Asp  Phe  Gly  Met  Tyr  Phe  Cys  Gln  Gln  Ser  Asn  Ser  Trp  Pro  His
                           85                       90                       95

Thr  Phe  Gly  Gly  Gly  Thr  Lys  Leu  Glu  Ile  Lys
                      100                      105
```

(2) INFORMATION FOR SEQ ID NO:63:

( i ) SEQUENCE CHARACTERISTICS:
    ( A ) LENGTH: 107 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:63:

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Ile Ser Asn Asn
             20                  25                  30
Leu His Trp Tyr Gln Gln Lys Pro Gly Gln Ala Pro Arg Leu Leu Ile
         35                  40                  45
Lys Tyr Ala Ser Gln Ser Ile Ser Gly Ile Pro Asp Arg Phe Ser Gly
     50                  55                  60
Ser Gly Ser Gly Thr Asp Phe Thr Leu Thr Ile Ser Arg Leu Glu Pro
 65                  70                  75                  80
Glu Asp Phe Ala Val Tyr Tyr Cys Gln Gln Ser Asn Ser Trp Pro His
                 85                  90                  95
Thr Phe Gly Gln Gly Thr Lys Val Glu Ile Lys
                100                 105
```

( 2 ) INFORMATION FOR SEQ ID NO:64:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

```
Glu Val Gln Leu Gln Gln Ser Gly Pro Glu Leu Val Lys Pro Gly Ala
  1               5                  10                  15
Ser Met Lys Ile Ser Cys Lys Ala Ser Val Tyr Ser Phe Thr Gly Tyr
             20                  25                  30
Thr Met Asn Trp Val Lys Gln Ser His Gly Gln Asn Leu Glu Trp Ile
         35                  40                  45
Gly Leu Ile Asn Pro Tyr Asn Gly Gly Thr Ser Tyr Asn Gln Lys Phe
     50                  55                  60
Lys Gly Lys Ala Thr Leu Thr Val Asp Lys Ser Ser Asn Thr Ala Tyr
 65                  70                  75                  80
Met Glu Leu Leu Ser Leu Thr Ser Ala Asp Ser Ala Val Tyr Tyr Cys
                 85                  90                  95
Thr Arg Arg Gly Phe Arg Asp Tyr Ser Met Asp Tyr Trp Gly Gln Gly
                100                 105                 110
Thr Ser Val Thr Val Ser Ser
                115
```

( 2 ) INFORMATION FOR SEQ ID NO:65:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:65:

```
Gln Val Gln Leu Val Gln Ser Gly Ala Glu Val Lys Lys Pro Gly Ser
 1               5                  10                  15

Ser Val Arg Val Ser Cys Lys Ala Ser Gly Tyr Ser Phe Thr Gly Tyr
             20                  25                  30

Thr Met Asn Trp Val Arg Gln Ala Pro Gly Lys Gly Leu Glu Trp Val
         35                  40                  45

Gly Leu Ile Asn Pro Tyr Asn Gly Gly Thr Ser Tyr Asn Gln Lys Phe
         50              55                  60

Lys Gly Arg Val Thr Val Ser Leu Lys Pro Ser Phe Asn Gln Ala Tyr
 65              70                  75                      80

Met Glu Leu Ser Ser Leu Phe Ser Glu Asp Thr Ala Val Tyr Tyr Cys
                 85                  90                  95

Thr Arg Arg Gly Phe Arg Asp Tyr Ser Met Asp Tyr Trp Gly Gln Gly
             100                 105                 110

Thr Leu Val Thr Val Ser Ser
             115
```

( 2 ) INFORMATION FOR SEQ ID NO:66:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..393

( x i ) SEQUENCE DESCRIPTION: SEQ ID NO:66:

```
ATG GAG AAA GAC ACA CTC CTG CTA TGG GTC CTG CTT CTC TGG GTT CCA      48
Met Glu Lys Asp Thr Leu Leu Leu Trp Val Leu Leu Leu Trp Val Pro
 1               5                  10                  15

GGT TCC ACA GGT GAC ATT GTG CTG ACC CAA TCT CCA GCT TCT TTG GCT      96
Gly Ser Thr Gly Asp Ile Val Leu Thr Gln Ser Pro Ala Ser Leu Ala
             20                  25                  30

GTG TCT CTA GGG CAG AGG GCC ACC ATC TCC TGC AGA GCC AGC GAA AGT     144
Val Ser Leu Gly Gln Arg Ala Thr Ile Ser Cys Arg Ala Ser Glu Ser
         35                  40                  45

GTT GAT AAT TAT GGC ATT AGT TTT ATG AAC TGG TTC CAA CAG AAA CCA     192
Val Asp Asn Tyr Gly Ile Ser Phe Met Asn Trp Phe Gln Gln Lys Pro
         50              55                  60

GGA CAG CCA CCC AAA CTC CTC ATC TAT GCT GCA TCC AAC CAA GGA TCC     240
Gly Gln Pro Pro Lys Leu Leu Ile Tyr Ala Ala Ser Asn Gln Gly Ser
 65              70                  75                      80

GGG GTC CCT GCC AGG TTT AGT GGC AGT GGG TCT GGG ACA GAC TTC AGC     288
Gly Val Pro Ala Arg Phe Ser Gly Ser Gly Ser Gly Thr Asp Phe Ser
             85                  90                  95

CTC AAC ATC CAT CCT ATG GAG GAG GAT GAT ACT GCA ATG TAT TTC TGT     336
Leu Asn Ile His Pro Met Glu Glu Asp Asp Thr Ala Met Tyr Phe Cys
             100                 105                 110

CAG CAA AGT AAG GAG GTT CCG TGG ACG TTC GGT GGA GGC ACC AAG CTG     384
Gln Gln Ser Lys Glu Val Pro Trp Thr Phe Gly Gly Gly Thr Lys Leu
             115                 120                 125

GAA ATC AAA                                                          393
Glu Ile Lys
 130
```

( 2 ) INFORMATION FOR SEQ ID NO:67:

( i ) SEQUENCE CHARACTERISTICS:
  ( A ) LENGTH: 131 amino acids
  ( B ) TYPE: amino acid
  ( D ) TOPOLOGY: linear ( i i ) MOLECULE TYPE: protein ( x i ) SEQUENCE DESCRIPTION: SEQ ID NO:67:

```
Met Glu Lys Asp Thr Leu Leu Leu Trp Val Leu Leu Leu Trp Val Pro
 1               5                  10                  15
Gly Ser Thr Gly Asp Ile Val Leu Thr Gln Ser Pro Ala Ser Leu Ala
            20                  25                  30
Val Ser Leu Gly Gln Arg Ala Thr Ile Ser Cys Arg Ala Ser Glu Ser
        35                  40                  45
Val Asp Asn Tyr Gly Ile Ser Phe Met Asn Trp Phe Gln Gln Lys Pro
    50                  55                  60
Gly Gln Pro Pro Lys Leu Leu Ile Tyr Ala Ala Ser Asn Gln Gly Ser
 65                 70                  75                  80
Gly Val Pro Ala Arg Phe Ser Gly Ser Gly Ser Gly Thr Asp Phe Ser
            85                  90                  95
Leu Asn Ile His Pro Met Glu Glu Asp Asp Thr Ala Met Tyr Phe Cys
           100                 105                 110
Gln Gln Ser Lys Glu Val Pro Trp Thr Phe Gly Gly Gly Thr Lys Leu
           115                 120                 125
Glu Ile Lys
   130
```

( 2 ) INFORMATION FOR SEQ ID NO:68:

( i ) SEQUENCE CHARACTERISTICS:
  ( A ) LENGTH: 405 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 1..405

( x i ) SEQUENCE DESCRIPTION: SEQ ID NO:68:

```
ATG GGA TGG AGC TGG ATC TTT CTC TTC CTC CTG TCA GGA ACT GCA GGC    48
Met Gly Trp Ser Trp Ile Phe Leu Phe Leu Leu Ser Gly Thr Ala Gly
 1               5                  10                  15

GTC CAC TCT GAG GTC CAG CTT CAG CAG TCA GGA CCT GAG CTG GTG AAA    96
Val His Ser Glu Val Gln Leu Gln Gln Ser Gly Pro Glu Leu Val Lys
            20                  25                  30

CCT GGG GCC TCA GTG AAG ATA TCC TGC AAG GCT TCT GGA TAC ACA TTC   144
Pro Gly Ala Ser Val Lys Ile Ser Cys Lys Ala Ser Gly Tyr Thr Phe
        35                  40                  45

ACT GAC TAC AAC ATG CAC TGG GTG AAG CAG AGC CAT GGA AAG AGC CTT   192
Thr Asp Tyr Asn Met His Trp Val Lys Gln Ser His Gly Lys Ser Leu
    50                  55                  60

GAG TGG ATT GGA TAT ATT TAT CCT TAC AAT GGT GGT ACT GGC TAC AAC   240
Glu Trp Ile Gly Tyr Ile Tyr Pro Tyr Asn Gly Gly Thr Gly Tyr Asn
 65                 70                  75                  80

CAG AAG TTC AAG AGC AAG GCC ACA TTG ACT GTA GAC AAT TCC TCC AGC   288
Gln Lys Phe Lys Ser Lys Ala Thr Leu Thr Val Asp Asn Ser Ser Ser
            85                  90                  95

ACA GCC TAC ATG GAC GTC CGC AGC CTG ACA TCT GAG GAC TCT GCA GTC   336
Thr Ala Tyr Met Asp Val Arg Ser Leu Thr Ser Glu Asp Ser Ala Val
```

|     |     |     |     |     | 100 |     |     |     |     | 105 |     |     |     |     | 110 |     |     |     |
| --- | --- | --- | --- | --- | --- | --- | --- | --- | --- | --- | --- | --- | --- | --- | --- | --- | --- | --- |
| TAT | TAC | TGT | GCA | AGA | GGG | CGC | CCC | GCT | ATG | GAC | TAC | TGG | GGT | CAA | GGA |     |     | 384 |
| Tyr | Tyr | Cys | Ala | Arg | Gly | Arg | Pro | Ala | Met | Asp | Tyr | Trp | Gly | Gln | Gly |     |     |     |
|     |     | 115 |     |     |     |     | 120 |     |     |     |     | 125 |     |     |     |     |     |     |
| ACC | TCA | GTC | ACC | GTC | TCC | TCA |     |     |     |     |     |     |     |     |     |     |     | 405 |
| Thr | Ser | Val | Thr | Val | Ser | Ser |     |     |     |     |     |     |     |     |     |     |     |     |
|     | 130 |     |     |     |     | 135 |     |     |     |     |     |     |     |     |     |     |     |     |

( 2 ) INFORMATION FOR SEQ ID NO:69:

( i ) SEQUENCE CHARACTERISTICS:
        ( A ) LENGTH: 135 amino acids
        ( B ) TYPE: amino acid
        ( D ) TOPOLOGY: linear ( i i ) MOLECULE TYPE: protein ( x i ) SEQUENCE DESCRIPTION: SEQ ID NO:69:

| Met | Gly | Trp | Ser | Trp | Ile | Phe | Leu | Phe | Leu | Leu | Ser | Gly | Thr | Ala | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Val | His | Ser | Glu | Val | Gln | Leu | Gln | Gln | Ser | Gly | Pro | Glu | Leu | Val | Lys |
|     |     |     | 20  |     |     |     |     | 25  |     |     |     |     | 30  |     |     |
| Pro | Gly | Ala | Ser | Val | Lys | Ile | Ser | Cys | Lys | Ala | Ser | Gly | Tyr | Thr | Phe |
|     |     |     | 35  |     |     |     |     | 40  |     |     |     |     | 45  |     |     |
| Thr | Asp | Tyr | Asn | Met | His | Trp | Val | Lys | Gln | Ser | His | Gly | Lys | Ser | Leu |
|     | 50  |     |     |     |     | 55  |     |     |     |     | 60  |     |     |     |     |
| Glu | Trp | Ile | Gly | Tyr | Ile | Tyr | Pro | Tyr | Asn | Gly | Gly | Thr | Gly | Tyr | Asn |
| 65  |     |     |     |     | 70  |     |     |     |     | 75  |     |     |     |     | 80  |
| Gln | Lys | Phe | Lys | Ser | Lys | Ala | Thr | Leu | Thr | Val | Asp | Asn | Ser | Ser | Ser |
|     |     |     |     | 85  |     |     |     |     | 90  |     |     |     |     | 95  |     |
| Thr | Ala | Tyr | Met | Asp | Val | Arg | Ser | Leu | Thr | Ser | Glu | Asp | Ser | Ala | Val |
|     |     |     | 100 |     |     |     |     | 105 |     |     |     |     | 110 |     |     |
| Tyr | Tyr | Cys | Ala | Arg | Gly | Arg | Pro | Ala | Met | Asp | Tyr | Trp | Gly | Gln | Gly |
|     |     | 115 |     |     |     |     | 120 |     |     |     |     | 125 |     |     |     |
| Thr | Ser | Val | Thr | Val | Ser | Ser |     |     |     |     |     |     |     |     |     |
|     | 130 |     |     |     |     | 135 |     |     |     |     |     |     |     |     |     |

( 2 ) INFORMATION FOR SEQ ID NO:70:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

| Asp | Ile | Gln | Met | Thr | Gln | Ser | Pro | Ser | Thr | Leu | Ser | Ala | Ser | Val | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asp | Arg | Val | Thr | Ile | Thr | Cys | Arg | Ala | Ser | Gln | Ser | Ile | Asn | Thr | Trp |
|     |     |     | 20  |     |     |     |     | 25  |     |     |     |     | 30  |     |     |
| Leu | Ala | Trp | Tyr | Gln | Gln | Lys | Pro | Gly | Lys | Ala | Pro | Lys | Leu | Leu | Met |
|     |     |     | 35  |     |     |     |     | 40  |     |     |     |     | 45  |     |     |
| Tyr | Lys | Ala | Ser | Ser | Leu | Glu | Ser | Gly | Val | Pro | Ser | Arg | Phe | Ile | Gly |
|     | 50  |     |     |     |     | 55  |     |     |     |     | 60  |     |     |     |     |
| Ser | Gly | Ser | Gly | Thr | Glu | Phe | Thr | Leu | Thr | Ile | Ser | Ser | Leu | Gln | Pro |
| 65  |     |     |     |     | 70  |     |     |     |     | 75  |     |     |     |     | 80  |
| Asp | Asp | Phe | Ala | Thr | Tyr | Tyr | Cys | Gln | Gln | Tyr | Asn | Ser | Asp | Ser | Lys |
|     |     |     |     | 85  |     |     |     |     | 90  |     |     |     |     | 95  |     |

Met Phe Gly Gln Gly Thr Lys Val Glu Val Lys
                         100                 105

(2) INFORMATION FOR SEQ ID NO:71:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Asn Tyr
                20                  25                  30

Gly Ile Ser Phe Met Asn Trp Phe Gln Gln Lys Pro Gly Lys Ala Pro
            35                  40                  45

Lys Leu Leu Ile Tyr Ala Ala Ser Asn Gln Gly Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys
                100                 105                 110

(2) INFORMATION FOR SEQ ID NO:72:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Ser
                20                  25                  30

Ala Ile Ile Trp Val Arg Gln Ala Pro Gly Gln Gly Leu Glu Trp Met
            35                  40                  45

Gly Gly Ile Val Pro Met Phe Gly Pro Pro Asn Tyr Ala Gln Lys Phe
        50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Glu Tyr Asn Gly Gly Leu
                100                 105                 110

Val Thr Val Ser Ser
            115

(2) INFORMATION FOR SEQ ID NO:73:

(i) SEQUENCE CHARACTERISTICS:
        (A) LENGTH: 116 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO:73:

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Asn | Met | His | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Tyr | Ile | Tyr | Pro | Tyr | Asn | Gly | Gly | Thr | Gly | Tyr | Asn | Gln | Lys | Phe |
|---|---|---|---|---|---|---|---|---|---|---|---|---|---|---|---|
| | 50 | | | | | 55 | | | | | 60 | | | | |

| Lys | Ser | Lys | Ala | Thr | Ile | Thr | Ala | Asp | Glu | Ser | Thr | Asn | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Arg | Pro | Ala | Met | Asp | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | 115 | |

(2) INFORMATION FOR SEQ ID NO:74:

(i) SEQUENCE CHARACTERISTICS:
(A) LENGTH: 132 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:74:

```
TATATCTAGA CCACCATGGG ATGGAGCTGG ATCTTTCTCT TCCTCCTGTC AGGAACTGCT      60
GGCGTCCACT CTCAGGTTCA GCTGGTGCAG TCTGGAGCTG AGGTGAAGAA GCCTGGGAGC     120
TCAGTGAAGG TT                                                         132
```

(2) INFORMATION FOR SEQ ID NO:75:

(i) SEQUENCE CHARACTERISTICS:
(A) LENGTH: 133 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:75:

```
AGCCGGTACC ACCATTGTAA GGATAAATAT ATCCAATCCA TTCCAGGCCT TGGCCAGGAG      60
CCTGCCTCAC CCAGTGCATG TTGTAGTCAG TGAAGGTGTA GCCAGAAGCT TTGCAGGAAA     120
CCTTCACTGA GCT                                                        133
```

(2) INFORMATION FOR SEQ ID NO:76:

(i) SEQUENCE CHARACTERISTICS:
(A) LENGTH: 112 base pairs
(B) TYPE: nucleic acid
(C) STRANDEDNESS: single
(D) TOPOLOGY: linear (ii) MOLECULE TYPE: DNA (oligonucleotide)

( x i ) SEQUENCE DESCRIPTION: SEQ ID NO:76:

| | | | | | | |
|---|---|---|---|---|---|---|
| TGGTGGTACC | GGCTACAACC | AGAAGTTCAA | GAGCAAGGCC | ACAATTACAG | CAGACGAGAG | 60 |
| TACTAACACA | GCCTACATGG | AACTCTCCAG | CCTGAGGTCT | GAGGACACTG | CA | 112 |

( 2 ) INFORMATION FOR SEQ ID NO:77:

( i ) SEQUENCE CHARACTERISTICS:
        ( A ) LENGTH: 111 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:77:

| | | | | | | |
|---|---|---|---|---|---|---|
| TATATCTAGA | GGCCATTCTT | ACCTGAAGAG | ACAGTGACCA | GAGTCCCTTG | GCCCCAGTAG | 60 |
| TCCATAGCGG | GGCGCCCTCT | TGCGCAGTAA | TAGACTGCAG | TGTCCTCAGA | C | 111 |

( 2 ) INFORMATION FOR SEQ ID NO:78:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:78:

| | | | | | | |
|---|---|---|---|---|---|---|
| TATATCTAGA | CCACCATGGA | GAAAGACACA | CTCCTGCTAT | GGGTCCTGCT | TCTCTGGGTT | 60 |
| CCAGGTTCCA | CAGGTGACAT | TCAGATGACC | CAGTCTCCGA | GCTCTCTGTC | CGCATCAGTA | 120 |
| GG | | | | | | 122 |

( 2 ) INFORMATION FOR SEQ ID NO:79:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:79:

| | | | | | | |
|---|---|---|---|---|---|---|
| TCAGAAGCTT | AGGAGCCTTC | CCGGGTTTCT | GTTGGAACCA | GTTCATAAAG | CTAATGCCAT | 60 |
| AATTGTCGAC | ACTTTCGCTG | GCTCTGCATG | TGATGGTGAC | CCTGTCTCCT | ACTGATGCGG | 120 |
| AC | | | | | | 122 |

( 2 ) INFORMATION FOR SEQ ID NO:80:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:80:

| | | | | | | |
|---|---|---|---|---|---|---|
| TCCTAAGCTT | CTGATTTACG | CTGCATCCAA | CCAAGGCTCC | GGGGTACCCT | CTCGCTTCTC | 60 |
| AGGCAGTGGA | TCTGGGACAG | ACTTCACTCT | CACCATTTCA | TCTCTGCAGC | CTGATGACT | 119 |

( 2 ) INFORMATION FOR SEQ ID NO:81:

( i ) SEQUENCE CHARACTERISTICS:
   ( A ) LENGTH: 118 base pairs
   ( B ) TYPE: nucleic acid
   ( C ) STRANDEDNESS: single
   ( D ) TOPOLOGY: linear ( i i ) MOLECULE TYPE: DNA (oligonucleotide)

( x i ) SEQUENCE DESCRIPTION: SEQ ID NO:81:

TATATCTAGA CTTTGGATTC TACTTACGTT TGATCTCCAC CTTGGTCCCT TGACCGAACG        60

TCCACGGAAC CTCCTTACTT TGCTGACAGT AATAGGTTGC GAAGTCATCA GGCTGCAG         118

( 2 ) INFORMATION FOR SEQ ID NO:82:

( i ) SEQUENCE CHARACTERISTICS:
      ( A ) LENGTH: 381 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 1..381

( x i ) SEQUENCE DESCRIPTION: SEQ ID NO:82:

```
ATG  GTT  TTC  ACA  CCT  CAG  ATA  CTT  GGA  CTT  ATG  CTT  TTT  TGG  ATT  TCA         48
Met  Val  Phe  Thr  Pro  Gln  Ile  Leu  Gly  Leu  Met  Leu  Phe  Trp  Ile  Ser
 1              5                        10                       15

GCC  TCC  AGA  GGT  GAT  ATT  GTG  CTA  ACT  CAG  TCT  CCA  GCC  ACC  CTG  TCT         96
Ala  Ser  Arg  Gly  Asp  Ile  Val  Leu  Thr  Gln  Ser  Pro  Ala  Thr  Leu  Ser
              20                       25                       30

GTG  ACT  CCG  GGA  GAT  AGC  GTC  AGT  CTT  TCC  TGC  AGG  GCC  AGC  CAA  AGT        144
Val  Thr  Pro  Gly  Asp  Ser  Val  Ser  Leu  Ser  Cys  Arg  Ala  Ser  Gln  Ser
         35                       40                       45

ATT  AGC  AAC  AAC  CTA  CAC  TGG  TAT  CAA  CAA  AAA  TCA  CAT  GAG  TCT  CCA        192
Ile  Ser  Asn  Asn  Leu  His  Trp  Tyr  Gln  Gln  Lys  Ser  His  Glu  Ser  Pro
    50                       55                       60

AGG  CTT  CTC  ATC  AAG  TAT  GCT  TCC  CAG  TCC  ATC  TCT  GGG  ATC  CCC  TCC        240
Arg  Leu  Leu  Ile  Lys  Tyr  Ala  Ser  Gln  Ser  Ile  Ser  Gly  Ile  Pro  Ser
65                       70                       75                       80

AGG  TTC  AGT  GGC  AGT  GGA  TCA  GGG  ACA  GAT  TTC  ACT  CTC  AGT  GTC  AAC        288
Arg  Phe  Ser  Gly  Ser  Gly  Ser  Gly  Thr  Asp  Phe  Thr  Leu  Ser  Val  Asn
                  85                       90                       95

GGT  GTG  GAG  ACT  GAA  GAT  TTT  GGA  ATG  TAT  TTC  TGT  CAA  CAG  AGT  AAC        336
Gly  Val  Glu  Thr  Glu  Asp  Phe  Gly  Met  Tyr  Phe  Cys  Gln  Gln  Ser  Asn
             100                      105                      110

AGT  TGG  CCT  CAT  ACG  TTC  GGA  GGG  GGG  ACC  AAG  CTG  GAA  ATA  AAA            381
Ser  Trp  Pro  His  Thr  Phe  Gly  Gly  Gly  Thr  Lys  Leu  Glu  Ile  Lys
         115                      120                      125
```

( 2 ) INFORMATION FOR SEQ ID NO:83:

( i ) SEQUENCE CHARACTERISTICS:
      ( A ) LENGTH: 127 amino acids
      ( B ) TYPE: amino acid
      ( D ) TOPOLOGY: linear ( i i ) MOLECULE TYPE: protein ( x i ) SEQUENCE DESCRIPTION: SEQ ID NO:83:

```
Met  Val  Phe  Thr  Pro  Gln  Ile  Leu  Gly  Leu  Met  Leu  Phe  Trp  Ile  Ser
 1              5                        10                       15

Ala  Ser  Arg  Gly  Asp  Ile  Val  Leu  Thr  Gln  Ser  Pro  Ala  Thr  Leu  Ser
```

```
                     20                        25                            30
Val  Thr  Pro  Gly  Asp  Ser  Val  Ser  Leu  Ser  Cys  Arg  Ala  Ser  Gln  Ser
          35                        40                        45

Ile  Ser  Asn  Asn  Leu  His  Trp  Tyr  Gln  Gln  Lys  Ser  His  Glu  Ser  Pro
 50                            55                             60

Arg  Leu  Leu  Ile  Lys  Tyr  Ala  Ser  Gln  Ser  Ile  Ser  Gly  Ile  Pro  Ser
 65                       70                        75                        80

Arg  Phe  Ser  Gly  Ser  Gly  Ser  Gly  Thr  Asp  Phe  Thr  Leu  Ser  Val  Asn
                    85                       90                            95

Gly  Val  Glu  Thr  Glu  Asp  Phe  Gly  Met  Tyr  Phe  Cys  Gln  Gln  Ser  Asn
               100                      105                     110

Ser  Trp  Pro  His  Thr  Phe  Gly  Gly  Gly  Thr  Lys  Leu  Glu  Ile  Lys
          115                      120                     125
```

( 2 ) INFORMATION FOR SEQ ID NO:84:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..414

( x i ) SEQUENCE DESCRIPTION: SEQ ID NO:84:

```
ATG  GGA  TGG  AGC  TGG  ATC  TTT  CTC  TTC  CTC  CTG  TCA  GGA  ACT  GCA  GGT       48
Met  Gly  Trp  Ser  Trp  Ile  Phe  Leu  Phe  Leu  Leu  Ser  Gly  Thr  Ala  Gly
 1                        5                         10                       15

GTC  CAC  TCT  GAG  GTC  CAG  CTG  CAA  CAG  TCT  GGA  CCT  GAG  CTG  GTG  AAG       96
Val  His  Ser  Glu  Val  Gln  Leu  Gln  Gln  Ser  Gly  Pro  Glu  Leu  Val  Lys
                20                            25                        30

CCT  GGA  GCT  TCA  ATG  AAG  ATA  TCC  TGC  AAG  GCT  TCT  GTT  TAC  TCA  TTC      144
Pro  Gly  Ala  Ser  Met  Lys  Ile  Ser  Cys  Lys  Ala  Ser  Val  Tyr  Ser  Phe
           35                            40                       45

ACT  GGC  TAC  ACC  ATG  AAC  TGG  GTG  AAG  CAG  AGC  CAT  GGA  CAG  AAC  CTT      192
Thr  Gly  Tyr  Thr  Met  Asn  Trp  Val  Lys  Gln  Ser  His  Gly  Gln  Asn  Leu
      50                            55                        60

GAG  TGG  ATT  GGA  CTT  ATT  AAT  CCT  TAC  AAT  GGT  GGT  ACT  AGC  TAC  AAC      240
Glu  Trp  Ile  Gly  Leu  Ile  Asn  Pro  Tyr  Asn  Gly  Gly  Thr  Ser  Tyr  Asn
 65                       70                        75                       80

CAG  AAG  TTC  AAG  GGG  AAG  GCC  ACA  TTA  ACT  GTA  GAC  AAG  TCA  TCC  AAC      288
Gln  Lys  Phe  Lys  Gly  Lys  Ala  Thr  Leu  Thr  Val  Asp  Lys  Ser  Ser  Asn
                     85                            90                       95

ACA  GCC  TAC  ATG  GAG  CTC  CTC  AGT  CTG  ACA  TCT  GCG  GAC  TCT  GCA  GTC      336
Thr  Ala  Tyr  Met  Glu  Leu  Leu  Ser  Leu  Thr  Ser  Ala  Asp  Ser  Ala  Val
                100                          105                      110

TAT  TAC  TGT  ACA  AGA  CGG  GGG  TTT  CGA  GAC  TAT  TCT  ATG  GAC  TAC  TGG      384
Tyr  Tyr  Cys  Thr  Arg  Arg  Gly  Phe  Arg  Asp  Tyr  Ser  Met  Asp  Tyr  Trp
           115                          120                      125

GGT  CAA  GGA  ACC  TCA  GTC  ACC  GTC  TCC  TCA                                    414
Gly  Gln  Gly  Thr  Ser  Val  Thr  Val  Ser  Ser
 130                      135
```

( 2 ) INFORMATION FOR SEQ ID NO:85:

( i ) SEQUENCE CHARACTERISTICS:
        ( A ) LENGTH: 138 amino acids
        ( B ) TYPE: amino acid
        ( D ) TOPOLOGY: linear ( i i ) MOLECULE TYPE: protein ( x i ) SEQUENCE DESCRIPTION: SEQ ID NO:85:

| Met | Gly | Trp | Ser | Trp | Ile | Phe | Leu | Phe | Leu | Leu | Ser | Gly | Thr | Ala | Gly |
|-----|-----|-----|-----|-----|-----|-----|-----|-----|-----|-----|-----|-----|-----|-----|-----|
| 1 | | | | 5 | | | | | 10 | | | | | 15 | |

| Val | His | Ser | Glu | Val | Gln | Leu | Gln | Gln | Ser | Gly | Pro | Glu | Leu | Val | Lys |
|-----|-----|-----|-----|-----|-----|-----|-----|-----|-----|-----|-----|-----|-----|-----|-----|
| | | | 20 | | | | | 25 | | | | | 30 | | |

| Pro | Gly | Ala | Ser | Met | Lys | Ile | Ser | Cys | Lys | Ala | Ser | Val | Tyr | Ser | Phe |
|-----|-----|-----|-----|-----|-----|-----|-----|-----|-----|-----|-----|-----|-----|-----|-----|
| | | | 35 | | | | 40 | | | | | 45 | | | |

| Thr | Gly | Tyr | Thr | Met | Asn | Trp | Val | Lys | Gln | Ser | His | Gly | Gln | Asn | Leu |
|-----|-----|-----|-----|-----|-----|-----|-----|-----|-----|-----|-----|-----|-----|-----|-----|
| | 50 | | | | | 55 | | | | | 60 | | | | |

| Glu | Trp | Ile | Gly | Leu | Ile | Asn | Pro | Tyr | Asn | Gly | Gly | Thr | Ser | Tyr | Asn |
|-----|-----|-----|-----|-----|-----|-----|-----|-----|-----|-----|-----|-----|-----|-----|-----|
| 65 | | | | | 70 | | | | | 75 | | | | | 80 |

| Gln | Lys | Phe | Lys | Gly | Lys | Ala | Thr | Leu | Thr | Val | Asp | Lys | Ser | Ser | Asn |
|-----|-----|-----|-----|-----|-----|-----|-----|-----|-----|-----|-----|-----|-----|-----|-----|
| | | | | 85 | | | | | 90 | | | | | 95 | |

| Thr | Ala | Tyr | Met | Glu | Leu | Leu | Ser | Leu | Thr | Ser | Ala | Asp | Ser | Ala | Val |
|-----|-----|-----|-----|-----|-----|-----|-----|-----|-----|-----|-----|-----|-----|-----|-----|
| | | | 100 | | | | | 105 | | | | | 110 | | |

| Tyr | Tyr | Cys | Thr | Arg | Arg | Gly | Phe | Arg | Asp | Tyr | Ser | Met | Asp | Tyr | Trp |
|-----|-----|-----|-----|-----|-----|-----|-----|-----|-----|-----|-----|-----|-----|-----|-----|
| | | 115 | | | | | 120 | | | | | 125 | | | |

| Gly | Gln | Gly | Thr | Ser | Val | Thr | Val | Ser | Ser |
|-----|-----|-----|-----|-----|-----|-----|-----|-----|-----|
| | 130 | | | | | 135 | | | |

( 2 ) INFORMATION FOR SEQ ID NO:86:

( i ) SEQUENCE CHARACTERISTICS:
 ( A ) LENGTH: 108 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:86:

| Glu | Ile | Val | Leu | Thr | Gln | Ser | Pro | Gly | Thr | Leu | Ser | Leu | Ser | Pro | Gly |
|-----|-----|-----|-----|-----|-----|-----|-----|-----|-----|-----|-----|-----|-----|-----|-----|
| 1 | | | | 5 | | | | | 10 | | | | | 15 | |

| Glu | Arg | Ala | Thr | Leu | Ser | Cys | Arg | Ala | Ser | Gln | Ser | Val | Ser | Ser | Gly |
|-----|-----|-----|-----|-----|-----|-----|-----|-----|-----|-----|-----|-----|-----|-----|-----|
| | | | 20 | | | | | 25 | | | | | 30 | | |

| Tyr | Leu | Gly | Trp | Tyr | Gln | Gln | Lys | Pro | Gly | Gln | Ala | Pro | Arg | Leu | Leu |
|-----|-----|-----|-----|-----|-----|-----|-----|-----|-----|-----|-----|-----|-----|-----|-----|
| | | 35 | | | | | 40 | | | | | 45 | | | |

| Ile | Tyr | Gly | Ala | Ser | Ser | Arg | Ala | Thr | Gly | Ile | Pro | Asp | Arg | Phe | Ser |
|-----|-----|-----|-----|-----|-----|-----|-----|-----|-----|-----|-----|-----|-----|-----|-----|
| | 50 | | | | | 55 | | | | | 60 | | | | |

| Gly | Ser | Gly | Ser | Gly | Thr | Asp | Phe | Thr | Leu | Thr | Ile | Ser | Arg | Leu | Glu |
|-----|-----|-----|-----|-----|-----|-----|-----|-----|-----|-----|-----|-----|-----|-----|-----|
| 65 | | | | | 70 | | | | | 75 | | | | | 80 |

| Pro | Glu | Asp | Phe | Ala | Val | Tyr | Tyr | Cys | Gln | Gln | Tyr | Gly | Ser | Leu | Gly |
|-----|-----|-----|-----|-----|-----|-----|-----|-----|-----|-----|-----|-----|-----|-----|-----|
| | | | | 85 | | | | | 90 | | | | | 95 | |

| Arg | Thr | Phe | Gly | Gln | Gly | Thr | Lys | Val | Glu | Ile | Lys |
|-----|-----|-----|-----|-----|-----|-----|-----|-----|-----|-----|-----|
| | | | 100 | | | | | 105 | | | |

( 2 ) INFORMATION FOR SEQ ID NO:87:

( i ) SEQUENCE CHARACTERISTICS:
 ( A ) LENGTH: 107 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:87:

| Glu | Ile | Val | Leu | Thr | Gln | Ser | Pro | Gly | Thr | Leu | Ser | Leu | Ser | Pro | Gly |
|-----|-----|-----|-----|-----|-----|-----|-----|-----|-----|-----|-----|-----|-----|-----|-----|

|  | 1 |  |  |  | 5 |  |  |  |  | 10 |  |  |  |  | 15 |
|---|---|---|---|---|---|---|---|---|---|---|---|---|---|---|---|
| Glu | Arg | Ala | Thr | Leu | Ser | Cys | Arg | Ala | Ser | Gln | Ser | Ile | Ser | Asn | Asn |
|  |  |  | 20 |  |  |  |  | 25 |  |  |  |  | 30 |  |  |
| Leu | His | Trp | Tyr | Gln | Gln | Lys | Pro | Gly | Gln | Ala | Pro | Arg | Leu | Leu | Ile |
|  |  |  | 35 |  |  |  | 40 |  |  |  |  | 45 |  |  |  |
| Lys | Tyr | Ala | Ser | Gln | Ser | Ile | Ser | Gly | Ile | Pro | Asp | Arg | Phe | Ser | Gly |
|  |  |  | 50 |  |  |  | 55 |  |  |  |  | 60 |  |  |  |
| Ser | Gly | Ser | Gly | Thr | Asp | Phe | Thr | Leu | Thr | Ile | Ser | Arg | Leu | Glu | Pro |
| 65 |  |  |  |  | 70 |  |  |  |  | 75 |  |  |  |  | 80 |
| Glu | Asp | Phe | Ala | Val | Tyr | Tyr | Cys | Gln | Gln | Ser | Asn | Ser | Trp | Pro | His |
|  |  |  |  | 85 |  |  |  |  | 90 |  |  |  |  | 95 |  |
| Thr | Phe | Gly | Gln | Gly | Thr | Lys | Val | Glu | Ile | Lys |  |  |  |  |  |
|  |  |  | 100 |  |  |  |  | 105 |  |  |  |  |  |  |  |

( 2 ) INFORMATION FOR SEQ ID NO:88:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:88:

| Gln | Val | Gln | Leu | Met | Gln | Ser | Gly | Ala | Glu | Val | Lys | Lys | Pro | Gly | Ser |
|---|---|---|---|---|---|---|---|---|---|---|---|---|---|---|---|
| 1 |  |  |  | 5 |  |  |  |  | 10 |  |  |  |  | 15 |  |
| Ser | Val | Arg | Val | Ser | Cys | Lys | Thr | Ser | Gly | Gly | Thr | Phe | Val | Asp | Tyr |
|  |  |  | 20 |  |  |  |  | 25 |  |  |  |  | 30 |  |  |
| Lys | Gly | Leu | Trp | Val | Arg | Gln | Ala | Pro | Gly | Lys | Gly | Leu | Glu | Trp | Val |
|  |  |  | 35 |  |  |  |  | 40 |  |  |  |  | 45 |  |  |
| Gly | Gln | Ile | Pro | Leu | Arg | Phe | Asn | Gly | Glu | Val | Lys | Asn | Pro | Gly | Ser |
|  |  |  | 50 |  |  |  | 55 |  |  |  |  | 60 |  |  |  |
| Val | Val | Arg | Val | Ser | Val | Ser | Leu | Lys | Pro | Ser | Phe | Asn | Gln | Ala | His |
| 65 |  |  |  |  | 70 |  |  |  |  | 75 |  |  |  |  | 80 |
| Met | Glu | Leu | Ser | Ser | Leu | Phe | Ser | Glu | Asp | Thr | Ala | Val | Tyr | Tyr | Cys |
|  |  |  |  | 85 |  |  |  |  | 90 |  |  |  |  | 95 |  |
| Ala | Arg | Glu | Tyr | Gly | Phe | Asp | Thr | Ser | Asp | Tyr | Tyr | Tyr | Tyr | Tyr | Trp |
|  |  |  | 100 |  |  |  |  | 105 |  |  |  |  | 110 |  |  |
| Gly | Gln | Gly | Thr | Leu | Val | Thr | Val | Ser | Ser |  |  |  |  |  |  |
|  |  |  | 115 |  |  |  |  | 120 |  |  |  |  |  |  |  |

( 2 ) INFORMATION FOR SEQ ID NO:89:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:89:

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 |  |  |  | 5 |  |  |  |  | 10 |  |  |  |  | 15 |  |
| Ser | Val | Arg | Val | Ser | Cys | Lys | Ala | Ser | Gly | Tyr | Ser | Phe | Thr | Gly | Tyr |
|  |  |  | 20 |  |  |  |  | 25 |  |  |  |  | 30 |  |  |
| Thr | Met | Asn | Trp | Val | Arg | Gln | Ala | Pro | Gly | Lys | Gly | Leu | Glu | Trp | Val |
|  |  |  | 35 |  |  |  |  | 40 |  |  |  |  | 45 |  |  |
| Gly | Leu | Ile | Asn | Pro | Tyr | Asn | Gly | Gly | Thr | Ser | Tyr | Asn | Gln | Lys | Phe |

|      | 50  |     |     |     |     | 55  |     |     |     |     | 60  |     |     |     |     |
|------|-----|-----|-----|-----|-----|-----|-----|-----|-----|-----|-----|-----|-----|-----|-----|
| Lys  | Gly | Arg | Val | Thr | Val | Ser | Leu | Lys | Pro | Ser | Phe | Asn | Gln | Ala | Tyr |
| 65   |     |     |     |     | 70  |     |     |     |     | 75  |     |     |     |     | 80  |
| Met  | Glu | Leu | Ser | Ser | Leu | Phe | Ser | Glu | Asp | Thr | Ala | Val | Tyr | Tyr | Cys |
|      |     |     |     | 85  |     |     |     |     | 90  |     |     |     |     | 95  |     |
| Thr  | Arg | Arg | Gly | Phe | Arg | Asp | Tyr | Ser | Met | Asp | Tyr | Trp | Gly | Gln | Gly |
|      |     |     | 100 |     |     |     |     | 105 |     |     |     |     | 110 |     |     |
| Thr  | Leu | Val | Thr | Val | Ser | Ser |     |     |     |     |     |     |     |     |     |
|      |     |     | 115 |     |     |     |     |     |     |     |     |     |     |     |     |

( 2 ) INFORMATION FOR SEQ ID NO:90:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:90:

```
TAGATCTAGA CCACCATGGT TTTCACACCT CAGATACTCA GACTCATGCT CTTCTGGATT    60
TCAGCCTCCA GAGGTGAAAT TGTGCTAACT CAGTCTCCAG GCACCCTAAG CTTATCACCG   120
GGAGAAAGG                                                           129
```

( 2 ) INFORMATION FOR SEQ ID NO:91:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:91:

```
TAGACAGAAT TCACGCGTAC TTGATAAGTA GACGTGGAGC TTGTCCAGGT TTTTGTTGGT    60
ACCAGTGTAG GTTGTTGCTA ATACTTTGGC TGGCCCTGCA GGAAAGTGTA GCCCTTTCTC   120
CCGGTGAT                                                            128
```

( 2 ) INFORMATION FOR SEQ ID NO:92:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:92:

```
AAGAGAATTC ACGCGTCCCA GTCCATCTCT GGAATACCCG ATAGGTTCAG TGGCAGTGGA    60
TCAGGGACAG ATTTCACTCT CACAATAAGT AGGCTCGAGC GGAAGATTT TGC           113
```

( 2 ) INFORMATION FOR SEQ ID NO:93:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:93:

```
TAGATCTAGA GTTGAGAAGA CTACTTACGT TTTATTTCTA CCTTGGTCCC TTGTCCGAAC      60
GTATGAGGCC AACTGTTACT CTGTTGACAA TAATACACAG CAAAATCTTC CGGCTC          116
```

( 2 ) INFORMATION FOR SEQ ID NO:94:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:94:

```
TATATCTAGA CCACCATGGG ATGGAGCTGG ATCTTTCTCT TCCTCCTGTC AGGAACTGCA      60
GGTGTCCACT CTCAAGTCCA ACTGGTACAG TCTGGAGCTG AGGTTAAAAA GCCTGGAAGT     120
TCAGTAAGAG TTTC                                                       134
```

( 2 ) INFORMATION FOR SEQ ID NO:95:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:95:

```
TATATAGGTA CCACCATGGG ATGGAGCTGG ATCTTTCTCT TCCTCCTGTC AGGAACTGCA      60
TGCCTGTCTC ACCCAGTTCA TGGTATACCC AGTGAATGAG TATCCGGAAG CTTTGCAGGA     120
AACTCTTACT GAAC                                                       134
```

( 2 ) INFORMATION FOR SEQ ID NO:96:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:96:

```
TATATAGGTA CCAGCTACAA CCAGAAGTTC AAGGGCAGAG TTACAGTTTC TTTGAAGCCT      60
TCATTTAACC AGGCCTACAT GGAGCTCAGT AGTCTGTTTT CTGAAGACAC TGCAGT          116
```

( 2 ) INFORMATION FOR SEQ ID NO:97:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:97:

```
TATATCTAGA GGCCATTCTT ACCTGAGGAG ACGGTGACTA AGGTTCCTTG ACCCCAGTAG      60
TCCATAGAAT AGTCTCGAAA CCCCCGTCTT GTACAGTAAT AGACTGCAGT GTCTTC          116
```

( 2 ) INFORMATION FOR SEQ ID NO:98:

( i ) SEQUENCE CHARACTERISTICS:
  ( A ) LENGTH: 408 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 1..408

( x i ) SEQUENCE DESCRIPTION: SEQ ID NO:98:

| ATG | CAT | CAG | ACC | AGC | ATG | GGC | ATC | AAG | ATG | GAA | TCA | CAG | ACT | CTG | GTC | 48 |
| Met | His | Gln | Thr | Ser | Met | Gly | Ile | Lys | Met | Glu | Ser | Gln | Thr | Leu | Val | |
| 1 | | | | 5 | | | | | 10 | | | | | 15 | | |

| TTC | ATA | TCC | ATA | CTG | CTC | TGG | TTA | TAT | GGT | GCT | GAT | GGG | AAC | ATT | GTT | 96 |
| Phe | Ile | Ser | Ile | Leu | Leu | Trp | Leu | Tyr | Gly | Ala | Asp | Gly | Asn | Ile | Val | |
| | | | 20 | | | | | 25 | | | | | 30 | | | |

| ATG | ACC | CAA | TCT | CCC | AAA | TCC | ATG | TAC | GTG | TCA | ATA | GGA | GAG | AGG | GTC | 144 |
| Met | Thr | Gln | Ser | Pro | Lys | Ser | Met | Tyr | Val | Ser | Ile | Gly | Glu | Arg | Val | |
| | | 35 | | | | | 40 | | | | | 45 | | | | |

| ACC | TTG | AGC | TGC | AAG | GCC | AGT | GAA | AAT | GTG | GAT | ACT | TAT | GTA | TCC | TGG | 192 |
| Thr | Leu | Ser | Cys | Lys | Ala | Ser | Glu | Asn | Val | Asp | Thr | Tyr | Val | Ser | Trp | |
| | 50 | | | | | 55 | | | | | 60 | | | | | |

| TAT | CAA | CAG | AAA | CCA | GAG | CAG | TCT | CCT | AAA | CTG | CTG | ATA | TAT | GGG | GCA | 240 |
| Tyr | Gln | Gln | Lys | Pro | Glu | Gln | Ser | Pro | Lys | Leu | Leu | Ile | Tyr | Gly | Ala | |
| 65 | | | | | 70 | | | | | 75 | | | | | 80 | |

| TCC | AAC | CGG | TAC | ACT | GGG | GTC | CCC | GAT | CGC | TTC | ACG | GGC | AGT | GGA | TCT | 288 |
| Ser | Asn | Arg | Tyr | Thr | Gly | Val | Pro | Asp | Arg | Phe | Thr | Gly | Ser | Gly | Ser | |
| | | | | 85 | | | | | 90 | | | | | 95 | | |

| GCA | ACA | GAT | TTC | ACT | CTG | ACC | ATC | AGC | AGT | GTG | CAG | GCT | GAA | GAC | CTT | 336 |
| Ala | Thr | Asp | Phe | Thr | Leu | Thr | Ile | Ser | Ser | Val | Gln | Ala | Glu | Asp | Leu | |
| | | | | 100 | | | | | 105 | | | | | 110 | | |

| GCA | GAT | TAT | CAC | TGT | GGA | CAG | AGT | TAC | AAC | TAT | CCA | TTC | ACG | TTC | GGC | 384 |
| Ala | Asp | Tyr | His | Cys | Gly | Gln | Ser | Tyr | Asn | Tyr | Pro | Phe | Thr | Phe | Gly | |
| | | | 115 | | | | | 120 | | | | | 125 | | | |

| TCG | GGG | ACA | AAG | TTG | GAA | ATA | AAG | | | | | | | | | 408 |
| Ser | Gly | Thr | Lys | Leu | Glu | Ile | Lys | | | | | | | | | |
| | | 130 | | | | | 135 | | | | | | | | | |

( 2 ) INFORMATION FOR SEQ ID NO:99:

( i ) SEQUENCE CHARACTERISTICS:
  ( A ) LENGTH: 136 amino acids
  ( B ) TYPE: amino acid
  ( D ) TOPOLOGY: linear ( i i ) MOLECULE TYPE: protein ( x i ) SEQUENCE DESCRIPTION: SEQ ID NO:99:

| Met | His | Gln | Thr | Ser | Met | Gly | Ile | Lys | Met | Glu | Ser | Gln | Thr | Leu | Val |
| 1 | | | | 5 | | | | | 10 | | | | | 15 | |

| Phe | Ile | Ser | Ile | Leu | Leu | Trp | Leu | Tyr | Gly | Ala | Asp | Gly | Asn | Ile | Val |
| | | | 20 | | | | | 25 | | | | | 30 | | |

| Met | Thr | Gln | Ser | Pro | Lys | Ser | Met | Tyr | Val | Ser | Ile | Gly | Glu | Arg | Val |
| | | 35 | | | | | 40 | | | | | 45 | | | |

| Thr | Leu | Ser | Cys | Lys | Ala | Ser | Glu | Asn | Val | Asp | Thr | Tyr | Val | Ser | Trp |
| | 50 | | | | | 55 | | | | | 60 | | | | |

| Tyr | Gln | Gln | Lys | Pro | Glu | Gln | Ser | Pro | Lys | Leu | Leu | Ile | Tyr | Gly | Ala |
| 65 | | | | | 70 | | | | | 75 | | | | | 80 |

| Ser | Asn | Arg | Tyr | Thr | Gly | Val | Pro | Asp | Arg | Phe | Thr | Gly | Ser | Gly | Ser |
| | | | | 85 | | | | | 90 | | | | | 95 | |

```
Ala Thr Asp Phe Thr Leu Thr Ile Ser Ser Val Gln Ala Glu Asp Leu
            100                 105             110

Ala Asp Tyr His Cys Gly Gln Ser Tyr Asn Tyr Pro Phe Thr Phe Gly
        115                 120             125

Ser Gly Thr Lys Leu Glu Ile Lys
    130                 135
```

( 2 ) INFORMATION FOR SEQ ID NO:100:

( i ) SEQUENCE CHARACTERISTICS:
        ( A ) LENGTH: 456 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..456

( x i ) SEQUENCE DESCRIPTION: SEQ ID NO:100:

```
ATG ACA TCA CTG TTC TCT CTA CAG TTA CCG AGC ACA CAG GAC CTC GCC      48
Met Thr Ser Leu Phe Ser Leu Gln Leu Pro Ser Thr Gln Asp Leu Ala
 1               5                  10                  15

ATG GGA TGG AGC TGT ATC ATC CTC TTC TTG GTA GCA ACA GCT ACA GGT      96
Met Gly Trp Ser Cys Ile Ile Leu Phe Leu Val Ala Thr Ala Thr Gly
            20                  25                  30

GTC CTC TCC CAG GTC CAA CTG CAG CAG CCT GGG GCT GAC CTT GTG ATG     144
Val Leu Ser Gln Val Gln Leu Gln Gln Pro Gly Ala Asp Leu Val Met
            35                  40                  45

CCT GGG GCT CCA GTG AAG CTG TCC TGC TTG GCT TCT GGC TAC ATC TTC     192
Pro Gly Ala Pro Val Lys Leu Ser Cys Leu Ala Ser Gly Tyr Ile Phe
 50                  55                  60

ACC AGC TCC TGG ATA AAC TGG GTG AAG CAG AGG CCT GGA CGA GGC CTC     240
Thr Ser Ser Trp Ile Asn Trp Val Lys Gln Arg Pro Gly Arg Gly Leu
 65                  70                  75                  80

GAG TGG ATT GGA AGG ATT GAT CCT TCC GAT GGT GAA GTT CAC TAC AAT     288
Glu Trp Ile Gly Arg Ile Asp Pro Ser Asp Gly Glu Val His Tyr Asn
                 85                  90                  95

CAA GAT TTC AAG GAC AAG GCC ACA CTG ACT GTA GAC AAA TCC TCC AGC     336
Gln Asp Phe Lys Asp Lys Ala Thr Leu Thr Val Asp Lys Ser Ser Ser
            100                 105                 110

ACA GCC TAC ATC CAA CTC AAC AGC CTG ACA TCT GAG GAC TCT GCG GTC     384
Thr Ala Tyr Ile Gln Leu Asn Ser Leu Thr Ser Glu Asp Ser Ala Val
            115                 120                 125

TAT TAC TGT GCT AGA GGA TTT CTG CCC TGG TTT GCT GAC TGG GGC CAA     432
Tyr Tyr Cys Ala Arg Gly Phe Leu Pro Trp Phe Ala Asp Trp Gly Gln
        130                 135                 140

GGG ACT CTG GTC ACT GTC TCT GCA                                     456
Gly Thr Leu Val Thr Val Ser Ala
145                 150
```

( 2 ) INFORMATION FOR SEQ ID NO:101:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:101:

```
Met Thr Ser Leu Phe Ser Leu Gln Leu Pro Ser Thr Gln Asp Leu Ala
```

```
              1                    5                          10                         15

Met  Gly  Trp  Ser  Cys  Ile  Ile  Leu  Phe  Leu  Val  Ala  Thr  Ala  Thr  Gly
                    20                        25                        30

Val  Leu  Ser  Gln  Val  Gln  Leu  Gln  Gln  Pro  Gly  Ala  Asp  Leu  Val  Met
               35                        40                        45

Pro  Gly  Ala  Pro  Val  Lys  Leu  Ser  Cys  Leu  Ala  Ser  Gly  Tyr  Ile  Phe
     50                        55                        60

Thr  Ser  Ser  Trp  Ile  Asn  Trp  Val  Lys  Gln  Arg  Pro  Gly  Arg  Gly  Leu
65                        70                        75                        80

Glu  Trp  Ile  Gly  Arg  Ile  Asp  Pro  Ser  Asp  Gly  Glu  Val  His  Tyr  Asn
                    85                        90                        95

Gln  Asp  Phe  Lys  Asp  Lys  Ala  Thr  Leu  Thr  Val  Asp  Lys  Ser  Ser  Ser
               100                       105                       110

Thr  Ala  Tyr  Ile  Gln  Leu  Asn  Ser  Leu  Thr  Ser  Glu  Asp  Ser  Ala  Val
               115                       120                       125

Tyr  Tyr  Cys  Ala  Arg  Gly  Phe  Leu  Pro  Trp  Phe  Ala  Asp  Trp  Gly  Gln
          130                       135                       140

Gly  Thr  Leu  Val  Thr  Val  Ser  Ala
145                       150
```

( 2 ) INFORMATION FOR SEQ ID NO:102:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:102:

```
Asp  Ile  Gln  Met  Thr  Gln  Ser  Pro  Ser  Thr  Leu  Ser  Ala  Ser  Val  Gly
1                   5                         10                        15

Asp  Arg  Val  Thr  Ile  Thr  Cys  Arg  Ala  Ser  Gln  Ser  Ile  Asn  Thr  Trp
               20                        25                        30

Leu  Ala  Trp  Tyr  Gln  Gln  Lys  Pro  Gly  Lys  Ala  Pro  Lys  Leu  Leu  Met
               35                        40                        45

Tyr  Lys  Ala  Ser  Ser  Leu  Glu  Ser  Gly  Val  Pro  Ser  Arg  Phe  Ile  Gly
     50                        55                        60

Ser  Gly  Ser  Gly  Thr  Glu  Phe  Thr  Leu  Thr  Ile  Ser  Ser  Leu  Gln  Pro
65                        70                        75                        80

Asp  Asp  Phe  Ala  Thr  Tyr  Tyr  Cys  Gln  Gln  Tyr  Asn  Ser  Asp  Ser  Lys
                    85                        90                        95

Met  Phe  Gly  Gln  Gly  Thr  Lys  Val  Glu  Val  Lys
                    100                       105
```

( 2 ) INFORMATION FOR SEQ ID NO:103:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:103:

```
Asp  Ile  Gln  Met  Thr  Gln  Ser  Pro  Ser  Thr  Leu  Ser  Ala  Ser  Val  Gly
1                   5                         10                        15

Asp  Arg  Val  Thr  Ile  Thr  Cys  Lys  Ala  Ser  Glu  Asn  Val  Asp  Thr  Tyr
```

|  |  |  |  |  | 20 |  |  |  | 25 |  |  |  |  | 30 |
|---|---|---|---|---|---|---|---|---|---|---|---|---|---|---|

Val Ser Trp Tyr Gln Gln Lys Pro Gly Lys Ala Pro Lys Leu Leu Ile
            35                40                45

Tyr Gly Ala Ser Asn Arg Tyr Thr Gly Val Pro Ser Arg Phe Ser Gly
    50                  55              60

Ser Gly Ser Gly Thr Asp Phe Thr Leu Thr Ile Ser Ser Leu Gln Pro
65              70                  75                      80

Asp Asp Phe Ala Thr Tyr Tyr Cys Gly Gln Ser Tyr Asn Tyr Pro Phe
                85              90                      95

Thr Phe Gly Gln Gly Thr Lys Val Glu Val Lys
            100             105

( 2 ) INFORMATION FOR SEQ ID NO:104:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:104:

Gln Val Gln Leu Val Gln Ser Gly Ala Glu Val Lys Lys Pro Gly Ser
1               5               10                      15

Ser Val Lys Val Ser Cys Lys Ala Ser Gly Gly Thr Phe Ser Arg Ser
            20                  25                  30

Ala Ile Ile Trp Val Arg Gln Ala Pro Gly Gln Gly Leu Glu Trp Met
            35                  40              45

Gly Gly Ile Val Pro Met Phe Gly Pro Pro Asn Tyr Ala Gln Lys Phe
    50                  55                  60

Gln Gly Arg Val Thr Ile Thr Ala Asp Glu Ser Thr Asn Thr Ala Tyr
65                  70                  75                      80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Glu Tyr Asn Gly Gly Leu
            100                 105                 110

Val Thr Val Ser Ser
            115

( 2 ) INFORMATION FOR SEQ ID NO:105:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:105:

Gln Val Gln Leu Val Gln Ser Gly Ala Glu Val Lys Lys Pro Gly Ser
1               5               10                      15

Ser Val Lys Val Ser Cys Lys Ala Ser Gly Tyr Ile Phe Thr Ser Ser
            20                  25                  30

Trp Ile Asn Trp Val Arg Gln Ala Pro Gly Gln Gly Leu Glu Trp Met
            35                  40              45

Gly Arg Ile Asp Pro Ser Asp Gly Glu Val His Tyr Asn Gln Asp Phe
    50                  55                  60

Lys Asp Arg Val Thr Ile Thr Ala Asp Glu Ser Thr Asn Thr Ala Tyr

|  | 65 |  |  |  | 70 |  |  |  | 75 |  |  |  | 80 |
|---|---|---|---|---|---|---|---|---|---|---|---|---|---|
| Met | Glu | Leu | Ser | Ser | Leu | Arg | Ser | Glu | Asp | Thr | Ala | Val | Tyr Tyr Cys |
|  |  |  |  | 85 |  |  |  |  | 90 |  |  |  | 95 |
| Ala | Arg | Gly | Phe | Leu | Pro | Trp | Phe | Ala | Asp | Trp | Gly | Gln | Gly Thr Leu |
|  |  |  | 100 |  |  |  |  | 105 |  |  |  | 110 |  |
| Val | Thr | Val | Ser | Ser |  |  |  |  |  |  |  |  |  |
|  |  |  | 115 |  |  |  |  |  |  |  |  |  |  |

( 2 ) INFORMATION FOR SEQ ID NO:106:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:106:

```
TTTTTCTAG  ACCACCATGG  AGACCGATAC  CCTCCTGCTA  TGGGTCCTCC  TGCTATGGGT      60
CCCAGGATCA  ACCGGAGATA  TTCAGATGAC  CCAGTCTCCG  TCGACCCTCT  CTGCT         115
```

( 2 ) INFORMATION FOR SEQ ID NO:107:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:107:

```
TTTTAAGCTT  GGGAGCTTTG  CCTGGCTTCT  GCTGATACCA  GGATACATAA  GTATCCACAT      60
TTTCACTGGC  CTTGCAGGTT  ATGGTGACCC  TATCCCCGAC  GCTAGCAGAG  AGGGTCGACG     120
```

( 2 ) INFORMATION FOR SEQ ID NO:108:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:108:

```
TTTTAAGCTT  CTAATTTATG  GGGCATCCAA  CCGGTACACT  GGGGTACCTT  CACGCTTCAG      60
TGGCAGTGGA  TCTGGGACCG  ATTTCACCCT  CACAATCAGC  TCTCTGCAGC  CAGATGAT      118
```

( 2 ) INFORMATION FOR SEQ ID NO:109:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:109:

```
TTTTTCTAG  AGCAAAAGTC  TACTTACGTT  TGACCTCCAC  CTTGGTCCCC  TGACCGAACG      60
TGAATGGATA  GTTGTAACTC  TGTCCGCAGT  AATAAGTGGC  GAAATCATCT  GGCTGCAGAG    120
```

( 2 ) INFORMATION FOR SEQ ID NO:110:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:110:

```
TTTTCTAGA  CCACCATGGG  ATGGAGCTGG  ATCTTTCTCT  TCCTCCTGTC  AGGTACCGCG      60
GGCGTGCACT  CTCAGGTCCA  GCTTGTCCAG  TCTGGGGCTG  AAGTCAAGAA  ACCT          114
```

( 2 ) INFORMATION FOR SEQ ID NO:111:

( i ) SEQUENCE CHARACTERISTICS:
        ( A ) LENGTH: 121 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:111:

```
TTTGAATTC   TCGAGACCCT  GTCCAGGGGC  CTGCCTTACC  CAGTTTATCC  AGGAGCTAGT     60
AAAGATGTAG  CCAGAAGCTT  TGCAGGAGAC  CTTCACGGAG  CTCCCAGGTT  TCTTGACTTC    120
A                                                                         121
```

( 2 ) INFORMATION FOR SEQ ID NO:112:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:112:

```
TTTTGAATTC  TCGAGTGGAT  GGGAAGGATT  GATCCTTCCG  ATGGTGAAGT  TCACTACAAT     60
CAAGATTTCA  AGGACCGTGT  TACAATTACA  GCAGACGAAT  CCACCAATAC  AGCCTACATG    120
GAACTGAGCA  GCCTGAG                                                       137
```

( 2 ) INFORMATION FOR SEQ ID NO:113:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:113:

```
TTTTCTAGA   GGTTTTAAGG  ACTCACCTGA  GGAGACTGTG  ACCAGGGTTC  CTTGGCCCCA     60
GTCAGCAAAC  CAGGGCAGAA  ATCCTCTTGC  ACAGTAATAG  ACTGCAGTGT  CCTCTGATCT    120
CAGGCTGCTC  AGTT                                                          134
```